(12) United States Patent
Reed et al.

(10) Patent No.: US 7,217,688 B2
(45) Date of Patent: May 15, 2007

(54) METHODS AND COMPOSITIONS FOR DEREPRESSION OF IAP-INHIBITED CASPASE

(75) Inventors: John C. Reed, Rancho Santa Fe, CA (US); Richard A. Houghten, Solana Beach, CA (US); Adel Nefzi, San Diego, CA (US); John M. Ostresh, Encinitas, CA (US); Clemencia Pinilla, Cardiff, CA (US); Kate Welsh, San Diego, CA (US)

(73) Assignees: The Burnham Institute, La Jolla, CA (US); Torrey Pines Institute for Molecular Studies, San Diego, CA (US)

( * ) Notice: Subject to any disclaimer, the term of this patent is extended or adjusted under 35 U.S.C. 154(b) by 0 days.

(21) Appl. No.: 11/186,629

(22) Filed: Jul. 19, 2005

(65) Prior Publication Data
US 2006/0211627 A1 Sep. 21, 2006

Related U.S. Application Data

(63) Continuation-in-part of application No. 11/084,714, filed on Mar. 17, 2005.

(51) Int. Cl.
*A01N 37/18* (2006.01)
(52) U.S. Cl. ............................... 514/2; 514/18
(58) Field of Classification Search ............... None
See application file for complete search history.

(56) References Cited

U.S. PATENT DOCUMENTS

| | | | |
|---|---|---|---|
| 4,631,211 A | 12/1986 | Houghten | |
| 5,223,409 A | 6/1993 | Ladner et al. | |
| 5,556,762 A | 9/1996 | Pinilla et al. | |
| 5,766,848 A | 6/1998 | Borden et al. | |
| 6,159,709 A | 12/2000 | Korneluk et al. | |
| 6,228,603 B1 | 5/2001 | Reed et al. | |
| 6,911,426 B2 | 6/2005 | Reed et al. | |
| 2003/0180805 A1* | 9/2003 | Reed et al. | 435/7.1 |
| 2005/0119176 A1* | 6/2005 | Reed et al. | 514/12 |

FOREIGN PATENT DOCUMENTS

WO WO 92/09300 6/1992

OTHER PUBLICATIONS

Ambrosini et al., "A novel anti-apoptosis gene, *survivin*, expressed in cancer and lymphoma," *Nature Med.* 3:917-921 (1997).
Bertin et al., "Apoptotic suppression by baculovirus P35 involves cleavage by and inhibition of a virus-induced CED-3/ICE-like protease," *J.Virol* 70:6251-6259 (1996).
Birnbaum et al., "An Apoptosis-inhibiting Gene from a Nuclear Polyhedrosis Virus Encoding a Polypeptide with Cys/His Sequence Motifs," *J. Virol.* 68:2521-2528 (1994).
Boldin et al., "Involvement of MACH, a Novel MORT1/FADD-Interacting Protease, in Fas/APO-1- and TNF Receptor-Induced Cell Death," *Cell* 85:803-815 (1996).
Bump et al., "Inhibition of ICE Family Proteases by Baculovirus Antiapoptotic protein p35," *Science* 269:1885-1888 (1995).
Casciola-Rosen et al., "Apopain/CPP32 Cleaves Proteins That Are Essential for Cellular Repair: A Fundamental Principle of Apoptotic Death," *J. Exp. Med.* 183:1957-1964 (1996).
Chai et al., "Structural and biochemical basis of apoptotic activation by Smac/DIABLO," *Nature* 406:855-862 (2000).
Chen et al., "A Human IAP-Family Gene, *Apollon*, Expressed in Human Brain Cancer Cells," *Biochem. Biophys. Res. Commun.* 264:847-854 (1999).
Deveraux et al., "IAPs block apoptotic events induced by caspase-8 and cytochrome c by direct inhibition of distinct caspases," *EMBO J.* 17:2215-2223 (1998).
Deveraux et al., "X-linked IAP is a direct inhibitor of cell-deaht proteases," *Nature* 388:300-304 (1997).
Deveraux and Reed, "IAP family proteins—suppressors of apoptosis," *Genes and Development* 13:239-252 (1999).
Dooley et al., "An All D-Amino Acid Opioid Peptide with Central Analgesic Activity from a Combinatorial Library," *Science* 266:2019-2022 (1994).
Du et al., "Smac, a Mitochondrial Protein that Promotes Cytochrome c-Dependent Caspase Activation by Eliminating IAP Inhibition," *Cell* 102:33-42 (2000).
Hawkins, et al. "Inhibition of interleukin 1β-converting enzyme-mediated apoptosis of mammalian cells by baculovirus IAP," *Proc. Nat'l Acad. Sci. USA* 93:13786-13790 (1996).
Houghten et al., "Generation and use of synthetic peptide combinatorial libraries for basic research and drug discovery," *Nature* 354:84-86 (1991).
Kasof and Gomes, "Livin, a Novel Inhibitor of Apoptosis Protein Family Member," *J. Biol. Chem.* 276:3238-3246 (2001).
Kharbanda et al., "Role for Bcl-$x_L$ as an inhibitor of cytosolic cytochrome C accumulation in DNA damage-induced apoptosis," *Proc. Natl. Acad. Sci. USA* 94:6939-6942 (1997).
Kluck et al., "The Release of Cytochrome c from Mitochondria: A Primary Site for Bcl-2 Regulation of Apoptosis," *Science* 275:1132-1136 (1997).

(Continued)

*Primary Examiner*—B. Dell Chism
*Assistant Examiner*—Hemant Khanna
(74) *Attorney, Agent, or Firm*—McDermott Will & Emery LLP

(57) ABSTRACT

The invention provides isolated agents having novel chemical structures and possessing superior activity as derepressors of IAP inhibited caspase. The invention further provides a method of derepressing an IAP-inhibited caspase. The invention further provides assay methods employing labeled compounds of the invention, especially fluorescent labeled compounds.

93 Claims, 158 Drawing Sheets

OTHER PUBLICATIONS

Li et al., "Cytochrome c and dATP-Dependent Formation of Apaf-1/Caspase-9 Complex Initiates an Apoptotic Protease Cascade," *Cell* 91:479-489 (1997).

Liston et al., "Suppression of apoptosis in mammalian cells by NAIP and a related family of IAP genes," *Nature* 379:349-353 (1996).

Liu et al., "Induction of Apoptotic Program in Cell-Free Extracts: Requirement for dATP and Cytochrome c," *Cell* 86:147-157 (1996).

Liu et al., "DFF, a Heterodimeric Protein That Functions Downstream of Caspase-3 to Trigger DNA Fragmentation during Apoptosis," *Cell* 89:175-184 (1997).

Liu et al., "Structural basis for binding of Smac/DIABLO to the XIAP BIR3 domain," *Nature* 408:1004-1008 (2000).

Martin and Green, "Protease Activation during Apoptosis: Death by a Thousand Cuts?" *Cell* 82:349-352 (1995).

Muzio et al., "FLICE, a Novel FADD-Homologous ICE/CED-3-like Protease, Is Recruited to the CD95 (Fas/APO-1) Death-Inducing Signaling Complex," *Cell* 85:817-827 (1996).

Reed and Tomaselli, "Drug discovery opportunities from apoptosis research," *Cur. Opin. Biotech.* 11:586-592 (2000).

Reed, "Apoptosis-regulating proteins as targets for drug discovery," *Trends Mol. Med.* 7:314-319 (2001).

Riedl et al., "Structural Basis for the Inhibition of Caspase-3 by XIAP," *Cell* 104:791-800 (2001).

Rothe et al., "The TNFR2-TRAF Signaling Complex Contains Two Novel Proteins Related to Baculoviral Inhibitor of Apoptosis Proteins," *Cell* 83:1243-1252 (1995).

Roy et al., "The c-IAP-1 and c-IAP-2 proteins are direct inhibitors of specific caspases," *EMBO J.* 16:6914-6925 (1997).

Sun et al., "NMR structure and mutagenesis of the inhibitor-of-apoptosis protein XIAP," *Nature* 401:818-822 (1999).

Srinivasula et al., "Molecular Determinants of the Caspase-promoting Activity of Smac/DIABLO and Its Role in the Death Receptor Pathway," *J. Bio. Chem.* 275:36152-36157 (2000).

Srinivasula et al., "A conserved XIAP-interaction motif in caspase-9 and Smac/DIABLO regulates caspase activity and apoptosis," *Nature* 410:112-116 (2001).

Takahashi et al., "Cleavage of lamin A by Mch2α but not CPP32: Multiple interleukin 1β-converting enzyme-related proteases with distinct substrate recognition properties are active in apoptosis," *Proc. Natl. Acad. Sci. USA* 93:8395-8400 (1996).

Takahashi et al., A Single BIR Domain of XIAP Sufficient for Inhibiting Caspases, *J. Biol. Chem.* 273:7787-7790 (1998).

Verhagen et al., "Identification of DIABLO, a Mammalian Protein that Promotes Apoptosis by Binding to and Antagonizing IAP Proteins," *Cell* 102:43-53 (2000).

Villa et al. "Caspases and caspase inhibitors," *TIBS.* 22:388-393 (1997).

Vucic et al., "ML-IAP, a novel inhibitor of apoptosis that is preferentially expressed in human melanomas," *Cur. Biol.* 10:1359-1366 (2000).

Wang et al., "Cleavage of sterol regulatory element binding proteins (SREBPs) by CPP32 during apoptosis," *EMBO J.* 15:1012-1020 (1996).

Wu et al., "Structural basis of IAP recognition by Smac/DIABLO," *Nature* 408:1008-1012 (2000).

Yang et al., "Prevention of Apoptosis by Bcl-2: Release of Cytochrome c from Mitochondria Blocked," *Science* 275:1129-1132 (1997).

Zhou et al., "Target Protease Specificity of the Viral Serpin CrmA. Analysis of Five Caspases," *J. Biol. Chem.* 272:7797-7800 (1997).

Zhou et al., "IL-10 Inhibits Apoptosis of Promyeloid Cells by Activating Insulin Receptor Substrate-2 and Phosphatidylinositol 3'- Kinase," *J. Immunol.* 167:4436-4442 (2001).

Zou et al., "Apaf-1, a Human Protein Homologous to *C. elegans* CED-4, Participates in Cytochrome c-Dependent Activation of Caspase-3," Cell 90:405-413 (1997).

Nefzi et al., "An efficient two-step synthesis of mono-, di- and triureas from resin bound amides," Tetrahedron Lett., 41:5441-5446 (2000).

* cited by examiner

TPI 1313

|  | 1 | 2 | 3 | 4 | | | | |
|---|---|---|---|---|---|---|---|---|
|  | L-Thiala | D-pCl-Phe | D-OEt-Tyr | D-pCl-Phe | | | Ratio>1.9 | |
|  | D-Thiala | D-OEt-Tyr | D-Nal | D-pNO2-Phe | | | | |
|  | Phe | D-Phe | | D-Thiala | | | | |
|  | | | | | | Ratio | | Ratio |
|  | | | | | | Caspase3/Xiap | | peptide/xiap |
| Vial# | 1 | 2 | 3 | 4 | | Avg | std | AVG | std |
| 1 | L-Thiala | D-pCl-Phe | D-OEt-Tyr | D-pCl-Phe | -NH2 | 0.9 | 0.036 | 1.3 | 0.20 |
| 2 | L-Thiala | D-pCl-Phe | D-OEt-Tyr | D-pNO2-Phe | -NH2 | 0.9 | 0.035 | 1.3 | 0.22 |
| 3 | L-Thiala | D-pCl-Phe | D-OEt-Tyr | D-Thiala | -NH2 | 0.9 | 0.031 | 0.9 | 0.10 |
| 4 | L-Thiala | D-pCl-Phe | D-Nal | D-pCl-Phe | -NH2 | 0.9 | 0.031 | 2.3 | 0.60 |
| 5 | L-Thiala | D-pCl-Phe | D-Nal | D-pNO2-Phe | -NH2 | 0.9 | 0.033 | 1.7 | 0.24 |
| 6 | L-Thiala | D-pCl-Phe | D-Nal | D-Thiala | -NH2 | 0.9 | 0.029 | 1.3 | 0.17 |
| 7 | L-Thiala | D-OEt-Tyr | D-OEt-Tyr | D-pCl-Phe | -NH2 | 0.9 | 0.024 | 2.7 | 0.37 |
| 8 | L-Thiala | D-OEt-Tyr | D-OEt-Tyr | D-pNO2-Phe | -NH2 | 0.9 | 0.027 | 1.4 | 0.21 |
| 9 | L-Thiala | D-OEt-Tyr | D-OEt-Tyr | D-Thiala | -NH2 | 0.9 | 0.032 | 0.9 | 0.05 |
| 10 | L-Thiala | D-OEt-Tyr | D-Nal | D-pCl-Phe | -NH2 | 0.9 | 0.029 | 0.7 | 0.09 |
| 11 | L-Thiala | D-OEt-Tyr | D-Nal | D-pNO2-Phe | -NH2 | 0.9 | 0.031 | 0.9 | 0.18 |
| 12 | L-Thiala | D-OEt-Tyr | D-Nal | D-Thiala | -NH2 | 0.9 | 0.029 | 0.9 | 0.13 |
| 13 | L-Thiala | D-Phe | D-OEt-Tyr | D-pCl-Phe | -NH2 | 0.9 | 0.028 | 0.6 | 0.08 |
| 14 | L-Thiala | D-Phe | D-OEt-Tyr | D-pNO2-Phe | -NH2 | 0.9 | 0.028 | 0.6 | 0.08 |
| 15 | L-Thiala | D-Phe | D-OEt-Tyr | D-Thiala | -NH2 | 0.9 | 0.025 | 0.6 | 0.07 |
| 16 | L-Thiala | D-Phe | D-Nal | D-pCl-Phe | -NH2 | 0.9 | 0.029 | 0.8 | 0.09 |
| 17 | L-Thiala | D-Phe | D-Nal | D-pNO2-Phe | -NH2 | 0.9 | 0.032 | 1.1 | 0.10 |
| 18 | L-Thiala | D-Phe | D-Nal | D-Thiala | -NH2 | 0.9 | 0.029 | 0.9 | 0.08 |
| 19 | D-Thiala | D-pCl-Phe | D-OEt-Tyr | D-pCl-Phe | -NH2 | 0.9 | 0.031 | 1.5 | 0.24 |
| 20 | D-Thiala | D-pCl-Phe | D-OEt-Tyr | D-pNO2-Phe | -NH2 | 0.8 | 0.042 | 1.3 | 0.30 |
| 21 | D-Thiala | D-pCl-Phe | D-OEt-Tyr | D-Thiala | -NH2 | 0.9 | 0.030 | 0.9 | 0.10 |
| 22 | D-Thiala | D-pCl-Phe | D-Nal | D-pCl-Phe | -NH2 | 0.9 | 0.030 | 1.0 | 0.14 |
| 23 | D-Thiala | D-pCl-Phe | D-Nal | D-pNO2-Phe | -NH2 | 0.9 | 0.022 | 1.0 | 0.10 |
| 24 | D-Thiala | D-pCl-Phe | D-Nal | D-Thiala | -NH2 | 0.9 | 0.024 | 1.3 | 0.16 |
| 25 | D-Thiala | D-OEt-Tyr | D-OEt-Tyr | D-pCl-Phe | -NH2 | 1.0 | 0.028 | 1.6 | 0.20 |
| 26 | D-Thiala | D-OEt-Tyr | D-OEt-Tyr | D-pNO2-Phe | -NH2 | 0.8 | 0.027 | 1.1 | 0.14 |
| 27 | D-Thiala | D-OEt-Tyr | D-OEt-Tyr | D-Thiala | -NH2 | 0.9 | 0.037 | 1.1 | 0.12 |
| 28 | D-Thiala | D-OEt-Tyr | D-Nal | D-pCl-Phe | -NH2 | 0.9 | 0.041 | 1.1 | 0.11 |
| 29 | D-Thiala | D-OEt-Tyr | D-Nal | D-pNO2-Phe | -NH2 | 0.9 | 0.032 | 1.1 | 0.14 |
| 30 | D-Thiala | D-OEt-Tyr | D-Nal | D-Thiala | -NH2 | 0.9 | 0.043 | 1.2 | 0.12 |
| 31 | D-Thiala | D-Phe | D-OEt-Tyr | D-pCl-Phe | -NH2 | 0.9 | 0.038 | 1.3 | 0.15 |
| 32 | D-Thiala | D-Phe | D-OEt-Tyr | D-pNO2-Phe | -NH2 | 1.0 | 0.036 | 1.1 | 0.08 |
| 33 | D-Thiala | D-Phe | D-OEt-Tyr | D-Thiala | -NH2 | 0.9 | 0.034 | 1.0 | 0.08 |
| 34 | D-Thiala | D-Phe | D-Nal | D-pCl-Phe | -NH2 | 0.9 | 0.027 | 1.0 | 0.13 |
| 35 | D-Thiala | D-Phe | D-Nal | D-pNO2-Phe | -NH2 | 0.9 | 0.029 | 0.9 | 0.12 |
| 36 | D-Thiala | D-Phe | D-Nal | D-Thiala | -NH2 | 0.9 | 0.032 | 1.1 | 0.13 |
| 37 | Phe | D-pCl-Phe | D-OEt-Tyr | D-pCl-Phe | -NH2 | 0.9 | 0.042 | 1.3 | 0.14 |
| 38 | Phe | D-pCl-Phe | D-OEt-Tyr | D-pNO2-Phe | -NH2 | 0.9 | 0.030 | 0.8 | 0.12 |
| 39 | Phe | D-pCl-Phe | D-OEt-Tyr | D-Thiala | -NH2 | 0.9 | 0.029 | 0.9 | 0.11 |
| 40 | Phe | D-pCl-Phe | D-Nal | D-pCl-Phe | -NH2 | 0.9 | 0.026 | 1.9 | 0.13 |
| 41 | Phe | D-pCl-Phe | D-Nal | D-pNO2-Phe | -NH2 | 1.0 | 0.120 | 0.9 | 0.07 |
| 42 | Phe | D-pCl-Phe | D-Nal | D-Thiala | -NH2 | 0.9 | 0.045 | 1.0 | 0.27 |
| 43 | Phe | D-OEt-Tyr | D-OEt-Tyr | D-pCl-Phe | -NH2 | 1.0 | 0.098 | 0.9 | 0.14 |
| 44 | Phe | D-OEt-Tyr | D-OEt-Tyr | D-pNO2-Phe | -NH2 | 1.0 | 0.139 | 1.0 | 0.07 |

Figure 2

TPI 1313

|  | 1 | 2 | 3 | 4 | | | | | |
|---|---|---|---|---|---|---|---|---|---|
|  | L-Thiala | D-pCl-Phe | D-OEt-Tyr | D-pCl-Phe | | | | Ratio>1.9 | |
|  | D-Thiala | D-OEt-Tyr | D-Nal | D-pNO2-Phe | | | | | |
|  | Phe | D-Phe | | D-Thiala | | | | | |
|  | | | | | | Ratio Caspase3/Xiap | | Ratio peptide/xiap | |
| Vial# | 1 | 2 | 3 | 4 | | Avg | std | AVG | std |
| 45 | Phe | D-OEt-Tyr | D-OEt-Tyr | D-Thiala | -NH2 | 1.0 | 0.114 | 0.8 | 0.23 |
| 46 | Phe | D-OEt-Tyr | D-Nal | D-pCl-Phe | -NH2 | 1.0 | 0.124 | 0.9 | 0.26 |
| 47 | Phe | D-OEt-Tyr | D-Nal | D-pNO2-Phe | -NH2 | 0.9 | 0.100 | 1.0 | 0.33 |
| 48 | Phe | D-OEt-Tyr | D-Nal | D-Thiala | -NH2 | 1.0 | 0.068 | 1.0 | 0.05 |
| 49 | Phe | D-Phe | D-OEt-Tyr | D-pCl-Phe | -NH2 | 1.0 | 0.057 | 1.1 | 0.09 |
| 50 | Phe | D-Phe | D-OEt-Tyr | D-pNO2-Phe | -NH2 | 0.9 | 0.106 | 0.9 | 0.07 |
| 51 | Phe | D-Phe | D-OEt-Tyr | D-Thiala | -NH2 | 1.0 | 0.056 | 0.9 | 0.03 |
| 52 | Phe | D-Phe | D-Nal | D-pCl-Phe | -NH2 | 0.9 | 0.083 | 1.0 | 0.14 |
| 53 | Phe | D-Phe | D-Nal | D-pNO2-Phe | -NH2 | 0.9 | 0.080 | 0.9 | 0.06 |
| 54 | Phe | D-Phe | D-Nal | D-Thiala | -NH2 | 1.0 | 0.127 | 0.9 | 0.03 |

Figure 2 (cont.)

TPI 882

TPI 759 N-Benzyl-1,4,5-trisubstited-2,3-diketopiperazines

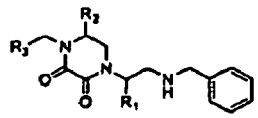

| Selections | R1 | | R2 | | R3 | |
|---|---|---|---|---|---|---|
| | 21 | Fmoc-Nle | 43 | Fmoc-leu | 65 | 4-Isobutyl-alpha-Methylphenylacetic Acid |
| | 22 | Fmoc-nle | 52 | Fmoc-NapAla | 67 | 3,5-Bis(Trifluoromethyl)-Phenylacetic Acid |
| | 25 | Fmoc-NapAla | 41 | Fmoc-phe | 72 | Heptanoic Acid |
| | 29 | Fmoc-chala | 31 | Fmoc-Phe | 60 | (Alpha-Alpha-Alpha-Trifluoro-m-Tolyl) acetic acid |
| | 28 | Fmoc-ChAla | 42 | Fmoc-Ile | 87 | 4-tert-Butyl-cyclohexanecarboxylic Acid |
| | 5 | Fmoc-Lys(Boc | 33 | Fmoc-Ile | 58 | m-Tolylacetic Acid |
| | 24 | Fmoc-nva | 46 | Fmoc-val | 66 | 3,4-Dichlorophenylacetic Acid |
| | 23 | Fmoc-Nva | 34 | Fmoc-Leu | 89 | 3,3-Diphenyl propionic Acid · |
| | 19 | Fmoc-val | | | 90 | Dicyclohexylacetic acid |
| | | | | | 81 | Cycloheptanecarboxylic Acid |
| | | | | | 61 | p-Tolylacetic Acid |
| | | | | | 80 | Cyclohexanebutyric Acid |

R1

21 Norleucine

22 norleucine

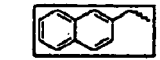
25 NapAla

29 cyclohexylalani

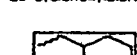
28 Cyclohexylalan

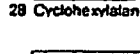
5 Lysine

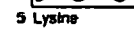
24 norvaline

23 Norvaline

19 valine

R2

43 leucine

52 NapAla

41 phenylalan

31 Phenylalar

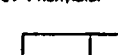
42 Isoleucine

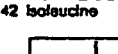
33 Isoleucine

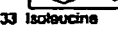
46 valine

34 Leucine

R3

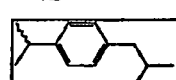
65 4-Isobutyl-alpha-methylphenylacetic acid

67 3,5-Bis(Trifluoromethyl)-phenylacetic acid

72 Heptanoic acid

60 (Alpha-alpha-alpha-trifluoro-m-tolyl)acetic acid

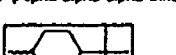
87 4-tert-Butyl-cyclohexanecarboxylic acid

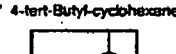
58 m-tolylacetic acid

66 3,4-Dichlorophenylacetic acid

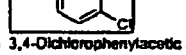
89 3,3-Diphenylpropionic acid

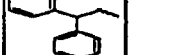
90 Dicyclohexylacetic acid

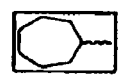
81 Cycloheptanecarboxylic acid

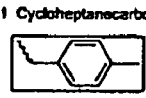
61 p-Tolylacetic acid

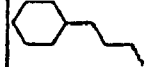
80 Cyclohexanebutyric acid

FIGURE 8

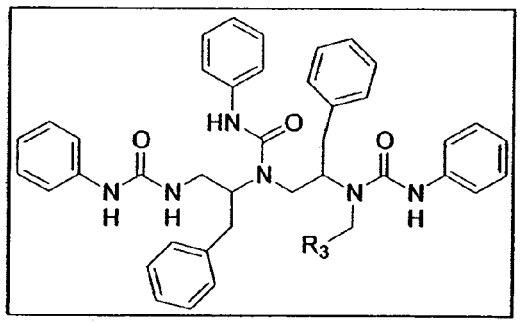
R3
tert-butyl
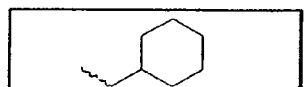
cyclohexylmethyl
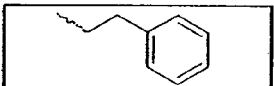
phenethyl
3-methoxybenzyl
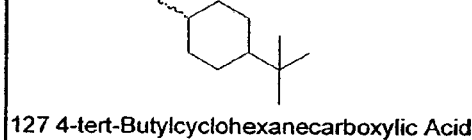
4-t-butyl-cyclohexyl
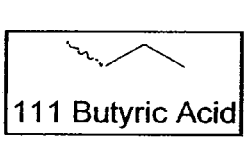
propyl
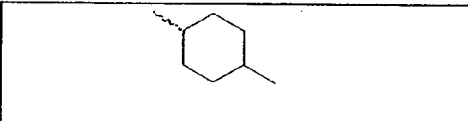
4-methylcyclohexyl
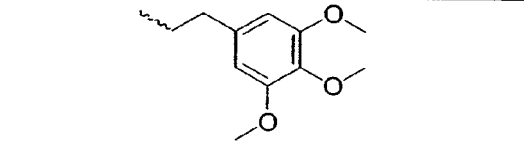
3,4,5-trimethoxyphenethyl
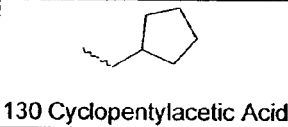
cyclopentylmethyl
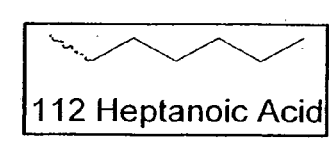
hexyl
Figure 9A

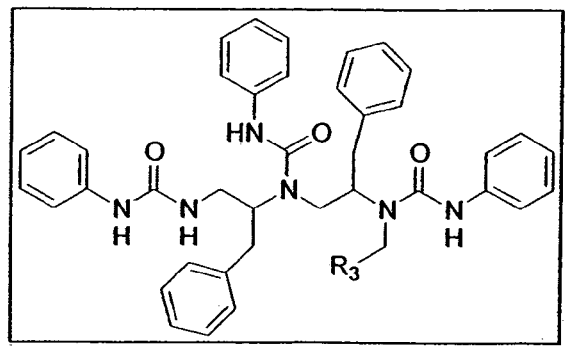

R3

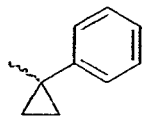

97 1-Phenyl-1-Cyclopropanecarboxylic Acid
1-phenyl-cyclopropyl

134 2-Norbornaneacetic Acid
2-norbornylmethyl

118 Cyclohexanecarboxylic Acid
cyclohexyl

125 Cyclohexanepropionic Acid
cyclohexylethyl

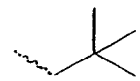

117 tert-Butyl acetic Acid
tert-butylmethyl

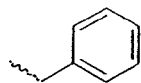

108 Phenylacetic Acid
benzyl

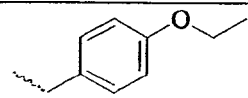

104 4-Ethoxyphenylacetic Acid
4-ethoxybenzyl

121 Cycloheptanecarboxylic Acid
cycloheptyl

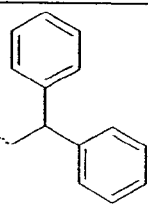

129 3,3-Diphenylpropionic Acid
2,2-diphenylethyl

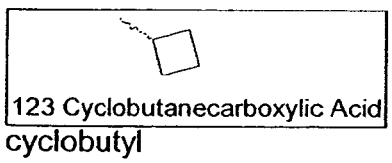

123 Cyclobutanecarboxylic Acid
cyclobutyl

Figure 9B

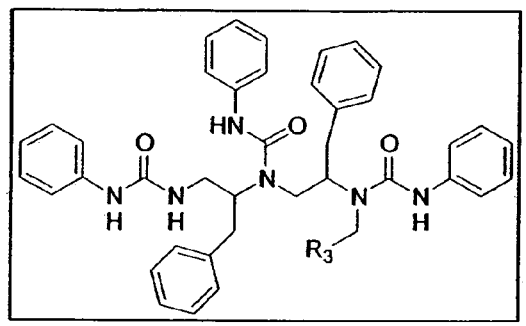
R3
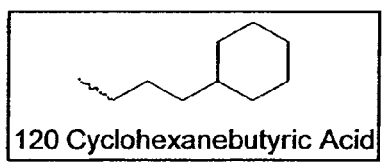
120 Cyclohexanebutyric Acid
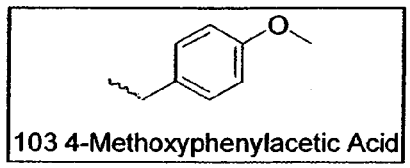
103 4-Methoxyphenylacetic Acid
4-methoxybenzyl
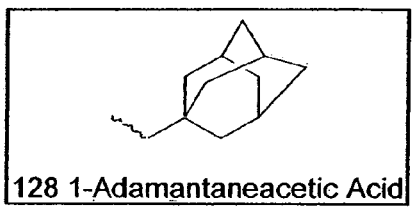
128 1-Adamantaneacetic Acid
1-adamantylmethyl
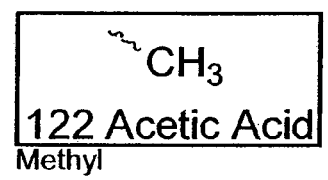
122 Acetic Acid
Methyl
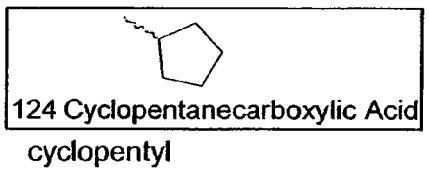
124 Cyclopentanecarboxylic Acid
cyclopentyl
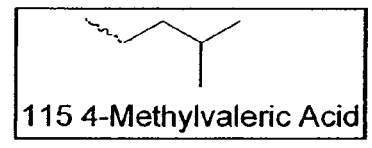
115 4-Methylvaleric Acid
3-methylbutyl
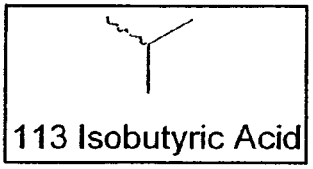
113 Isobutyric Acid
isopropyl
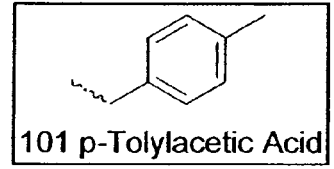
101 p-Tolylacetic Acid
4-methylbenzyl
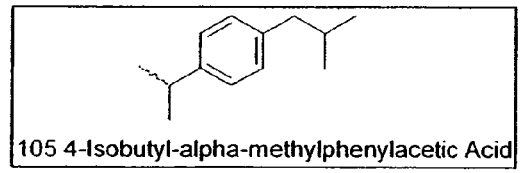
105 4-Isobutyl-alpha-methylphenylacetic Acid
1-(4-isobutyl-phenyl)-ethyl
Figure 9C TPI 882 controls
All the compounds below have activity at 8 ug/ml Hexape-1
TPI 1239      All mix are N-terminal free and C-terminal amide
Caspase 3-XIAP
From File 032001-IC50 of selected TPI 1239
Note that Smac is only tested at 1 mM TPI1239 dose responses (sort)

Caspase effect

| | 2 ug/ml | | 1ug/ml | | 0.5 ug/ml | | 0.25 ug/ml | |
|---|---|---|---|---|---|---|---|---|
| | Avg | std | Avg | std | Avg | std | Avg | std |
| Caspase 3 | 1.0 | 0.0 | 1.0 | 0.0 | 1.0 | 0.0 | 1.0 | 0.0 |
| Xiap+C3 | 0.4 | 0.0 | 0.4 | 0.0 | 0.4 | 0.0 | 0.4 | 0.0 |
| SMAC | 0.9 | 0.1 | 0.9 | 0.1 | 0.9 | 0.1 | 0.9 | 0.1 |
| XXXAWW | 1.0 | 0.0 | 1.1 | 0.0 | 1.1 | 0.0 | 1.0 | 0.0 |
| XXXHWW | 1.0 | 0.1 | 1.1 | 0.0 | 1.1 | 0.0 | 1.0 | 0.1 |
| XXXKWW | 1.0 | 0.1 | 1.0 | 0.0 | 1.0 | 0.0 | 1.1 | 0.1 |
| XXXNWW | 1.0 | 0.0 | 1.0 | 0.0 | 1.0 | 0.0 | 1.0 | 0.0 |
| XXXQWW | 1.0 | 0.0 | 1.0 | 0.0 | 1.0 | 0.0 | 1.0 | 0.0 |
| XXXRWW | 1.0 | 0.0 | 1.0 | 0.0 | 1.0 | 0.0 | 1.0 | 0.0 |
| XXXSWW | 1.0 | 0.0 | 1.0 | 0.0 | 1.0 | 0.0 | 1.0 | 0.1 |
| XXXTWW | 1.1 | 0.0 | 1.1 | 0.0 | 1.1 | 0.0 | 1.0 | 0.0 |

Figure 11A

Hexape-1
TPI 1239
Caspase 3-XIAP    All mix are N-terminal free and C-terminal amide
From File 032001-IC50 of selected TPI 1239
Note that Smac is only tested at 1 mM TPI1239 dose responses (sort)

| | 2 ug/ml | | 1ug/ml | | 0.5 ug/ml | | 0.25 ug/ml | |
|---|---|---|---|---|---|---|---|---|
| | Avg | std | Avg | std | Avg | std | Avg | std |
| XXXVWW | 1.0 | 0.0 | 0.9 | 0.0 | 1.0 | 0.1 | 1.0 | 0.0 |
| XXXXWW | 1.0 | 0.0 | 1.1 | 0.1 | 1.0 | 0.0 | 1.1 | 0.0 |

XIAP effect

| | 2 ug/ml | | 1ug/ml | | 0.5 ug/ml | | 0.25 ug/ml | |
|---|---|---|---|---|---|---|---|---|
| | Avg | std | Avg | std | Avg | std | Avg | std |
| Caspase 3 | 2.2 | 0.0 | 2.2 | 0.0 | 2.2 | 0.0 | 2.2 | 0.0 |
| Xiap + C3 | 1.0 | 0.1 | 1.0 | 0.0 | 1.0 | 0.0 | 1.0 | 0.0 |
| SMAC | 2.0 | 0.1 | 2.0 | 0.1 | 2.0 | 0.1 | 2.0 | 0.1 |
| XXXAWW | 2.2 | 0.0 | 2.0 | 0.0 | 1.7 | 0.0 | 1.4 | 0.0 |
| XXXKWW | 2.2 | 0.1 | 2.0 | 0.2 | 1.6 | 0.1 | 1.2 | 0.1 |
| XXXTWW | 2.1 | 0.0 | 1.8 | 0.0 | 1.6 | 0.0 | 1.2 | 0.1 |
| XXXSWW | 2.1 | 0.2 | 1.8 | 0.0 | 1.4 | 0.1 | 1.3 | 0.3 |

Figure 11B

Hexape-1
TPI 1239        All mix are N-terminal free and C-terminal amide
Caspase 3-XIAP
From File 032001-IC50 of selected TPI 1239
Note that Smac is only tested at 1 mM TPI1239 dose responses (sort)

| | 2 ug/ml | | 1ug/ml | | 0.5 ug/ml | | 0.25 ug/ml | |
|---|---|---|---|---|---|---|---|---|
| | Avg | std | Avg | std | Avg | std | Avg | std |
| XXXNWW | 1.8 | 0.2 | 1.4 | 0.0 | 1.2 | 0.1 | 1.1 | 0.1 |
| XXXVWW | 1.7 | 0.0 | 1.4 | 0.0 | 1.2 | 0.2 | 1.0 | 0.1 |
| XXXXWW | 1.8 | 0.1 | 1.4 | 0.1 | 1.1 | 0.1 | 1.1 | 0.3 |
| XXXHWW | 1.8 | 0.1 | 1.4 | 0.1 | 1.1 | 0.1 | 1.0 | 0.1 |
| XXXRWW | 1.4 | 0.1 | 1.1 | 0.0 | 1.1 | 0.1 | 0.9 | 0.1 |
| XXXQWW | 1.54 | 0.0 | 1.3 | 0.0 | 1.1 | | 0.9 | 0.1 |

Figure 11C

Tetra-peptide antagonists of XIAP
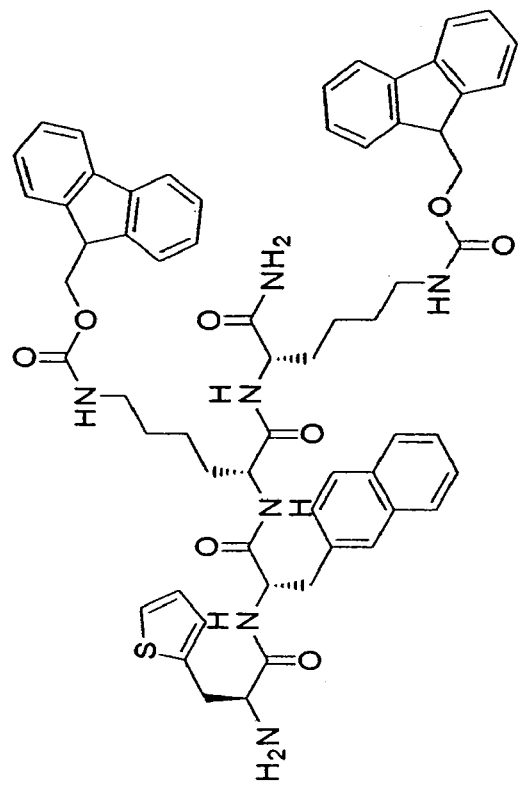
792-35
Exact Mass: 1067.46153
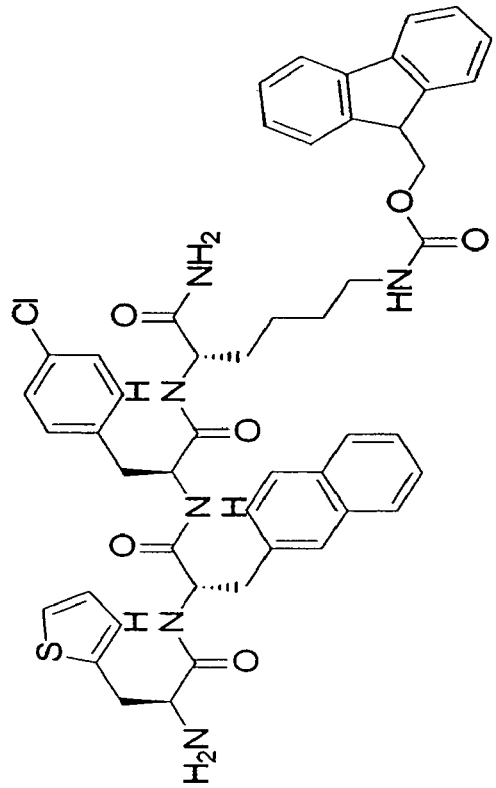
792-33
Exact Mass: 898.32793
Figure 12

A     TPI 1391
N-Benzyl-1,4,5-trisubstited-2,3-diketopiperazines
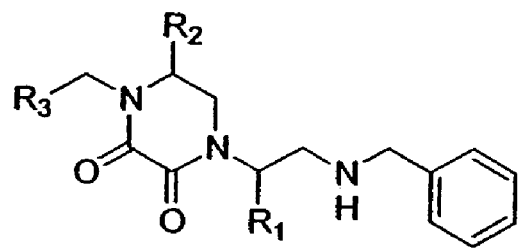
TPI 1396
Polyphenylureas
Diphenyl or Triphenylureas
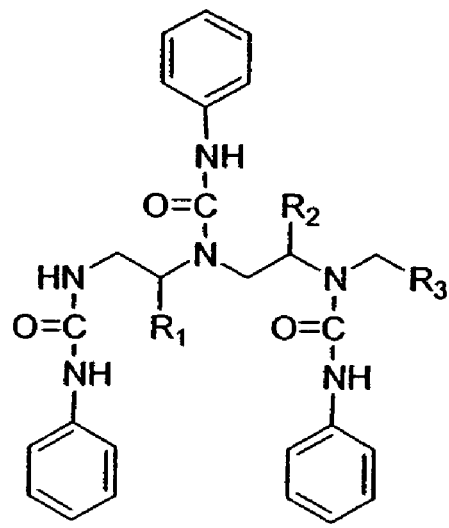
Figure 14A B
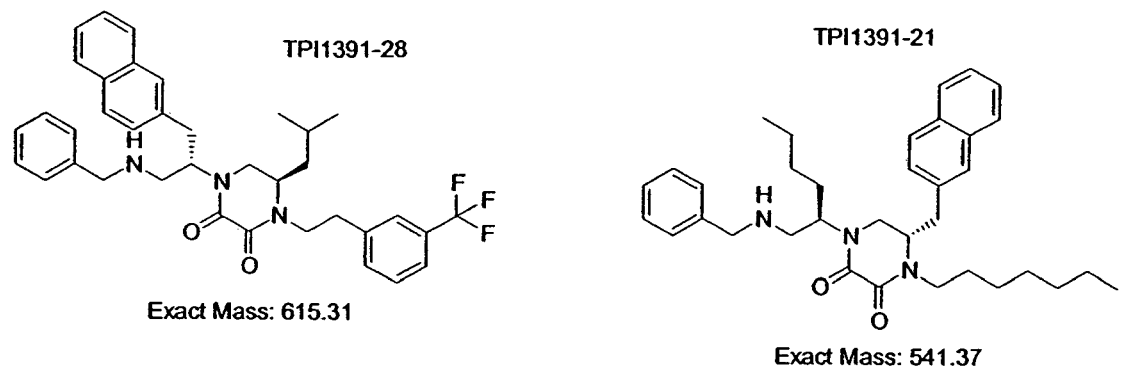
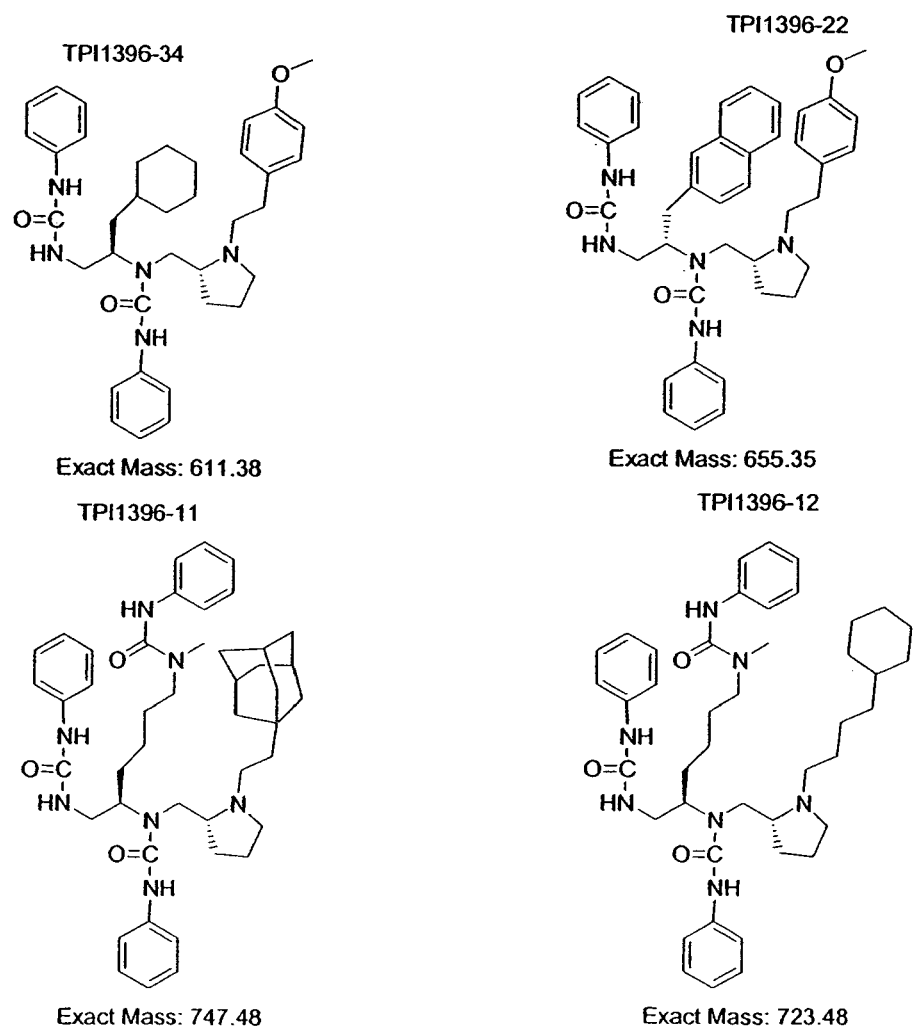
Figure 14B

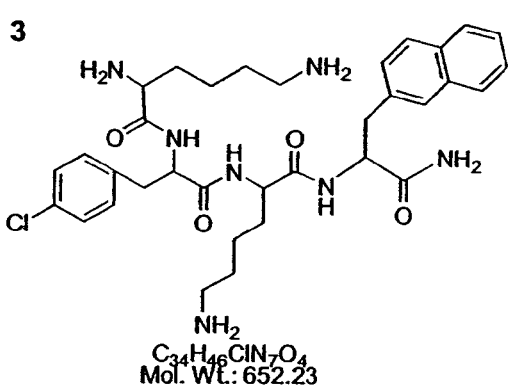
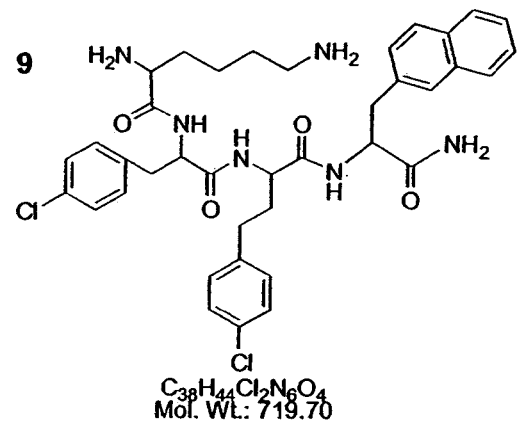
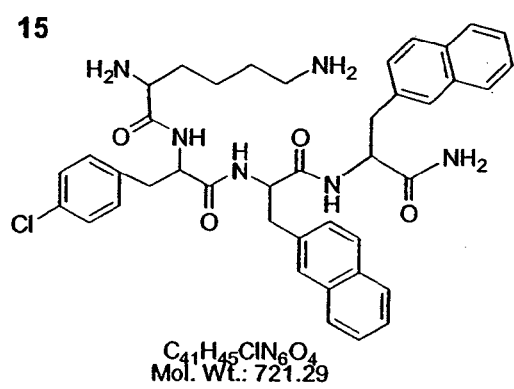
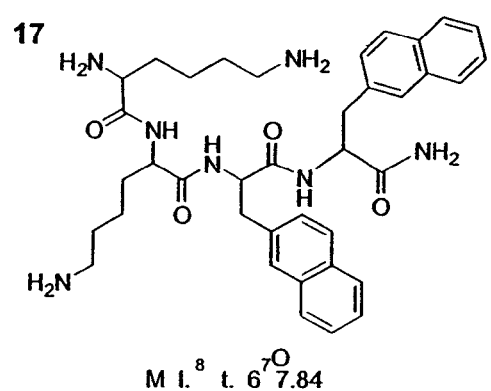
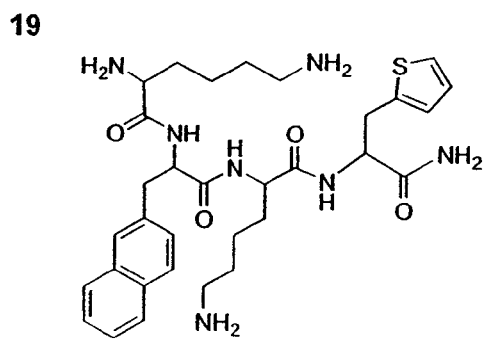
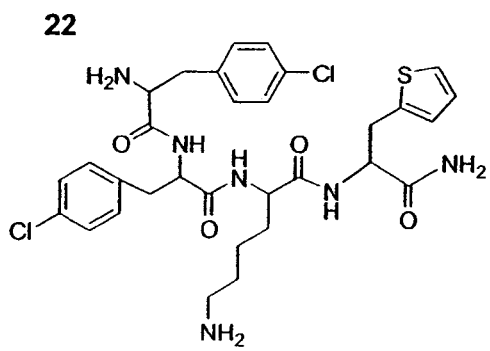
Figure 20A

27
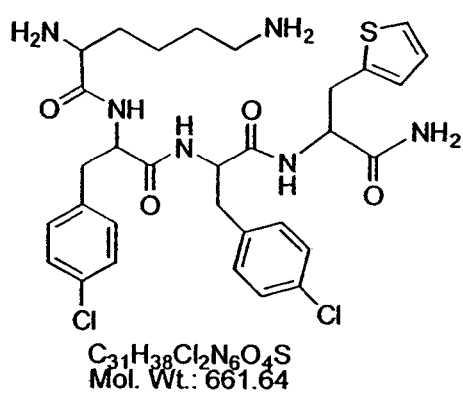
C31H38Cl2N6O4S
Mol. Wt.: 661.64
33
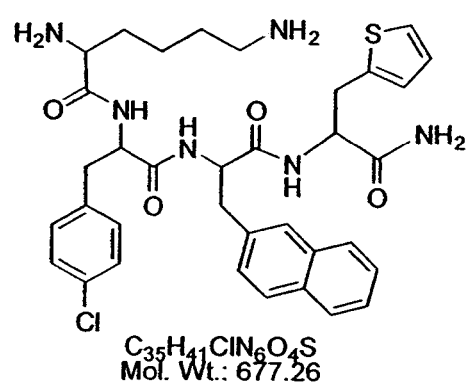
C35H41ClN6O4S
Mol. Wt.: 677.26
35
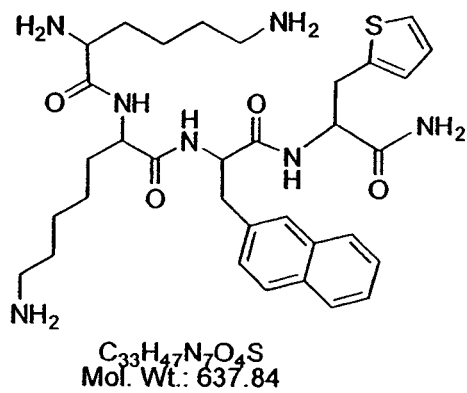
C33H47N7O4S
Mol. Wt.: 637.84
Figure 20B

| TPI1349 | Structures | MW | Exact Mass | [lowest] ug/ml * |
|---|---|---|---|---|
| 1 | 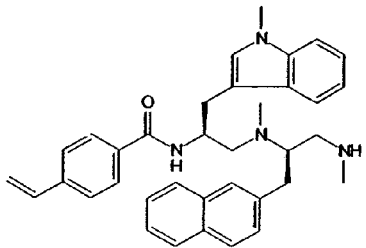 [Boc-D-(2-Naphthyl)-alanine][Boc-L-Tryptophan(Formyl)][4-Vinylbenzoic acid] | 544.74 | 544.32 | 1 |
| 2 | 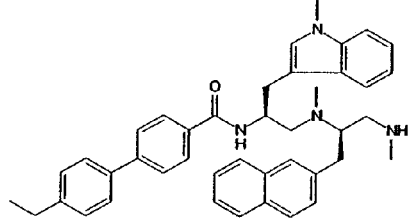 [Boc-D-(2-Naphthyl)-alanine][Boc-L-Tryptophan(Formyl)][4-Ethyl-4-Biphenylcarboxylic acid] | 622.86 | 622.37 | 5 |
| 3 | 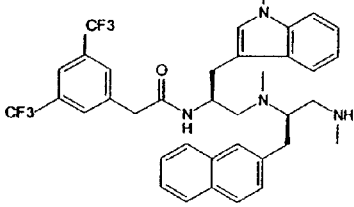 [Boc-D-(2-Naphthyl)-alanine][Boc-L-Tryptophan(Formyl)][3,5-Bis-(trifluoromethyl)-phenylacetic acid] | 668.73 | 668.29 | 5 |
Figure 21A

| TPI1349 | Structures | MW | Exact Mass | [lowest] ug/ml * |
|---|---|---|---|---|
| 4 | 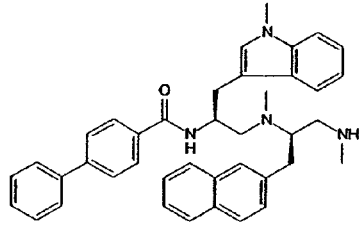 [Boc-D-(2-Naphthyl)-alanine][Boc-L-Tryptophan(Formyl)][4-Biphenylcarboxylic acid] | 594.80 | 594.34 | 5 |
| 5 | 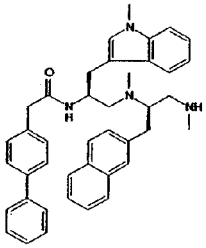 [Boc-D-(2-Naphthyl)-alanine][Boc-L-Tryptophan(Formyl)][4-Biphenylacetic acid] | 608.83 | 608.35 | 5 |
| 6 | 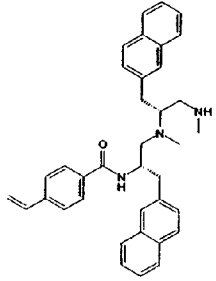 [Boc-D-(2-Naphthyl)-alanine][Boc-L-(2-Naphthyl)-alanine][4-Vinylbenzoic acid] | 541.74 | 541.31 | 5 |
Figure 21A (cont.)

| TPI1349 | Structures | MW | Exact Mass | [lowest] ug/ml * |
|---|---|---|---|---|
| 7 | 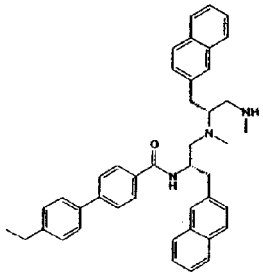 [Boc-D-(2-Naphthyl)-alanine][Boc-L-(2-Naphthyl)-alanine][4-Ethyl-4-Biphenylcarboxylic acid] | 619.85 | 619.36 | 5 |
| 8 | 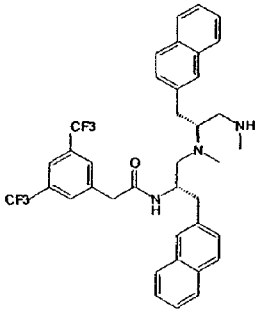 [Boc-D-(2-Naphthyl)-alanine][Boc-L-(2-Naphthyl)-alanine][3,5-Bis-(trifluoromethyl)-phenylacetic acid] | 665.72 | 665.28 | 1 |
| 9 | 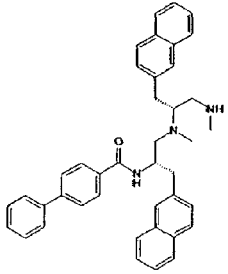 [Boc-D-(2-Naphthyl)-alanine][Boc-L-(2-Naphthyl)-alanine][4-Biphenylcarboxylic acid] | 591.80 | 591.32 | 15 |
Figure 21A (cont.)

| TPI1349 | Structures | MW | Exact Mass | [lowest] ug/ml * |
|---|---|---|---|---|
| 10 | 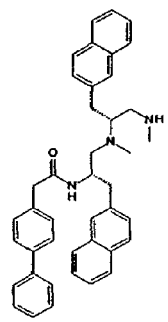 [Boc-D-(2-Naphthyl)-alanine][Boc-L-(2-Naphthyl)-alanine][4-Biphenylacetic acid] | 605.83 | 605.34 | 25 |
| 11 | 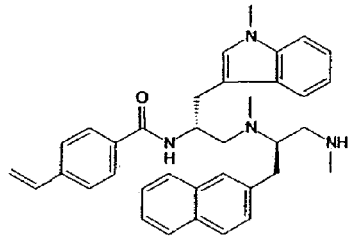 [Boc-D-(2-Naphthyl)-alanine][Boc-D-Tryptophan][4-Vinylbenzoic acid] | 544.74 | 544.32 | 15 |
| 12 | 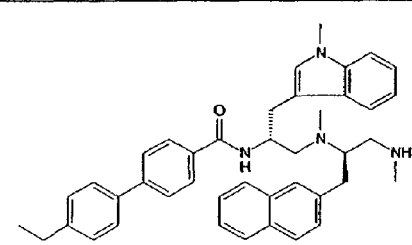 [Boc-D-(2-Naphthyl)-alanine][Boc-D-Tryptophan][4-Ethyl-4-Biphenylcarboxylic acid] | 622.86 | 622.37 | 15 |
Figure 21A (cont.)

| TPI1349 | Structures | MW | Exact Mass | [lowest] ug/ml * |
|---|---|---|---|---|
| 13 | 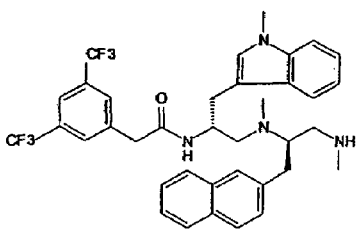 [Boc-D-(2-Naphthyl)-alanine][Boc-D-Tryptophan][3,5-Bis-(trifluoromethyl)-phenylacetic acid] | 668.73 | 668.29 | 25 |
| 14 | 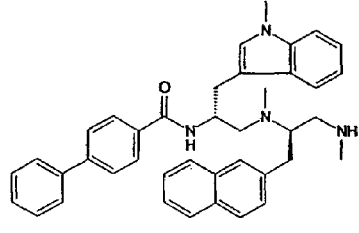 [Boc-D-(2-Naphthyl)-alanine][Boc-D-Tryptophan][4-Biphenylcarboxylic acid] | 594.80 | 594.34 | 15 |
| 15 | 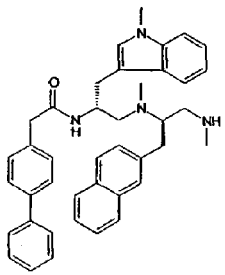 [Boc-D-(2-Naphthyl)-alanine][Boc-D-Tryptophan][4-Biphenylacetic acid] | 608.83 | 608.35 | 25 |
Figure 21A (cont.)

| TPI1349 | Structures | MW | Exact Mass | [lowest] ug/ml * |
|---|---|---|---|---|
| 16 | 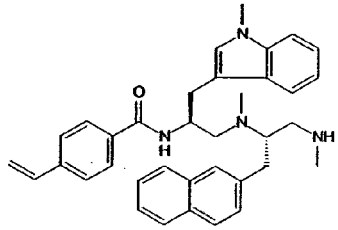 [Boc-L-(2-Naphthyl)-alanine][Boc-L-Tryptophan(Formyl)][4-Vinylbenzoic acid] | 544.74 | 544.32 | 15 |
| 17 | 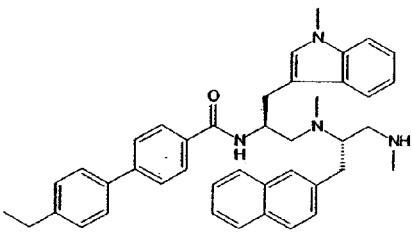 [Boc-L-(2-Naphthyl)-alanine][Boc-L-Tryptophan(Formyl)][4-Ethyl-4-Biphenylcarboxylic acid] | 622.86 | 622.37 | 5 |
| 18 | 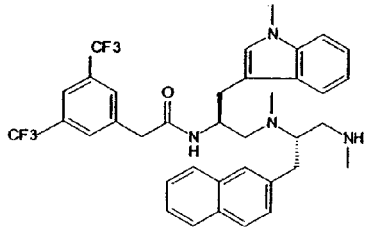 [Boc-L-(2-Naphthyl)-alanine][Boc-L-Tryptophan(Formyl)][3,5-Bis-(trifluoromethyl)-phenylacetic acid] | 668.73 | 668.29 | 25 |
Figure 21A (cont.)

| TPI1349 | Structures | MW | Exact Mass | [lowest] ug/ml * |
|---|---|---|---|---|
| 19 | 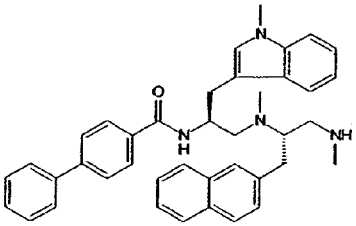 [Boc-L-(2-Naphthyl)-alanine][Boc-L-Tryptophan(Formyl)][4-Biphenylcarboxylic acid] | 594.80 | 594.34 | 5 |
| 20 | 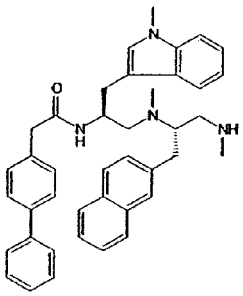 [Boc-L-(2-Naphthyl)-alanine][Boc-L-Tryptophan(Formyl)][4-Biphenylacetic acid] | 608.83 | 608.35 | 5 |
| 21 | 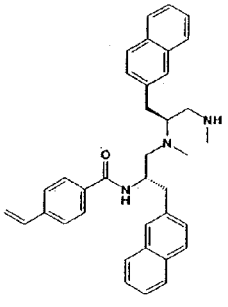 [Boc-L-(2-Naphthyl)-alanine][Boc-L-(2-Naphthyl)-alanine][4-Vinylbenzoic acid] | 541.74 | 541.31 | 15 |
Figure 21A (cont.)

| TPI1349 | Structures | MW | Exact Mass | [lowest] ug/ml * |
|---|---|---|---|---|
| 22 | 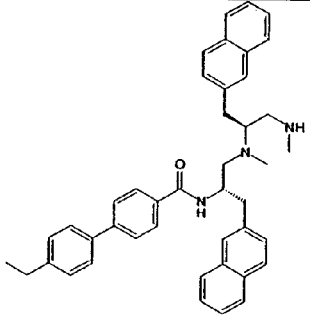 [Boc-L-(2-Naphthyl)-alanine][Boc-L-(2-Naphthyl)-alanine][4-Ethyl-4-Biphenylcarboxylic acid] | 619.85 | 619.36 | 5 |
| 23 | 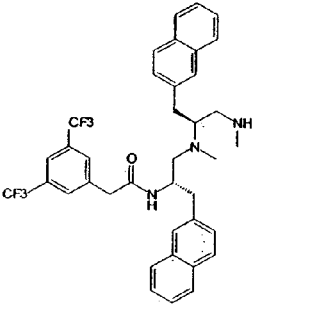 [Boc-L-(2-Naphthyl)-alanine][Boc-L-(2-Naphthyl)-alanine][3,5-Bis-(trifluoromethyl)-phenylacetic acid] | 665.72 | 665.28 | 5 |
| 24 | 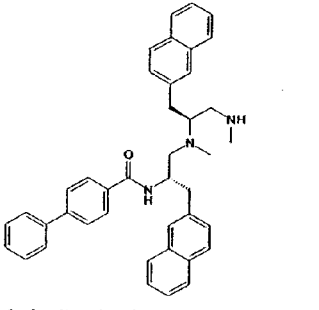 [Boc-L-(2-Naphthyl)-alanine][Boc-L-(2-Naphthyl)-alanine][4-Biphenylcarboxylic acid] | 591.80 | 591.32 | 1 |
Figure 21A (cont.)

| TPI1349 | Structures | MW | Exact Mass | [lowest] ug/ml * |
|---|---|---|---|---|
| 25 | 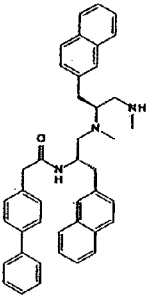 [Boc-L-(2-Naphthyl)-alanine][Boc-L-(2-Naphthyl)-alanine][4-Biphenylacetic acid] | 605.83 | 605.34 | 1 |
| 26 | 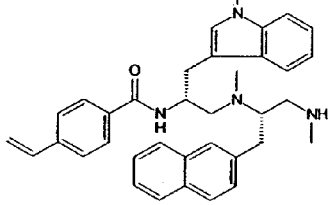 [Boc-L-(2-Naphthyl)-alanine][Boc-D-Tryptophan][4-Vinylbenzoic acid] | 544.74 | 544.32 | 5 |
| 27 | 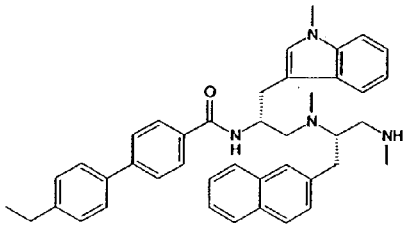 [Boc-L-(2-Naphthyl)-alanine][Boc-D-Tryptophan][4-Ethyl-4-Biphenylcarboxylic acid] | 622.86 | 622.37 | 5 |
Figure 21A (cont.)

| TPI1349 | Structures | MW | Exact Mass | [lowest] ug/ml * |
|---|---|---|---|---|
| 28 | 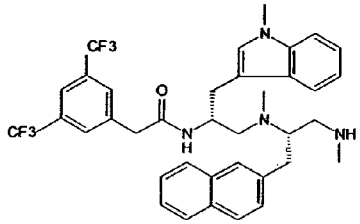 [Boc-L-(2-Naphthyl)-alanine][Boc-D-Tryptophan][3,5-Bis-(trifluoromethyl)-phenylacetic acid] | 668.73 | 668.29 | 5 |
| 29 | 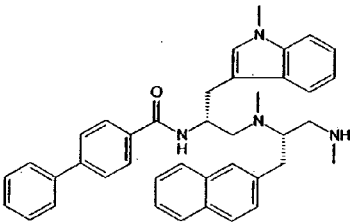 [Boc-L-(2-Naphthyl)-alanine][Boc-D-Tryptophan][4-Biphenylcarboxylic acid] | 594.80 | 594.34 | 5 |
| 30 | 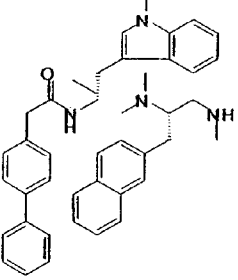 [Boc-L-(2-Naphthyl)-alanine][Boc-D-Tryptophan][4-Biphenylacetic acid] | 608.83 | 608.35 | 5 |
Figure 21A (cont.)

| TPI1349 | Structures | MW | Exact Mass | [lowest] ug/ml * |
|---|---|---|---|---|
| 31 | 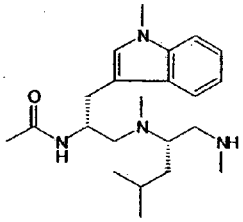 [Boc-L-Leucine][Boc-D-Tryptophan][Acetic acid] | 372.56 | 372.29 | 25 |
| 32 | 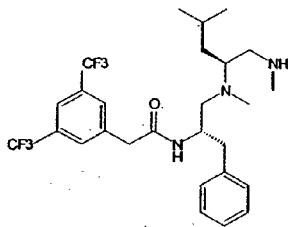 [Boc-L-Leucine][Boc-L-Phenylalanine][3,5-Bis-(trifluoromethyl)-phenylacetic acid] | 531.58 | 531.27 | 1 |
| 33 | 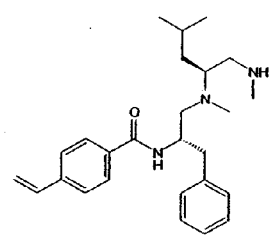 [Boc-L-Leucine][Boc-L-Phenylalanine][4-Vinylbenzoic acid] | 407.60 | 407.29 | >25 |
Figure 21A (cont.)

| TPI1349 | Structures | MW | Exact Mass | [lowest] ug/ml * |
|---|---|---|---|---|
| 34 | [Boc-L-Leucine][Boc-L-Phenylalanine][4-Ethyl-4-Biphenylcarboxylic acid] | 485.72 | 485.34 | >25 |

| TP1396 | CHEMISTRY | MW | Exact Mass | Name | M Log P | H Bond Acceptor | H Bond Donor | Rule Of Five |
|---|---|---|---|---|---|---|---|---|
| 6 | 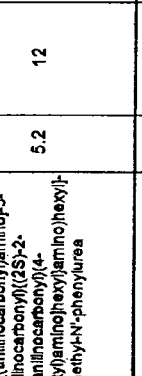 [Boc-D-Lysine(2-Cl-Z)][Boc-L-Norleucine][Cyclohexanebutyric acid] | 859.2 | 858.6 | N-[(5R)-6-[(anilinocarbonyl)amino]-5-[((anilinocarbonyl)((2S)-2-((anilinocarbonyl)(4-cyclohexylbutyl)amino)hexyl)-N-methyl-N'-phenylurea | 5.2 | 12 | 5 | 3 |
| 7 | 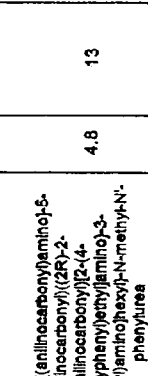 [Boc-D-Lysine(2-Cl-Z)][Boc-D-Phenylalanine][4-Methoxyphenylacetic acid] | 889.1 | 888.5 | N-[(5R)-6-[(anilinocarbonyl)amino]-5-[((anilinocarbonyl)((2R)-2-((anilinocarbonyl)[2-(4-methoxyphenyl)ethyl]amino)-3-phenylpropyl)amino]hexyl)-N-methyl-N'-phenylurea | 4.8 | 13 | 5 | 3 |
| 8 | 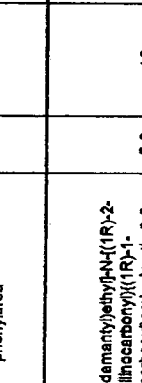 [Boc-D-Lysine(2-Cl-Z)][Boc-D-Phenylalanine][1-Adamantaneacetic acid] | 917.2 | 916.5 | N-[2-(1-adamantyl)ethyl]-N-[(1R)-2-((anilinocarbonyl)(methyl)amino)-5-((anilinocarbonyl)(methyl)amino)pentyl)amino)-1-benzylethyl]-N'-phenylurea | 5.8 | 12 | 5 | 3 |
| 9 | 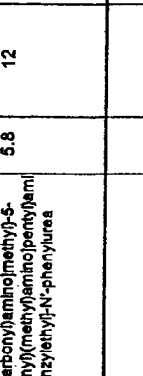 [Boc-D-Lysine(2-Cl-Z)][Boc-D-Phenylalanine][Cyclohexanebutyric acid] | 893.2 | 892.5 | N-[(6R)-6-[(anilinocarbonyl)amino]-5-[((anilinocarbonyl)((2R)-2-((anilinocarbonyl)(4-cyclohexylbutyl)amino]-3-phenylpropyl)amino]hexyl)-N-methyl-N'-phenylurea | 5.5 | 12 | 5 | 3 |
| 10 | 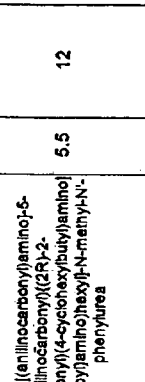 [Boc-D-Lysine(2-Cl-Z)][Boc-L-Proline][4-Methoxyphenylacetic acid] | 719.9 | 719.4 | N-[(5R)-6-[(anilinocarbonyl)amino]-5-[((anilinocarbonyl)(((2S)-1-(2-(4-methoxyphenyl)ethyl]pyrrolidin-2-yl)methyl)amino]hexyl)-N-methyl-N'-phenylurea | 3.7 | 11 | 4 | 2 |

Figure 22A (cont.)

| TPI1396 | CHEMISTRY | MW | Exact Mass | Name | M Log P | H Bond Acceptor | H Bond Donor | Rule Of Five |
|---|---|---|---|---|---|---|---|---|
| 11 | 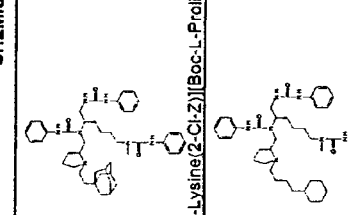 [Boc-D-Lysine(2-Cl-Z)][Boc-L-Proline][1-Adamantaneacetic acid] | 748.0 | 747.5 | N-(((2S)-1-(2-(1-adamantyl)ethyl)pyrrolidin-2-yl)methyl)-N-((R)-1-(((anilinocarbonyl)(methyl)amino)pentyl)-N'-phenylurea | 4.9 | 10 | 4 | 2 |
| 12 | 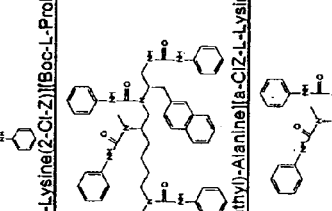 [Boc-D-Lysine(2-Cl-Z)][Boc-L-Proline][Cyclohexanebutyric acid] | 724.0 | 723.5 | N-[(5R)-6-((anilinocarbonyl)amino)-5-(((anilinocarbonyl)((2S)-1-(4-cyclohexylbutyl)pyrrolidin-2-yl)methyl)amino)-2-N-methyl-N'-phenylurea | 4.8 | 10 | 4 | 2 |
| 13 | 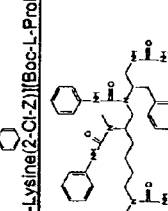 [Boc-L-3-(2-Naphthyl)-Alanine][a-ClZ-L-Lysine(e-Boc)][4-Methoxyphenylacetic acid] | 939.2 | 938.5 | N-[(1S)-2-(((anilinocarbonyl)amino)-1-(2-naphthylmethyl)ethyl]-N-((2S)-6-((anilinocarbonyl)amino)-1-(2-(4-methoxyphenyl)acetyl)amino)-2-((anilinocarbonyl)(methyl)amino)hexyl)-N'-phenylurea | 6.2 | 13 | 5 | 3 |
| 14 | 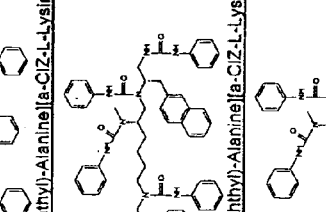 [Boc-L-3-(2-Naphthyl)-Alanine][a-ClZ-L-Lysine(e-Boc)][1-Adamantaneacetic acid] | 967.3 | 966.6 | N-[2-(1-adamantyl)ethyl]-N-((5S)-6-((anilinocarbonyl)amino)-1-(2-naphthylmethyl)ethyl]-N-((2S)-2-((anilinocarbonyl)(methyl)amino)hexyl)-5-phenylurea | 6.2 | 12 | 5 | 3 |
| 15 | 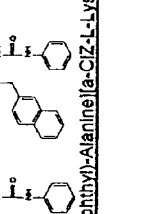 [Boc-L-3-(2-Naphthyl)-Alanine][a-ClZ-L-Lysine(e-Boc)][Cyclohexanebutyric acid] | 943.2 | 942.6 | N-[(1S)-2-[((anilinocarbonyl)amino)-1-(2-naphthyl)methyl)ethyl]-N-((2S)-6-((anilinocarbonyl)(4-cyclohexylbutyl)amino)-2-((anilinocarbonyl)(methyl)amino)hexyl)-N'-phenylurea | 5.9 | 12 | 5 | 3 |

Figure 22A (cont.)

| TPI1396 | CHEMISTRY | MW | Exact Mass | Name | M Log P | H Bond Acceptor | H Bond Donor | Rule Of Five |
|---|---|---|---|---|---|---|---|---|
| 16 | [Boc-L-3-(2-Naphthyl)-Alanine][Boc-L-Norleucine][4-Methoxyphenylacetic acid] | 791.0 | 790.4 | N-{(1S)-2-[(anilinocarbonyl)amino]-1-(2-naphthylmethyl)ethyl]-N-((2S)-2-[(anilinocarbonyl)](2-4-methoxyphenyl)ethyl]amino]hexyl)-N'-phenylurea | 5.6 | 10 | 4 | 2 |
| 17 | [Boc-L-3-(2-Naphthyl)-Alanine][Boc-L-Norleucine][1-Adamantaneacetic acid] | 819.1 | 818.5 | N-[2-(1-adamantyl)ethyl]-N-((1S)-1-[(anilinocarbonyl)](1S)-2-[(anilinocarbonyl)amino]-1-(2-naphthylmethyl)ethyl]amino]methyl)pentyl]-N'-phenylurea | 6.3 | 9 | 4 | 2 |
| 18 | [Boc-L-3-(2-Naphthyl)-Alanine][Boc-L-Norleucine][Cyclohexanebutyric acid] | 795.1 | 794.5 | N-{(1S)-2-[(anilinocarbonyl)amino]-1-(2-naphthylmethyl)ethyl]-N-((2S)-2-[(anilinocarbonyl)](4-cyclohexylbutyl)amino]hexyl)-N'-phenylurea | 6.0 | 9 | 4 | 2 |
| 19 | [Boc-L-3-(2-Naphthyl)-Alanine][Boc-D-Phenylalanine][4-Methoxyphenylacetic acid] | 825.0 | 824.4 | N-{(1S)-2-[(anilinocarbonyl)amino]-1-(2-naphthylmethyl)ethyl]-N-((2S)-2-[(anilinocarbonyl)](2-4-methoxyphenyl)amino]-3-phenylpropyl)-N'-phenylurea | 5.9 | 10 | 4 | 2 |
| 20 | [Boc-L-3-(2-Naphthyl)-Alanine][Boc-D-Phenylalanine][1-Adamantaneacetic acid] | 853.1 | 852.5 | N-{2-(1-adamantyl)ethyl]-N-((1S)-2-[(anilinocarbonyl)](1S)-2-[(anilinocarbonyl)amino]-1-(2-naphthylmethyl)ethyl]amino]-1-benzylethyl)-N'-phenylurea | 6.6 | 9 | 4 | 2 |

Figure 22A (cont.)

| TPI1396 | CHEMISTRY | MW | Exact Mass | Name | M Log P | H Bond Acceptor | H Bond Donor | Rule Of Five |
|---|---|---|---|---|---|---|---|---|
| 21 | [Boc-L-3-(2-Naphthyl)-Alanine][Boc-D-Phenylalanine][Cyclohexanebutyric acid] | 829.1 | 828.5 | N-{(1S)-2-[(anilinocarbonyl)amino]-1-(2-naphthylmethyl)ethyl]-N-((2S)-2-[(anilinocarbonyl)(4-cyclohexylbutyl)amino]-3-phenylpropyl)-N'-phenylurea | 6.3 | 9 | 4 | 2 |
| 22 | [Boc-L-3-(2-Naphthyl)-Alanine][Boc-L-Proline][4-Methoxyphenylacetic acid] | 655.8 | 655.4 | N-{(1S)-2-[(anilinocarbonyl)amino]-1-(2-naphthylmethyl)ethyl]-N-(((2S)-1-(2-(4-methoxyphenyl)ethyl]pyrrolidin-2-yl)methyl)-N'-phenylurea | 4.6 | 8 | 3 | 2 |
| 23 | [Boc-L-3-(2-Naphthyl)-Alanine][Boc-L-Proline][1-Adamantaneacetic acid] | 683.9 | 683.4 | N-(((2S)-1-{2-(1-adamantyl)ethyl]pyrrolidin-2-yl}methyl)-N-{(1S)-2-[(anilinocarbonyl)amino]-1-(2-naphthylmethyl)ethyl]-N'-phenylurea | 5.8 | 7 | 3 | 2 |
| 24 | [Boc-L-3-(2-Naphthyl)-Alanine][Boc-L-Proline][Cyclohexanebutyric acid] | 659.9 | 659.4 | N-{(1S)-2-[(anilinocarbonyl)amino]-1-(2-naphthylmethyl)ethyl]-N-{((2S)-1-(4-cyclohexylbutyl)pyrrolidin-2-yl)methyl)-N'-phenylurea | 5.4 | 7 | 3 | 2 |
| 25 | [Boc-D-Cyclohexylalanine][e-CIZ-L-Lysine(e-Boc)][4-Methoxyphenylacetic acid] | 895.2 | 894.5 | N-{(1R)-2-{[(anilinocarbonyl)amino]-1-(cyclohexylmethyl)ethyl]-N-((2S)-6-[(anilinocarbonyl)[2-(4-methoxyphenyl)ethyl]amino]-2-[(anilinocarbonyl)(methyl)amino]hexyl)-N'-phenylurea | 4.6 | 13 | 5 | 3 |

Figure 22A (cont.)

| TPI1396 | CHEMISTRY | MW | Exact Mass | Name | M Log P | H Bond Acceptor | H Bond Donor | Rule Of Five |
|---|---|---|---|---|---|---|---|---|
| 26 | [Boc-D-Cyclohexylalanine][a-ClZ-L-Lysine(e-Boc)][1-Adamantaneacetic acid] | 923.3 | 922.6 | N-{2-(1-adamantyl)ethyl}-N-((5S)-6-{(anilinocarbonyl)[(1R)-2-(cyclohexylmethyl)ethyl]amino}-5-{(anilinocarbonyl)(methyl)amino]-6-[(anilinocarbonyl)(methyl)amino]hexyl}-N'-phenylurea | 6.0 | 12 | 5 | 3 |
| 27 | [Boc-D-Cyclohexylalanine][a-ClZ-L-Lysine(e-Boc)][Cyclohexanebutyric acid] | 899.2 | 898.6 | N-{(1R)-2-{(anilinocarbonyl)amino}-1-(cyclohexylmethyl)ethyl}-N-((2S)-6-[(anilinocarbonyl)(4-cyclohexylbutyl)amino]-2-[(anilinocarbonyl)(methyl)amino]hexyl}-N'-phenylurea | 5.7 | 12 | 5 | 3 |
| 28 | [Boc-D-Cyclohexylalanine][Boc-L-Norleucine][4-Methoxyphenylacetic acid] | 747.0 | 746.5 | N-{(1R)-2-{(anilinocarbonyl)amino}-1-(cyclohexylmethyl)ethyl}-N-((2S)-2-{(anilinocarbonyl)[2-(4-methoxyphenyl)ethyl]amino}hexyl)-N'-phenylurea | 4.9 | 10 | 4 | 2 |
| 29 | [Boc-D-Cyclohexylalanine][Boc-L-Norleucine][1-Adamantaneacetic acid] | 775.1 | 774.5 | N-{2-(1-adamantyl)ethyl}-N-((1S)-1-{((anilinocarbonyl)[(1R)-2-(cyclohexylmethyl)ethyl]amino]-1-methyl}pentyl)-N'-phenylurea | 6.1 | 9 | 4 | 2 |
| 30 | [Boc-D-Cyclohexylalanine][Boc-L-Norleucine][Cyclohexanebutyric acid] | 751.1 | 750.5 | N-{(1R)-2-{(anilinocarbonyl)amino}-1-(cyclohexylmethyl)ethyl}-N-((2S)-2-{(anilinocarbonyl)(4-cyclohexylbutyl)amino}hexyl)-N'-phenylurea | 5.8 | 9 | 4 | 2 |

Figure 22A (cont.)

| TPI1396 | CHEMISTRY | MW | Exact Mass | Name | M Log P | H Bond Acceptor | H Bond Donor | Rule Of Five |
|---|---|---|---|---|---|---|---|---|
| 31 | 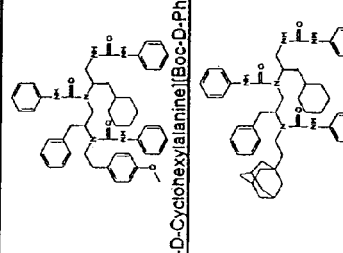 [Boc-D-Cyclohexylalanine][Boc-D-Phenylalanine][4-Methoxyphenylacetic acid] | 781.0 | 780.4 | N-((1R)-2-((anilinocarbonyl)amino)-1-(cyclohexylmethyl)ethyl)-N-((2R)-2-[(anilinocarbonyl)amino]-3-methoxyphenyl)methyl]amino}-3-phenylpropyl)-N'-phenylurea | 5.2 | 10 | 4 | 2 |
| 32 | 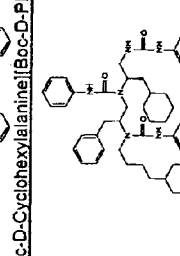 [Boc-D-Cyclohexylalanine][Boc-D-Phenylalanine][1-Adamantaneacetic acid] | 809.1 | 808.5 | N-[2-(1-adamantyl)ethyl]-N-((1R)-2-[(anilinocarbonyl)amino]-1-(cyclohexylmethyl)ethyl]amino}-1-benzylethyl)-N'-phenylurea | 6.4 | 9 | 4 | 2 |
| 33 | 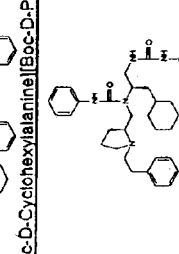 [Boc-D-Cyclohexylalanine][Boc-D-Phenylalanine][Cyclohexanebutyric acid] | 785.1 | 784.5 | N-((1R)-2-((anilinocarbonyl)amino)-1-(cyclohexylmethyl)ethyl)-N-((2R)-2-[(anilinocarbonyl)(4-cyclohexylbutyl)amino]-3-phenylpropyl)-N'-phenylurea | 6.0 | 9 | 4 | 2 |
| 34 | 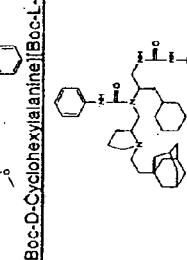 [Boc-D-Cyclohexylalanine][Boc-L-Proline][4-Methoxyphenylacetic acid] | 811.8 | 811.4 | N-((1R)-2-((anilinocarbonyl)amino)-1-(cyclohexylmethyl)ethyl)-N-((2S)-1-[2-(4-methoxyphenyl)ethyl]pyrrolidin-2-yl)methyl)-N'-phenylurea | 4.3 | 8 | 3 | 2 |
| 35 | 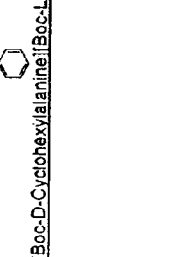 [Boc-D-Cyclohexylalanine][Boc-L-Proline][1-Adamantaneacetic acid] | 839.9 | 839.5 | N-(((2S)-1-[2-(1-adamantyl)ethyl]pyrrolidin-2-yl]methyl)-N-((1R)-2-[(anilinocarbonyl)amino]-1-(cyclohexylmethyl)ethyl)-N'-phenylurea | 5.5 | 7 | 3 | 2 |

Figure 22A (cont.)

| TPI1396 | CHEMISTRY | MW | Exact Mass | Name | M Log P | H Bond Acceptor | H Bond Donor | Rule Of Five |
|---|---|---|---|---|---|---|---|---|
| 36 | [Boc-D-Cyclohexylalanine][Boc-L-Proline][Cyclohexanebutyric acid] | 815.9 | 815.5 | N-((1R)-2-[(anilinocarbonyl)amino]-1-(cyclohexylmethyl)ethyl)-N'-[((2S)-1-(4-cyclohexylbutyl)pyrrolidin-2-yl]methyl)-N'-phenylurea | 5.1 | 7 | 3 | 2 |
| 37 | [Boc-L-Phenylalanine][Boc-L-Phenylalanine][1-Phenyl-1-Cyclopropanecarboxylic acid] | 771.0 | 770.4 | N-((1S)-2-[(anilinocarbonyl)amino]-1-benzylethyl)-N-((2S)-2-((anilinocarbonyl)[(1-phenylcyclopropyl)methyl]amino)-3-phenylpropyl)-N'-phenylurea | 6.7 | 9 | 4 | 2 |
| 38 | [Boc-L-Phenylalanine][Boc-L-Phenylalanine][p-Tolylacetic acid] | 759.0 | 758.4 | N-((1S)-2-[(anilinocarbonyl)amino]-1-benzylethyl)-N-((2S)-2-[(anilinocarbonyl)(4-methylphenyl)ethyl]amino)-3-phenylpropyl)-N'-phenylurea | 5.9 | 9 | 4 | 2 |
| 39 | [Boc-L-Phenylalanine][Boc-L-Phenylalanine][3-Methoxyphenylacetic acid] | 775.0 | 774.4 | N-((1S)-2-[(anilinocarbonyl)amino]-1-benzylethyl)-N-((2S)-2-[(anilinocarbonyl)(3-methoxyphenyl)ethyl]amino)-3-phenylpropyl)-N'-phenylurea | 5.4 | 10 | 4 | 2 |
| 40 | [Boc-L-Phenylalanine][Boc-L-Phenylalanine][4-Methoxyphenylacetic acid] | 775.0 | 774.4 | N-((1S)-2-[(anilinocarbonyl)amino]-1-benzylethyl)-N-((2S)-2-[(anilinocarbonyl)(4-methoxyphenyl)ethyl]amino)-3-phenylpropyl)-N'-phenylurea | 5.4 | 10 | 4 | 2 |

Figure 22A (cont.)

| TPI1396 | CHEMISTRY | MW | Exact Mass | Name | M Log P | H Bond Acceptor | H Bond Donor | Rule Of Five |
|---|---|---|---|---|---|---|---|---|
| 41 | [Boc-L-Phenylalanine][Boc-L-Phenylalanine][4-Ethoxyphenylacetic acid] | 789.0 | 788.4 | N-{(1S)-2-[(anilinocarbonyl)amino]-1-benzylethyl}-N-{(2S)-2-[(anilinocarbonyl)[(2-(4-ethoxyphenyl)ethyl]amino]-3-phenylpropyl}-N'-phenylurea | 5.6 | 10 | 4 | 2 |
| 42 | [Boc-L-Phenylalanine][Boc-L-Phenylalanine][Phenylacetic acid] | 744.9 | 744.4 | N-{(1S)-2-[(anilinocarbonyl)amino]-1-benzylethyl}-N-{(2S)-2-[(anilinocarbonyl)(2-phenylethyl)amino]-3-phenylpropyl}-N'-phenylurea | 5.7 | 9 | 4 | 2 |
| 43 | [Boc-L-Phenylalanine][Boc-L-Phenylalanine][Hydrocinnamic acid] | 759.0 | 758.4 | N-{(1S)-2-[(anilinocarbonyl)amino]-1-benzylethyl}-N-{(2S)-2-[(anilinocarbonyl)(3-phenylpropyl)amino]-3-phenylpropyl}-N'-phenylurea | 5.9 | 9 | 4 | 2 |
| 44 | [Boc-L-Phenylalanine][Boc-L-Phenylalanine][Butyric acid] | 696.9 | 696.4 | N-{(1S)-2-[(anilinocarbonyl)amino]-1-benzylethyl}-N-{(2S)-2-[(anilinocarbonyl)(butyl)amino]-3-phenylpropyl}-N'-phenylurea | 5.3 | 9 | 4 | 2 |
| 45 | [Boc-L-Phenylalanine][Boc-L-Phenylalanine][Heptanoic acid] | 739.0 | 738.4 | N-{(1S)-2-[(anilinocarbonyl)amino]-1-benzylethyl}-N-{(2S)-2-[(anilinocarbonyl)(heptyl)amino]-3-phenylpropyl}-N'-phenylurea | 5.8 | 9 | 4 | 2 |

Figure 22A (cont.)

| TP11396 | CHEMISTRY | MW | Exact Mass | Name | M Log P | H Bond Acceptor | H Bond Donor | Rule Of Five |
|---|---|---|---|---|---|---|---|---|
| 46 | [Boc-L-Phenylalanine][Boc-L-Phenylalanine][Isobutyric acid] | 696.9 | 696.4 | N-((1S)-2-{(anilinocarbonyl)amino}-1-benzylethyl)-N-((2S)-2-[(anilinocarbonyl)(isobutyl)amino]-3-phenylpropyl)-N'-phenylurea | 5.3 | 9 | 4 | 2 |
| 47 | [Boc-L-Phenylalanine][Boc-L-Phenylalanine][4-Methylvaleric acid] | 724.9 | 724.4 | N-((1S)-2-{(anilinocarbonyl)amino}-1-benzylethyl)-N-((2S)-2-[(anilinocarbonyl)(4-methylpentyl)amino]-3-phenylpropyl)-N'-phenylurea | 5.8 | 9 | 4 | 2 |
| 48 | [Boc-L-Phenylalanine][Boc-L-Phenylalanine][Trimethylacetic acid] | 710.9 | 710.4 | N-((1S)-2-{(anilinocarbonyl)amino}-1-benzylethyl)-N-((2S)-2-[(anilinocarbonyl)(neopentyl)amino]-3-phenylpropyl)-N'-phenylurea | 5.4 | 9 | 4 | 2 |
| 49 | [Boc-L-Phenylalanine][Boc-L-Phenylalanine][tert-Butylacetic acid] | 724.9 | 724.4 | N-((1S)-2-{(anilinocarbonyl)amino}-1-benzylethyl)-N-((2S)-2-[(anilinocarbonyl)(3,3-dimethylbutyl)amino]-3-phenylpropyl)-N'-phenylurea | 5.6 | 9 | 4 | 2 |
| 50 | [Boc-L-Phenylalanine][Boc-L-Phenylalanine][Cyclohexanecarboxylic acid] | 737.0 | 736.4 | N-((1S)-2-{(anilinocarbonyl)amino}-1-benzylethyl)-N-((2S)-2-[(anilinocarbonyl)(cyclohexymethyl)amino]-3-phenylpropyl)-N'-phenylurea | 5.4 | 9 | 4 | 2 |

Figure 22A (cont.)

| TPI1396 | CHEMISTRY | MW | Exact Mass | Name | M Log P | H Bond Acceptor | H Bond Donor | Rule Of Five |
|---|---|---|---|---|---|---|---|---|
| 51 | [Boc-L-Phenylalanine][Boc-L-Phenylalanine][Cyclohexylacetic acid] | 751.0 | 750.4 | N-{(1S)-2-[(anilinocarbonyl)amino]-1-benzylethyl}-N-((2S)-2-[(anilinocarbonyl)(2-cyclohexylethyl)amino]-3-phenylpropyl)-N'-phenylurea | 5.5 | 9 | 4 | 2 |
| 52 | [Boc-L-Phenylalanine][Boc-L-Phenylalanine][Cyclohexanebutyric acid] | 779.0 | 778.5 | N-{(1S)-2-[(anilinocarbonyl)amino]-1-benzylethyl}-N-((2S)-2-[(anilinocarbonyl)(4-cyclohexylbutyl)amino]-3-phenylpropyl)-N'-phenylurea | 5.8 | 9 | 4 | 2 |
| 53 | [Boc-L-Phenylalanine][Boc-L-Phenylalanine][Cycloheptanecarboxylic acid] | 751.0 | 750.4 | N-{(1S)-2-[(anilinocarbonyl)amino]-1-benzylethyl}-N-((2S)-2-[(anilinocarbonyl)(cycloheptylmethyl)amino]-3-phenylpropyl)-N'-phenylurea | 5.5 | 9 | 4 | 2 |
| 54 | [Boc-L-Phenylalanine][Boc-L-Phenylalanine][Acetic acid] | 668.8 | 668.3 | N-{(1S)-2-[(anilinocarbonyl)amino]-1-benzylethyl}-N-((2S)-2-[(anilinocarbonyl)(ethyl)amino]-3-phenylpropyl)-N'-phenylurea | 4.9 | 9 | 4 | 2 |
| 55 | [Boc-L-Phenylalanine][Boc-L-Phenylalanine][Cyclobutanecarboxylic acid] | 708.9 | 708.4 | N-{(1S)-2-[(anilinocarbonyl)amino]-1-benzylethyl}-N-((2S)-2-[(anilinocarbonyl)(cyclobutylmethyl)amino]-3-phenylpropyl)-N'-phenylurea | 5.0 | 9 | 4 | 2 |

Figure 22A (cont.)

| TPI1396 | CHEMISTRY | MW | Exact Mass | Name | M Log P | H Bond Acceptor | H Bond Donor | Rule Of Five |
|---|---|---|---|---|---|---|---|---|
| 56 | 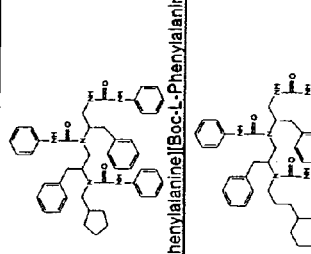 [Boc-L-Phenylalanine][Boc-L-Phenylalanine][Cyclopentanecarboxylic acid] | 722.9 | 722.4 | N-{(1S)-2-{(anilinocarbonyl)amino}-1-benzylethyl]-N-((2S)-2-{(anilinocarbonyl)(cyclopentylmethyl)amino}-3-phenylpropyl)-N'-phenylurea | 5.2 | 9 | 4 | 2 |
| 57 | 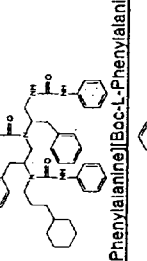 [Boc-L-Phenylalanine][Boc-L-Phenylalanine][Cyclohexanepropionic acid] | 765.0 | 764.4 | N-{(1S)-2-{(anilinocarbonyl)amino}-1-benzylethyl]-N-((2S)-2-{(anilinocarbonyl)(3-cyclohexylpropyl)amino}-3-phenylpropyl)-N'-phenylurea | 5.7 | 9 | 4 | 2 |
| 58 | 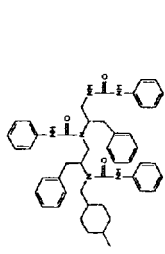 [Boc-L-Phenylalanine][Boc-L-Phenylalanine][4-Methyl-1-cyclohexanecarboxylic acid] | 751.0 | 750.4 | N-{(1S)-2-{(anilinocarbonyl)amino}-1-benzylethyl]-N-((2S)-2-{(anilinocarbonyl)[(4-methylcyclohexyl)methyl]amino}-3-phenylpropyl)-N'-phenylurea | 5.5 | 9 | 4 | 2 |
| 59 | 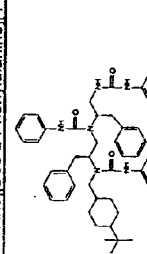 [Boc-L-Phenylalanine][Boc-L-Phenylalanine][4-tert-Butyl-cyclohexanecarboxylic acid] | 793.1 | 792.5 | N-{(1S)-2-{(anilinocarbonyl)amino}-1-benzylethyl]-N-((2S)-2-{(anilinocarbonyl)[(4-tert-butylcyclohexyl)methyl]amino}-3-phenylpropyl)-N'-phenylurea | 6.0 | 9 | 4 | 2 |
| 60 | 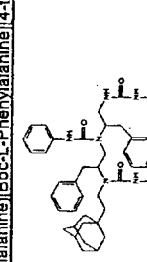 [Boc-L-Phenylalanine][Boc-L-Phenylalanine][1-Adamantaneacetic acid] | 803.1 | 802.5 | N-{2-(1-adamantyl)ethyl)-N'-{(1S)-2-{(anilinocarbonyl)amino}-1-benzylethyl]amino}-1-benzylethyl]-N'-phenylurea | 6.2 | 9 | 4 | 2 |

Figure 22A (cont.)

| TPI1396 | CHEMISTRY | MW | Exact Mass | Name | M Log P | H Bond Acceptor | H Bond Donor | Rule Of Five |
|---|---|---|---|---|---|---|---|---|
| 61 | [Boc-L-Phenylalanine][Boc-L-Phenylalanine][3,3-Diphenylpropionic acid] | 835.1 | 834.4 | N-((1S)-2-[(anilinocarbonyl)amino]-1-benzylethyl)-N'-((2S)-2-[(anilinocarbonyl)](3,3-diphenylpropyl)amino]-3-phenylpropyl)-N'-phenylurea | 6.6 | 9 | 4 | 2 |
| 62 | [Boc-L-Phenylalanine][Boc-L-Phenylalanine][Cyclopentylacetic acid] | 737.0 | 736.4 | N-((1S)-2-[(anilinocarbonyl)amino]-1-benzylethyl)-N'-((2S)-2-[(anilinocarbonyl)](2-cyclopentylethyl)amino]-3-phenylpropyl)-N'-phenylurea | 5.4 | 9 | 4 | 2 |
| 63 | [Boc-L-Phenylalanine][Boc-L-Phenylalanine][Indole-3-acetic acid] | 784.0 | 783.4 | N-((1S)-2-[(anilinocarbonyl)amino]-1-benzylethyl)-N'-((2S)-2-[(anilinocarbonyl)](2-(1H-indol-3-yl)ethyl)amino]-3-phenylpropyl)-N'-phenylurea | 4.8 | 10 | 5 | 2 |
| 64 | [Boc-L-Phenylalanine][Boc-L-Phenylalanine][3-(3,4,5)-Trimethoxyphenylpropionic acid] | 849.0 | 848.4 | N-((1S)-2-[(anilinocarbonyl)amino]-1-benzylethyl)-N'-((2S)-2-[(anilinocarbonyl)](3-(3,4,5-trimethoxyphenyl)propyl)amino]-3-phenylpropyl)-N'-phenylurea | 4.5 | 12 | 4 | 3 |
| 65 | [Boc-L-Phenylalanine][Boc-L-Phenylalanine][2-Norbornaneacetic acid] | 783.0 | 762.4 | N-((1S)-2-[(anilinocarbonyl)amino]-1-benzylethyl)-N'-((2S)-2-[(anilinocarbonyl)](2-bicyclo[2.2.1]hept-2-ylethyl)amino]-3-phenylpropyl)-N'-phenylurea | 5.7 | 9 | 4 | 2 |

Figure 22A (cont.)

Selected TPI 1396

| TPI 1396 | Caspase 3-XIAP IC-50 (µM) | | Caspase 3-XIAP-BIR2 IC-50 (µM) | |
|---|---|---|---|---|
| | AVG | STD | AVG | STD |
| 11 | 32.1 | 3.8 | 7.9 | 0.3 |
| 12 | 53.0 | 8.3 | 14.4 | 1.1 |
| 22 | 45.3 | 3.3 | 9.5 | 2.2 |
| 28 | >134 | | 134.1 | 0.3 |
| 34 | 77.1 | 11.0 | 13.6 | 0.9 |

FIGURE 22D

| TPI1391 | Structures | MW | Exact Mass | Name | M Log P | H Bond Donor | H Bond Donor | Rule Of Five |
|---|---|---|---|---|---|---|---|---|
| 1 | [Fmoc-L-Norleucine][Fmoc-D-Leucine][4-Isobutyl-alpha-Methylphenyl acetic Acid] | 533.8 | 533.4 | (5R)-1-((1S)-1-((benzylamino)methyl)pentyl)-5-isobutyl-4-[2-(4-isobutylphenyl)propyl]piperazine-2,3-dione | 4.6 | 5 | 1 | 2 |
| 2 | [Fmoc-L-Norleucine][Fmoc-D-Leucine][3,5-bis(trifluoromethyl)phenyl acetic acid] | 599.7 | 599.3 | (5R)-1-((1S)-1-((benzylamino)methyl)pentyl)-4-(2-[3,5-bis(trifluoromethyl)phenyl]ethyl)-5-isobutylpiperazine-2,3-dione | 5.4 | 5 | 1 | 2 |
| 3 | Accord For Excel - New Chemistry [Fmoc-D-Leucine][Heptenoic acid] | 457.7 | 457.4 | (5R)-1-((1S)-1-((benzylamino)methyl)-4-heptyl-5-isobutylpiperazine-2,3-dione | 3.7 | 5 | 1 | 0 |
| 4 | [Fmoc-L-Norleucine][Fmoc-D-Leucine][(Alpha-Alpha-Trifluoro-m-Tolyl) acetic acid] | 531.7 | 531.3 | (5R)-1-((1S)-1-((benzylamino)methyl)pentyl)-5-isobutyl-4-(2-(3-(trifluoromethyl)phenyl)ethyl)piperazine-2,3-dione | 4.4 | 5 | 1 | 2 |
| 5 | [Fmoc-L-Norleucine][Fmoc-D-Leucine][4-tert-Butyl-cyclohexanecarboxylic acid] | 511.8 | 511.4 | (5R)-1-((1S)-1-((benzylamino)methyl)pentyl)-4-(4-tert-butylcyclohexyl)methyl-5-isobutylpiperazine-2,3-dione | 4.6 | 5 | 1 | 2 |
| 6 | [Fmoc-L-Norleucine][Fmoc-D-Leucine][m-Tolylacetic acid] | 477.7 | 477.3 | (5R)-1-((1S)-1-((benzylamino)methyl)pentyl)-5-isobutyl-4-(2-(3-methylphenyl)ethyl)piperazine-2,3-dione | 3.9 | 5 | 1 | 0 |

Figure 23A

| TPI1391 | Structures | MW | Exact Mass | Name | M Log P | H Bond Donor | H Bond Donor | Rule Of Five |
|---|---|---|---|---|---|---|---|---|
| 7 | [Fmoc-L-Norleucine][Fmoc-L-2-Naphthylalanine][4-Isobutyl-alpha-Methylphenylacetic Acid] | 617.9 | 617.4 | (5S)-1-((1S)-1-((benzylamino)methyl)pentyl)-4-(2-(4-isobutylphenyl)propyl)-5-(2-naphthylmethyl)piperazine-2,3-dione | 5.4 | 6 | 1 | 2 |
| 8 | [Fmoc-L-Norleucine][Fmoc-L-2-Naphthylalanine][3,5-Bis(Trifluoromethyl)-Phenylacetic Acid] | 683.7 | 683.3 | (5S)-1-((1S)-1-((benzylamino)methyl)pentyl)-4-(2-(3,5-bis(trifluoromethyl)phenyl)ethyl)-5-(2-naphthylmethyl)piperazine-2,3-dione | 6.2 | 5 | 1 | 2 |
| 9 | [Fmoc-L-Norleucine][Fmoc-L-2-Naphthylalanine][Heptanoic acid] | 541.8 | 541.4 | (5S)-1-((1S)-1-((benzylamino)methyl)pentyl)-4-heptyl-5-(2-naphthylmethyl)piperazine-2,3-dione | 4.8 | 5 | 1 | 2 |
| 10 | [Fmoc-L-Norleucine][Fmoc-L-2-Naphthylalanine][Alpha-Alpha-Alpha-Trifluoro-m-Tolyl) acetic ac] | 615.7 | 615.3 | (5S)-1-((1S)-1-((benzylamino)methyl)pentyl)-4-(2-(3-naphthylmethyl)phenyl)ethyl)-5-(2-naphthylmethyl)piperazine-2,3-dione | 5.3 | 5 | 1 | 2 |
| 11 | [Fmoc-L-Norleucine][Fmoc-L-2-Naphthylalanine][4-tert-Butyl-cyclohexanecarboxylic acid] | 595.9 | 595.4 | (5S)-1-((1S)-1-((benzylamino)methyl)pentyl)-4-(4-tert-butylcyclohexyl)methyl)-5-(2-naphthylmethyl)piperazine-2,3-dione | 5.3 | 5 | 1 | 2 |
| 12 | [Fmoc-L-Norleucine][Fmoc-L-2-Naphthylalanine][m-Tolylacetic acid] | 561.8 | 561.3 | (5S)-1-((1S)-1-((benzylamino)methyl)pentyl)-4-(2-(3-methylphenyl)ethyl)-5-(2-naphthylmethyl)piperazine-2,3-dione | 4.7 | 5 | 1 | 2 |

Figure 23A (cont.)

| TPI1391 | Structures | MW | Exact Mass | Name | M Log P | H Bond Donor | H Bond Donor | Rule Of Five |
|---|---|---|---|---|---|---|---|---|
| 13 | [Fmoc-D-Norleucine][Fmoc-D-Leucine][4-Isobutyl-alpha-Methylphenylacetic Acid] | 533.8 | 533.4 | (5R)-1-[(1R)-1-[(benzylamino)methyl]pentyl]-5-isobutyl-4-[2-(4-isobutylphenyl)propyl)piperazine-2,3-dione | 4.8 | 6 | 1 | 2 |
| 14 | [Fmoc-D-Norleucine][Fmoc-D-Leucine][3,5-Bis(Trifluoromethyl)-Phenylacetic Acid] | 599.7 | 599.3 | (5R)-1-[(1R)-1-[(benzylamino)methyl]pentyl]-4-(2-[3,5-bis(trifluoromethyl)phenyl]ethyl)-5-isobutylpiperazine-2,3-dione | 5.4 | 5 | 1 | 2 |
| 15 | [Fmoc-D-Norleucine][Fmoc-D-Leucine][Heptanoic acid] | 457.7 | 457.4 | (5R)-1-[(1R)-1-[(benzylamino)methyl]pentyl]-4-heptyl-5-isobutylpiperazine-2,3-dione | 3.7 | 5 | 1 | 0 |
| 16 | [Fmoc-D-Norleucine][Fmoc-D-Leucine][(Alpha-Alpha-Alpha-Trifluoro-m-Tolyl) acetic acid] | 531.7 | 531.3 | (5R)-1-[(1R)-1-[(benzylamino)methyl]pentyl]-5-isobutyl-4-[2-(3-(trifluoromethyl)phenyl]ethyl)piperazine-2,3-dione | 4.4 | 5 | 1 | 2 |
| 17 | [Fmoc-D-Norleucine][Fmoc-D-Leucine][4-tert-Butyl-cyclohexanecarboxylic acid] | 511.8 | 511.4 | (5R)-1-[(1R)-1-[(benzylamino)methyl]pentyl]-4-(4-tert-butylcyclohexyl)methyl]-5-isobutylpiperazine-2,3-dione | 4.5 | 5 | 1 | 2 |
| 18 | [Fmoc-D-Norleucine][Fmoc-D-Leucine][m-Tolylacetic acid] | 477.7 | 477.3 | (5R)-1-[(1R)-1-[(benzylamino)methyl]pentyl]-5-isobutyl-4-[2-(3-methylphenyl)ethyl]piperazine-2,3-dione | 3.9 | 5 | 1 | 0 |

Figure 23A (cont.)

| TPI1391 | Structures | MW | Exact Mass | Name | M Log P | H Bond Donor | H Bond Donor | Rule Of Five |
|---|---|---|---|---|---|---|---|---|
| 19 | [Fmoc-D-Norleucine][Fmoc-L-2-Naphthylalanine][4-Isobutyl-alpha-Methyl-phenylacetic Acid] | 617.9 | 617.4 | (5S)-1-((1R)-1-((benzylamino)methyl)pentyl)-4-(2-(4-isobutylphenyl)propyl)-5-(2-naphthylmethyl)piperazine-2,3-dione | 6.4 | 5 | 1 | 2 |
| 20 | [Fmoc-D-Norleucine][Fmoc-L-2-Naphthylalanine][3,5-Bis(Trifluoromethyl)-Phenylacetic Acid] | 683.7 | 683.3 | (5S)-1-((1R)-1-((benzylamino)methyl)pentyl)-4-(2-(3,5-bis(trifluoromethyl)phenyl)ethyl)-5-(2-naphthylmethyl)piperazine-2,3-dione | 6.2 | 5 | 1 | 2 |
| 21 | FALSE | 541.8 | 541.4 | (5S)-1-((1R)-1-((benzylamino)methyl)pentyl)-4-heptyl-5-(2-naphthylmethyl)piperazine-2,3-dione | 4.8 | 5 | 1 | 2 |
| 22 | [Fmoc-D-Norleucine][Fmoc-L-2-Naphthylalanine][(Alpha-Alpha-Alpha-Trifluoro-m-Tolyl) acetic ac] | 615.7 | 615.3 | (5S)-1-((1R)-1-((benzylamino)methyl)pentyl)-5-(2-naphthylmethyl)-4-(2-(3-(trifluoromethyl)phenyl)ethyl)piperazine-2,3-dione | 5.3 | 5 | 1 | 2 |
| 23 | [Fmoc-D-Norleucine][Fmoc-L-2-Naphthylalanine][4-tert-Butyl-cyclohexanecarboxylic acid] | 595.9 | 595.4 | (5S)-1-((1R)-1-((benzylamino)methyl)pentyl)-4-((4-tert-butyl)cyclohexyl)methyl)-5-(2-naphthylmethyl)piperazine-2,3-dione | 5.3 | 5 | 1 | 2 |
| 24 | [Fmoc-D-Norleucine][Fmoc-L-2-Naphthylalanine][m-Tolylacetic acid] | 561.8 | 561.3 | (5S)-1-((1R)-1-((benzylamino)methyl)pentyl)-4-(2-(3-methylphenyl)ethyl)-5-(2-naphthylmethyl)piperazine-2,3-dione | 4.7 | 5 | 1 | 2 |

Figure 23A (cont.)

| TPI1391 | Structures | MW | Exact Mass | Name | M Log P | H Bond Donor | H Bond Donor | Rule Of Five |
|---|---|---|---|---|---|---|---|---|
| 25 | [Fmoc-L-2-Naphthylalanine][Fmoc-D-Leucine][4-Isobutyl-alpha-Methylphenylacetic Acid] | 617.9 | 617.4 | (5R)-1-[(1S)-2-(benzylamino)-1-(2-naphthylmethyl)ethyl]-4-[2-(4-isobutylphenyl)propyl]piperazine-2,3-dione | 5.4 | 5 | 1 | 2 |
| 26 | [Fmoc-L-2-Naphthylalanine][Fmoc-D-Leucine][3,5-Bis(Trifluoromethyl)-Phenylacetic Acid] | 683.7 | 683.3 | (5R)-1-[(1S)-2-(benzylamino)-1-(2-naphthylmethyl)ethyl]-4-[2-(3,5-bis(trifluoromethyl)phenyl]ethyl]-5-isobutyl)piperazine-2,3-dione | 6.2 | 5 | 1 | 2 |
| 27 | [Fmoc-L-2-Naphthylalanine][Fmoc-D-Leucine]Heptanoic acid] | 541.8 | 541.4 | (5R)-1-[(1S)-2-(benzylamino)-1-(2-naphthylmethyl)ethyl]-4-heptyl-5-isobutyl)piperazine-2,3-dione | 4.8 | 5 | 1 | 2 |
| 28 | [Fmoc-L-2-Naphthylalanine][Fmoc-D-Leucine][Alpha-Alpha-Alpha-Trifluoro-m-Tolyl) acetic acid] | 615.7 | 615.3 | (5R)-1-[(1S)-2-(benzylamino)-1-(2-naphthylmethyl)ethyl]-5-isobutyl-4-[2-(3-(trifluoromethyl)phenyl]ethyl)piperazine-2,3-dione | 5.3 | 5 | 1 | 2 |
| 29 | [Fmoc-L-2-Naphthylalanine][Fmoc-D-Leucine][4-tert-Butyl-cyclohexanecarboxylic acid] | 595.9 | 595.4 | (5R)-1-[(1S)-2-(benzylamino)-1-(2-naphthylmethyl)ethyl]-4-((4-tert-butylcyclohexyl)methyl)-5-isobutyl)piperazine-2,3-dione | 6.3 | 5 | 1 | 2 |
| 30 | [Fmoc-L-2-Naphthylalanine][Fmoc-D-Leucine][m-Tolylacetic acid] | 561.8 | 561.3 | (5R)-1-[(1S)-2-(benzylamino)-1-(2-naphthylmethyl)ethyl]-5-isobutyl-4-[2-(3-methylphenyl)ethyl]piperazine-2,3-dione | 4.7 | 5 | 1 | 2 |

Figure 23A (cont.)

| TPI1391 | Structures | MW | Exact Mass | Name | M Log P | H Bond Donor | H Bond Donor | Rule Of Five |
|---|---|---|---|---|---|---|---|---|
| 31 | [Fmoc-L-2-Naphthylalanine][Fmoc-L-2-Naphthylalanine][4-Isobutyl-alpha-Methylphenylacetic Acid] | 702.0 | 701.4 | (5S)-1-((1S)-2-(benzylamino)-1-(2-naphthylmethyl)ethyl]-4-(2-(4-isobutylphenyl)propyl]-5-(2-naphthylmethyl)piperazine-2,3-dione | 6.2 | 5 | 1 | 2 |
| 32 | [Fmoc-L-2-Naphthylalanine][Fmoc-L-2-Naphthylalanine][3,5-Bis(Trifluoromethyl)-Phenylacetic Acid] | 767.8 | 767.3 | (5S)-1-((1S)-2-(Benzylamino)-1-(2-naphthylmethyl)ethyl]-4-(2-(3,5-bis(trifluoromethyl)phenyl)ethyl]-5-(2-naphthylmethyl)piperazine-2,3-dione | 7.0 | 5 | 1 | 2 |
| 33 | [Fmoc-L-2-Naphthylalanine][Fmoc-L-2-Naphthylalanine][Heptanoic acid] | 625.9 | 625.4 | (5S)-1-((1S)-2-(benzylamino)-1-(2-naphthylmethyl)ethyl]-4-heptyl-5-(2-naphthylmethyl)piperazine-2,3-dione | 5.4 | 5 | 1 | 2 |
| 34 | [Fmoc-L-2-Naphthylalanine][Fmoc-L-2-Naphthylalanine][Alpha-Alpha-Alpha-Trifluoro-m-Tolyl] acetic acid] | 699.8 | 699.3 | (5S)-1-((1S)-2-(benzylamino)-1-(2-naphthylmethyl)ethyl]-4-(2-(3-(trifluoromethyl)phenyl)ethyl]-5-(2-naphthylmethyl)piperazine-2,3-dione | 6.1 | 5 | 1 | 2 |
| 35 | [Fmoc-L-2-Naphthylalanine][Fmoc-L-2-Naphthylalanine][4-tert-Butyl-cyclohexanecarboxylic acid] | 679.9 | 679.4 | (5S)-1-((1S)-2-(benzylamino)-1-(2-naphthylmethyl)ethyl]-4-((4-tert-butylcyclohexyl)methyl]-5-(2-naphthylmethyl)piperazine-2,3-dione | 6.1 | 5 | 1 | 2 |
| 36 | [Fmoc-L-2-Naphthylalanine][Fmoc-L-2-Naphthylalanine][m-Tolylacetic acid] | 645.8 | 645.3 | (5S)-1-((1S)-2-(benzylamino)-1-(2-naphthylmethyl)ethyl]-4-(2-(3-methylphenyl)ethyl]-5-(2-naphthylmethyl)piperazine-2,3-dione | 5.8 | 6 | 1 | 2 |

Figure 23A (cont.)

Selected TPI 1391

| TPI 1391 | Caspase 3-XIAP IC-50 (µM) | |
|---|---|---|
|  | AVG | STD |
| 1 | 29.6 | 2.9 |
| 4 | 28.0 | 2.1 |
| 5 | 29.9 | 2.5 |
| 7 | >162 |  |
| 17 | 57.3 | 16.1 |
| 21 | 33.6 | 0.7 |
| 25 | 29.0 | 2.8 |
| 28 | 25.1 | 5.9 |
| 34 | 39.4 | 0.5 |
| 35 | 32.6 | 1.2 |

FIGURE 23D

| TPI1400 | Structures | MW | Exact Mass | Name | M. Log P | H. Bond Acceptor | H Bond Donor | Rule Of Five |
|---|---|---|---|---|---|---|---|---|
| 1 | [Boc-L-Cyclohexylalanine][4-Biphenylacetic acid][4-Ethoxyphenylacetic acid] | 606.9 | 606.4 | N-(3-((2S,5S)-1-(2-(1,1'-biphenyl-4-yl)ethyl)-5-(cyclohexylmethyl)-2,3,5,6-tetrahydro-1H-imidazo[1,2-a]imidazol-2-yl)propyl)-2-(4-ethoxyphenyl)acetamide | 5.8 | 6 | 1 | 2 |
| 2 | [Boc-L-Cyclohexylalanine][Phenylacetic acid][4-Ethoxyphenylacetic acid] | 530.8 | 530.4 | N-(3-((2S,5S)-5-(cyclohexylmethyl)-1-(2-phenylethyl)-2,3,5,6-tetrahydro-1H-imidazo[1,2-a]imidazol-2-yl)propyl)-2-(4-ethoxyphenyl)acetamide | 4.7 | 6 | 1 | 2 |
| 3 | [Boc-L-Cyclohexylalanine][4-Phenylbutyric acid][4-Ethoxyphenylacetic acid] | 558.8 | 558.4 | N-(3-((2S,5S)-5-(cyclohexylmethyl)-1-(4-phenylbutyl)-2,3,5,6-tetrahydro-1H-imidazo[1,2-a]imidazol-2-yl)propyl)-2-(4-ethoxyphenyl)acetamide | 5.1 | 6 | 1 | 2 |
| 4 | [Boc-L-Cyclohexylalanine][Heptanoic acid][4-Ethoxyphenylacetic acid] | 524.8 | 524.4 | N-(3-((2S,5S)-5-(cyclohexylmethyl)-1-heptyl-2,3,5,6-tetrahydro-1H-imidazo[1,2-a]imidazol-2-yl)propyl)-2-(4-ethoxyphenyl)acetamide | 4.8 | 6 | 1 | 2 |
| 5 | [Boc-L-Cyclohexylalanine][Cyclohexanecarboxylic acid][4-Ethoxyphenylacetic acid] | 522.8 | 522.4 | N-(3-((2S,5S)-1,5-bis(cyclohexylmethyl)-2,3,5,6-tetrahydro-1H-imidazo[1,2-a]imidazol-2-yl)propyl)-2-(4-ethoxyphenyl)acetamide | 4.8 | 6 | 1 | 2 |
| 6 | [Boc-L-Cyclohexylalanine][4-tert-Butyl-cyclohexanecarboxylic acid][4-Ethoxyphenylacetic acid] | 578.9 | 578.5 | N-(3-((2S,5S)-1-((4-tert-butylcyclohexyl)methyl)-5-(cyclohexylmethyl)-2,3,5,6-tetrahydro-1H-imidazo[1,2-a]imidazol-2-yl)propyl)-2-(4-ethoxyphenyl)acetamide | 5.6 | 6 | 1 | 2 |

Figure 24A

| TPI1400 | Structures | MW | Exact Mass | Name | M Log P | H Bond Acceptor | H Bond Donor | Rule Of Five |
|---|---|---|---|---|---|---|---|---|
| 7 | [Boc-L-Cyclohexylalanine][1-Adamantaneacetic acid][4-Ethoxyphenylacetic acid] | 588.9 | 588.4 | N-{3-[(2S,5S)-1-[2-(1-adamantyl)ethyl]-5-(cyclohexylmethyl)-2,3,5,6-tetrahydro-1H-imidazo[1,2-a]imidazol-2-yl]propyl}-2-(4-ethoxyphenyl)acetamide | 5.7 | 6 | 1 | 2 |
| 8 | [Boc-D-Cyclohexylalanine][4-Biphenylacetic acid][4-Ethoxyphenylacetic acid] | 606.9 | 606.4 | N-{3-[(2S,5R)-1-[2-(1,1'-biphenyl-4-yl)methyl]-5-(cyclohexylmethyl)-2,3,5,6-tetrahydro-1H-imidazo[1,2-a]imidazol-2-yl]propyl}-2-(4-ethoxyphenyl)acetamide | 5.8 | 6 | 1 | 2 |
| 9 | [Boc-D-Cyclohexylalanine][Phenylacetic acid][4-Ethoxyphenylacetic acid] | 530.8 | 530.4 | N-{3-[(2S,5R)-5-(cyclohexylmethyl)-1-(2-phenylethyl)-2,3,5,6-tetrahydro-1H-imidazo[1,2-a]imidazol-2-yl]propyl}-2-(4-ethoxyphenyl)acetamide | 4.7 | 6 | 1 | 2 |
| 10 | [Boc-D-Cyclohexylalanine][Phenylbutyric acid][4-Ethoxyphenylacetic acid] | 558.8 | 558.4 | N-{3-[(2S,5R)-5-(cyclohexylmethyl)-1-(4-phenylbutyl)-2,3,5,6-tetrahydro-1H-imidazo[1,2-a]imidazol-2-yl]propyl}-2-(4-ethoxyphenyl)acetamide | 5.1 | 6 | 1 | 2 |
| 11 | [Boc-D-Cyclohexylalanine][Heptanoic acid][4-Ethoxyphenylacetic acid] | 524.8 | 524.4 | N-{3-[(2S,5R)-5-(cyclohexylmethyl)-1-naphtyl-2,3,5,6-tetrahydro-1H-imidazo[1,2-a]imidazol-2-yl]propyl}-2-(4-ethoxyphenyl)acetamide | 4.8 | 6 | 1 | 2 |
| 12 | [Boc-D-Cyclohexylalanine][Cyclohexanecarboxylic acid][4-Ethoxyphenylacetic acid] | 522.8 | 522.4 | N-{3-[(2S,5R)-1,5-bis(cyclohexylmethyl)-2,3,5,6-tetrahydro-1H-imidazo[1,2-a]imidazol-2-yl]propyl}-2-(4-ethoxyphenyl)acetamide | 4.8 | 6 | 1 | 2 |

Figure 24A (cont.)

| TPI1400 | Structures | MW | Exact Mass | Name | M Log P | H Bond Acceptor | H Bond Donor | Rule Of Five |
|---|---|---|---|---|---|---|---|---|
| 13 | [Boc-D-Cyclohexylalanine][4-tert-Butyl-cyclohexanecarboxylic acid][4-Ethoxyphenylacetic acid] | 578.9 | 578.8 | N-(3-((2S,5R))-1-((4-tert-butylcyclohexyl)methyl)-5-(cyclohexylmethyl)-2,3,5,6-tetrahydro-1H-imidazo[1,2-a]imidazol-2-yl)propyl)-2-(4-ethoxyphenyl)acetamide | 5.5 | 6 | 1 | 2 |
| 14 | [Boc-D-Cyclohexylalanine][1-Adamantaneacetic acid][4-Ethoxyphenylacetic acid] | 588.9 | 588.4 | N-(3-((2S,5R))-1-(2-(1-adamantyl)ethyl)-5-(cyclohexylmethyl)-2,3,5,6-tetrahydro-1H-imidazo[1,2-a]imidazol-2-yl)propyl)-2-(4-ethoxyphenyl)acetamide | 5.7 | 6 | 1 | 2 |
| 15 | [Boc-L-Naphthylalanine][4-Biphenylacetic acid][4-Ethoxyphenylacetic acid] | 650.9 | 650.4 | N-(3-((2S,5S))-1-(2-(1,1'-biphenyl-4-yl)ethyl)-6-(2-naphthylmethyl)-2,3,5,6-tetrahydro-1H-imidazo[1,2-a]imidazol-2-yl)propyl)-2-(4-ethoxyphenyl)acetamide | 6.9 | 6 | 1 | 2 |
| 16 | [Boc-L-Naphthylalanine][Phenylacetic acid][4-Ethoxyphenylacetic acid] | 574.8 | 574.3 | 2-(4-ethoxyphenyl)-N-(3-((2S,5S))-5-(2-naphthylmethyl)-1-(2-phenylethyl)-2,3,5,6-tetrahydro-1H-imidazo[1,2-a]imidazol-2-yl)propyl)acetamide | 5.1 | 6 | 1 | 2 |
| 17 | [Boc-L-Naphthylalanine][4-Phenylbutyric acid][4-Ethoxyphenylacetic acid] | 602.8 | 602.4 | 2-(4-ethoxyphenyl)-N-(3-((2S,5S))-5-(2-naphthylmethyl)-1-(4-phenylbutyl)-2,3,5,6-tetrahydro-1H-imidazo[1,2-a]imidazol-2-yl)propyl)acetamide | 5.4 | 6 | 1 | 2 |
| 18 | [Boc-L-Naphthylalanine][Heptanoic acid][4-Ethoxyphenylacetic acid] | 588.8 | 588.4 | 2-(4-ethoxyphenyl)-N-(3-((2S,5S))-1-heptyl-5-(2-naphthylmethyl)-2,3,5,6-tetrahydro-1H-imidazo[1,2-a]imidazol-2-yl)propyl)acetamide | 5.1 | 6 | 1 | 2 |

Figure 24A (cont.)

| TPI1400 | Structures | MW | Exact Mass | Name | M Log P | H Bond Acceptor | H Bond Donor | Rule Of Five |
|---|---|---|---|---|---|---|---|---|
| 19 | [Boc-L-Naphthylalanine][Cyclohexanecarboxylic acid][4-Ethoxyphenylacetic acid] | 588.8 | 588.4 | N-{3-[(2S,5S)-1-(cyclohexylmethyl)-5-(2-naphthylmethyl)-2,3,5,8-tetrahydro-1H-imidazo[1,2-a]imidazol-2-yl]propyl}-2-(4-ethoxyphenyl)acetamide | 5.1 | 6 | 1 | 2 |
| 20 | [Boc-L-Naphthylalanine][4-tert-Butyl-cyclohexanecarboxylic acid][4-Ethoxyphenylacetic acid] | 622.9 | 622.4 | N-{3-[(2S,5S)-1-((4-tert-butylcyclohexyl)methyl)-5-(2-naphthylmethyl)-2,3,5,8-tetrahydro-1H-imidazo[1,2-a]imidazol-2-yl]propyl}-2-(4-ethoxyphenyl)acetamide | 5.8 | 6 | 1 | 2 |
| 21 | [Boc-L-Naphthylalanine][1-Adamantaneacetic acid][4-Ethoxyphenylacetic acid] | 632.9 | 632.4 | N-{3-[(2S,5S)-1-(2-(1-adamantyl)ethyl)-5-(2-naphthylmethyl)-2,3,5,8-tetrahydro-1H-imidazo[1,2-a]imidazol-2-yl]propyl}-2-(4-ethoxyphenyl)acetamide | 6.0 | 6 | 1 | 2 |
| 22 | [Boc-L-Naphthylalanine][4-Biphenylacetic acid][4-Ethoxyphenylacetic acid] | 650.9 | 650.4 | N-{3-[(2S,5R)-1-(2-(1,1'-biphenyl-4-yl)ethyl)-5-(2-naphthylmethyl)-2,3,5,8-tetrahydro-1H-imidazo[1,2-a]imidazol-2-yl]propyl}-2-(4-ethoxyphenyl)acetamide | 5.9 | 6 | 1 | 2 |
| 23 | [Boc-D-Naphthylalanine][Phenylacetic acid][4-Ethoxyphenylacetic acid] | 574.8 | 574.3 | 2-(4-ethoxyphenyl)-N-{3-[(2S,5R)-5-(2-naphthylmethyl)-1-(2-phenylethyl)-2,3,5,8-tetrahydro-1H-imidazo[1,2-a]imidazol-2-yl]propyl}acetamide | 5.1 | 6 | 1 | 2 |
| 24 | [Boc-D-Naphthylalanine][4-Phenylbutyric acid][4-Ethoxyphenylacetic acid] | 602.8 | 602.4 | 2-(4-ethoxyphenyl)-N-{3-[(2S,5R)-5-(2-naphthylmethyl)-1-(4-phenylbutyl)-2,3,5,8-tetrahydro-1H-imidazo[1,2-a]imidazol-2-yl]propyl}acetamide | 5.4 | 6 | 1 | 2 |

Figure 24A (cont.)

| TPI1400 | Structures | MW | Exact Mass | Name | M Log P | H Bond Acceptor | H Bond Donor | Rule Of Five |
|---|---|---|---|---|---|---|---|---|
| 25 | [Boc-D-Naphthylalanine][Heptanoic acid][4-Ethoxyphenylacetic acid] | 566.8 | 566.4 | 2-(4-ethoxyphenyl)-N-{3-[(2S,5R)-1-heptyl-5-(2-naphthylmethyl)-2,3,5,6-tetrahydro-1H-imidazo[1,2-a]imidazol-2-yl]propyl}acetamide | 5.1 | 6 | 1 | 2 |
| 26 | [Boc-D-Naphthylalanine][Cyclohexanecarboxylic acid][4-Ethoxyphenylacetic acid] | 566.8 | 566.4 | N-(3-{(2S,5R)-1-(cyclohexylmethyl)-5-(2-naphthylmethyl)-2,3,5,6-tetrahydro-1H-imidazo[1,2-a]imidazol-2-yl]propyl)-2-(4-ethoxyphenyl)acetamide | 5.1 | 6 | 1 | 2 |
| 27 | [Boc-D-Naphthylalanine][4-tert-Butyl-Cyclohexaneacetic acid][4-Ethoxyphenylacetic acid] | 622.9 | 622.4 | N-{3-[(2S,5R)-1-[(4-tert-butylcyclohexyl)methyl]-5-(2-naphthylmethyl)-2,3,5,6-tetrahydro-1H-imidazo[1,2-a]imidazol-2-yl]propyl}-2-(4-ethoxyphenyl)acetamide | 5.8 | 6 | 1 | 2 |
| 28 | [Boc-D-Naphthylalanine][1-Adamantaneacetic acid][4-Ethoxyphenylacetic acid] | 632.9 | 632.4 | N-(3-{(2S,5R)-1-[2-(1-adamantyl)ethyl]-5-(2-naphthylmethyl)-2,3,5,6-tetrahydro-1H-imidazo[1,2-a]imidazol-2-yl]propyl)-2-(4-ethoxyphenyl)acetamide | 6.0 | 6 | 1 | 2 |
| 29 | [Boc-L-Cyclohexylalanine][Phenylacetic acid][Phenylacetic acid] | 486.7 | 486.3 | N-{3-[(2S,5S)-5-(cyclohexylmethyl)-1-(2-phenylethyl)-2,3,5,6-tetrahydro-1H-imidazo[1,2-a]imidazol-2-yl]propyl}-2-phenylacetamide | 4.9 | 6 | 1 | 1 |
| 30 | [Boc-D-Cyclohexylalanine][Phenylacetic acid][Phenylacetic acid] | 486.7 | 486.3 | N-{3-[(2S,5R)-5-(cyclohexylmethyl)-1-(2-phenylethyl)-2,3,5,6-tetrahydro-1H-imidazo[1,2-a]imidazol-2-yl]propyl}-2-phenylacetamide | 4.9 | 5 | 1 | 1 |

Figure 24A (cont.)

| TPI1400 | Structures | MW | Exact Mass | Name | M Log P | H Bond Acceptor | H Bond Donor | Rule Of Five |
|---|---|---|---|---|---|---|---|---|
| 31 | [Boc-D-p-Chloro-Phenylalanine][Phenylacetic acid] | 515.1 | 514.2 | N-{3-[(2S,5R)-5-(4-chlorobenzyl)-1-(2-phenylethyl)-2,3,5,6-tetrahydro-1H-imidazo[1,2-a]imidazol-2-yl]propyl}-2-phenylacetamide | 5.1 | 5 | 1 | 2 |
| 32 | [Boc-D-p-Fluoro-Phenylalanine][Phenylacetic acid] | 498.6 | 498.3 | N-{3-[(2S,5R)-5-(4-fluorobenzyl)-1-(2-phenylethyl)-2,3,5,6-tetrahydro-1H-imidazo[1,2-a]imidazol-2-yl]propyl}-2-phenylacetamide | 5.0 | 5 | 1 | 1 |
| 33 | [Boc-L-p-Fluoro-Phenylalanine][Phenylacetic acid] | 498.6 | 498.3 | N-{3-[(2S,5S)-5-(4-fluorobenzyl)-1-(2-phenylethyl)-2,3,5,6-tetrahydro-1H-imidazo[1,2-a]imidazol-2-yl]propyl}-2-phenylacetamide | 5.0 | 5 | 1 | 1 |
| 34 | [Boc-D-2-Chloro-Phenylalanine][Phenylacetic acid] | 515.1 | 514.2 | N-{3-[(2S,5R)-5-(2-chlorobenzyl)-1-(2-phenylethyl)-2,3,5,6-tetrahydro-1H-imidazo[1,2-a]imidazol-2-yl]propyl}-2-phenylacetamide | 5.1 | 5 | 1 | 2 |
| 35 | [Boc-L-O-Ethyl-Tyrosine][Phenylacetic acid] | 524.7 | 524.3 | N-{3-[(2S,5S)-5-(4-ethoxybenzyl)-1-(2-phenylethyl)-2,3,5,6-tetrahydro-1H-imidazo[1,2-a]imidazol-2-yl]propyl}-2-phenylacetamide | 4.5 | 6 | 1 | 2 |
| 36 | [Boc-D-O-Ethyl-Tyrosine][Phenylacetic acid] | 524.7 | 524.3 | N-{3-[(2S,5R)-5-(4-ethoxybenzyl)-1-(2-phenylethyl)-2,3,5,6-tetrahydro-1H-imidazo[1,2-a]imidazol-2-yl]propyl}-2-phenylacetamide | 4.5 | 6 | 1 | 2 |

Figure 24A (cont.)

| TPI1400 | Structures | MW | Exact Mass | Name | M. Log P | H Bond Acceptor | H Bond Donor | Rule Of Five |
|---|---|---|---|---|---|---|---|---|
| 37 | [Boc-L-O-Methyl-Tyrosine][Phenylacetic acid][Phenylacetic acid] | 510.7 | 510.3 | N-(3-((2S,6R)-5-(4-methoxybenzyl)-1-(2-phenylethyl)-2,3,5,6-tetrahydro-1H-imidazo[1,2-a]imidazol-2-yl)propyl)-2-phenylacetamide | 4.3 | 6 | 1 | 2 |
| 38 | [Boc-L-3,5-Diiodo-Tyrosine(Bzl)][Phenylacetic acid] | 748.4 | 748.1 | N-(3-((2S,6S)-5-(4-hydroxy-3,5-diiodobenzyl)-1-(2-phenylethyl)-2,3,5,6-tetrahydro-1H-imidazo[1,2-a]imidazol-2-yl)propyl)-2-phenylacetamide | 5.4 | 6 | 2 | 2 |
| 39 | [Boc-L-Naphthylalanine][Phenylacetic acid] | 530.7 | 530.3 | N-(3-((2S,5S)-5-(2-naphthylmethyl)-1-(2-phenylethyl)-2,3,5,6-tetrahydro-1H-imidazo[1,2-a]imidazol-2-yl)propyl)-2-phenylacetamide | 5.2 | 5 | 1 | 2 |
| 40 | [Boc-D-Naphthylalanine][Phenylacetic acid] | 530.7 | 530.3 | N-(3-((2S,5R)-5-(2-naphthylmethyl)-1-(2-phenylethyl)-2,3,5,6-tetrahydro-1H-imidazo[1,2-a]imidazol-2-yl)propyl)-2-phenylacetamide | 5.2 | 5 | 1 | 2 |
| 41 | [Boc-L-4,4'-Biphenyl-Alanine][Phenylacetic acid] | 556.8 | 556.3 | N-(3-((2S,5S)-5-(1,1'-biphenyl-4-ylmethyl)-1-(2-phenylethyl)-2,3,5,6-tetrahydro-1H-imidazo[1,2-a]imidazol-2-yl)propyl)-2-phenylacetamide | 5.5 | 5 | 1 | 2 |
| 42 | [Boc-L-Phenylalanine][p-Tolylacetic acid][Phenylacetic acid] | 494.7 | 494.3 | N-(3-((2S,6S)-5-benzyl-1-(2-(4-methylphenyl)ethyl)-2,3,5,6-tetrahydro-1H-imidazo[1,2-a]imidazol-2-yl)propyl)-2-phenylacetamide | 4.8 | 5 | 1 | 1 |

Figure 24A (cont.)

| TPI1400 | Structures | MW | Exact Mass | Name | M.Log P | H Bond Acceptor | H Bond Donor | Rule Of Five |
|---|---|---|---|---|---|---|---|---|
| 43 | [Boc-L-Phenylalanine][4-Fluorophenylacetic acid] | 498.8 | 498.3 | N-{3-[(2S,5S)-5-benzyl-1-[2-(4-fluorophenyl)ethyl]-2,3,5,6-tetrahydro-1H-imidazo[1,2-a]imidazol-2-yl]propyl}-2-phenylacetamide | 5.0 | 5 | 1 | 1 |
| 44 | [Boc-L-Phenylalanine][3-Methoxyphenylacetic acid] | 510.7 | 510.3 | N-{3-[(2S,5S)-5-benzyl-1-[2-(3-methoxyphenyl)ethyl]-2,3,5,6-tetrahydro-1H-imidazo[1,2-a]imidazol-2-yl]propyl}-2-phenylacetamide | 4.3 | 6 | 1 | 2 |
| 45 | [Boc-L-Phenylalanine][4-Methoxyphenylacetic acid] | 510.7 | 510.3 | N-{3-[(2S,5S)-5-benzyl-1-[2-(4-methoxyphenyl)ethyl]-2,3,5,6-tetrahydro-1H-imidazo[1,2-a]imidazol-2-yl]propyl}-2-phenylacetamide | 4.3 | 6 | 1 | 2 |
| 46 | [Boc-L-Phenylalanine][4-Ethoxyphenylacetic acid] | 524.7 | 524.3 | N-{3-[(2S,5S)-5-benzyl-1-[2-(4-ethoxyphenyl)ethyl]-2,3,5,6-tetrahydro-1H-imidazo[1,2-a]imidazol-2-yl]propyl}-2-phenylacetamide | 4.5 | 6 | 1 | 2 |
| 47 | [Boc-L-Phenylalanine][4-Biphenylacetic acid] | 556.8 | 556.3 | N-{3-[(2S,5S)-5-benzyl-1-[2-(1,1'-biphenyl-4-yl)ethyl]-2,3,5,6-tetrahydro-1H-imidazo[1,2-a]imidazol-2-yl]propyl}-2-phenylacetamide | 5.5 | 5 | 1 | 2 |
| 48 | [Boc-L-Phenylalanine][4-Phenylbutyric acid] | 508.7 | 508.3 | N-{3-[(2S,5S)-5-benzyl-1-(4-phenylbutyl)-2,3,5,6-tetrahydro-1H-imidazo[1,2-a]imidazol-2-yl]propyl}-2-phenylacetamide | 5.0 | 5 | 1 | 2 |

Figure 24A (cont.)

| TPI1400 | Structures | MW | Exact Mass | Name | M. Log P | H Bond Acceptor | H Bond Donor | Rule Of Five |
|---|---|---|---|---|---|---|---|---|
| 49 | [Boc-L-Phenylalanine][Heptanoic acid][Phenylacetic acid] | 474.7 | 474.3 | N-{3-[(2S,5S)-5-benzyl-1-heptyl-2,3,5,6-tetrahydro-1H-imidazo[1,2-a]imidazol-2-yl]propyl}-2-phenylacetamide | 4.7 | 5 | 1 | 1 |
| 50 | [Boc-L-Phenylalanine][3-Methylvaleric acid][Phenylacetic acid] | 460.7 | 460.3 | N-{3-[(2S,5S)-5-benzyl-1-(3-methylpentyl)-2,3,5,6-tetrahydro-1H-imidazo[1,2-a]imidazol-2-yl]propyl}-2-phenylacetamide | 4.5 | 5 | 1 | 1 |
| 51 | [Boc-L-Phenylalanine][4-Methylvaleric acid][Phenylacetic acid] | 460.7 | 460.3 | N-{3-[(2S,5S)-5-benzyl-1-(4-methylpentyl)-2,3,5,6-tetrahydro-1H-imidazo[1,2-a]imidazol-2-yl]propyl}-2-phenylacetamide | 4.5 | 5 | 1 | 1 |
| 52 | [Boc-L-Phenylalanine][Phenylacetic acid][4-Biphenylacetic acid] | 556.8 | 556.3 | N-{3-[(2S,5S)-5-benzyl-1-(2-phenylethyl)-2,3,5,6-tetrahydro-1H-imidazo[1,2-a]imidazol-2-yl]propyl}-2-(1,1'-biphenyl-4-yl)acetamide | 5.5 | 5 | 1 | 2 |
| 53 | [Boc-L-Phenylalanine][Phenylacetic acid][Cyclohexanecarboxylic acid] | 472.7 | 472.3 | N-{3-[(2S,5S)-5-benzyl-1-(2-phenylethyl)-2,3,5,6-tetrahydro-1H-imidazo[1,2-a]imidazol-2-yl]propyl}cyclohexanecarboxamide | 4.7 | 5 | 1 | 1 |
| 54 | [Boc-L-Phenylalanine][Phenylacetic acid][Cyclohexaneacetic acid] | 486.7 | 486.3 | N-{3-[(2S,5S)-5-benzyl-1-(2-phenylethyl)-2,3,5,6-tetrahydro-1H-imidazo[1,2-a]imidazol-2-yl]propyl}-2-cyclohexylacetamide | 4.9 | 5 | 1 | 1 |

Figure 24A (cont.)

| TPI1400 | Structures | MW | Exact Mass | Name | M Log P | H Bond Acceptor | H Bond Donor | Rule Of Five |
|---|---|---|---|---|---|---|---|---|
| 55 | [Boc-L-Phenylalanine][Phenylacetic acid][Cyclohexanebutyric acid] | 514.8 | 514.4 | N-(3-((2S,5S)-5-benzyl-1-(2-phenylethyl)-2,3,5,6-tetrahydro-1H-imidazo[1,2-a]imidazol-2-yl)propyl)-4-cyclohexylbutanamide | 5.2 | 5 | 1 | 2 |
| 56 | [Boc-L-Phenylalanine][Phenylacetic acid][Cycloheptanecarboxylic acid] | 486.7 | 486.3 | N-(3-((2S,5S)-5-benzyl-1-(2-phenylethyl)-2,3,5,6-tetrahydro-1H-imidazo[1,2-a]imidazol-2-yl)propyl)cycloheptanecarboxamide | 4.9 | 5 | 1 | 1 |
| 57 | [Boc-L-Phenylalanine][Phenylacetic acid][3-Cyclopentylpropionic acid] | 486.7 | 486.3 | N-(3-((2S,5S)-5-benzyl-1-(2-phenylethyl)-2,3,5,6-tetrahydro-1H-imidazo[1,2-a]imidazol-2-yl)propyl)-3-cyclopentylpropanamide | 4.9 | 5 | 1 | 1 |
| 58 | [Boc-L-Phenylalanine][Phenylacetic acid][3,5-bis-(Trifluoromethyl)-phenylacetic acid] | 618.6 | 618.3 | N-(3-((2S,5S)-5-benzyl-1-(2-phenylethyl)-2,3,5,6-tetrahydro-1H-imidazo[1,2-a]imidazol-2-yl)propyl)-2-(3,5-bis(trifluoromethyl)phenyl)acetamide | 6.4 | 5 | 1 | 2 |

Figure 24A (cont.)

Selected TPI 1400

| TPI 1400- | Caspase 3-XIAP IC-50 (µM) | |
|---|---|---|
| | AVG | STD |
| 6 | 26.6 | 4.6 |
| 7 | 40.2 | 8.7 |
| 14 | 31.2 | 6.8 |
| 13 | 157.2 | |
| 33 | >200 | |
| 37 | 157.6 | |
| 43 | 169.5 | |
| 44 | 120.2 | |

FIGURE 24F

| ID # | Name | MW | Structure | Relative caspase 3 activity * | | TPI 1396- |
|---|---|---|---|---|---|---|
| | | | | @ 25 ug/ml | [lowest] ug/ml ** | L-proline |
| TPI 1509-1 | N-((5R)-6-[(anilinocarbonyl)amino]-5-[((2R)-1-[2-(4-methoxyphenyl)ethyl]pyrrolidin-2-yl)methyl]amino]hexyl)-N-methyl-N'-phenylurea | 719.9 | 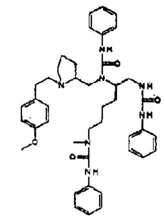 | 2.2 | 6.25 | 10 |
| TPI 1509-2 | N-(((2R)-1-[2-(1-adamantyl)ethyl]pyrrolidin-2-yl)methyl)-N-((1R)-1-{[(anilinocarbonyl)amino]methyl}-5-[((anilinocarbonyl)(methyl)amino]pentyl)-N'-phenylurea | 748.0 | 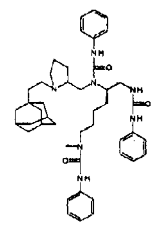 | 2.5 | 12.5 | 11 |
| TPI 1509-3 | N-[(5R)-6-[(anilinocarbonyl)amino]-5-((anilinocarbonyl)[((2R)-1-(4-cyclohexylbutyl)pyrrolidin-2-yl]methyl)amino]hexyl)-N-methyl-N'-phenylurea | 724.0 | 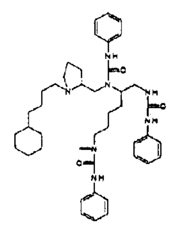 | 2.4 | 12.5 | 12 |
| TPI 1509-4 | N-[(1S)-2-[(anilinocarbonyl)amino]-1-(2-naphthylmethyl)ethyl]-N-(((2R)-1-[2-(4-methoxyphenyl)ethyl]pyrrolidin-2-yl)methyl)-N'-phenylurea | 655.8 | 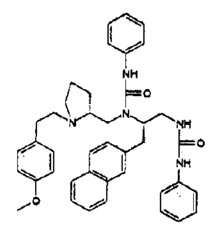 | 2.4 | 25 | 22 |

Figure 34

| ID # | Name | MW | Structure | @ 25 ug/ml | [lowest] ug/ml ** | L-proline |
|---|---|---|---|---|---|---|
| TPI 1509-5 | N-(((2R)-1-[2-(1-adamantyl)ethyl]pyrrolidin-2-yl)methyl)-N-[(1S)-2-[(anilinocarbonyl)amino]-1-(2-naphthylmethyl)ethyl]-N'-phenylurea | 683.9 | 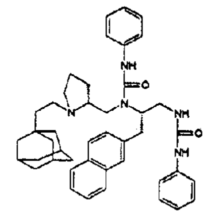 | 2.5 | 25 | 23 |
| TPI 1509-6 | N-[(1S)-2-[(anilinocarbonyl)amino]-1-(2-naphthylmethyl)ethyl]-N-[((2R)-1-(4-cyclohexylbutyl)pyrrolidin-2-yl)methyl]-N'-phenylurea | 659.9 | 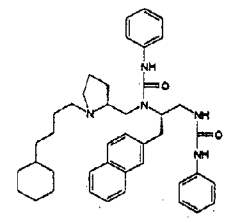 | 2.0 | 12.5 | 24 |
| TPI 1509-7 | N-[(1R)-2-[(anilinocarbonyl)amino]-1-(cyclohexylmethyl)ethyl]-N-(((2R)-1-[2-(4-methoxyphenyl)ethyl]pyrrolidin-2-yl)methyl)-N'-phenylurea | 611.8 | 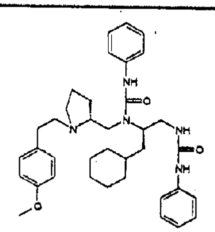 | 2.4 | 25 | 34 |
| TPI 1509-8 | N-(((2R)-1-[2-(1-adamantyl)ethyl]pyrrolidin-2-yl)methyl)-N-[(1R)-2-[(anilinocarbonyl)amino]-1-(cyclohexylmethyl)ethyl]-N'-phenylurea | 639.9 | 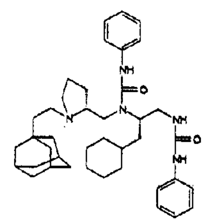 | 2.2 | 25 | 35 |

Figure 34 (cont.)

| ID # | Name | MW | Structure | @ 25 ug/ml | [lowest] ug/ml ** | L-proline |
|---|---|---|---|---|---|---|
| TPI 1509-9 | N-[(1R)-2-[(anilinocarbonyl)amino]-1-(cyclohexylmethyl)ethyl]-N-[[(2R)-1-(4-cyclohexylbutyl)pyrrolidin-2-yl]methyl]-N'-phenylurea | 615.9 | 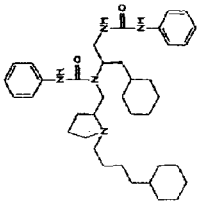 | 2.2 | 25 | 36 |

Relative caspase-3* activity in the XIAP derepression assay was calculated as the ratio of the Vmax in the presence of each compound divided by the Vmax of the controls ha

[lowest] ug/ml **: lowest concentration in which the relative caspase 3 activity was 1.8

Figure 34 (cont.)

TPI 1640
Code: 1077
Modifications of TPI1509-7

TPI1509-7 Parent compound
D-Cyclohexylalanine, D-Proline

Lipinski Alerts: MW>500, MlogP > 4.15, HBD>5, HBA>10

| | Structure | MW | Modification | R group | Yield (mg) | MLogP | Hydrogen Bond Donors | Hydrogen Bond Acceptors | Lipinski Alerts |
|---|---|---|---|---|---|---|---|---|---|
| | | | | | | 4.26 | 3 | 8 | 2 |
| 6 | L-cyclohexylalanine analog | 611.38 | Sterochemistry | R1 | 54.3 | 4.26 | 3 | 8 | 2 |
| 7 | L-Proline, L-cyclohexylalanine analog | 611.38 | Sterochemistry | R1 and R2 | 64.4 | 4.26 | 3 | 8 | 2 |
| 8 | Split parent compound-Left side | 353.21 | Removal of R1 and associated urea | R1 | 14.8 | 2.63 | 2 | 5 | 0 |
| 9 | Split parent compound-Right side | 394.24 | Removal of R2 and R3 | R2 and R3 | 32 | 3.02 | 4 | 6 | 0 |
| 10 | Remove R3 | 477.31 | Removal of R3 | R3 | 5.6 | 3.29 | 4 | 7 | 0 |
| 11 | Remove R3-Acetyl substitution (ethyl) | 505.3 | Replacement of R3 with ethyl | R3 | 51.1 | 3.68 | 3 | 7 | 1 |
| 12 | Remove R2-Glycine substitution | 565.37 | Removal of R2 | R2 | 56.1 | 3.90 | 3 | 8 | 1 |

Figure 35A

| Structure | MW | Modification | R group | Yield (mg) | MLogP | Hydrogen Bond Donors | Hydrogen Bond Acceptors | Lipinski Alerts |
|---|---|---|---|---|---|---|---|---|
| 13 Remove R2-(D-Alanine) substitution | 599.38 | Replacement of pyrrolidine with N-metylalanine | R2 | 60.2 | 4.08 | 3 | 8 | 1 |
| 14 Remove urea 2-methyl substitution | 506.36 | Removal of N-urea | Urea | 48.7 | 3.89 | 2 | 6 | 1 |
| 15 Remove R1-Glycine substitution | 515.2 | Removal of R1 | R1 | 51.2 | 2.97 | 3 | 8 | 1 |
| 16 Remove R1-(D-Alanine) substitution | 529.31 | Replacement of R1 with methyl | R1 | 51.5 | 3.16 | 3 | 8 | 1 |
| 17 Remove urea 1-methyl substitution | 506.36 | Removal of N'-urea | Urea | 10.3 | 3.89 | 2 | 6 | 1 |
| 18 Remove ureas-benzoyl substitution | 581.36 | Replacement of phenylurea with phenylacyl | Urea | 15.2 | 4.95 | 1 | 6 | 2 |
| 19 Remove ureas-acetylate | 457.33 | Replacement of phenylurea with acetyl | Urea | 18.8 | 3.01 | 1 | 6 | 0 |
| 20 Urea substitution-ethyl isocyanate | 515.38 | Replacement of phenylurea with ethylurea | Urea | 53 | 2.71 | 3 | 8 | 1 |

Figure 35A (cont.)

| Structure | MW | Modification | R group | Yield (mg) | MLogP | Hydrogen Bond Donors | Hydrogen Bond Acceptors | Lipinski Alerts |
|---|---|---|---|---|---|---|---|---|
| 21 Urea substitution-4-methylphenylisocyanate | 639.41 | Replacement of phenylurea with p-methylphenylurea | Urea | 67.7 | 4.61 | 3 | 8 | 2 |
| 22 Urea substitution-4-fluorophenylisocyanate | 647.36 | Replacement of phenylurea with p-fluorophenylurea | Urea | 72.2 | 4.70 | 3 | 8 | 2 |
| 23 Urea substitution-4-nitrophenylisocyanate | 701.35 | Replacement of phenylurea with p-nitrophenylurea | Urea | 66.4 | 4.39 | 3 | 14 | 3 |

Figure 35A (cont.)

SAR of active poly-phenylurea (TPI 1509-7)

| TPI 1540- | Structure | MW | Modification | R group | Caspase 3-XIAP derepression Ratio** 100 ug/ml | 25 ug/ml | IC-50 uM | Summ activity | TPIMS IC-50-MTT uM*** Jurkatt | MCF-7 | Annexin-V Jurkatt IC-50 uM |
|---|---|---|---|---|---|---|---|---|---|---|---|
| TPI 1509-7 | | 611.82 | Native-R2=D-proline | | 2.4 | 1.7 | 36.0 | ++ | 10.8 | >163 | 5.2 |
| TPI 1507 21 30 (TPI 1396-34) | | 611.82 | R2=L-Proline | | 2.2 | 1.6 | 57.2 | ++ | 14.7 | >163 | N.T |
| 6 | | 611.38 | Sterochemistry | R1 | 2.2 | 1.8 | 39.3 | ++ | 9.8 | 74.7 | N.T |
| 15 | | 515.2 | Removal of R1 | R1 | 2 | 1.4 | 97.0 | ++ | 11.5 | 15.5 | 6.3 |
| 16 | | 529.31 | Replacement of R1 with methyl | R1 | 2 | 1.3 | 102.0 | ++ | 15.4 | 18.4 | >30 |
| 8 | | 353.21 | Removal of R1 and associated urea | R1 | 1.2 | 0.9 | >283 | − | 247.0 | 259.3 | N.T |
| 7 | | 611.38 | Sterochemistry | R1 and R2 | 2.3 | 1.7 | 40.9 | ++ | 53.5 | 155.1 | N.T |
| 12 | | 585.37 | Removal of R2 | R2 | 2.2 | 1.6 | 54.7 | ++ | 43.9 | >171 | 7.1 |
| 13 | | 599.38 | Replacement of pyrrolidine with N-methylalanine | R2 | 2.3 | 1.7 | 45.0 | ++ | 15.8 | >167 | 4.9 |
| 9 | | 394.24 | Removal of R2 and R3 | R2 and R3 | 1.1 | 0.9 | >254 | − | >254 | 142.3 | N.T |

FIGURE 35B

| TPI 1540- | Structure | MW | Modification | R group | Ratio** 100 ug/ml | Ratio** 25 ug/ml | IC-50 uM | Summ activity | IC-50-MTT uM ***Jurkatt Jurkatt | IC-50-MTT uM ***Jurkatt MCF-7 | IC-50 uM Jurkatt |
|---|---|---|---|---|---|---|---|---|---|---|---|
| 10 | 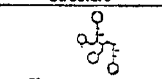 | 477.31 | Removal of R3 | R3 | 1.5 | 0.9 | >210 | - | 128.8 | 150.0 | N.T |
| 11 | 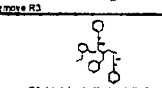 | 505.3 | Replacement of R3 with ethyl | R3 | 2.2 | 1.7 | 49.5 | ++ | 16.0 | 25.7 | 7.6 |
| 14 | 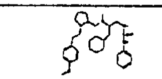 | 508.38 | Removal of N-urea | Urea | 2 | 1.8 | 43.4 | ++ | 19.2 | 21.4 | 7.3 |
| 17 | 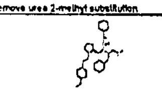 | 508.36 | Removal of N'-urea | Urea | 1.7 | 1.4 | 175.8 | + | 16.0 | 10.0 | N.T |
| 18 | 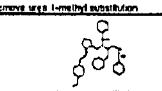 | 581.36 | Replacement of phenylurea with phenylacyl | Urea | 1.8 | 1.2 | 154.6 | + | 38.9 | 24.5 | N.T |
| 19 | 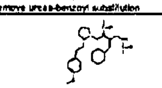 | 457.33 | Replacement of phenylurea with acetyl | Urea | 1.2 | 0.8 | 218.7 | - | 127.9 | 87.4 | N.T |
| 20 | 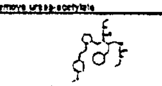 | 515.38 | Replacement of phenylurea with ethylurea | Urea | 1.8 | 1 | 194.0 | - | 92.9 | >194 | >30 |
| 21 | 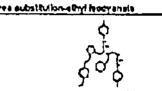 | 639.41 | Replacement of phenylurea with p-methylphenylurea | Urea | 2.3 | 1.7 | 42.2 | ++ | 32.1 | >156 | 5.4 |
| 22 | 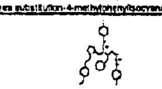 | 647.36 | Replacement of phenylurea with p-fluorophenylurea | Urea | 1.1 | 1.5 | 55.6 | ++ | 14.5 | 102.0 | 3.9 |
| 23 | 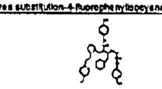 | 701.35 | Replacement of phenylurea with p-nitrophenylurea | Urea | 1.6 | 1.2 | >143 | + | 74.0 | 117.2 | N.T |

Caspase-XIAP derepression assay*: crude compounds/080603
Ratio** =Vmax compound+C3+XIAP/Vmax C3+XIAP
++: As active as native or not more than 20 % decrease
+: less active, ~30 % reduction
-:No activity at 100 ug/ml
MTT data***activity for crude and pur compounds, pure ones are:11,12,13,14,15,16,20,21,22
11,12,13,14,15,16,20,21,22

FIGURE 35B (cont.)

| TPI1332 | Structure | MW |
|---|---|---|
| 1 | [L-Ala][L-Trp(CHO)][L-Trp(CHO)][L-ThiAla] | 613.74 |
| 2 | [L-Ala][L-Trp(CHO)][L-Trp(CHO)][L-pClPhe] | 642.16 |
| 3 | [L-Ala][L-Trp(CHO)][L-Trp(CHO)][L-Nal] | 657.77 |
| 4 | [L-Ala][L-Trp(CHO)][L-Trp(CHO)][D-Nal] | 657.77 |
| 5 | [L-Ala][L-Trp(CHO)][L-Trp(CHO)][L-3I-Tyr] | 749.61 |
| 6 | [L-Ala][D-Trp(CHO)][L-Trp(CHO)][L-ThiAla] | 613.74 |
| 7 | [L-Ala][D-Trp(CHO)][L-Trp(CHO)][L-pClPhe] | 642.16 |

Figure 36A

| TPI1332 | Structure | MW |
|---|---|---|
| 8 | 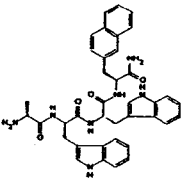 [L-Ala][D-Trp(CHO)][L-Trp(CHO)][L-Nal] | 657.77 |
| 9 | 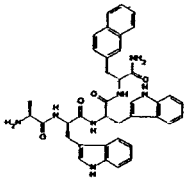 [L-Ala][D-Trp(CHO)][L-Trp(CHO)][D-Nal] | 657.77 |
| 10 | 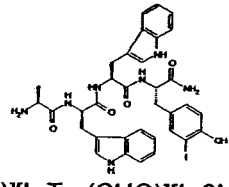 [L-Ala][D-Trp(CHO)][L-Trp(CHO)][L-3I-Tyr] | 749.61 |
| 11 | 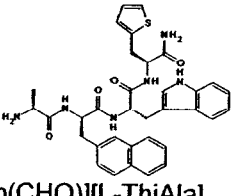 [L-Ala][D-Nal][L-Trp(CHO)][L-ThiAla] | 624.76 |
| 12 | 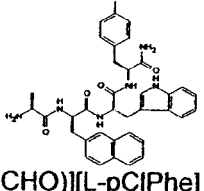 [L-Ala][D-Nal][L-Trp(CHO)][L-pClPhe] | 653.18 |
| 13 | 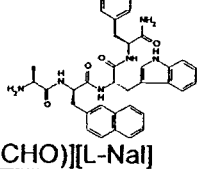 [L-Ala][D-Nal][L-Trp(CHO)][L-Nal] | 668.80 |
| 14 | 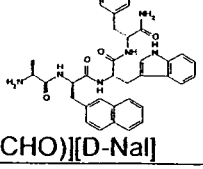 [L-Ala][D-Nal][L-Trp(CHO)][D-Nal] | 668.80 |
Figure 36A (cont.)

| TPI1332 | Structure | MW |
|---|---|---|
| 15 | 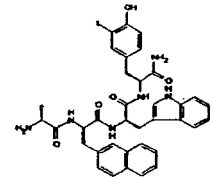 [L-Ala][D-Nal][L-Trp(CHO)][L-3I-Tyr] | 760.63 |
| 16 | 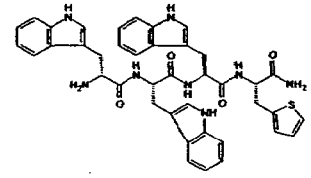 [D-Trp(CHO)][L-Trp(CHO)][L-Trp(CHO)][L-ThiAla] | 728.88 |
| 17 | 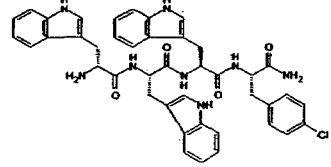 [D-Trp(CHO)][L-Trp(CHO)][L-Trp(CHO)][L-pClPhe] | 757.29 |
| 18 | 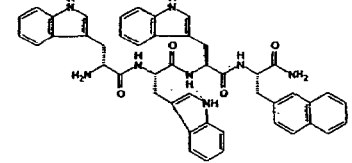 [D-Trp(CHO)][L-Trp(CHO)][L-Trp(CHO)][L-Nal] | 772.91 |
| 19 | 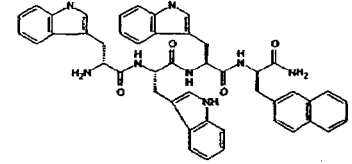 [D-Trp(CHO)][L-Trp(CHO)][L-Trp(CHO)][D-Nal] | 772.91 |
| 20 | 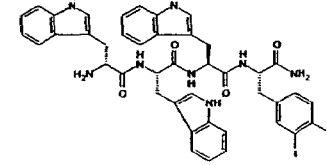 [D-Trp(CHO)][L-Trp(CHO)][L-Trp(CHO)][L-3I-Tyr] | 864.74 |
| 21 | 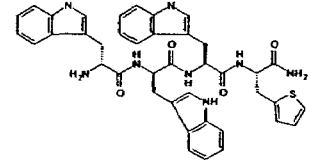 [D-Trp(CHO)][D-Trp(CHO)][L-Trp(CHO)][L-ThiAla] | 728.88 |
Figure 36A (cont.)

| TPI1332 | Structure | MW |
|---|---|---|
| 22 | [D-Trp(CHO)][D-Trp(CHO)][L-Trp(CHO)][L-pClPhe] 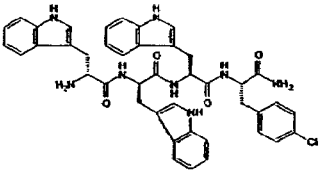 | 757.29 |
| 23 | [D-Trp(CHO)][D-Trp(CHO)][L-Trp(CHO)][L-Nal] 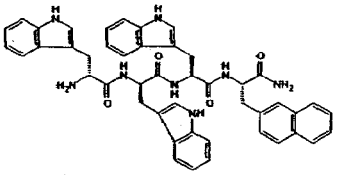 | 772.91 |
| 24 | [D-Trp(CHO)][D-Trp(CHO)][L-Trp(CHO)][D-Nal] 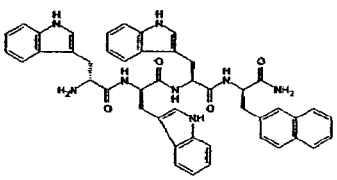 | 772.91 |
| 25 | [D-Trp(CHO)][D-Trp(CHO)][L-Trp(CHO)][L-3I-Tyr] 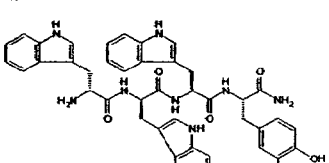 | 864.74 |
| 26 | [D-Trp(CHO)][D-Nal][L-Trp(CHO)][L-ThiAla] 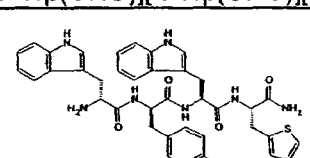 | 739.90 |
| 27 | [D-Trp(CHO)][D-Nal][L-Trp(CHO)][L-pClPhe] 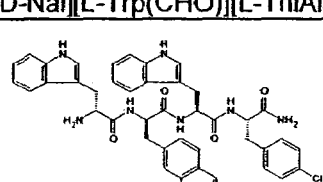 | 768.32 |
| 28 | [D-Trp(CHO)][D-Nal][L-Trp(CHO)][L-Nal] 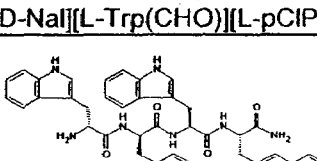 | 783.93 |
Figure 36A (cont.)

| TPI1332 | Structure | MW |
|---|---|---|
| 29 | [D-Trp(CHO)][D-Nal][L-Trp(CHO)][D-Nal] 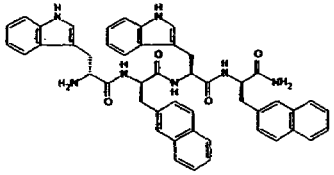 | 783.93 |
| 30 | [D-Trp(CHO)][D-Nal][L-Trp(CHO)][L-3I-Tyr] 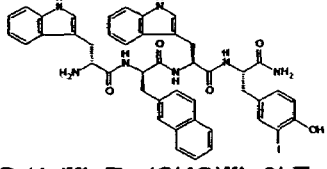 | 875.77 |
| 31 | [L-Cha][L-Trp(CHO)][L-Trp(CHO)][L-ThiAla] 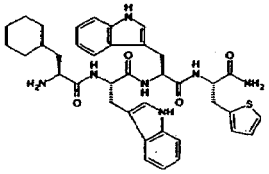 | 695.89 |
| 32 | [L-Cha][L-Trp(CHO)][L-Trp(CHO)][L-pClPhe] 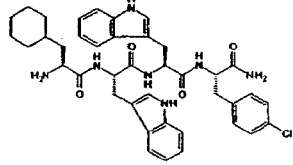 | 724.31 |
| 33 | [L-Cha][L-Trp(CHO)][L-Trp(CHO)][L-Nal] 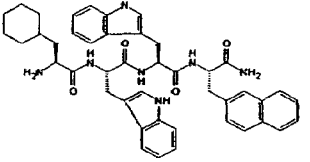 | 739.92 |
| 34 | [L-Cha][L-Trp(CHO)][L-Trp(CHO)][D-Nal] 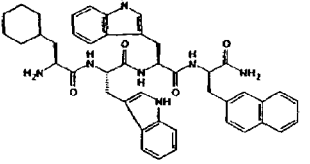 | 739.92 |
| 35 | [L-Cha][L-Trp(CHO)][L-Trp(CHO)][L-3I-Tyr] 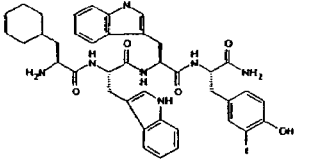 | 831.76 |
Figure 36A (cont.)

| TPI1332 | Structure | MW |
|---|---|---|
| 36 | [L-Cha][D-Trp(CHO)][L-Trp(CHO)][L-ThiAla] 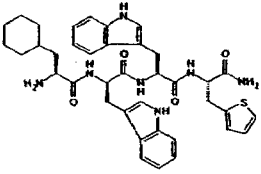 | 695.89 |
| 37 | [L-Cha][D-Trp(CHO)][L-Trp(CHO)][L-pClPhe] 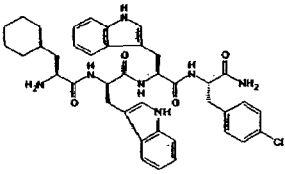 | 724.31 |
| 38 | [L-Cha][D-Trp(CHO)][L-Trp(CHO)][L-Nal] 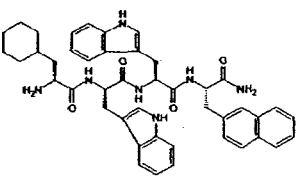 | 739.92 |
| 39 | [L-Cha][D-Trp(CHO)][L-Trp(CHO)][D-Nal] 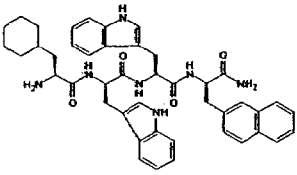 | 739.92 |
| 40 | [L-Cha][D-Trp(CHO)][L-Trp(CHO)][L-3I-Tyr] 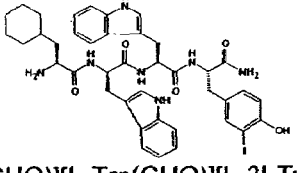 | 831.76 |
| 41 | [L-Cha][D-Nal][L-Trp(CHO)][L-ThiAla] 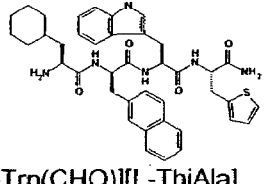 | 706.91 |
| 42 | [L-Cha][D-Nal][L-Trp(CHO)][L-pClPhe] 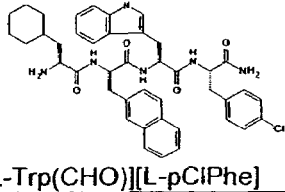 | 735.33 |
Figure 36A (cont.)

| TPI1332 | Structure | MW |
|---|---|---|
| 43 | [L-Cha][D-Nal][L-Trp(CHO)][L-Nal] 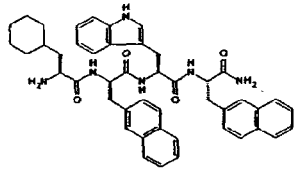 | 750.94 |
| 44 | [L-Cha][D-Nal][L-Trp(CHO)][D-Nal] 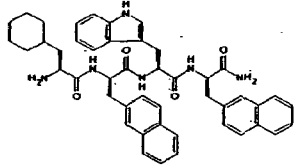 | 750.94 |
| 45 | [L-Cha][D-Nal][L-Trp(CHO)][L-3I-Tyr] 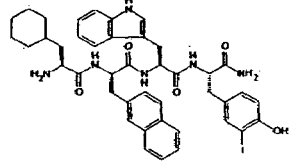 | 842.78 |
| 46 | [L-Ala][D-Trp(CHO)][L-Trp(CHO)][D-Trp(CHO)] 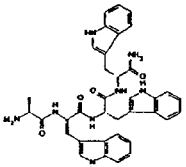 | 646.75 |
| 47 | [L-Ala][D-Trp(CHO)][L-Trp(CHO)][L-ThiAla] 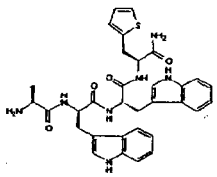 | 613.74 |
| 48 | [L-Ala][D-Trp(CHO)][D-Phe][D-Trp(CHO)] 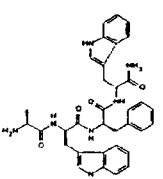 | 607.71 |
| 49 | [L-Ala][D-Trp(CHO)][D-Phe][L-ThiAla] 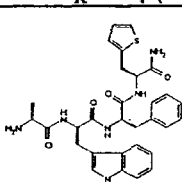 | 574.70 |
Figure 36A (cont.)

| TPI1332 | Structure | MW |
|---|---|---|
| 50 | [L-Ala][D-Cha][L-Trp(CHO)][D-Trp(CHO)] 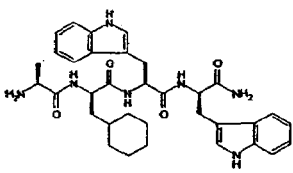 | 613.76 |
| 51 | [L-Ala][D-Cha][L-Trp(CHO)][L-ThiAla] 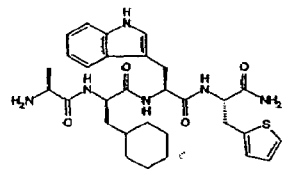 | 580.75 |
| 52 | [L-Ala][D-Cha][D-Phe][D-Trp(CHO)] 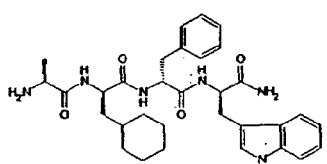 | 574.73 |
| 53 | [L-Ala][D-Cha][D-Phe][L-ThiAla] 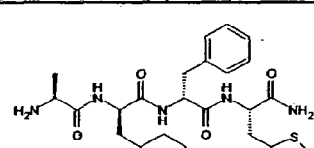 | 541.71 |
| 54 | [L-Ala][D-ThiAla][L-Trp(CHO)][D-Trp(CHO)] 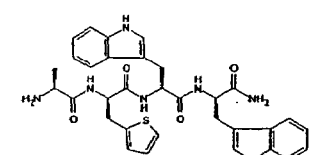 | 613.74 |
| 55 | [L-Ala][D-ThiAla][L-Trp(CHO)][L-ThiAla] 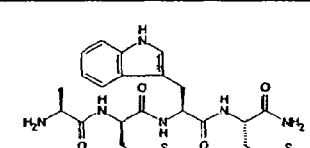 | 580.73 |
| 56 | [L-Ala][D-ThiAla][D-Phe][D-Trp(CHO)] 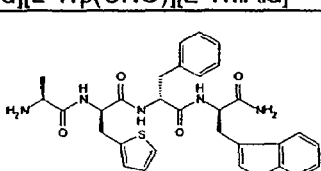 | 574.70 |
Figure 36A (cont.)

| TPI1332 | Structure | MW |
|---|---|---|
| 57 | [L-Ala][D-ThiAla][D-Phe][L-ThiAla] 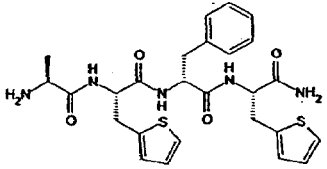 | 541.69 |
| 58 | [L-Ala][D-pIPhe][L-Trp(CHO)][D-Trp(CHO)] 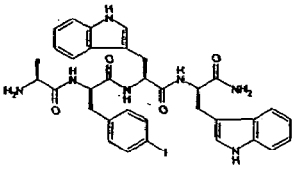 | 733.61 |
| 59 | [L-Ala][D-pIPhe][L-Trp(CHO)][L-ThiAla] 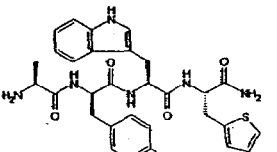 | 700.60 |
| 60 | [L-Ala][D-pIPhe][D-Phe][D-Trp(CHO)] 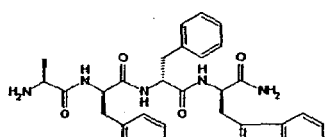 | 694.57 |
| 61 | [L-Ala][D-pIPhe][D-Phe][L-ThiAla] 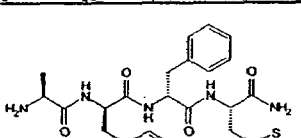 | 661.56 |
| 62 | [L-Nal][D-Trp(CHO)][L-Trp(CHO)][D-Trp(CHO)] 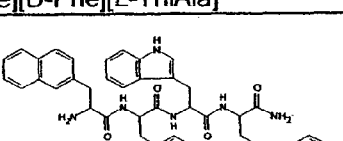 | 772.91 |
| 63 | [L-Nal][D-Trp(CHO)][L-Trp(CHO)][L-ThiAla] 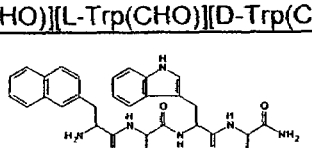 | 739.90 |
Figure 36A (cont.)

| TPI1332 | Structure | MW |
|---|---|---|
| 64 | [L-Nal][D-Trp(CHO)][D-Phe][D-Trp(CHO)] | 733.87 |
| 65 | [L-Nal][D-Trp(CHO)][D-Phe][L-ThiAla] | 700.86 |
| 66 | [L-Nal][D-Cha][L-Trp(CHO)][D-Trp(CHO)] | 739.92 |
| 67 | [L-Nal][D-Cha][L-Trp(CHO)][L-ThiAla] | 706.91 |
| 68 | [L-Nal][D-Cha][D-Phe][D-Trp(CHO)] | 700.88 |
| 69 | [L-Nal][D-Cha][D-Phe][L-ThiAla] | 667.87 |
| 70 | [L-Nal][D-ThiAla][L-Trp(CHO)][D-Trp(CHO)] | 739.90 |

Figure 36A (cont.)

| TPI1332 | Structure | MW |
|---|---|---|
| 71 | [L-Nal][D-ThiAla][L-Trp(CHO)][L-ThiAla] | 706.89 |
| 72 | [L-Nal][D-ThiAla][D-Phe][D-Trp(CHO)] | 700.86 |
| 73 | [L-Nal][D-ThiAla][D-Phe][L-ThiAla] | 667.85 |
| 74 | [L-Nal][D-pIPhe][L-Trp(CHO)][D-Trp(CHO)] | 859.77 |
| 75 | [L-Nal][D-pIPhe][L-Trp(CHO)][L-ThiAla] | 826.76 |
| 76 | [L-Nal][D-pIPhe][D-Phe][D-Trp(CHO)] | 820.73 |
| 77 | [L-Nal][D-pIPhe][D-Phe][L-ThiAla] | 787.72 |

Figure 36A (cont.)

| TPI1332 | Structure | MW |
|---|---|---|
| 78 | [L-3I-Tyr][D-Trp(CHO)][L-Trp(CHO)][D-Trp(CHO)] | 864.74 |
| 79 | [L-3I-Tyr][D-Trp(CHO)][L-Trp(CHO)][L-ThiAla] | 831.73 |
| 80 | [L-3I-Tyr][D-Trp(CHO)][D-Phe][D-Trp(CHO)] | 825.71 |
| 81 | [L-3I-Tyr][D-Trp(CHO)][D-Phe][L-ThiAla] | 792.70 |
| 82 | [L-3I-Tyr][D-Cha][L-Trp(CHO)][D-Trp(CHO)] | 831.76 |
| 83 | [L-3I-Tyr][D-Cha][L-Trp(CHO)][L-ThiAla] | 798.74 |
| 84 | [L-3I-Tyr][D-Cha][D-Phe][D-Trp(CHO)] | 792.72 |

Figure 36A (cont.)

| TPI1332 | Structure | MW |
|---|---|---|
| 85 | [L-3I-Tyr][D-Cha][D-Phe][L-ThiAla] | 759.71 |
| 86 | [L-3I-Tyr][D-ThiAla][L-Trp(CHO)][D-Trp(CHO)] | 831.73 |
| 87 | [L-3I-Tyr][D-ThiAla][L-Trp(CHO)][L-ThiAla] | 798.72 |
| 88 | [L-3I-Tyr][D-ThiAla][D-Phe][D-Trp(CHO)] | 792.70 |
| 89 | [L-3I-Tyr][D-ThiAla][D-Phe][L-ThiAla] | 759.69 |
| 90 | [L-3I-Tyr][D-pIPhe][L-Trp(CHO)][D-Trp(CHO)] | 951.60 |
| 91 | [L-3I-Tyr][D-pIPhe][L-Trp(CHO)][L-ThiAla] | 918.59 |

Figure 36A (cont.)

| TPI1332 | Structure | MW |
|---|---|---|
| 92 | 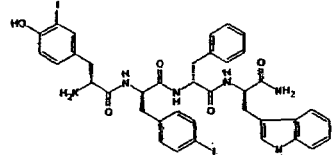 [L-3I-Tyr][D-pIPhe][D-Phe][D-Trp(CHO)] | 912.57 |
| 93 | 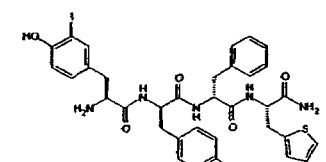 [L-3I-Tyr][D-pIPhe][D-Phe][L-ThiAla] | 879.56 |
Figure 36A (cont.)

XIAP inhibitors-Tetrapeptides

| | | MW | Competition assay Smac-7 mer/XIAP-BI IC-50 uM AVG | STD |
|---|---|---|---|---|
| TPI 1453-1 (TPI 792-33) | [L-ThiAla]-[L-Nal]-[p-ClPhe]-[L-LyseFmoc] Exact Mass: 898.32793 | 900.9 | 48.4 | 10 |
| TPI 1453-6 (TPI 792-35) | [L-ThiAla]-[L-Nal]-[p-ClPhe]-[L-LyseFmoc] | 1068.8 | 12.6 | 4.8 |
| TPI 1332-4 | [L-Ala][L-Trp(CHO)][L-Trp(CHO)][D-Nal] | 657.8 | 3.9 | 3.6 |
| TPI 1332-24 | [D-Trp(CHO)][D-Trp(CHO)][L-Trp(CHO)][D- | 772.9 | 5.0 | 4.8 |
| TPI 1332-41 | [L-Cha][D-Nal][L-Trp(CHO)][L-ThiAla] | 706.9 | 48.5 | 0.9 |
| TPI 1332-69 | [L-Nal][D-Cha][D-Phe][L-ThiAla] | 667.9 | >150 | |
| TPI 1332-76 | [L-Nal][D-pIPhe][D-Phe][D-Trp(CHO)] | 820.7 | 36.2 | 20.9 |
| TPI 1332-77 | [L-Nal][D-pIPhe][D-Phe][L-ThiAla] | 787.7 | 66.7 | 32.4 |
| Smac 7-mer | AVPIAQK-NH$_2$ | 724.4 | 18.8 | 4 |
| Smac 4-mer | AVPI-NH$_2$ | 397.2 | 30.3 | |

FIGURE 36B

TPI 1495-1 is the same as TPI 1332-69

TPI 1495-

| | | | | | | | MW | XIAP-FL derepression IC50 uM | Competitive binding assay IC-50 uM | STD |
|---|---|---|---|---|---|---|---|---|---|---|
| 1 | H- | L-Nal | D-Cha | D-Phe | L-ThiaAla | -NH2 | 667.3 | 33.9 | >150 | |
| 2 | H- | G | D-Cha | D-Phe | L-ThiaAla | -NH2 | 527.3 | >189.7 | >190 | |
| 3 | H- | L-Nal | G | D-Phe | L-ThiaAla | -NH2 | 571.2 | >175.1 | >175 | |
| 4 | H- | L-Nal | D-Cha | G | L-ThiaAla | -NH2 | 577.3 | >173.2 | >175 | |
| 5 | H- | L-Nal | D-Cha | D-Phe | G | -NH2 | 571.3 | 67.4 | 29.7 | 23.4 |
| 6 | H- | A | D-Cha | D-Phe | L-ThiaAla | -NH2 | 541.3 | >184.8 | >185 | |
| 7 | H- | L-Nal | A | D-Phe | L-ThiaAla | -NH2 | 585.2 | >170.9 | >170 | |
| 8 | H- | L-Nal | D-Cha | A | L-ThiaAla | -NH2 | 591.3 | >169.1 | >170 | |
| 9 | H- | L-Nal | D-Cha | D-Phe | A | -NH2 | 585.3 | 149.0 | >170 | |

| TPI 1237-14 | Smac 7 mer | | | | | | 724.4 | | 18.8 | 4.0 |
| TPI 1425-1 | Smac 4 mer | | | | | | 397.2 | | 30.3 | |

FIGURE 37

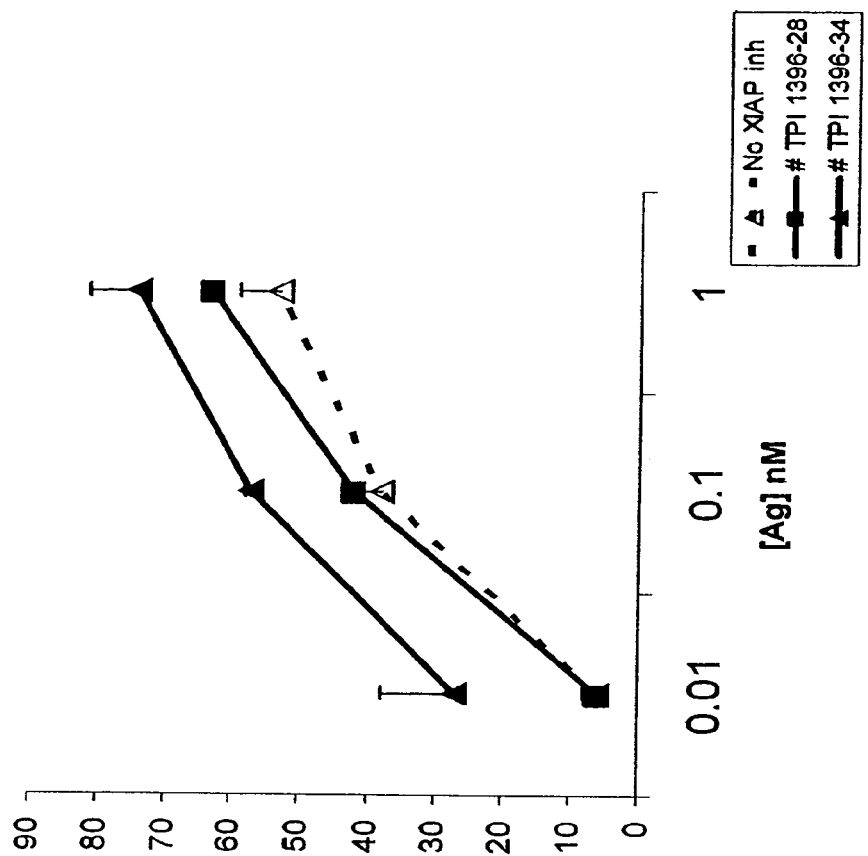
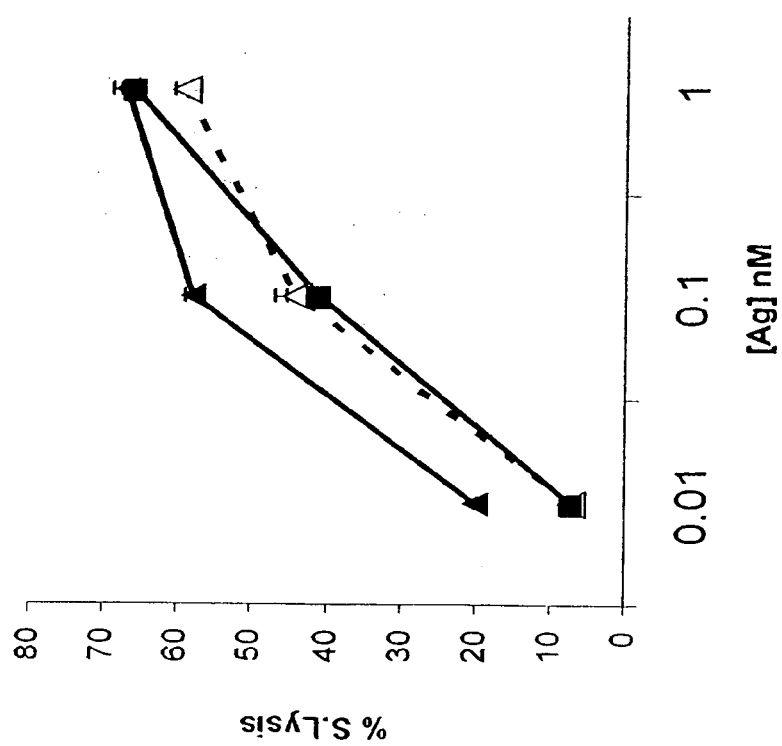
Figure 39

| TPI 1453 | | | | | | MW | XIAP-FL derepression data | | | Competitive binding assay | |
|---|---|---|---|---|---|---|---|---|---|---|---|
| | | | | | | | lowest ratio 1.8 | AVG IC-50 uM | STD | IC-50 uM | STD |
| 1 | L-Thiala | L-Nal | pCl-L-f | Lys eFm | -NH₂ | 900.9 | 12.5 | 21.0 | 10.3 | 48.4 | 10.0 |
| 2 | G | L-Nal | pCl-L-f | Lys eFm | -NH₂ | 803.7 | 6.25 | 14.1 | 0.6 | 10.1 | 9.0 |
| 3 | L-Thiala | G | pCl-L-f | Lys eFm | -NH₂ | 759.5 | ~100 | ~131.7 | | 57.7 | 15.6 |
| 4 | L-Thiala | L-Nal | G | Lys eFm | -NH₂ | 775.2 | 25 | 69.0 | | 38.5 | 16.4 |
| 5 | L-Thiala | L-Nal | pCl-L-f | G | -NH₂ | 607.3 | >100 | > 164.7 | | >165 | na |
| 6 | L-Thiala | L-Nal | dLysFm | Lys eFm | -NH₂ | 1068.8 | 3.13 | 6.1 | 2.1 | 12.6 | 4.8 |
| 7 | G | L-Nal | dLysFm | Lys eFm | -NH₂ | 971.6 | 6.25 | 36.4 | 16.7 | 4.2 | 1.1 |
| 8 | L-Thiala | G | dLysFm | Lys eFm | -NH₂ | 927.4 | 3.13 | 24.0 | 1.7 | 7.1 | 6.9 |
| 4 | L-Thiala | L-Nal | G | Lys eFm | -NH₂ | 775.2 | 25 | 69.0 | | 38.5 | 16.4 |
| 9 | L-Thiala | L-Nal | dLysFm | G | -NH₂ | 775.2 | 6.25 | 19.0 | 8.6 | 3.8 | 3.6 |
| TPI 1237-14 | Smac 7 mer | | | | | 724.4 | | | | 18.8 | 4.0 |
| TPI 1425-1 | Smac 4 mer | | | | | 397.2 | | | | 30.3 | |

TPI 1453-1=TPI 792-33 and TPI 1408-3.
TPI 1453-6=TPI 792-35

TPI 1554 Biotinylated Tetrapeptides

| TPI 1554 # | Non-Biotin Synthesis # | Sequence | 1 | 2 | 3 | 4 | 5 | 6 | 7 | | MW |
|---|---|---|---|---|---|---|---|---|---|---|---|
| TPI 1554-1 | TPI 792-33, TPI 1408-3, TPI 1453- | H- | L-Thiala | L-Nal | pCl-L-f | Lys eFm | (Biotin) | (6aha) | Kboc/fmoc | -NH2 | 1365.6 |
| TPI 1554-2 | TPI 792-35, TPI 1453-6 | H- | L-Thiala | L-Nal | dLysFm | Lys eFm | (Biotin) | (6aha) | Kboc/fmoc | -NH2 | 1534.7 |
| TPI 1554-3 | TPI 1332-4 | H- | Boc-L-Ala | Boc-L-Trp(CHO) | Boc-L-Trp(CHO) | Boc-D-Nal | (Biotin) | (6aha) | Kboc/fmoc | -NH2 | 1124.5 |
| TPI 1554-4 | TPI 1332-41 | H- | Boc-L-Cha | Boc-D-Nal | Boc-L-Trp(CHO) | Boc-L-ThiaAla | (Biotin) | (6aha) | Kboc/fmoc | -NH2 | 1173.6 |
| TPI 1554-5 | TPI 1332-89 | H- | Boc-L-Nal | Boc-D-Cha | Boc-D-Phe | Boc-L-ThiaAla | (Biotin) | (6aha) | Kboc/fmoc | -NH2 | 1134.6 |
| TPI 1554-6 | TPI 1332-77 | H- | Boc-L-Nal | Boc-D-plPhe | Boc-D-Phe | Boc-L-ThiaAla | (Biotin) | (6aha) | Kboc/fmoc | -NH2 | 1254.4 |
| TPI 1554-7 | TPI 1495-19 | H- | L-Nal | pCl-L-f | Lys eFm | (Biotin) | (6aha) | Kboc/fmoc | | -NH2 | 1212.6 |
| TPI 1554-8 | TPI 1495-20 | H- | L-Thiala | L-Nal | dLysFm | (Biotin) | (6aha) | Kboc/fmoc | | -NH2 | 1184.6 |

FIGURE 44

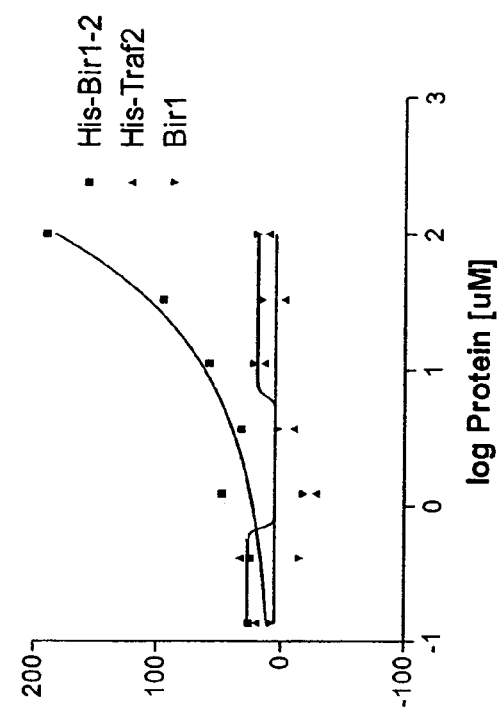
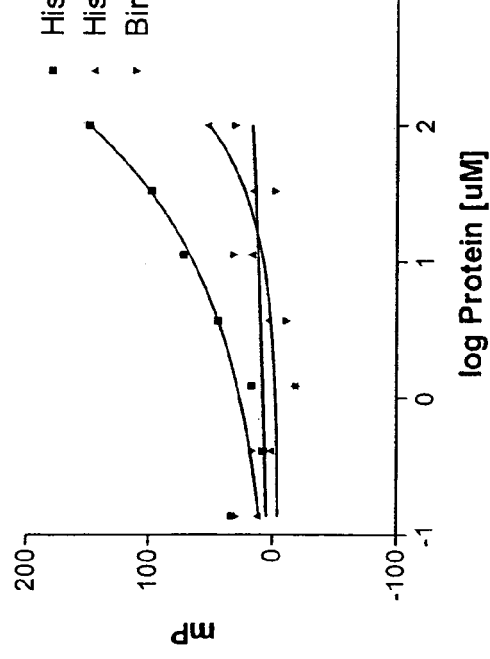
Figure 50

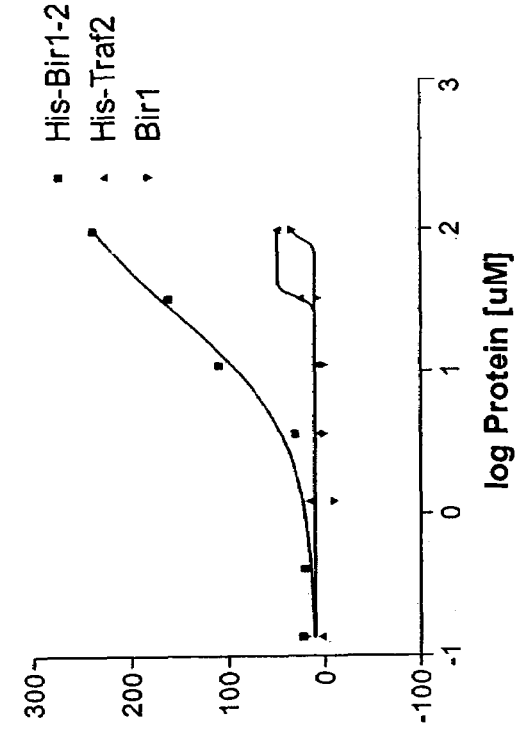
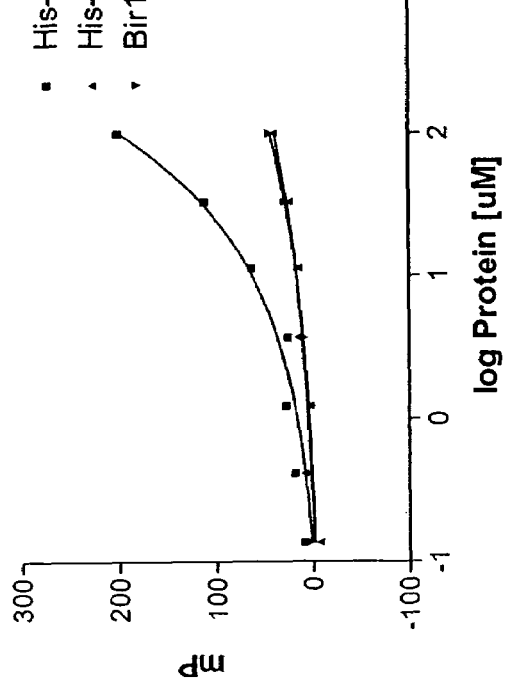
Figure 52

SEQUENCE LISTING

```
<160> NUMBER OF SEQ ID NOS: 16

<210> SEQ ID NO 1
<211> LENGTH: 5
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: 4
<223> OTHER INFORMATION: Xaa = Any Amino Acid

<400> SEQUENCE: 1

Gln Ala Cys Xaa Gly
 1               5

<210> SEQ ID NO 2
<211> LENGTH: 4
<212> TYPE: PRT
<213> ORGANISM: Artificial Sequence
<220> FEATURE:
<223> OTHER INFORMATION: synthetic construct

<400> SEQUENCE: 2

Asp Glu Val Asp
 1

<210> SEQ ID NO 3
<211> LENGTH: 4
<212> TYPE: PRT
<213> ORGANISM: Artificial Sequence
<220> FEATURE:
<223> OTHER INFORMATION: synthetic construct

<400> SEQUENCE: 3

Tyr Val Ala Asp
 1

<210> SEQ ID NO 4
<211> LENGTH: 4
<212> TYPE: PRT
<213> ORGANISM: Artificial Sequence
<220> FEATURE:
<223> OTHER INFORMATION: synthetic construct

<400> SEQUENCE: 4

Ala Val Pro Ile
 1

<210> SEQ ID NO 5
<211> LENGTH: 7
<212> TYPE: PRT
<213> ORGANISM: Artificial Sequence
<220> FEATURE:
<223> OTHER INFORMATION: synthetic construct
<220> FEATURE:
<221> NAME/KEY: AMIDATION
<222> LOCATION: 7
<223> OTHER INFORMATION: at the C-terminus
<220> FEATURE:
```

```
<221> NAME/KEY: MOD_RES
<222> LOCATION: 1
<223> OTHER INFORMATION: hydrogenated at the N-terminus

<400> SEQUENCE: 5

Ala Val Pro Ile Ala Gln Lys
 1               5

<210> SEQ ID NO 6
<211> LENGTH: 4
<212> TYPE: PRT
<213> ORGANISM: Artificial Sequence
<220> FEATURE:
<223> OTHER INFORMATION: synthetic peptide

<400> SEQUENCE: 6

Ala Val Pro Ser
 1

<210> SEQ ID NO 7
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (1)...(2)
<223> OTHER INFORMATION: Xaa = any amino acid

<400> SEQUENCE: 7

Xaa Xaa Ala Ala Trp Trp
 1               5

<210> SEQ ID NO 8
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (1)...(2)
<223> OTHER INFORMATION: Xaa = any amino acid

<400> SEQUENCE: 8

Xaa Xaa Gly Ala Trp Trp
 1               5

<210> SEQ ID NO 9
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (1)...(2)
<223> OTHER INFORMATION: Xaa = any amino acid

<400> SEQUENCE: 9

Xaa Xaa Arg Ala Trp Trp
 1               5

<210> SEQ ID NO 10
<211> LENGTH: 6
<212> TYPE: PRT
<213> ORGANISM: Artificial Sequence
<220> FEATURE:
```

-continued

```
<223> OTHER INFORMATION: synthetic peptide
<220> FEATURE:
<221> NAME/KEY: VARIANT
<222> LOCATION: (1)...(2)
<223> OTHER INFORMATION: Xaa = any amino acid

<400> SEQUENCE: 10

Xaa Xaa Cys Lys Trp Trp
1               5

<210> SEQ ID NO 11
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 1, 2
<223> OTHER INFORMATION: Xaa = Any Amino Acid

<400> SEQUENCE: 11

Xaa Xaa Phe Trp Trp Trp
1               5

<210> SEQ ID NO 12
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 1, 2
<223> OTHER INFORMATION: Xaa = Any Amino Acid

<400> SEQUENCE: 12

Xaa Xaa Leu Trp Trp Trp
1               5

<210> SEQ ID NO 13
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 1, 2
<223> OTHER INFORMATION: Xaa = Any Amino Acid

<400> SEQUENCE: 13

Xaa Xaa Trp Leu Trp Trp
1               5

<210> SEQ ID NO 14
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: 1, 2
<223> OTHER INFORMATION: Xaa = Any Amino Acid

<400> SEQUENCE: 14

Xaa Xaa Trp Trp Trp Trp
1               5
```

-continued

```
<210> SEQ ID NO 15
<211> LENGTH: 6
<212> TYPE: PRT
<213> ORGANISM: Artificial Sequence
<220> FEATURE:
<223> OTHER INFORMATION: synthetic peptide
<220> FEATURE:
<221> NAME/KEY: VARIANT
<222> LOCATION: (1)...(2)
<223> OTHER INFORMATION: Xaa=any amino acid

<400> SEQUENCE: 15

Xaa Xaa Leu Lys Trp Trp
 1               5

<210> SEQ ID NO 16
<211> LENGTH: 68
<212> TYPE: PRT
<213> ORGANISM: Artificial Sequence
<220> FEATURE:
<223> OTHER INFORMATION: consensus sequence
<220> FEATURE:
<221> NAME/KEY: VARIANT
<222> LOCATION: 1-3,6,9,10,13,14,16,18-21,24,30,32,33,35,37,40,42-44,46,
      47,49-51,53-57,59,61,62,64,66
<223> OTHER INFORMATION: Xaa=Any amino acid
<220> FEATURE:
<221> NAME/KEY: VARIANT
<222> LOCATION: 15
<223> OTHER INFORMATION: Xaa=any amino acid that may or may not be
      present
<220> FEATURE:
<221> NAME/KEY: VARIANT
<222> LOCATION: 5,17,28,29,45,68
<223> OTHER INFORMATION: Xaa=a hydrophobic amino acid
<220> FEATURE:
<221> NAME/KEY: VARIANT
<222> LOCATION: 7
<223> OTHER INFORMATION: Xaa=serine or threonine
<220> FEATURE:
<221> NAME/KEY: VARIANT
<222> LOCATION: 8,67
<223> OTHER INFORMATION: Xaa=phenylalanine or tyrosine
<220> FEATURE:
<221> NAME/KEY: VARIANT
<222> LOCATION: (12)...(12)
<223> OTHER INFORMATION: Xaa=proline that may or may not be present
<220> FEATURE:
<221> NAME/KEY: VARIANT
<222> LOCATION: (52)...(52)
<223> OTHER INFORMATION: Xaa=aspartic or glutamic acid
<220> FEATURE:
<221> NAME/KEY: VARIANT
<222> LOCATION: (60)...(60)
<223> OTHER INFORMATION: Xaa=a basic amino acid (e.g. Arg, His, or Lys)

<400> SEQUENCE: 16

Xaa Xaa Xaa Arg Xaa Xaa Xaa Xaa Xaa Trp Xaa Xaa Xaa Xaa Xaa
 1               5                  10                  15

Xaa Xaa Xaa Xaa Xaa Leu Ala Xaa Ala Gly Phe Xaa Xaa Xaa Gly Xaa
            20                  25                  30

Xaa Asp Xaa Val Xaa Cys Phe Xaa Cys Xaa Xaa Xaa Xaa Xaa Trp
        35                  40                  45

Xaa Xaa Xaa Xaa Xaa Xaa Xaa Xaa Xaa His Xaa Xaa Xaa Xaa Pro Xaa
    50                  55                  60

Cys Xaa Xaa Xaa
65
```

METHODS AND COMPOSITIONS FOR DEREPRESSION OF IAP-INHIBITED CASPASE

This application is a continuation-in-part of U.S. application Ser. No. 11/084,714, filed Mar. 17, 2005, which is incorporated herein by reference.

This invention was made with government support under grant number CA78040 awarded by The National Institute of Health/National Cancer Institute. The United States Government has certain rights in this invention.

BACKGROUND OF THE INVENTION

The present invention relates generally to molecular medicine and more specifically to compositions and methods for altering molecular interactions involved in regulating programmed cell death.

Normal tissues in the body are formed either by cells that have reached a terminally differentiated state and no longer divide or by cells that die after a period of time and are replaced from a pool of dividing cells. For example, nervous tissue is formed early in development and the cells of the nervous system reach a terminally differentiated state soon after birth. In contrast, the body has a number of self renewing tissues such as skin, gut, bone marrow and sex organs which undergo a balanced flux of cell birth and death. This flux, which results in the production of 50–70 billion cells per day in an average adult and amounting to a mass of cells equivalent to an entire body weight over a years time, is balanced by the regulated eradication of an equivalent number of cells. In self renewing tissues the eradication is maintained, in part, due to the process of programmed cell death, known as apoptosis, in which the cells are genetically "programmed" to die after a certain period of time.

Apoptosis is particularly prominent during the development of an organism, where cells that perform transitory functions are programmed to die after their function no longer is required. In addition, apoptosis can occur in cells that have undergone major genetic alterations, thus providing the organism with a means to rid itself of defective and potentially cancer forming cells. Apoptosis also can be induced due to exposure of an organism to various external stimuli, including, for example, bacterial toxins, ethanol and ultraviolet radiation. Chemotherapeutic agents for treating cancer also are potent inducers of apoptosis.

The regulation of programmed cell death is a complex process involving numerous pathways and, on occasion, defects occur in the regulation of programmed cell death. Given the critical role of this process in maintaining a steady-state number of cells in a tissue or in maintaining the appropriate cells during development of an organism, defects in programmed cell death often are associated with pathologic conditions. It is estimated that either too little or too much cell death is involved in over half of the diseases for which adequate therapies do not currently exist.

Various disease states occur due to aberrant regulation of programmed cell death in an organism. For example, defects that result in a decreased level of apoptosis in a tissue as compared to the normal level required to maintain the steady-state of the tissue can result in an increased number of cells in the tissue. Such a mechanism of increasing cell numbers has been identified in various cancers, where the formation of a tumor occurs not because the cancer cells necessarily are dividing more rapidly than their normal counterparts, but because the cells are not dying at their normal rate.

Thus, a need exists for agents capable of modulating programmed cell death pathways and methods for treating individuals experiencing diseases associated with aberrant regulation of programmed cell death. The present invention satisfies this need and provides additional advantages as well.

SUMMARY OF THE INVENTION

The invention provides isolated agents having one of the structures TPI 1577-1, TPI 1577-2, TPI 1577-3, TPI 1567-5, TPI 1577-6, TPI 1577-7, TPI 1577-8, TPI 1577-9, TPI 1567-11, TPI 1567-12, TPI 1567-13, TPI 1567-14, TPI 1567-23, TPI 1567-24, TPI 1567-18, TPI 1572-8, TPI 1572-15, TPI 1572-16, TPI 1572-10, TPI 1572-11; TPI 1572-14; TPI 1572-17, TPI 1572-18, TPI 1572-19, TPI 1572-20, TPI 1572-21, TPI 1572-22 or TPI 1572-23. These compounds are derepressors of IAP-inhibited caspase. The invention further provides a method of derepressing an IAP-inhibited caspase. The method comprises contacting an IAP-inhibited caspase with an effective amount of one of the agents. The invention also provides a method for promoting apoptosis in a cell and for reducing the severity of a pathology characterized by reduced levels of apoptosis.

The invention further provides assay methods for identifying an IAP inhibited caspase derepressor. One method involves providing a labeled candidate agent and measuring a label signal in the presence and absence of IAP or a fragment of IAP. The difference in label signal in the presence and absence of IAP or fragment thereof is a measure of the degree of binding of the candidate agent to IAP or fragment thereof. The method optionally includes creating a binding curve, plotting the concentration of either IAP (or its fragment) or the candidate agent against the difference between bound and unbound label signal.

The invention further provides another assay method for identifying an IAP inhibited caspase derepressor. A labeled candidate agent is first provided. A label signal is measured for the labeled candidate agent in the absence of IAP and fragments thereof. Then a label signal is obtained for the labeled candidate agent in the presence of a known IAP-binding agent and IAP or a fragment thereof. The difference between the first and second label signals corresponds to the relative affinity of the candidate agent for IAP, and is thus predictive of the IAP inhibited caspase derepressor activity of the candidate agent. The method optionally includes creating a binding curve, plotting the concentration of either IAP (or its fragment) or the candidate agent against the difference between bound and unbound label signal.

The invention provides isolated agents having a core peptide selected from the group consisting of Core peptides 4 through 39 and 42 through 55, wherein the agent derepresses an IAP-inhibited caspase. Also provided is an isolated agent having a core structure selected from any of the structures shown in FIGS. 5, 9, 10, 14B, 21–24, 34, 35 and 36, wherein the agent derepresses an IAP-inhibited caspase. The invention further provides a method of derepressing an IAP-inhibited caspase. The method consists of contacting an IAP-inhibited caspase with an effective amount of an agent to derepress an IAP-inhibited caspase, the agent having a core motif selected from the group consisting of a core peptide having a sequence set forth in any of Core peptides 4 through 39 and 42 through 55; a core structure selected from the group consisting of TPI759, TPI 882, TPI 914 or TPI 927; and a core structure selected from TPI 1391, TPI 1349, TPI 1396, TPI 1509, TPI 1540, TPI 1400, TPI 792 and TPI 1332. The invention also provides methods for promoting apoptosis in a cell and for reducing the severity of a pathology characterized by reduced levels of apoptosis. Methods for identifying agents that derepress an IAP-inhibited caspase further are provided.

The invention further provides a homogeneous radioassay method of identifying an agent that binds IAP. The method includes providing a scintillation bead that is linked to IAP or a fragment of IAP and a compound known to bind to IAP or a fragment of IAP. The known IAP binding compound is radiolabeled, for example with a tritium label. The scintiallation bead is then contacted with the radiolabeled IAP binding compound in the presence of a candidate compound. Binding of the known IAP binding compound is measured by scintillation counting by the scintillation proximity method. A decrease in scintillation counts in the presence of a candidate compound indicates that the candidate compound competes with the known IAP binding compound. Thus, a candidate compound that causes a decrease in scintillation counts in this assay is identified as an IAP binding compound. The binding constant of the candidate compound can be prepared by titrating the candidate compound against a known concentration of known IAP binding compound, for example.

The invention also provides another method of identifying an agent that binds IAP. The method is a non-homogeneous competition assay, which involves immobilizing the IAP or fragment of IAP on a support, such as a commercially available 96 well plate. The immobilized IAP or fragment of IAP is then contacted with a known compound that binds IAP. The known compound is labeled with a suitable label, such as a fluorescent label, a radiolabel, biotin, an ezyme, etc. The known compound and the IAP or fragment of IAP form a bound complex, which remains immobilized even upon washing. A signal can be obtained from the bound complex, which represents a negative control. The bound complex is contacted with a candidate agent. If the candidate agent competitively binds IAP or a fragment of IAP, it will displace the labeled known compound from the bound complex. After washing, it is a label signal is then determined for the complex. A decrease in the label signal from the negative control label signal indicates that the candidate compound competitively binds IAP or a fragment of IAP. Thus, a candidate compound that causes a decrease in label signal is identified as an IAP binding compound.

BRIEF DESCRIPTION OF THE DRAWINGS

FIG. 2 shows a table listing individual tetrapeptides of the TPI 1313 library and the ratio of $V_{max}$ for hydrolysis of Ac-DEVD-AFC in the presence and absence of each peptide species. The ratio=($V_{max}$ when peptide, caspase 3 and XIAP are present)/($V_{max}$ when caspase 3 and XIAP are present).

FIG. 8 shows structures of the defined functionalities in the mixtures found to be derepressors of an XIAP-inhibited caspase in the TPI759 N-benzyl-1,4,5-trisusbstituted-2,3-diketopiperazine positional scanning combinatorial library. The chemical name listed below each box is the reagent from which the R group was derived. Each functional group has the same stereochemistry as the reagent from which it was derived.

FIGS. 9A–9C show structures for individual compounds found to be derepressors of an XIAP-inhibited caspase in the TPI927 polyphenylurea library. The chemical name in each box is the reagent from which the R group was derived. Each functional group has the same stereochemistry as the reagent from which it was derived.

FIGS. 11A–11C show dose response of mixtures identified as derepressors of XIAP-inhibited caspase from the TPI 1239 library. Values shown are for the ratio of $V_{max}$ for hydrolysis of AC-DEVD-AFC in the presence and absence of each mixture. TPI 1239 mixtures were present at the doses listed at the top of each column.

FIG. 12 shows the structures of L-3-(2-thienyl)-alanyl-L-(2-naphthyl)-alanyl-L-p-chloro-phenylalanyl-L-(e-fluorenylmethyloxycarbonyl)-lysine (TPI792-33; Core peptide 16) and L-3-(2-thienyl)-alanyl, L-(2-naphthyl)-alanyl-D-(e-fluorenylmethyloxycarbonyl)-lysyl-L-(e-fluorenylmethyloxycarbonyl)-lysine (TPI792-35; Core peptide 17).

FIGS. 14A–14B show the generalized structures for phenyl urea compounds in the TPI 1396 library and diketopiperazine compounds in the TPI 1391 library (Panel A) and structures for compounds TPI 1391-28, TPI 1391-21, TPI 1396-34, TPI 1396-22, TPI 1396-11, TPI 1396-12 (Panel B).

FIGS. 20A–20B show structures for TPI792-3, TPI792-9, TPI792-15, TPI792-17, TPI792-19, TPI792-22, TPI792-27, TPI792-33 and TPI792-35.

FIG. 21A shows structures for TPI 1349-1 through TPI 1349-34 along with respective molecular weights, masses and lowest concentration of each agent having a ratio of 1.8 or higher in SMAC competition assays.

FIG. 22D shows a table indicating the activities of TPI 1396-11, -12, -22, -28, and -34 in the derepression assay using full length XIAP and the XIAP BIR2 domain.

FIG. 23A shows structures of TPI 1391-1 through TPI 1391-36 along with respective molecular weights, masses and lowest concentration of each agent having a ratio of 1.8 or higher in SMAC competition assays. FIG. 23D shows a table indicating the activities of TPI 1391-1, -4, -5, 7, -17, -21, -25, -28, -34 and -35 in the derepression assay using full length XIAP.

FIG. 24A shows structures of TPI 1400-1 through TPI 1400-58 along with respective molecular weights, masses and lowest concentration of each agent having a ratio of 1.8 or higher in SMAC competition assays. FIG. 24F shows a table indicating the activities of TPI 1400-6, -7, 13, -14, -33, -37, -43, -44 in the derepression assay using full length XIAP.

FIG. 25a and b show screening of small molecule poly-phenylurea compounds in a Caspase derepression assay to identify compounds that overcome XIAP-mediated repression of Caspase-3. FIG. 25a shows the results using aliquots from the poly-phenylurea library mixtures and FIG. 25b shows the results for 36 individual compounds based on deconvolution of the poly-phenylurea library.

FIG. 26a, b, c, and d show the results of a Caspase derepression assay using poly-phenylurea compounds with XIAP and Caspase-3 (a), XIAP and Caspase-9 (b), BIR-2 and Caspase-3 (c) and p35 and Caspase-3 (d).

FIG. 27a and b show cell death after incubation of Jurkat leukemia cells with various poly-phenylurea compounds (a) or TPI 1396-34 (b).

FIG. 28a shows the result of cell growth of sixty human tumor cell lines cultured with TPI 1396-34 or TPI 1396-28 compared to cells treated with solvent alone. Each line represents a tumor cell line.

FIG. 30a shows viability of DU145 prostate cancer cells cultured with Etoposide (VP16), Doxorubicin (DOX) or Paclitaxel (Tax) with or without TPI 1396-34.

FIG. 32a shows colony number of two prostate cancer cell lines, PC-3 and LNCaP, cultured with TPI 1396-34. Control compound is represented by the bars, showing only the 10 μM dose results.

FIG. 33a shows tumor volume of Balb/C nu–/nu– mice injected with PPC-1 prostate cancer cells treated with TPI 1396-22, TPI 1396-34 or solvent control.

FIG. 34 shows structures of agents TPI 1509-1 through TPI 1509-9 along with respective molecular weights, masses and lowest concentration of each agent having a ratio of 1.8.

FIGS. 35A and B show compound modifications of R groups based on TPI 1509-7 as an example of SAR studies for poly-phenylurea compounds.

FIG. 36A shows structures of TPI 1332-1 through TPI 1332-93 along with respective molecular weights. FIG. 36B shows structures of selected TPI 1332 compounds, including TPI 1332-4, TPI 1332-24, TPI 1332-41, TPI 1332-69, TPI 1332-76, and TPI 1332-77 along with respective molecular weights and the activity of the compounds in competing with XIAP BIR2 domain binding to the SMAC peptide.

FIG. 37 shows that none of TPI 1495-1, -2, -3, -4, -6, -7, -8 or -9 tetrapeptide series compete with XIAP binding to the SMAC peptide, while TPI 1495-5 does compete with XIAP binding to the SMAC peptide; also shown is that TPI 1495-2, -3, -4, -6, -7, and -8 are inactive in the derepression assay using full length XIAP, while TPI 1495-1, -5, and -9 are active in the derepression assay.

FIG. 39 shows that TPI 1396-34 enhances cytotoxicity of antigen-specific CTL. Tumor cells treated with specific antigen were incubated with antigen-specific T cells at an effector:target ratio of either 5 (FIG. 39B) or 10 (FIG. 39A). Percent cell lysis as a function of antigen concentration is shown.

FIG. 40A shows an immunoblot of tumor tissue from animals treated with control or TPI 1396-12, performed using antibodies specific for cleaved caspase-3 or actin. FIG. 40B shows immunohistochemistry of tumor tissues from animals treated with control or TPI 1396-12, performed using hematoxylin and eosin (nuclear stain) (A and B); caspase-3 antibodies and PCNA antibodies(C and D); caspase-6 antibodies (E and F) and DFF 40 antibodies (G and H).

FIG. 43 shows the activity of TPI 1453-1 (also referred to as TPI 792-33 or TPI 1408-3), TPI 1453-2, TPI 1453-3, TPI 1453-4,TPI 1453-5, TPI 1453-6 (also referred to as TPI 792-35), TPI 1453-7, TPI 1453-8, and TPI 1453-9, in the derepression assay using full length XIAP (XIAP-FL derepression data), as well as in the SMAC competition assay (Competitive binding assay).

FIG. 44 shows a table of biotinylated tetrapeptides of the TPI 1554 series, as well as the corresponding peptide number for the original tetrapeptides (Non-biotin Synthesis #) and molecular weights (MW).

FIG. 46B showing results using 0.5 μg/ml XIAP BIR2, and FIG. 46C showing results using 0.25 μg/ml XIAP BIR2.

FIG. 50 shows binding of labeled TPI 1540-14 (TPI 1576-37, peaks 1 and 2) to His-BIR1-2, His-Traf2 (negative protein control) and BIR1. Rhodamine labeled TPI 1540-14 (TPI 1576-37 pk1 or TPI 1576-37 pk2) were present at 2.5 μM in 50 mM Tris at pH 8.8/50 mM NaCl/1.25 mM DTT. His-BIR1-2 of XIAP, His-Traf2 and BIR1 of XIAP was present at 0, 0.14, 0.41, 1.23, 3.70, 11.11, 33.33 and 100 μM. Plates were incubated for 1 hour at room temperature and read in an LJL Analyst HT in fluorescence polarization mode with rhodamine filters (excitation 530 nm; emission 580 nm) and a rhodamine dichroic mirror at 565 nm. Data was fit in Prism™ by nonlinear regression for a sigmoidal dose-response curve with variable slope.

FIG. 52 shows binding of labeled TPI 1540 (TPI 1576-41, peaks 1 and 2) to His-BIR1-2, His-Traf2 (negative protein control) and BIR1. Rhodamine labeled TPI 1540-14 (TPI 1576-41 pk1 or TPI 1576-41 pk2) were present at 2.5 μM in 50 mM Tris at pH 8.8/50 mM NaCl/1.25 mM DTT. His-BIR1-2 of XIAP, His-Traf2 and Bir1 of XIAP was present at 0, 0.14, 0.41, 1.23, 3.70, 11.11, 33.33 and 100 μM. Plates were incubated for 1 hour at room temperature and read in an LJL Analyst HT in fluorescence polarization mode with rhodamine filters (excitation 530 nm; emission 580 nm) and a rhodamine dichroic mirror at 565 nm. Data was fit in Prism by nonlinear regression for a sigmoidal dose-response curve with variable slope.

DETAILED DESCRIPTION OF THE INVENTION

Figure 1:
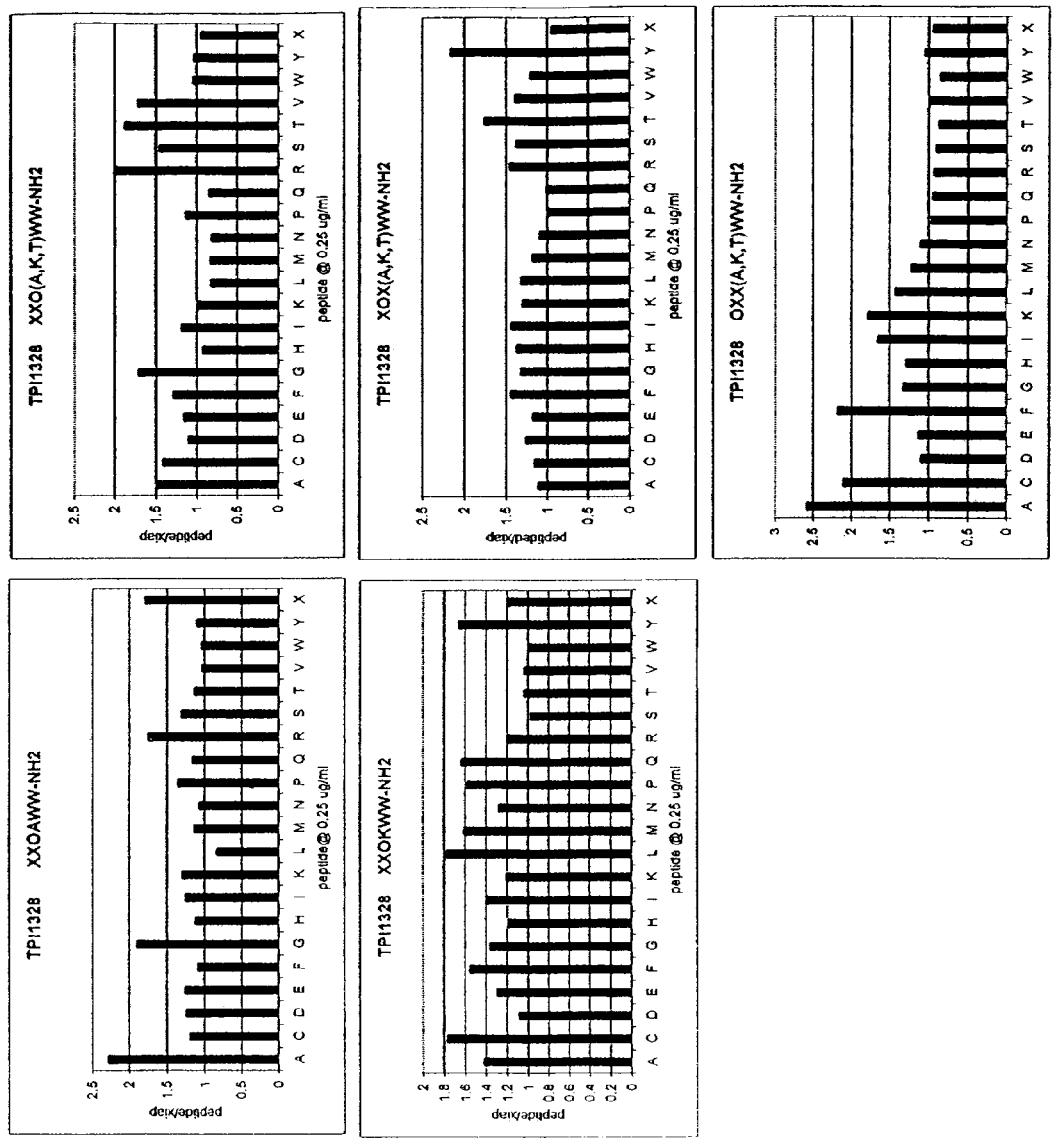
FIG. 1 shows a plot of values obtained for the ratio of $V_{max}$ (where $V_{max}$ is equal to RFU/min) for hydrolysis of Acetyl-DEVD-7-amino-4-trifluoromethyl-coumarin (Ac-DEVD-AFC) in the presence and absence of each species of the TPI 1328 library, composed of mixtures of hexapeptides.
Figure 3A:
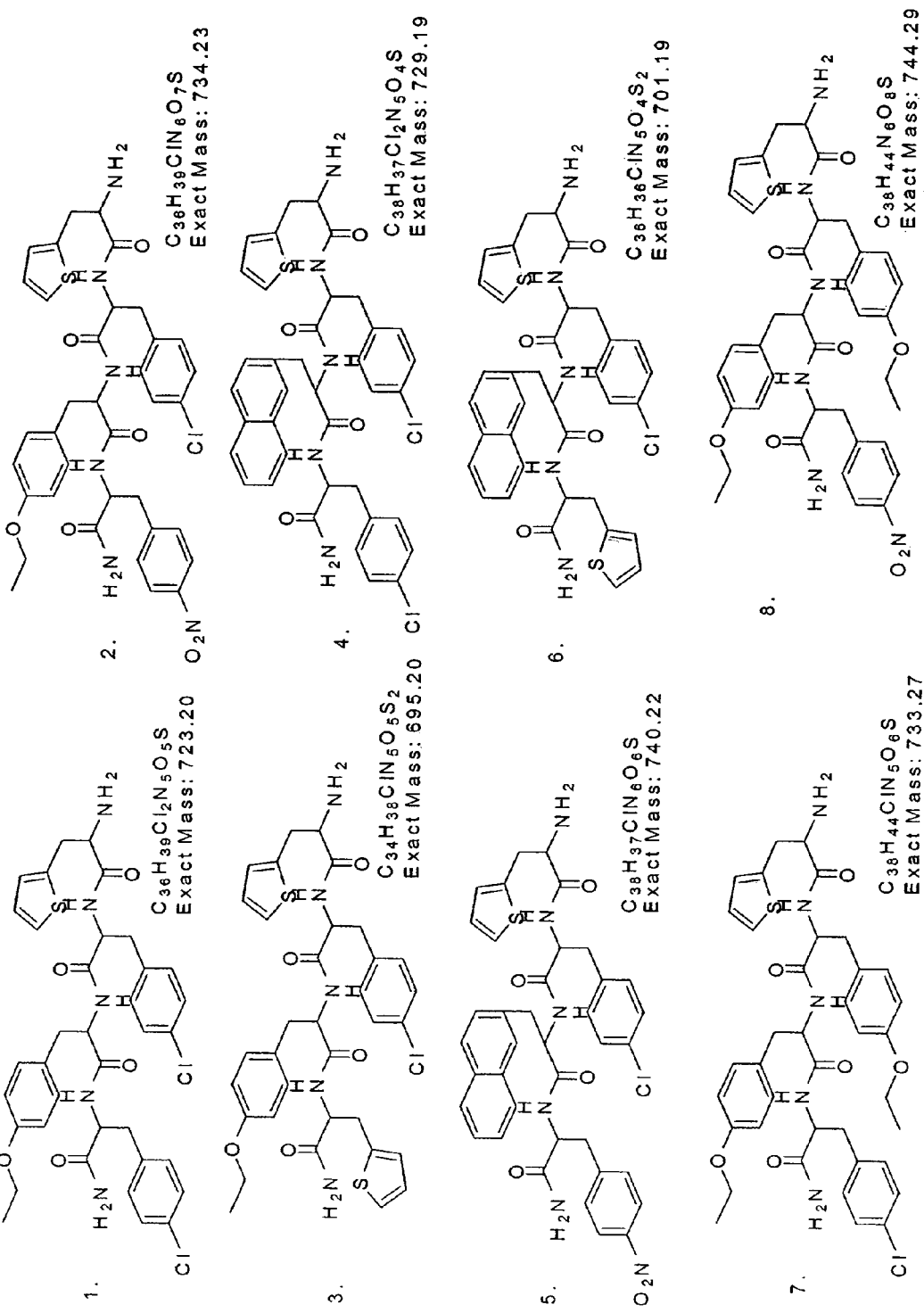
FIGS. 3A–3I show structures for the individual species of tetrapeptides in the TPI 1313 library.
Figure 3B:
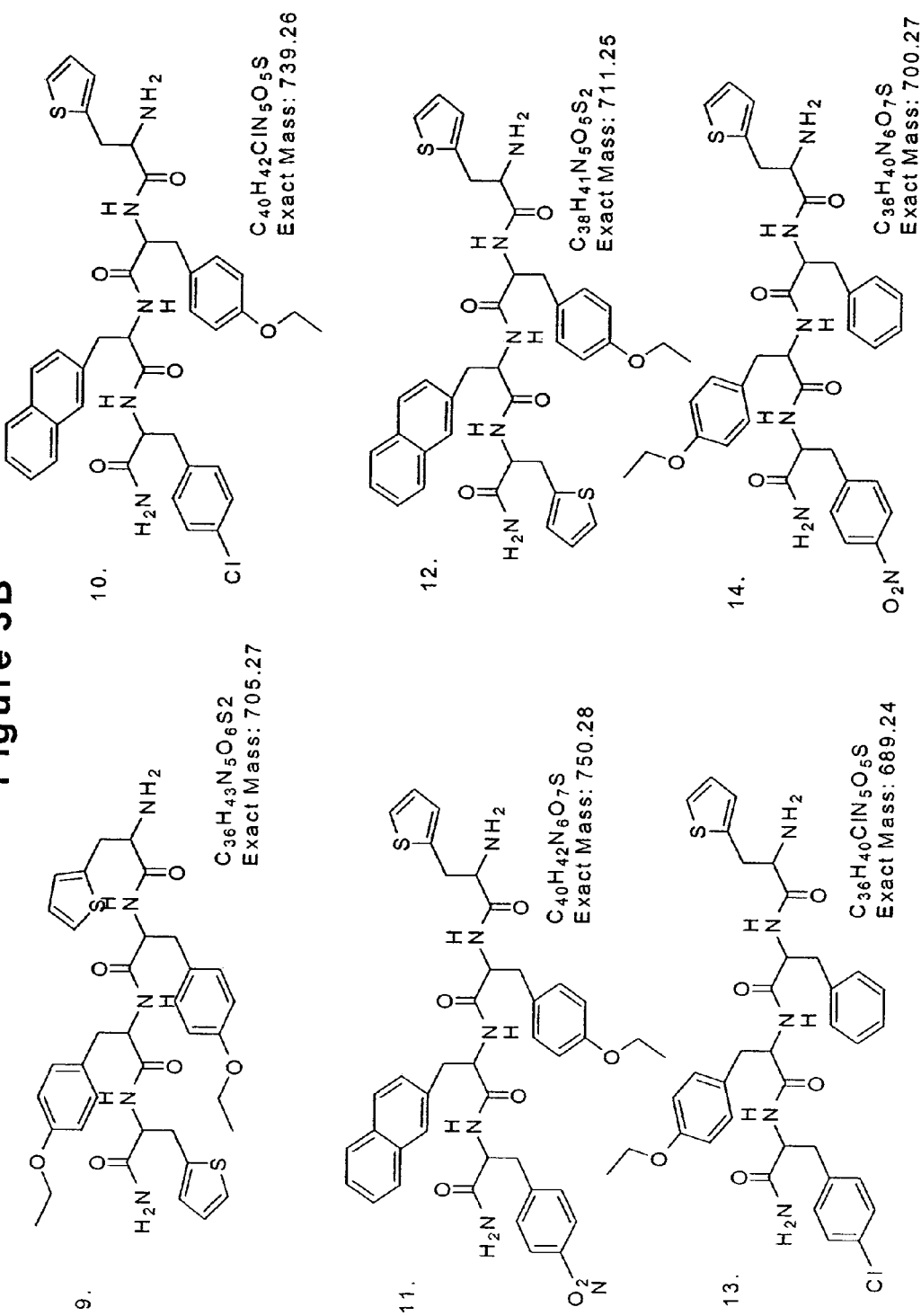
Figure 3C:
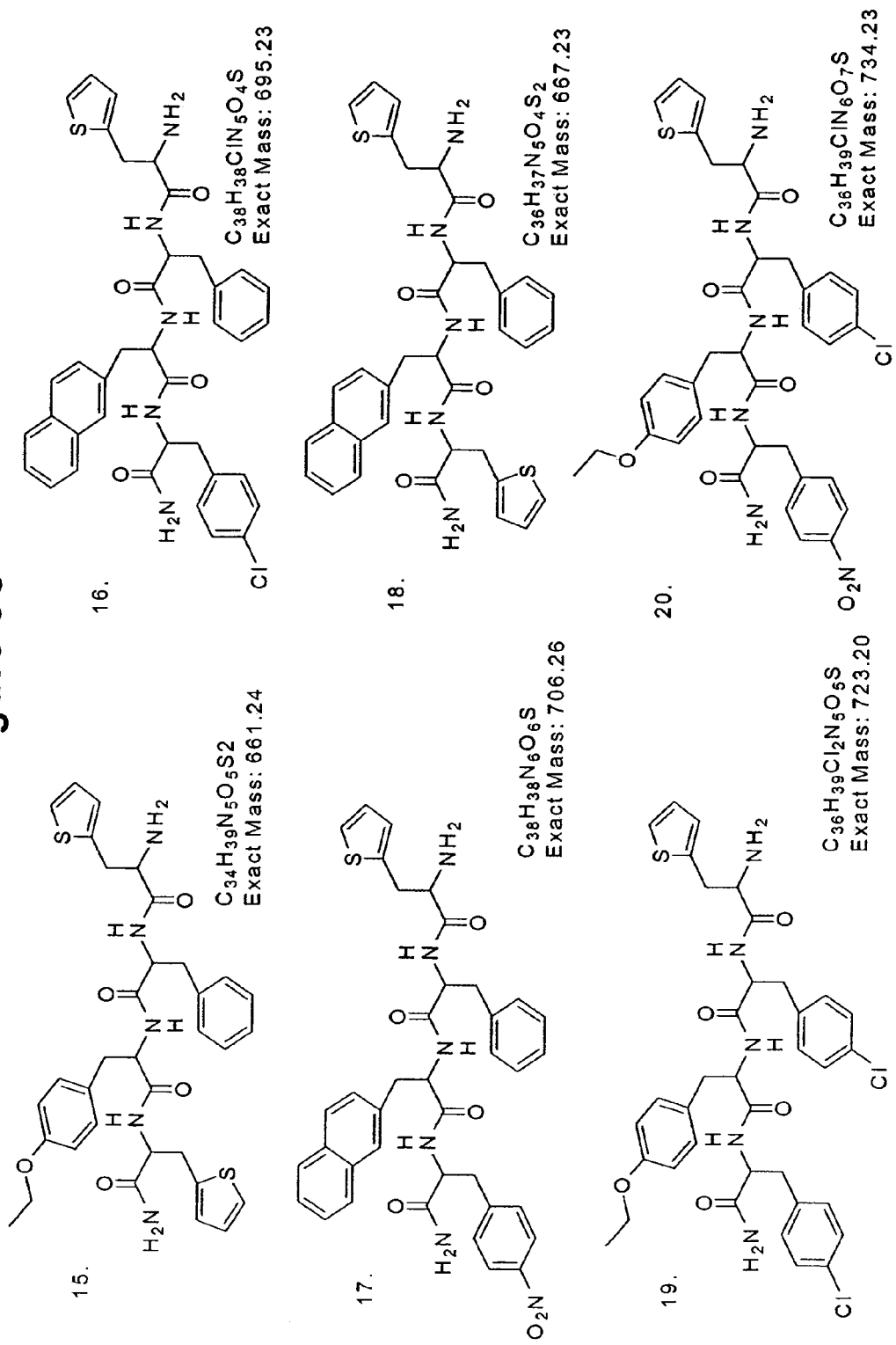
Figure 3D:
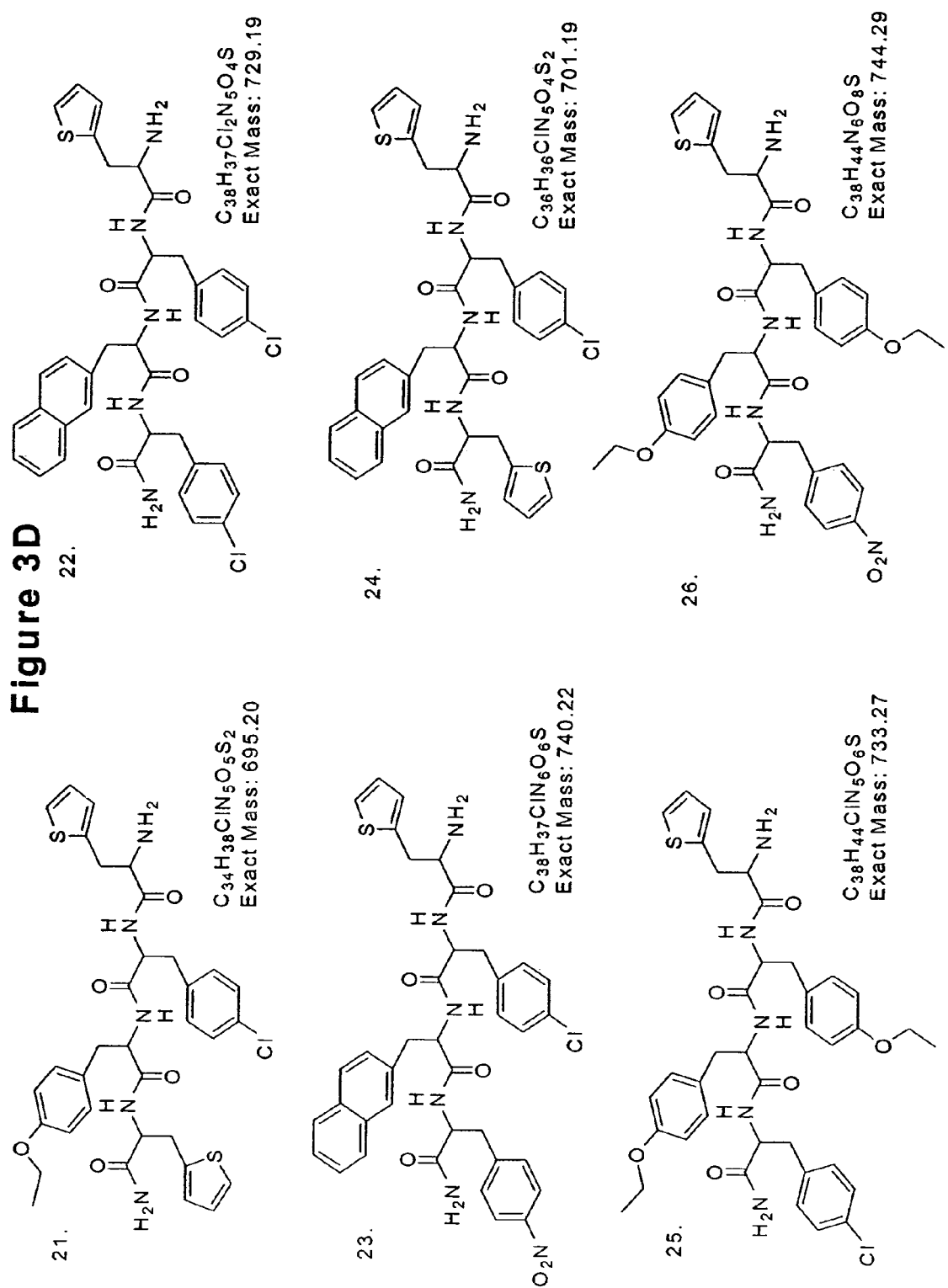
Figure 3E:
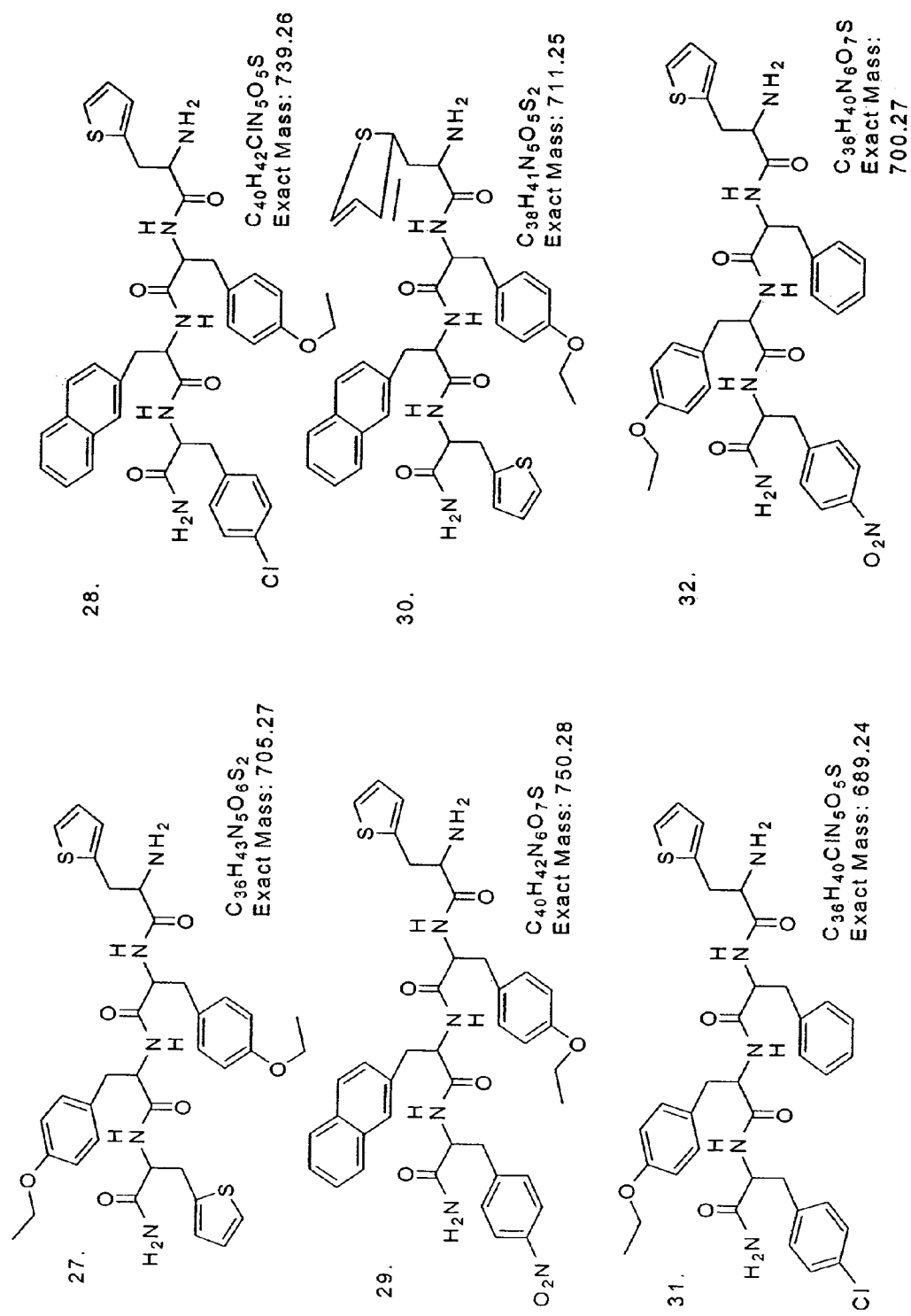
Figure 3F:
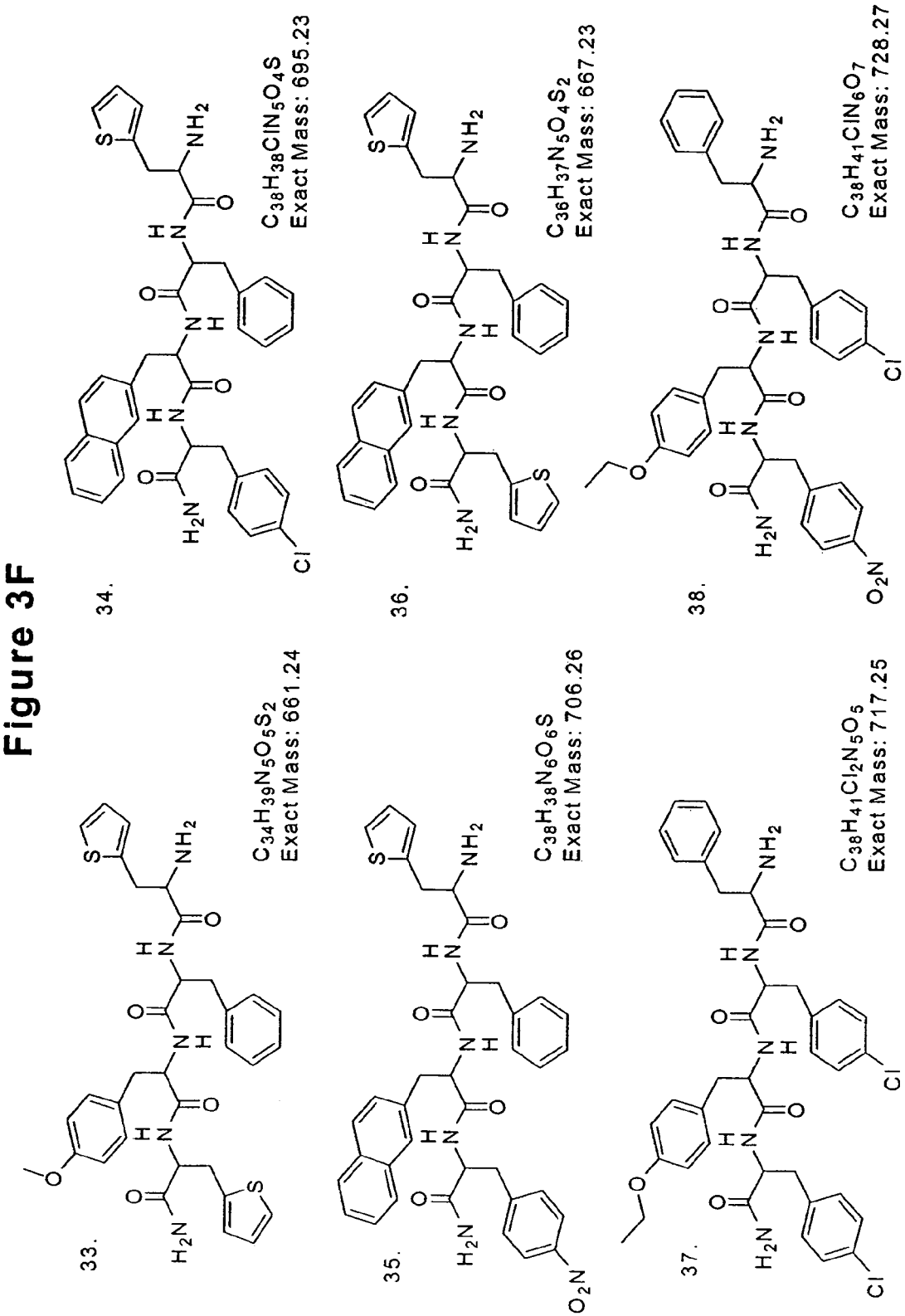
Figure 3G:
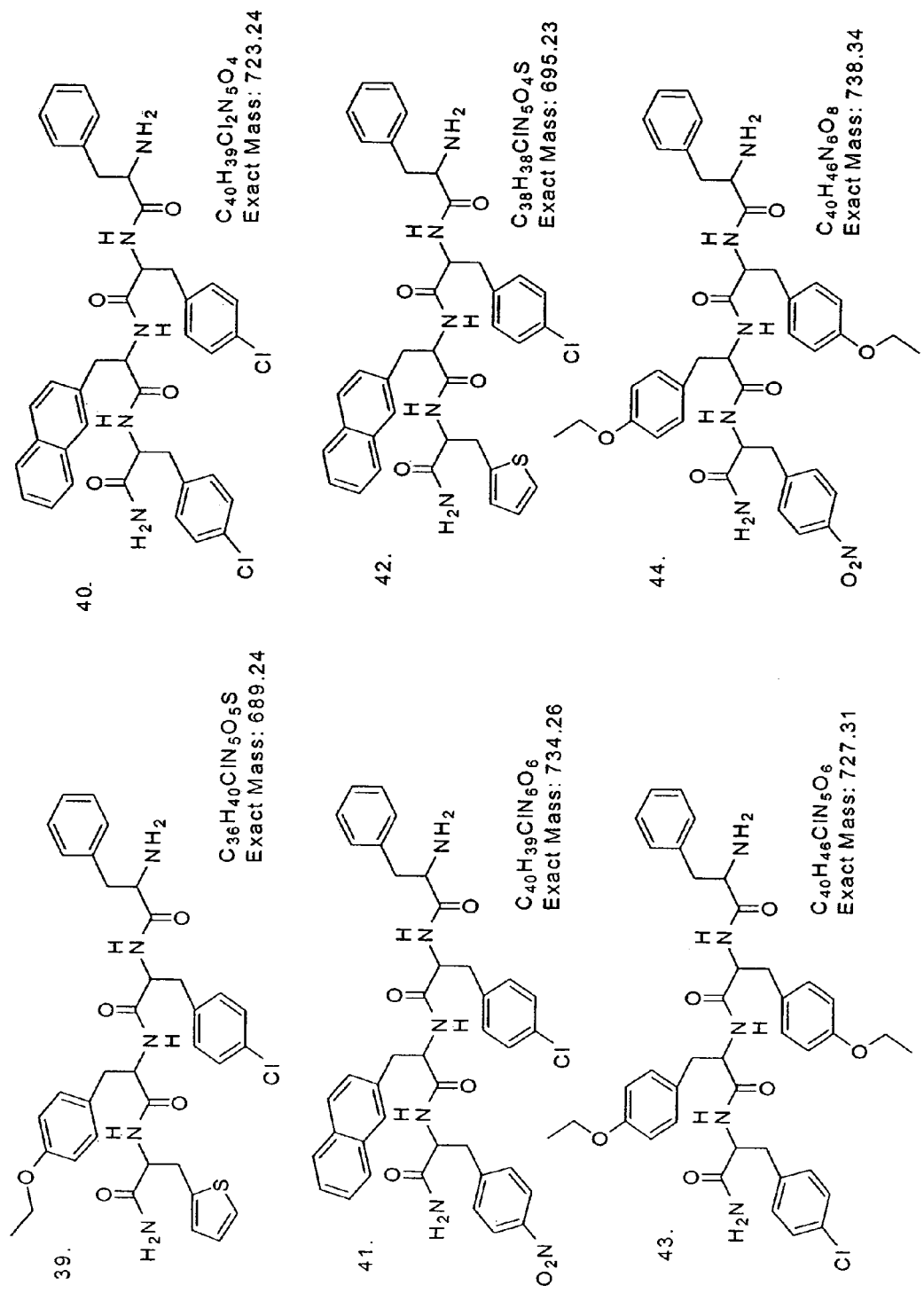
Figure 3H:
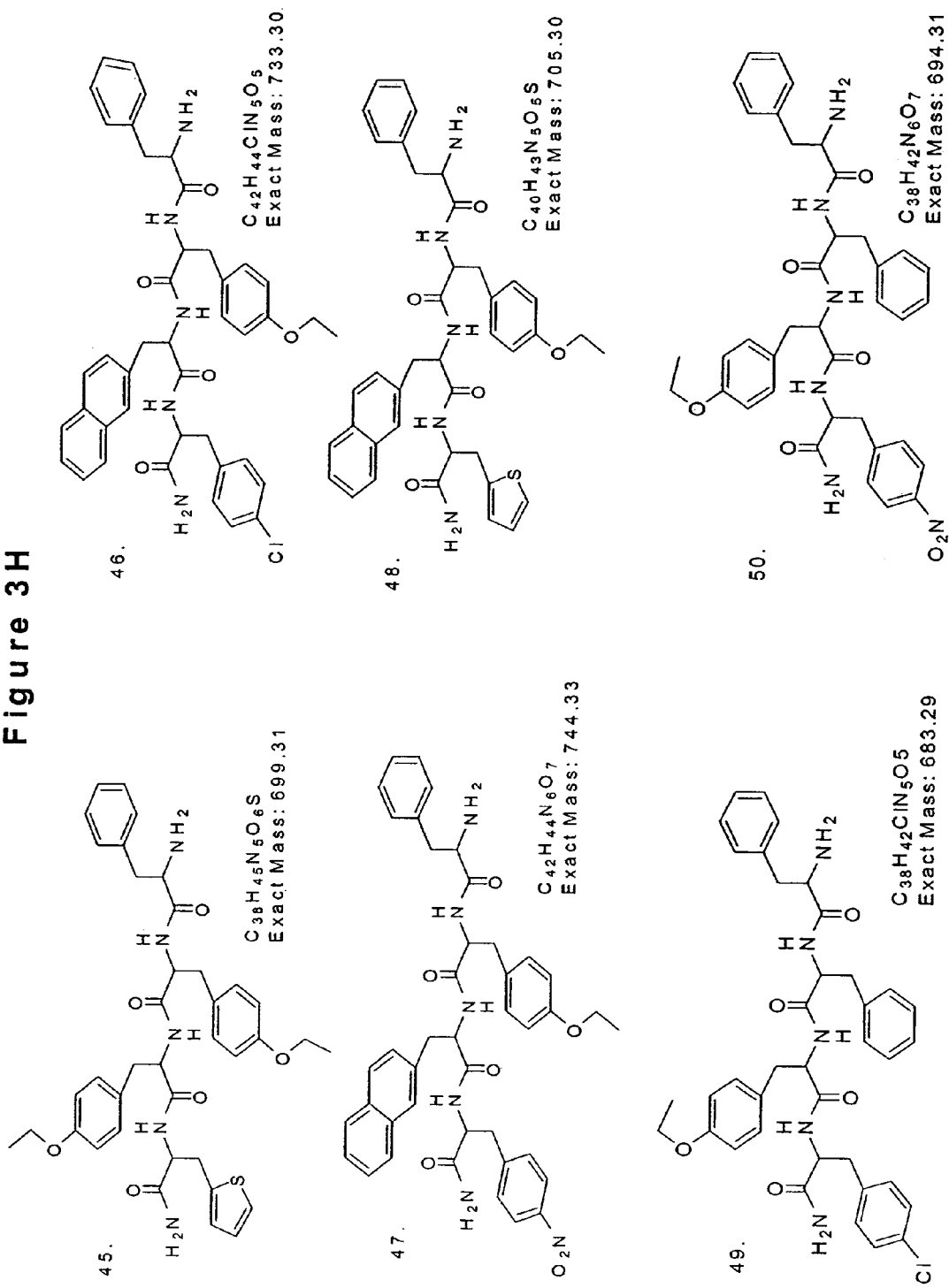
Figure 3I:
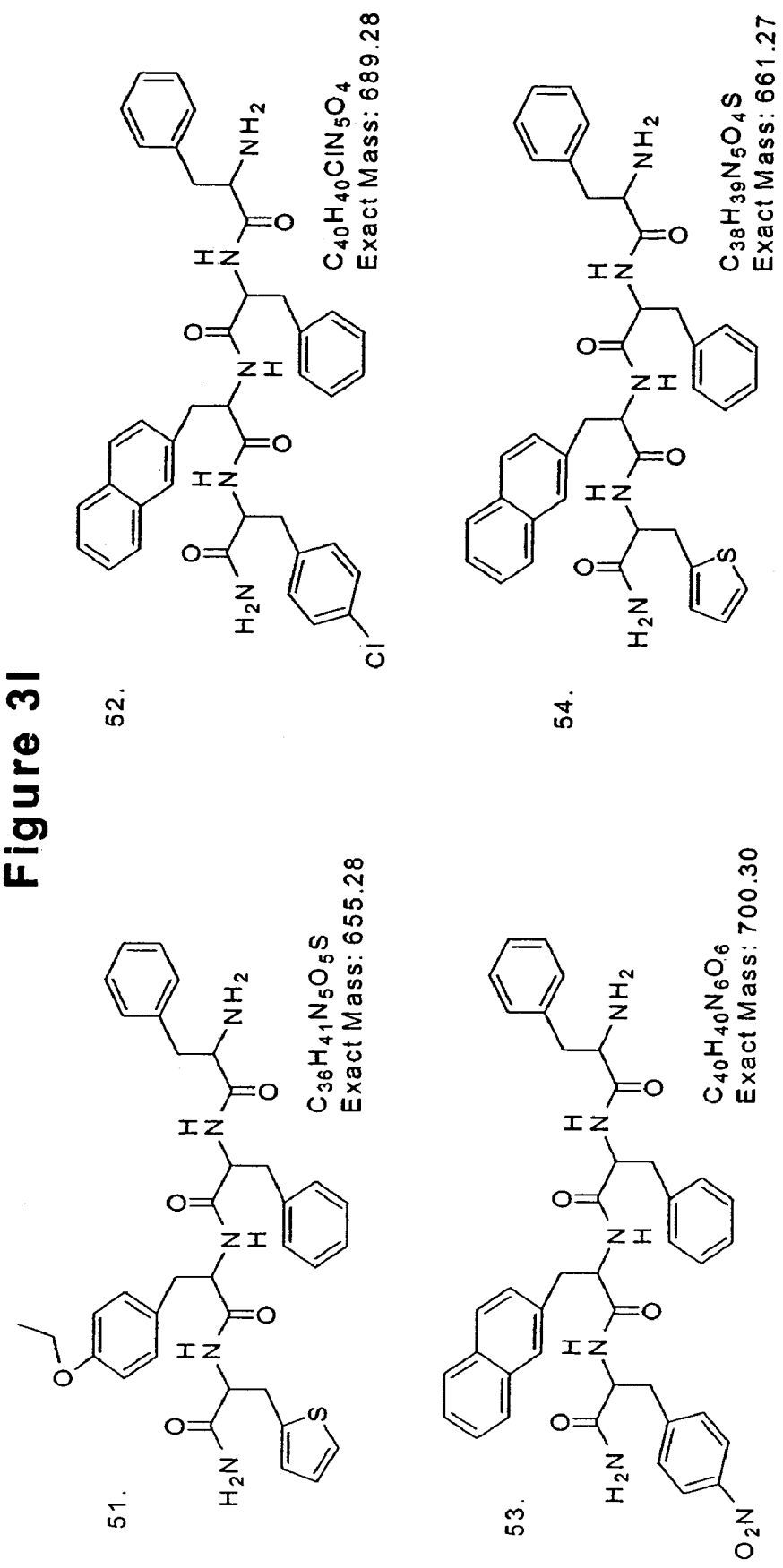

The present invention provides agents that suppress an inhibitor of apoptosis protein (IAP) from inhibiting the protease activity of a caspase or from binding to a caspase. An advantage of an agent of the invention is that it can be used to allow apoptosis to occur in a cell where apoptosis is being prevented by the regulatory activity of an IAP. Accordingly, the invention provides methods for reducing the ability of a population of cells to survive in vitro or ex vivo by administering to the cells an agent that derepresses an IAP-inhibited caspase. Use of an agent having specificity for a particular IAP-inhibited caspase in such a method can selectively target and kill a sub-population of cells in a larger mixed population. Also provided is a method of treating an individual having a condition characterized by a pathologically reduced level of apoptosis, such as cancer or hyperplasia, by administering to the individual an agent of the invention, wherein the agent derepresses an IAP inhibited caspase, thereby increasing the level of apoptosis.

The invention further provides methods for identifying agents that modulate inhibitors of apoptosis. Using the methods of the invention a candidate agent can be tested for the ability to suppress an inhibitor of apoptosis (IAP) protein from inhibiting a protease activity of a caspase or from binding to a caspase. A caspase when uninhibited mediates apoptosis. Thus, an agent determined by the methods to derepress an IAP-inhibited caspase is identified as an agent that allows apoptosis to occur in the presence of negative regulatory components. An advantage of the methods of the invention is that they can be performed in a high throughput format such that large libraries of candidate agents can be efficiently screened for identification of a variety of derepressors of an IAP-inhibited caspase.

As used herein the term "caspase" is intended to mean a member of the family of cysteine aspartyl-specific proteases that cleave C-terminal to an aspartic acid residue in a polypeptide and are involved in cell death pathways leading to apoptosis. The term is intended to be consistent with its use in the art as described, for example, in Martin and Green, *Cell* 82:349–352 (1995). The caspases previously were referred to as the "Ice" proteases, based on their homology to the first identified member of the family, the interleukin-1β (IL-1β) converting enzyme (Ice), which converts the inactive 33 kiloDalton (kDa) form of IL-1β to the active 17.5 kDa form. The Ice protease was found to be homologous to the *Caenorhabditis elegans* ced-3 gene, which is involved in apoptosis during *C. elegans* development, and transfection experiments showed that expression of Ice in fibroblasts induced apoptosis in the cells (see Martin and Green, supra, 1995). Therefore, the term includes Ice and ced-3.

Additional polypeptides sharing homology with Ice and ced-3 have been identified and are referred to as caspases, each caspase being distinguished by a number. For example, the originally identified Ice protease now is referred to as caspase-1, the protease referred to as caspase-3 previously was known variously as CPP32, YAMA and apopain, and the protease now designated caspase-9 previously was known as Mch6 or ICE-LAP6. The caspase family of proteases are characterized in that each is a cysteine protease that cleaves C-terminal to an aspartic acid residue and each has a conserved active site cysteine comprising generally the amino acid sequence QACXG (SEQ ID NO:1), where X can be any amino acid and often is arginine. The caspases are further subcategorized into those that have DEVD (SEQ ID NO:2) cleaving activity, including caspase-3 and caspase-7, and those that have YVAD (SEQ ID NO:3) cleaving activity, including caspase-1 (Martin and Green, supra, 1995).

As used herein the term "IAP" or "inhibitor of apoptosis protein" is intended to mean a protein that inhibits the proteolytic activity of a caspase. The term can include a protein that when bound to a caspase inhibits the proteolytic activity of the caspase. The term can also include a protein that inhibits the proteolytic activity of a downstream caspase by inhibiting the ability of an upstream caspase to process a precursor of the caspase to a mature form. Also included in the term is a protein that induces ubiquitination and degradation of a caspase.

Members of the Inhibitor of Apoptosis (IAP) protein family of antiapoptotic proteins are conserved across evolution with homologues found in both vertebrate and invertebrate animal species. The baculovirus IAPs, Cp-IAP and Op-IAP, were the first members of this family to be identified based on their ability to functionally complement defects in the cell death inhibitor p35, a baculovirus protein that binds to and inhibits caspase. Subsequently, at least seven additional human homologues have been identified and demonstrated to inhibit cell death including X chromosome linked IAP (XIAP, GenBank accession number U32974); cellular IAP proteins, c-IAP-1/HIAP-2/hMIHB and c-IAP-2/HIAP-1/hMIHC (Liston et al., *Nature* 379: 349–353 (1996); Rothe et al., *Cell* 83:1243–1252 (1995)); neuronal apoptosis inhibitory protein, NAIP (Roy et al., *Cell* 80:167–178 (1995)); ML-IAP also referred to as LIVIN (Vucic et al., *Cur. Biol.* 10:1359–1366 (2000) and Kasof et al., *J. Biol. Chem.* 276:3238–3246 (2001)); Apollon (Chen et al., *Biochem. Biophys. Res. Commun.* 264:847–854 (1999)); and survivin (Ambrosini et al., *Nature Med.* 3:917–921 (1997)). Two *Drosophila* homologues (DIAP1 and DIAP2) have also been identified and demonstrated to inhibit cell death (Deveraux et al., *Genes and Development* 13:239–252 (1999)). A central role for IAP-family proteins in programmed cell death regulation in *Drosophila* has been suggested by the finding that several apoptosis-inducing proteins in flies, including reaper, hid, and grim bind to IAPs as part of their cytotoxic mechanism. Other IAP proteins include viral IAPs such as CiIAP, PoIAP, CpIAP and ASFIAP (Deveraux et al., supra (1999)).

IAP proteins targeted by an agent of the invention include those that inhibit the activity of an effector caspase such as caspase-3 or caspase-7 and those that inhibit an initiator caspase such as caspase-9. The human IAPs (XIAP, cIAP1, and cIAP2) have been reported to bind and potently inhibit caspase-3 and -7, with $K_i$s in the range of 0.2–10 nM. These caspases operate in the distal portions of apoptotic protease cascades, functioning as effectors rather than initiators of apoptosis.

A common structural feature of all IAP family members is a ~70 amino acid motif termed baculoviral IAP repeat (BIR), which is present in one to three copies as described, for example, in Deveraux et al., *Genes and Development* 13:239–252 (1999). The conserved presence and spacing of cysteine and histidine residues observed within BIR domains indicates that the structure represents a zinc binding domain. BIR domains have been shown to exhibit distinct functions. For example, the second BIR domain of XIAP (BIR2) is a potent inhibitor for caspase-3, whereas the third BIR domain of XIAP (BIR3) targets caspase-9 (see Wu et al., *Nature* 408:1008–1012 (2000)). In addition to the BIR motif located at the N-terminal and central portions of IAP, a RING finger domain is located in the C-terminal portion of members of the IAP protein family (Birnbaum et al., *J. Virol.* 68:2521–2528 (1994)). A BIR domain corresponds to an amino acid sequence having the consensus sequence: Xaa1-Xaa1-Xaa1-Arg-Xaa3-Xaa1-Xaa4-Xaa5-Xaa1-Xaa1-Trp-Xaa6-Xaa1-Xaa1-Xaa2-Xaa1-Xaa3-Xaa1-Xaa1-Xaa1-Xaa1-Leu-Ala-Xaa1-Ala-Gly-Phe-Xaa3-Xaa3-Xaa1-Gly-Xaa1-Xaa1-Asp-Xaa1-Val-Xaa1-Cys-Phe-Xaa1-Cys-Xaa1-Xaa1-Xaa1-Xaa3-Xaa1-Xaa1-Trp-Xaa1-Xaa1-Xaa1-Xaa7-Xaa1-Xaa1-Xaa1-Xaa1-Xaa1-His-Xaa1-Xaa8-Xaa1-Xaa1-Pro-Xaa1-Cys-Xaa1-Xaa5-Xaa3 (SEQ ID NO: 16), wherein Xaa1 is any amino acid, Xaa2 is any amino acid or is absent, Xaa3 is a hydrophobic amino acid (for example, Ala, Cys, Ile, Leu, Met, Phe, Pro, Trp, Tyr, or Val), Xaa4 is serine or threonine, Xaa5 is phenylalanine or tyrosine, Xaa6 is proline or is absent, Xaa7 is aspartic or glutamic acid, and Xaa8 is a basic amino acid (for example, Arg, His, or Lys).

As used herein the term "IAP-inhibited caspase" is intended to mean a cysteine aspartyl-specific protease that is prevented or suppressed from proteolytic activity due to the presence of an inhibitor of apoptosis protein. The term can include a cysteine aspartyl-specific protease having reduced activity due to a bound inhibitor of apoptosis protein. The term can also include a cysteine aspartyl-specific protease that is prevented or suppressed from being processed to a mature form capable of proteolytic activity due to the presence of an inhibitor of apoptosis protein. An example of a non-processed cysteine aspartyl-specific protease that is useful in the invention is a pro-caspase having an attached pro-domain. Alternatively, the compositions and methods of the invention can be directed to an IAP-inhibited caspase that does not contain a prodomain or is not a procaspase.

As used herein the term "derepress," when used in reference to an IAP-inhibited caspase, is intended to mean reduction, inhibition or prevention of the ability of the IAP to inhibit the proteolytic activity of the caspase. Accordingly, a derepressor of a IAP-inhibited caspase is a molecule that inhibits or prevents the ability of the IAP to inhibit caspase proteolytic activity. The term can include inhibition or prevention of the ability of an IAP to induce ubiquitination and degradation of caspases.

As used herein, the term "agent" means a synthetic or isolated biological molecule such as a simple or complex organic molecule, a peptide, a peptidomimetic, a protein or an oligonucleotide that is capable of derepressing an IAP-inhibited caspase.

As used herein, the term "pharmaceutically acceptable carrier" is intended to mean a medium having sufficient purity and quality for use in humans. Such a medium can be a human pharmaceutical grade, sterile medium, such as water, sodium phosphate buffer, phosphate buffered saline, normal saline or Ringer's solution or other physiologically buffered saline, or other solvent or vehicle such as a glycol, glycerol, an oil such as olive oil or an injectable organic ester. Pharmaceutically acceptable media are substantially free from contaminating particles and organisms.

As used herein the term "inhibiting," when used in reference to a protein activity, is intended to mean a reduction in the activity by decreasing affinity of the protein for a substrate or decreasing the catalytic rate at which the protein converts a substrate to product. The term includes, for example, decreasing the affinity of an IAP for a caspase substrate, decreasing the affinity of a caspase for a polypeptide substrate, decreasing the rate at which a caspase cleaves a polypeptide C-terminal to an aspartic acid residue, or decreasing the rate at which a caspase is ubiquitinated or proteolytically degraded.

As used herein the term "isolated," when used in reference to an agent, means that the agent is separated from 1 or more reagent, precursor or other reaction product. Therefore, an isolated agent is an agent that is free from one or more compounds found in the synthetic reaction or reaction pathway that produces the agent. Also included in the term is an agent that is free from one or more compound that it is found with in nature. An isolated agent also includes a substantially pure agent. The term can include a molecule that has been produced by a combinatorial chemistry method and separated from precursors and other products by chemical purification or by binding to second molecule with sufficient stability to be co-purified with the second molecule. The term can include naturally occurring agents such as products of biosynthetic reactions or non-naturally occurring agents.

As used herein the term "peptide" refers to a molecule containing two or more amino acids linked by a covalent bond between the carboxyl of one amino acid and the amino group of another. Invention peptides can be included in larger molecules or agents, such as larger peptides, proteins, fragments of proteins, peptoids, peptidomimetics and the like. A peptide can be a non-naturally occurring molecule, which does not occur in nature, but is produced as a result of in vitro methods, or can be a naturally occurring molecule such as a protein or fragment thereof expressed from a cDNA library. Peptides can be either linear, cyclic or multivalent, and the like, which conformations can be achieved using methods well-known in the art. The term includes molecules having naturally occurring proteogenic amino acids as well as non-naturally occurring amino acids such as D-amino acids and amino acid analogs, any of which can be incorporated into a peptide using methods known in the art. In view of this definition, one skilled in the art would know that reference herein to an amino acid, unless specifically indicated otherwise, includes, for example, naturally occurring proteogenic L-amino acids, D-amino acids, chemically modified amino acids such as amino acid analogs, naturally occurring non-proteogenic amino acids such as norleucine, and chemically synthesized agents. Exemplary amino acids useful in the invention are described further below.

As used herein, the term "proteogenic," when used in reference to an amino acid, indicates that the amino acid can be incorporated into a protein in a cell through well known metabolic pathways. The amino acids are designated as D or L in reference to the configuration at the alpha carbon. Amino acids referred to herein without specific reference to configuration are understood to have the L configuration at the alpha carbon. Proteogenic amino acids are indicated herein using the single letter or three letter code and are intended to be consistent with the nomenclature used in the art as described for Example in Branden and Tooze *Introduction to Protein Structure*, Garland Publishing, New York, pp6–7 (1991). Other amino acids are indicated using nomenclature known in the art, wherein, for example, pClPhe refers to p-chloro-phenylalanine, ThiAla refers to 2-thienyl-alanine, Nal refers to 3-(2-napthyl)-alanine, 3I-Tyr refers to 3-iodo-Tyrosine, Cha refers to cyclohexylalanine, Lys-e-Fmoc refers to lysine(e-fluorenylmethloxycarbonyl) and OEt-Tyr refers to Tyrosine(O-ethyl).

As used herein the term "core" is intended to mean a chemical structure or motif of a molecule, or portion thereof. The chemical structure or motif can be, for example, an amino acid sequence of a peptide or peptide containing molecule, or a chemical formula representing the covalent attachment of atoms in a molecule. A chemical structure or motif included in the term can be further defined with respect to chirality. A core peptide or other chemical entity need not be located at the center of a molecule.

The present invention provides isolated agents that derepresses an IAP-inhibited caspase. An agent that derepresses an IAP-inhibited caspase can have a core peptide or amino acid sequence motif corresponding to:

(L-Ala)-$X_1$-(L-Trp)-$X_2$   (Core peptide 4)

where $X_1$ is L-Trp or D-Trp and $X_2$ is L-ThiAla or L-pClPhe. Exemplary core peptides included in Core peptide 4 include, for example:

(L-Ala)-(L-Trp)-(L-Trp)-(L-ThiAla)(Core peptide 5), (L-Ala)-(L-Trp)-(L-Trp)-(L-pClPhe)(Core peptide 6) and (L-Ala)-(D-Trp)-(L-Trp)-(L-ThiAla)(Core peptide 7).

An agent that derepresses an IAP-inhibited caspase can have a core peptide or amino acid sequence motif corresponding to:

$X_1$—$X_2$—$X_3$—$X_4$   (Core peptide 23)

where $X_1$ is L-Ala, L-Cha, L-Nal, D-Trp or D-Trp(CHO); $X_2$ is D-Nal, D-Trp, D-Trp(CHO), L-Trp, L-Trp(CHO), D-Cha or D-ThiAla; $X_3$ is L-Trp, L-Trp(CHO) or D-Phe; and $X_4$ is L-Nal, D-Nal, D-Trp, D-Trp(CHO), L-ThiAla, L-3I-Tyr or L-pClPhe. Exemplary core peptides included in Core peptide 23 include, for example:

(L-Ala)-(D-Nal)-(L-Trp)-(L-Nal)(Core peptide 24)

(D-Trp)-(D-Trp)-(L-Trp)-(D-Nal)(Core peptide 25)

(L-Cha)-(D-Nal)-(L-Trp)-(L-ThiAla)(Core peptide 26)

(L-Ala)-(L-Trp)-(L-Trp)-(L-3I-Tyr)(Core peptide 27)

(L-Ala)-(D-Trp)-(L-Trp)-(L-ThiAla)(Core peptide 28)

(L-Cha)-(L-Trp)-(L-Trp)-(L-pClPhe)(Core peptide 29)

(L-Ala)-(D-Trp)-(L-Trp)-(D-Trp)(Core peptide 30)

(L-Ala)-(D-Trp)-(D-Phe)-(D-Trp)(Core peptide 31)

(L-Nal)-(D-Trp)-(D-Phe)-(D-Trp)(Core peptide 32)

(L-Nal)-(D-Cha)-(L-Trp)-(D-Trp)(Core peptide 33)

(L-Nal)-(D-ThiAla)-(D-Phe)-(D-Trp)(Core peptide 34).

An agent that derepresses an IAP-inhibited caspase can have a core peptide or amino acid sequence motif corresponding to:

$X_1$—$X_2$—$X_3$—$X_4$   (Core peptide 8)

where $X_1$ is D-Nal or L-ThiAla; $X_2$ is Lys-εFmoc, D-pClPhe or L-Nal; $X_3$ is D-Nal, L-pClPhe or D-Lys(Fm); and $X_4$ is Lys-εFmoc or D-pFPhe. Exemplary core peptides included in Core peptide 8 include, for example:

(D-Nal)-(Lys-εFmoc)-(L-pClPhe)-(Lys-εFmoc)(Core peptide 9)

-continued (D-Nal)-(D-pClPhe)-(L-pClPhe)-(Lys-εFmoc)(Core peptide 10)

(D-Nal)-(L-Nal)-(L-pClPhe)-(Lys-εFmoc)(Core peptide 11)

(D-Nal)-(L-Nal)-(D-Lys-εFmoc)-(Lys-εFmoc)(Core peptide 12)

(L-ThiAla)-(Lys-εFmoc)-(D-Nal)-(Lys-εFmoc)(Core peptide 13)

(L-ThiAla)-(Lys-εFmoc)-(L-pClPhe)-(pF-D-F)(Core peptide 14)

(L-ThiAla)-(D-pClPhe)-(L-pClPhe)-(Lys-εFmoc)(Core peptide 15)

(L-ThiAla)-(L-Nal)-(L-pClPhe)-(Lys-εFmoc)(Core peptide 16)

(L-ThiAla)-(L-Nal)-(D-Lys-εFmoc)-(Lys-εFmoc)(Core peptide 17).

An agent that derepresses an IAP-inhibited caspase can have a core peptide or amino acid sequence motif corresponding to:

$X_1$—$X_2$—$X_3$—$X_4$ (Core peptide 35)

where $X_1$ is L-ThiAla or Phe; $X_2$ is D-pClPhe or D-OEt-Tyr; $X_3$ is D-Nal, or D-OEt-Tyr; and $X_4$ is D-pClPhe or D-pNO$_2$Phe. Exemplary core peptides included in Core peptide 35 include, for example:

(L-ThiAla)-(D-pClPhe)-(D-Nal)-(D-pClPhe)(Core peptide 36)

(L-ThiAla)-(D-pClPhe)-(D-Nal)-(D-pNO$_2$Phe)(Core peptide 37)

(L-ThiAla)-(D-OEt-Tyr)-(D-OEt-Tyr)-(D-pClPhe)(Core peptide 38)

(Phe)-(D-pClPhe)-(D-Nal)-(D-pClPhe)(Core peptide 39).

An agent that derepresses an IAP-inhibited caspase can have a core peptide or amino acid sequence motif corresponding to:

A-$X_1$—$X_2$—$X_3$ (Core peptide 18)

where $X_1$ is Met, Ser, Thr, Trp, or ThiAla and $X_2$ and $X_3$ are selected from Ala, Asp, Glu, Phe, Gly, His, Ile, Lys, Leu, Met, Asn, Pro, Gln, Arg, Ser, Thr, Val, Trp, Tyr, D-Ala, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, D-Tyr, L-Nle, D-Nle, L-Cha, D-Cha, L-PyrAla, D-PyrAla, L-ThiAla, D-ThiAla, L-Tic, D-Tic, L-pClPhe, D-pClPhe, L-pIPhe, D-pIPhe, L-pNO$_2$Phe, D-pNO$_2$Phe, L-Nal, D-Nal, beta-Ala, e-Aminocaproic acid, L-Met[O$_2$], L-dehydPro, or L-31-Tyr.

An agent that derepresses an IAP-inhibited caspase can have a core peptide or amino acid sequence motif corresponding to:

$X_1$—$X_2$-(L-Trp)-(D-Trp) (Core peptide 19)

where $X_1$ and $X_2$ are selected from Ala, Asp, Glu, Phe, Gly, His, Ile, Lys, Leu, Met, Asn, Pro, Gln, Arg, Ser, Thr, Val, Trp, Tyr, D-Ala, D-Asp, D-Glu, D-Phe, D-His, D-Ile, D-Lys, D-Leu, D-Met, D-Asn, D-Pro, D-Gln, D-Arg, D-Ser, D-Thr, D-Val, D-Trp, D-Tyr, L-Nle, D-Nle, L-Cha, D-Cha, L-PyrAla, D-PyrAla, L-ThiAla, D-ThiAla, L-Tic, D-Tic, L-pClPhe, D-pClPhe, L-pIPhe, D-pIPhe, L-pNO$_2$Phe, D-pNO$_2$Phe, L-Nal, D-Nal, beta-Ala, e-Aminocaproic acid, L-Met[O2], L-dehydPro, or L-31-Tyr.

An agent that derepresses an IAP-inhibited caspase can have a core peptide or amino acid sequence motif corresponding to:

$X_1$—$X_2$—$X_3$—$X_4$—W—W (Core peptide 55), where $X_1$, $X_2$ and $X_3$ are selected from Ala, Asp, Glu, Phe, Gly, His, Ile, Lys, Leu, Met, Asn, Pro, Gln, Arg, Ser, Thr, Val, Trp, Cys or Tyr and $X_4$ is selected from Ala, His, Lys, Asn, Gln, Arg, Ser, Thr or Val.

An agent that derepresses an IAP-inhibited caspase can have a core peptide or amino acid sequence motif corresponding to any of:

$X_1$-$X_2$-A-A-W-W(Core peptide 43), SEQ ID NO: 7

$X_1$-$X_2$-G-A-W-W(Core peptide 44), SEQ ID NO: 8

$X_1$-$X_2$-R-A-W-W(Core peptide 45), SEQ ID NO: 9

$X_1$-$X_2$-$X_4$-A-W-W(Core peptide 46), $X_1$-$X_2$-C-K-W-W(Core peptide 47), SEQ ID NO: 10

$X_1$-$X_2$-L-$X_3$-W-W(Core peptide 20), $X_1$-$X_2$-R-$X_3$-W-W(Core peptide 21), $X_1$-$X_2$-G-$X_3$-W-W(Core peptide 22), $X_1$-$X_2$-T-$X_3$-W-W(Core peptide 42), $X_1$-$X_2$-V-$X_3$-W-W(Core peptide 48), $X_1$-T-$X_2$-$X_3$-W-W(Core peptide 49), $X_1$-Y-$X_2$-$X_3$-W-W(Core peptide 50), A-$X_1$-$X_2$-$X_3$-W-W(Core peptide 51), C-$X_1$-$X_2$-$X_3$-W-W(Core peptide 52), F-$X_1$-$X_2$-$X_3$-W-W(Core peptide 53), or K-$X_1$-$X_2$-$X_3$-W-W(Core peptide 54), where $X_1$, $X_2$ and $X_4$ are selected from Ala, Asp, Glu, Phe, Gly, His, Ile, Lys, Leu, Met, Asn, Pro, Gln, Arg, Ser, Thr, Val, Trp, Cys or Tyr and $X_3$ is selected from Ala, Lys, Ser or Thr.

The core peptide sequences of the invention can be those of a molecule or a portion of a molecule. For example, the above-described sequences having four positions can be tetrapeptide molecules and the above-described sequences having four or six positions can be hexapeptide molecules. A core peptide of the invention can also be included in larger molecules including, for example, a molecule having at least 5 amino acids, at least 6 amino acids, at least 7 amino acids, at least 8 amino acids, at least 9 amino acids, at least 10 amino acids, at least 20 amino acids or at least 25 amino acids. In some embodiments, the amino acid lengths of molecules comprising invention peptides can be defined by a maximum length including, for example, no more than about 4, no more than about 5, no more than about 6, no more than about 7, no more than about 8, no more than about 9, no more than about 10, no more than about 20, no more than about 25, no more than about 50, no more than about 100, no more than about 150, or no more than about 200 or more amino acids in length so long as the peptide is capable of derepressing an IAP-inhibited caspase. A molecule having a core peptide of the invention can also be defined within a size range delimited by a combination of any of the above described minimum and maximum lengths.

The invention further provides agents that are effective derepressors of an IAP-inhibited caspase having non-peptide based core structures. Thus, the invention provides an agent that derepresses an IAP-inhibited caspase and having a core structure corresponding to an N-benzyl-1,4,5-trisubstituted-2,3-diketopiperazine such as TPI 759 shown in FIG. 8. An agent having the TPI 759 core structure can be substituted, for example, at position R1 derived from an amino acid side chain group of norleucine, NapAla, cyclohexylalanine, Lys, norvaleucine or valine; at R2 derived from an amino acid side chain group of Leu, NapAla, Phe, Ile or Val; and at R3 with the functional group derived from 4-isobutyl-alpha-methylphenylacetic acid, 3,5-bis(trifluoromethyl)-phenylacetic acid, heptanoic acid, (alpha-alpha-alpha-trifluoro-m-tolyl)acetic acid, 4-tert-butyl-cyclohexane carboxylic acid, m-tolylacetic acid, 3,4-dichlorophenylacetic acid, 3,3-diphenyl propionic acid, dicyclohexylacetic acid, cycloheptanecarboxylic acid, p-Tolylacetic acid or cyclohexanebutyric acid as shown in FIG. 8.

Figure 7:
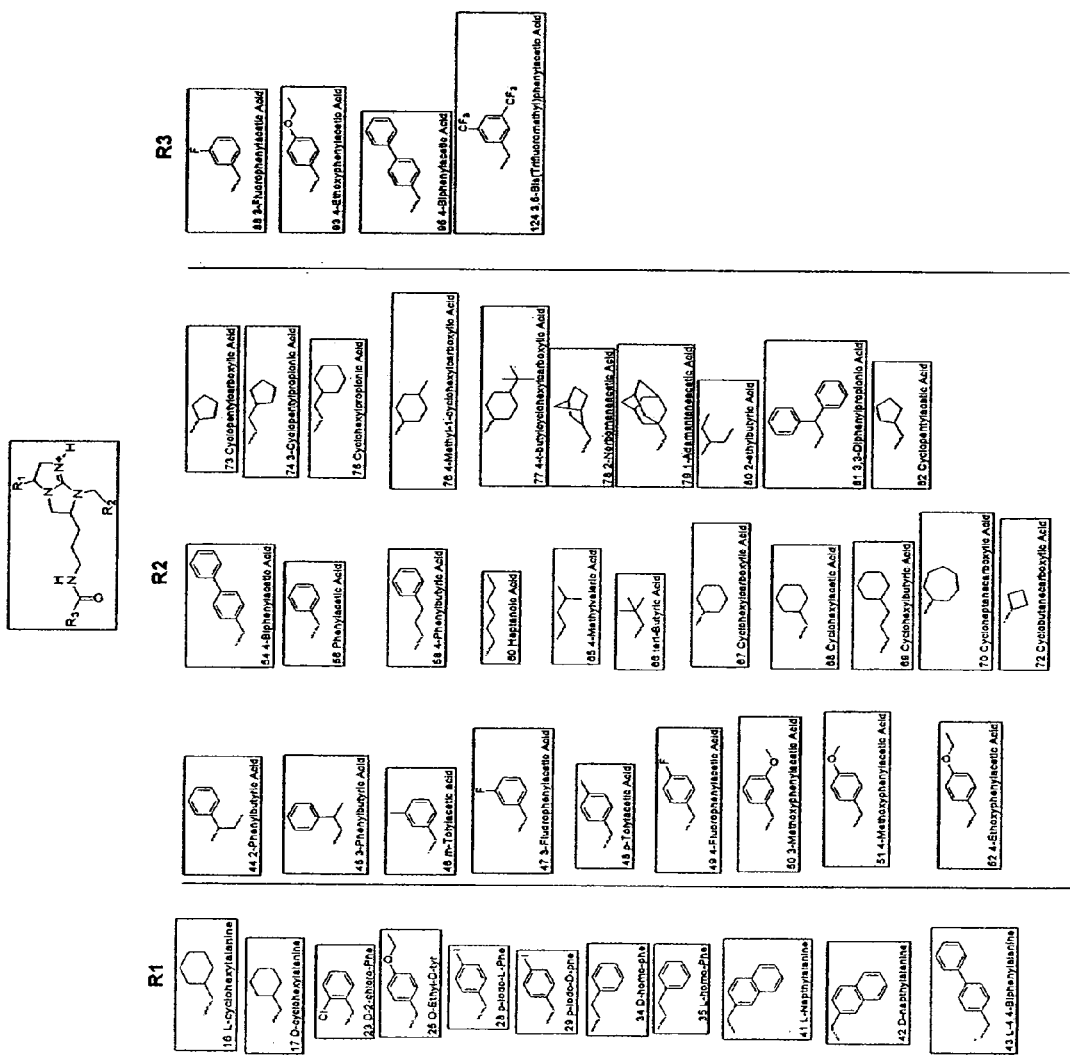
FIG. 7 shows structures of the defined functionalities in the mixtures found to be derepressors of an XIAP-inhibited caspase in the TPI882 C-6-acylamino bicyclic guanidine library. The chemical name in each box is the reagent from which the R group was derived. Each functional group has the same stereochemistry as the reagent from which it was derived.
Figure 10:
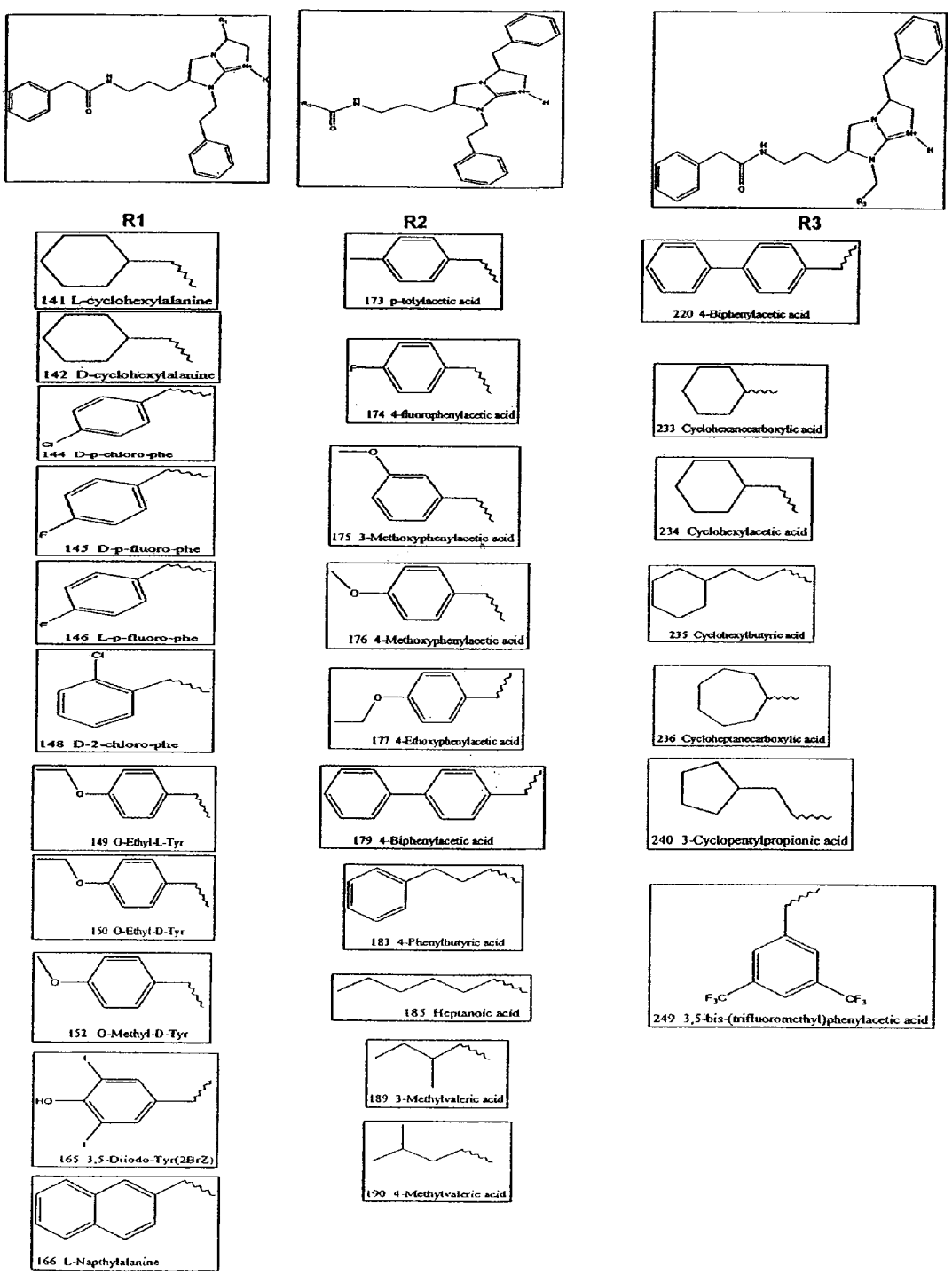
FIG. 10 shows structures for individual compounds found to be derepressors of an XIAP-inhibited caspase in the TPI882 C-6-acylamino bicyclic guanidine library. The chemical name in each box is the reagent from which the R group was derived. Each functional group has the same stereochemistry as the reagent from which it was derived.

An agent that derepresses an IAP-inhibited caspase can have a core structure corresponding to a C-6-acylamino bicyclic guanidine such as TPI 882 shown in FIG. 7. An agent having the TPI 882 core structure can be substituted, for example, at position R1 derived from an amino acid side chain group of L-cyclohexylalanine, D-cyclohexylalanine, D-2-chloroPhe, O-ethyl-D-Tyr, p-iodo-L-Phe, p-iodo-D-Phe, D-homo-Phe, L-homo-Phe, L-napthylAla, D-napthylAla or L-4,4-biphenylalanine; at position R2 with the functional group derived from 2-phenylbutyric acid, 3-phenylbutyric acid, m-tolylacetic acid, 3-fluorophenylacetic acid, p-tolylacetic acid, 4-fluorophenylacetic acid, 3-methoxyphenylacetic acid, 4-methoxyphenylacetic acid, 4-ethoxyphenylacetic acid, 4-biphenylacetic acid, phenylacetic acid, 4-phenylbutyric acid, heptanoic acid, 4-methylvaleric acid, tert-butyric acid, cyclohexylcarboxylic acid, cyclohexylacetic acid, cyclohexylbutyric acid, cycloheptanecarboxylic acid, cyclobutanecarboxylic acid, cyclopentylcarboxylic acid, 3-cyclopentylpropionic acid, cyclohexylpropionic acid, 4-methyl- 1-cyclohexylcarboxylic acid, 4-t-butylcyclohexylcarboxylic acid, 2-norbornaneacetic acid, 1-adamantane acetic acid, 2-ethylbutyric acid, 3,3-diphenylpropionic acid or cyclopentylacetic acid; and at position R3 with the functional group derived from 3-fluorophenylacetic acid, 4-ethoxyphenylacetic acid, 4-biphenylacetic acid or 3,5-bis(trifluoromethyl)phenylacetic acid as shown in FIG. 7. An agent having the TPI 882 core structure can be substituted at R2 and R3 with the functional group derived from phenylacetic acid and at R1 derived from an amino acid side chain group of L-cyclohexylalanine, D-cyclohexylalanine, D-p-chloro-Phe, D-p-fluoro-Phe, L-p-fluoro-Phe, D-2-chloro-Phe, O-ethyl-L-Tyr, O-ethyl-D-Tyr, O-methyl-D-Tyr, 3,5-diiodo-Tyr or L-napthylAla; at R1 with an amino acid side chain group of Phe; at R3 with the functional group derived from phenylacetic acid and at R2 with the functional group derived from p-tolylacetic acid, 4-fluorophenylacetic acid, 3-methoxyphenylacetic acid, 4-methoxyphenylacetic acid, 4-ethoxyphenylacetic acid, 4-biphenylacetic acid, phenylacetic acid, 4-phenylbutyric acid, heptanoic acid, 3-methylvaleric acid or 4-methylvaleric acid; or at R1 with an amino acid side chain group of Phe; at R2 with the functional group derived from phenylacetic acid; and at R3 with the functional group derived from 4-biphenylacetic acid, cyclohexanecarboxylic acid, cyclohexylacetic acid, cyclohexylbutyric acid, cycloheptanecarboxylic acid, 3-cyclopentylpropionic acid or 3,5-bis (trifluoromethyl)phenylacetic acid as shown in FIG. 10.

An agent that derepresses an IAP-inhibited caspase can have a core structure corresponding to a polyphenylurea such as TPI 927 shown in FIG. 6. An agent having the TPI 927 core structure can be substituted, for example, at position R1 derived from an amino acid side chain group of D-Lys(Me), L-3-(2Nap)Ala, D-Chala, L-Phe, Pro, Leu or Ser; at position R2 derived from an amino acid side chain group of ε-Lys, L-Nle, D-Phe, Pro, D-Orn(Me), Gln, L-3-(2-Nap)Ala or D-Thr; and at position R3 with the functional group derived from 4-methoxyphenylacetic acid, 1-adamantaneacetic acid, cyclohexanebutyric acid, 4-tert-butylcyclohexanecarboxylic acid, cycloheptanecarboxylic acid, 3-fluorophenylacetic acid, 3,3-diphenylpropionic acid, 4-ethoxyphenylacetic acid, 1-phenyl-1-cyclopropanecarboxylic acid, 1-napthylacetic acid, or cyclobutane carboxylic acid as shown in FIG. 6. An agent having the TPI 927 core structure can be substituted at R1 and R2 with an amino acid side chain group of Phe and at R3 with the functional group derived from trimethylacetic acid, hydrocinnamic acid, 4-tert-butylcyclohexane carboxylic acid, 4-methyl-1-cyclohexanecarboxylic acid, cyclopentylacetic acid, 1-phenyl-1-cyclopropanecarboxylic acid, cyclohexanecarboxylic acid, phenylacetic acid, cycloheptanecarboxylic acid, cyclobutane carboxylic acid, cyclohexanebutyric acid, 1-adamantaneacetic acid, cyclopentanecarboxylic acid, isobutyric acid, cyclohexylacetic acid; 3-methoxyphenylacetic acid, butyric acid, 3-(3,4,5)-trimethoxyphenylpropionic acid; heptanoic acid;. 2-norbornaneacetic acid, cyclohexanepropionic acid, tert-butyric acid, 4-ethoxyphenylacetic acid, 3,3-diphenylpropionic acid, 4-methoxyphenylacetic acid, acetic acid, methylvaleric acid p-tolylacetic acid or 4-isobutyl-alpha-methylphenylacetic acid as shown in FIG. 9.

Figure 4:
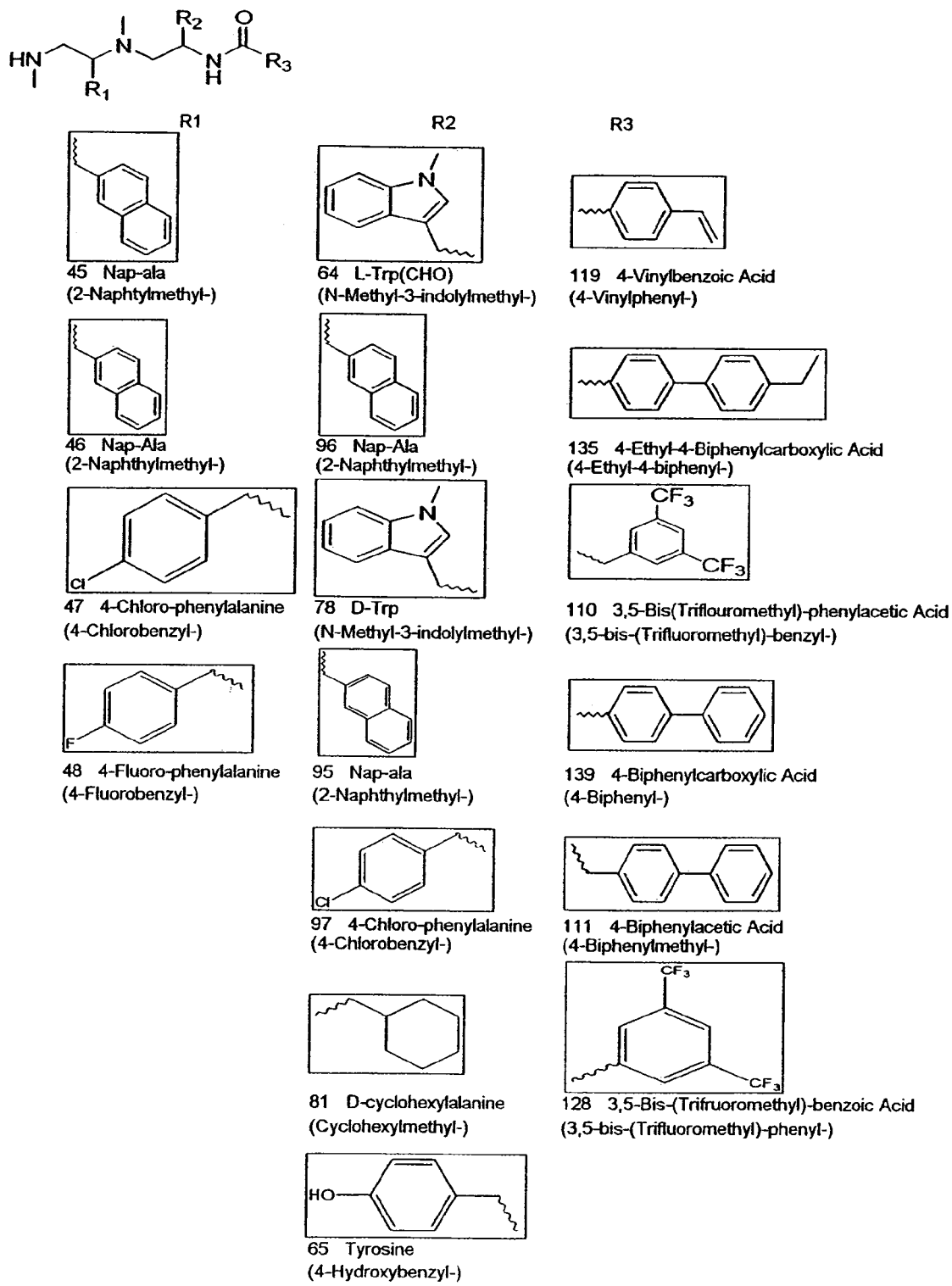
FIG. 4 shows structures of the defined functionalities in the mixtures found to be derepressors of an XIAP-inhibited caspase in the TPI914 N-acyltriamine positional scanning combinatorial library. The chemical name listed below each box is the reagent from which the R group was derived. Each functional group has the same stereochemistry as the reagent from which it was derived.
Figure 5:
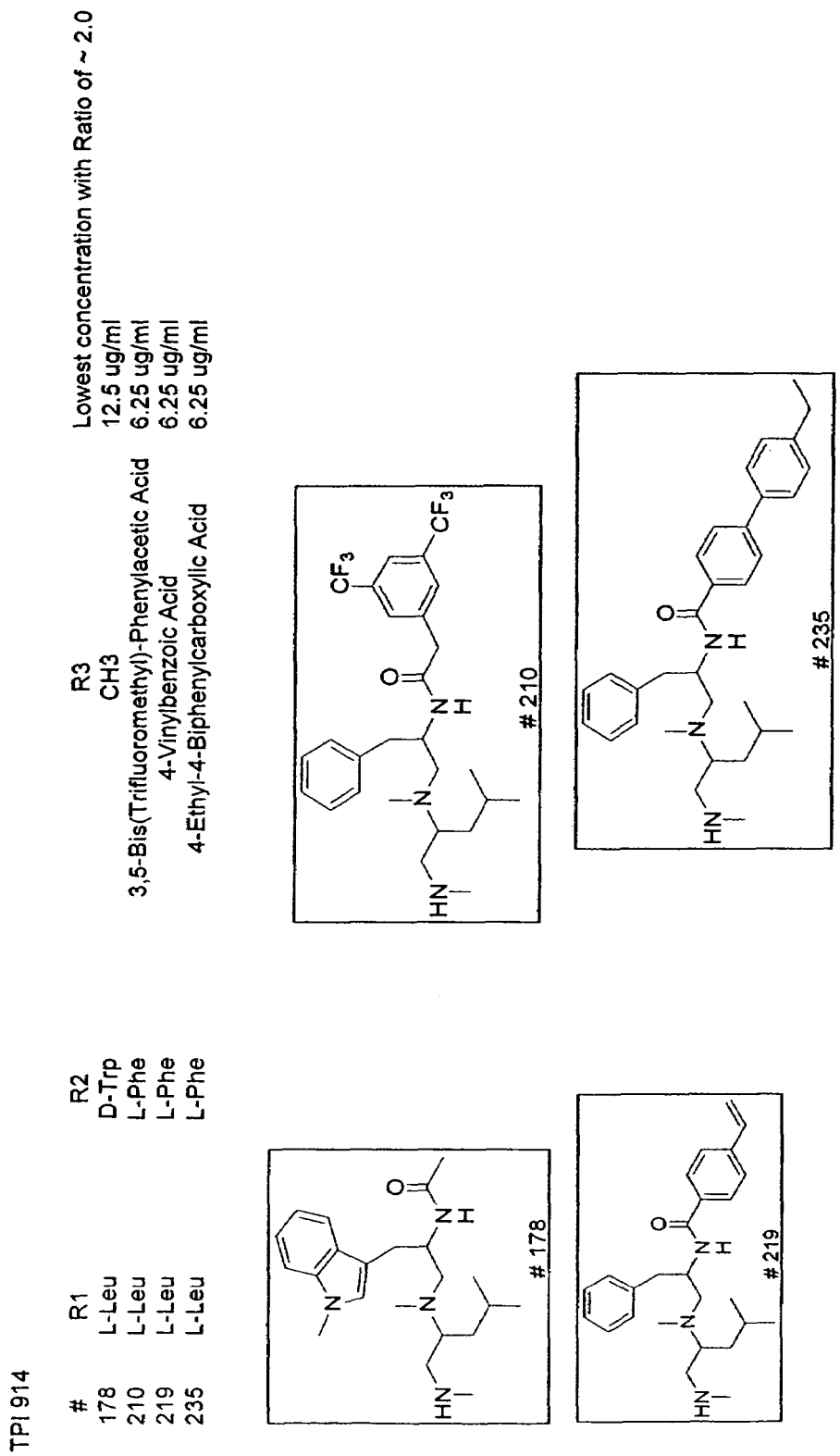
FIG. 5 shows structures for the individual compounds found to be derepressors of an XIAP-inhibited caspase in the TPI914 N-acyltriamine library. The chemical name listed at each table entry is the reagent from which the R group was derived. Each functional group has the same stereochemistry as the reagent from which it was derived.
Figure 6A:
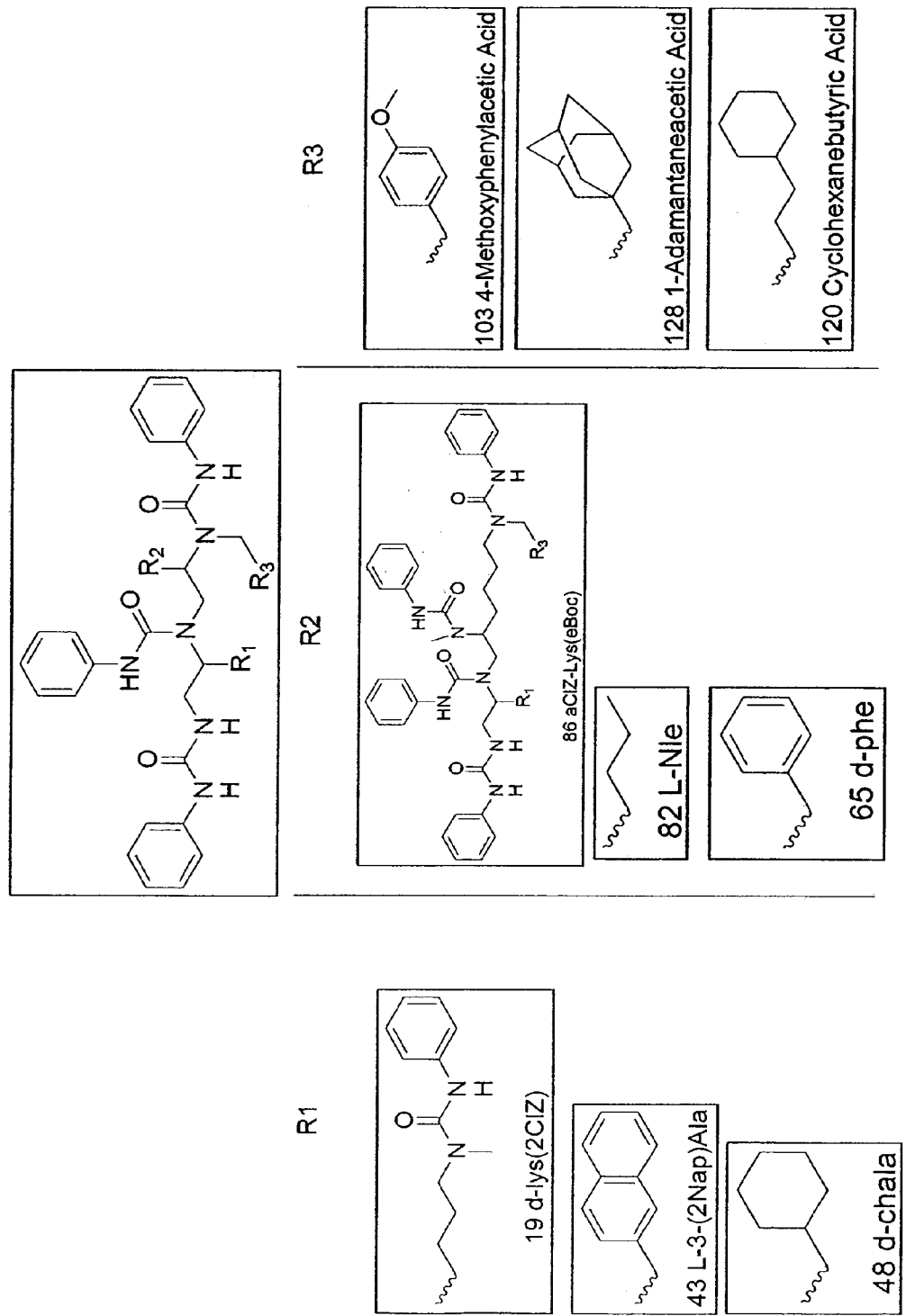
FIGS. 6A–6D show structures of the defined functionalities in the mixtures found to be derepressors of an XIAP-inhibited caspase in the TPI927 polyphenylurea positional scanning combinatorial library. The chemical name in each box is the reagent from which the R group was derived. Each functional group has the same stereochemistry as the reagent from which it was derived. For structures 25, 73, 86 and 88, where the core structure of the molecule is modified, the resulting modified core structure and R group is shown.
Figure 6B:
Figure 6C:
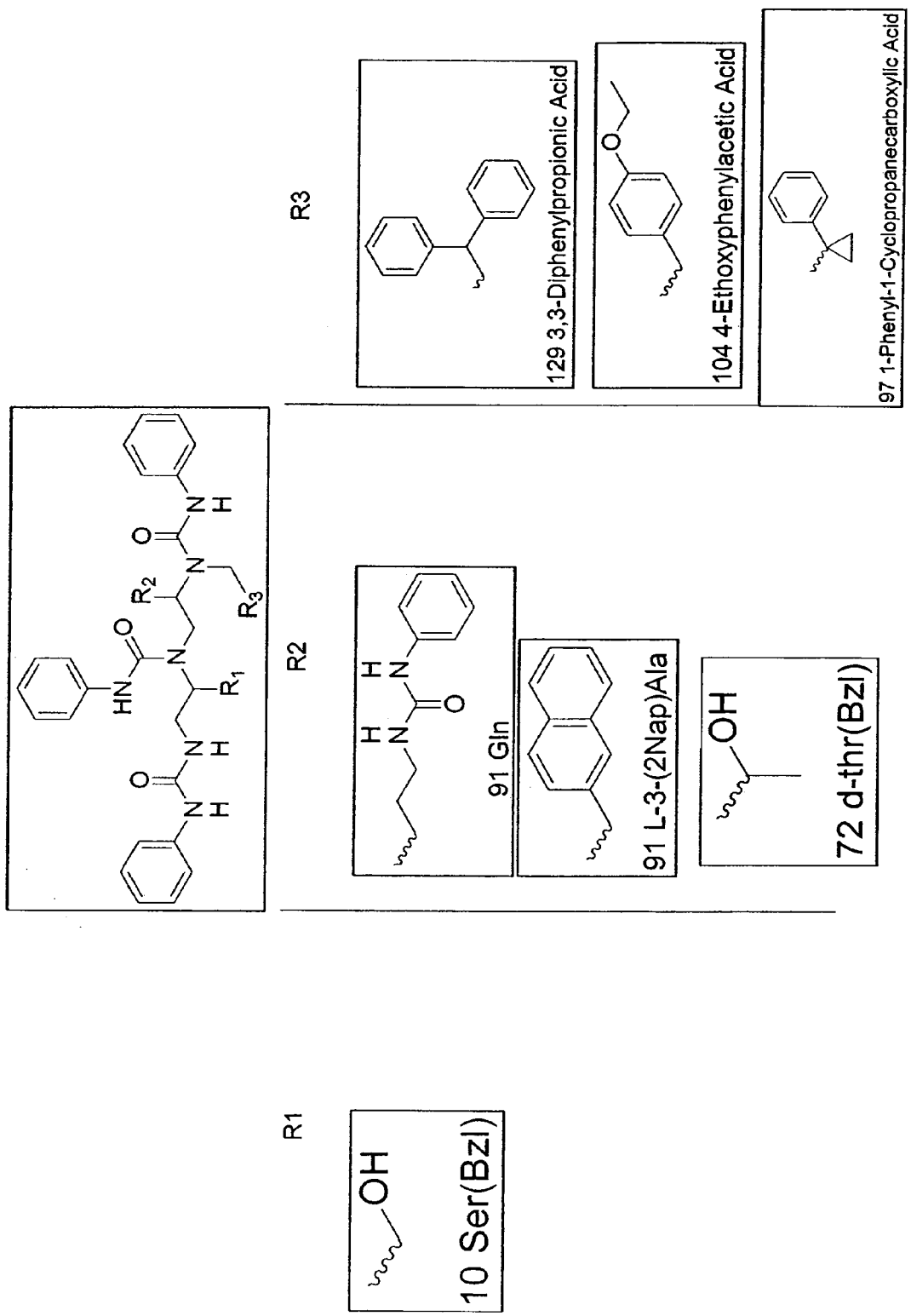
Figure 6D:
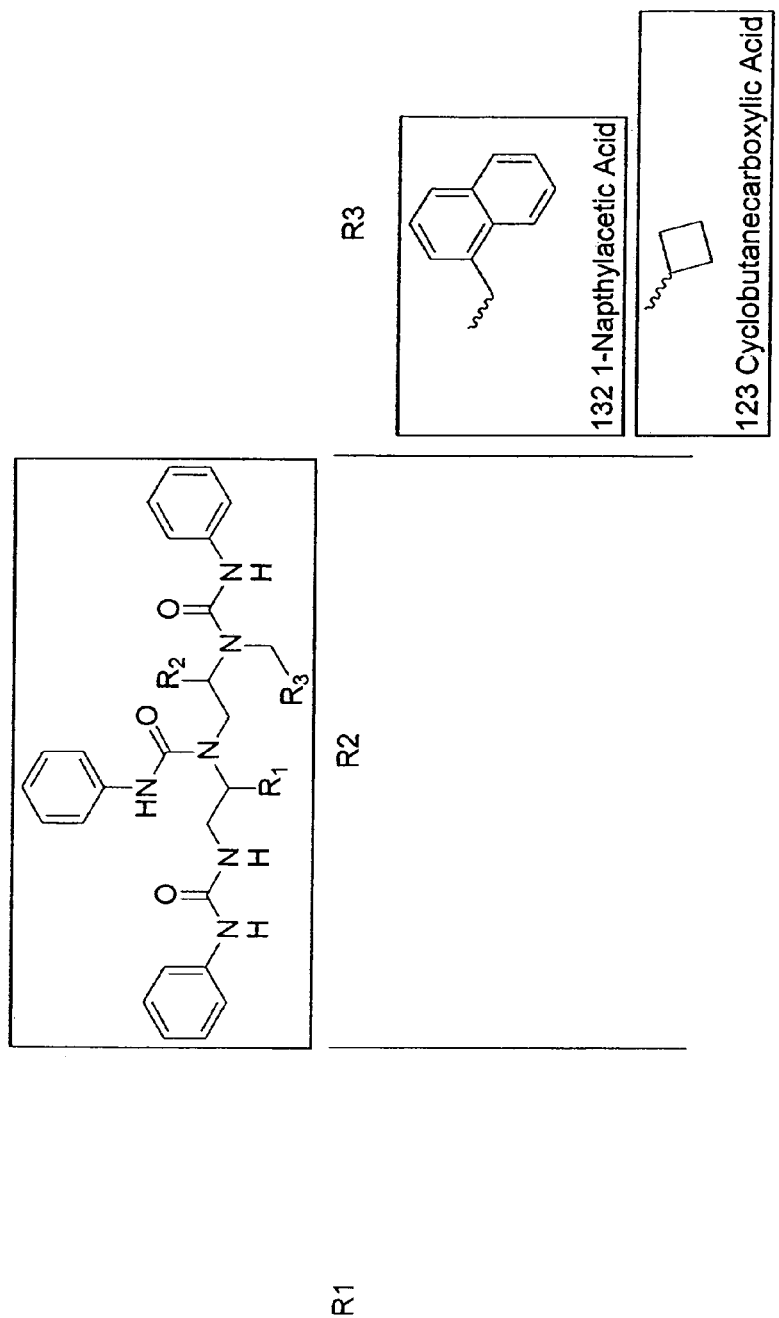

An agent that derepresses an IAP-inhibited caspase can have a core structure corresponding to an N-acyltriamine such as TPI 914 shown in FIG. 4. An agent having the TPI 914 core structure can be substituted, for example, at position R1 derived from an amino acid side chain group of Nap-Ala or 4-Fluoro-phenylalanine; at position R2 derived from an amino acid side chain group of L-Trp, Nap-Ala, D-Trp, 4-chlorophenylalanine, D-cyclohexylalanine or Tyr; and at R3 with the functional group derived from 4-vinylbenzoic acid, 4-ethyl-4-biphenylcarboxylic acid, 3,5-Bis(trifluoromethyl)-phenylacetic acid, 4-biphenylcarboxylic acid, 4-biphenylacetic acid or 3,5-bis-(trifluoromethyl)-benzoic acid as shown in FIG. 4. An agent having the TPI 914 core structure can be substituted at R1 with a functional group derived from an amino acid side chain group of Leu, at R2 with a functional group derived from an amino acid side chain group of D-Trp and at R3 with methyl; at R1 with a functional group derived from an amino acid side chain group of Leu, at R2 with a functional group derived from an amino acid side chain group of Phe and at R3 with the functional group derived from 3,5-Bis(trifluoromethyl)-phenylacetic acid; at R1 with a functional group derived from an amino acid side chain group of Leu, at R2 with a functional group derived from an amino acid side chain group of Phe and at R3 with the functional group derived from 4-vinylbenzoic acid; or at R1 with a functional group derived from an amino acid side chain group of Leu, at R2 with a functional group derived from an amino acid side chain group of Phe and at R3 with the functional group derived from 4-ethyl-4-biphenylcarboxylic acid each as shown in FIG. 5.

Those skilled in the art will recognize that libraries having the core structure of TPI 914, TPI 927, TPI 759, TPI 882, can be combinatorialized at one or more position. A combinatorialized position refers to a position which is variously substituted with different moieties such that a library of molecules combinatorialized at the position is a mixture of molecules that differ in chemical structure at that position. Such libraries can be used to identify agents that derepress an IAP-inhibited caspase, for example, in a screen utilizing positional scanning as described in Example VI. Thus, any one of positions R1, R2 or R3 can be held fixed to a discrete moiety while the remaining two positions are combinatorialized, thereby generating sublibraries based on which position is fixed. Moreover, one can add additional positions to the core structure that can be combinatorialized or held constant while one or more other positions are combinatorialized. Thus, different or more diverse libraries can be created based on a particular core structure or on a species identified from the library as capable of derepressing an IAP-inhibited caspase.

Those skilled in the art will understand that an agent of the invention having a core structure corresponding to TPI 914, TPI 927, TPI 759, TPI 882, such as a compound of the TPI 1396, TPI 1349, TPI 1391 or TPI 1400 series, can further include one or more attached moieties such as a peptide moiety. An agent of the invention can be multivalent, as described above, in which case the attached moiety can be one or more core structures corresponding to TPI 914, TPI 927, TPI 759, TPI 882, a core peptide having a sequence described above; or a combination of one or more of these core structures and core peptides.

An agent that is capable of derepressing an IAP-inhibited caspase, whether based on a peptide or non-peptide core structure can include a moiety known to naturally occur in biological proteins. Such moieties when part of a protein are commonly referred to as amino acid R-groups. These R groups can be characterized by a variety of physical or chemical properties. Taking the essential amino acids as an example, the R groups found on Gly, Ala, Val, Leu, or Ile have the characteristic of being non-polar; polar R groups include the sulfhydryl moiety of Cys, the thioether of Met, hydroxyl moieties of Ser and Thr, and amide moieties of Asn and Gln; Asp and Glu are characterized as polar acidic groups due to the presence of carboxylic acid moieties; polar basic R groups include Lys which has an amino moiety, Arg which has a guanidino moiety and His which has an imidazole with secondary amines; and Phe, Trp, Tyr, and His are characterized as aromatic amino acids due to the presence of phenyl or heterocyclic rings. An agent of the invention can include one or more of these moieties or characteristics, thereby rendering the agent capable of derepressing an IAP-inhibited caspase.

An agent of the invention can also be described or characterized according to other moieties or combinations of moieties that when present renders the agent capable of derepressing an IAP-inhibited caspase. Definitions for various moieties that can be present in the agents of the invention are set forth below.

As used herein, the term "alkyl," alone or in combination, refers to a saturated, straight-chain or branched-chain hydrocarbon moiety containing from 1 to 10, preferably from 1 to 6 and more preferably from 1 to 4, carbon atoms. Examples of such moieties include, but are not limited to, methyl, ethyl, n-propyl, iso-propyl, n-butyl, iso-butyl, sec-butyl, tert-butyl, pentyl, iso-amyl, hexyl, decyl and the like.

The term "alkene," alone or in combination, refers to a straight-chain or branched-chain hydrocarbon moiety having at least one carbon-carbon double bond in a total of from 2 to 10, preferably from 2 to 6 and more preferably from 2 to 4, carbon atoms. Examples of such moieties include, but are not limited to, ethenyl, E- and Z-propenyl, isopropenyl, E- and Z-butenyl, E- and Z-isobutenyl, E- and Z-pentenyl, decenyl, methylidene (=$CH_2$), ethylidene (—CH=CH—), propylidene (—$CH_2$—CH=CH—) and the like.

The term "alkyne," alone or in combination, refers to a straight-chain or branched-chain hydrocarbon moiety having at least one carbon-carbon triple bond in a total of from 2 to 10, preferably from 2 to 6 and more preferably from 2 to 4, carbon atoms. Examples of such moieties include, but are not limited to, ethynyl (acetylenyl), propynyl (propargyl), butynyl, hexynyl, decynyl and the like.

The term "cycloalkyl," alone or in combination, refers to a saturated, cyclic arrangement of carbon atoms which number from 3 to 8 and preferably from 3 to 6, carbon atoms. Examples of such cycloalkyl moieties include, but are not limited to, cyclopropyl, cyclobutyl, cyclopentyl, cyclohexyl and the like.

The term "aryl" refers to a carbocyclic (consisting entirely of carbon and hydrogen) aromatic group selected from the group consisting of phenyl, naphthyl, indenyl, indanyl, azulenyl, fluorenyl, and anthracenyl; or a heterocyclic aromatic group selected from the group consisting of furyl, thienyl, pyridyl, pyrrolyl, oxazolyly, thiazolyl, imidazolyl, pyrazolyl, 2-pyrazolinyl, pyrazolidinyl, isoxazolyl, isothiazolyl, 1,2,3-oxadiazolyl, 1,2,3-triazolyl, 1,3,4-thiadiazolyl, pyridazinyl, pyrimidinyl. pyrazinyl, 1,3,5-triazinyl, 1,3,5-trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl, carbazolyl, acridinyl, phenazinyl, phenothiazinyl, and phenoxazinyl.

"Aryl" groups, as defined in this application may independently contain one to four substituents which are independently selected from the group consisting of hydrogen, halogen, hydroxyl, amino, nitro, trifluoromethyl, trifluoromethoxy, alkyl, alkenyl, alkynyl, cyano, carboxy, carboalkoxy, 1,2-dioxyethylene, alkoxy, alkenoxy or alkynoxy, alkylamino, alkenylamino, alkynylamino, aliphatic or aromatic acyl, alkoxy-carbonylamino, alkylsulfonylamino, morpholinocarbonylamino, thiomorpholinocarbonylamino, N-alkyl guanidino, aralkylaminosulfonyl; aralkoxyalkyl; N-aralkoxyurea; N-hydroxylurea; N-alkenylurea; N,N-(alkyl, hydroxyl)urea; heterocyclyl; thioaryloxy-substituted aryl; N,N-(aryl, alkyl)hydrazino; Ar'-substituted sulfonylheterocyclyl; aralkyl-substituted heterocyclyl; cycloalkyl and cycloakenyl-substituted heterocyclyl; cycloalkyl-fused aryl; aryloxy-substituted alkyl; heterocyclylamino; aliphatic or aromatic acylaminocarbonyl; aliphatic or aromatic acyl-substituted alkenyl; Ar'-substituted aminocarbonyloxy; Ar', Ar'-disubstituted aryl; aliphatic or aromatic acyl-substituted acyl; cycloalkylcarbonylalkyl; cycloalkyl-substituted amino; aryloxycarbonylalkyl; phosphorodiamidyl acid or ester;

"Ar'" is a carbocyclic or heterocyclic aryl group as defined above having one to three substituents selected from the group consisting of hydrogen, halogen, hydroxyl, amino, nitro, trifluoromethyl, trifluoromethoxy, alkyl, alkenyl, alkynyl, 1,2-dioxymethylene, 1,2-dioxyethylene, alkoxy, alkenoxy, alkynoxy, alkylamino, alkenylamino or alkynylamino, alkylcarbonyloxy, aliphatic or aromatic acyl, alkylcarbonylamino, alkoxycarbonylamino, alkylsulfonylamino, N-alkyl or N,N-dialkyl urea.

The term "alkoxy," alone or in combination, refers to an alkyl ether moiety, wherein the term "alkyl" is as defined above. Examples of suitable alkyl ether moieties include, but are not limited to, methoxy, ethoxy, n-propoxy, iso-propoxy, n-butoxy, iso-butoxy, sec-butoxy, tert-butoxy and the like.

The term "alkenoxy," alone or in combination, refers to a moiety of formula alkenyl-O—, wherein the term "alkenyl" is as defined above. Examples of suitable alkenoxy moieties include, but are not limited to, allyloxy, E- and Z-3-methyl-2-propenoxy and the like.

The term "thioalkoxy" refers to a thioether moiety of formula alkyl-S—, wherein alkyl is as defined above.

The term "alkylamino," alone or in combination, refers to a mono- or di-alkyl-substituted amino group (i.e., a group of formula alkyl-NH— or (alkyl)$_2$-N—), wherein the term "alkyl" is as defined above. Examples of suitable alkylamino moieties include, but are not limited to, methylamino, ethylamino, propylamino, isopropylamino, t-butylamino, N,N-diethylamino and the like.

The term "amide" refers to either —N(R$^1$)—C(=O)— or —C(=O)—N (R$^1$)— where (R$^1$) is defined herein to include hydrogen as well as other groups. The term "substituted amide" refers to the situation where (R$^1$) is not hydrogen, while the term "unsubstituted amide" refers to the situation where (R$^1$) is hydrogen.

The term "aryloxy," alone or in combination, refers to a moiety of formula aryl-O—, wherein aryl is as defined above. Examples of aryloxy moieties include, but are not limited to, phenoxy, naphthoxy, pyridyloxy and the like.

The term "arylamino," alone or in combination, refers to a moiety of formula aryl-NH—, wherein aryl is as defined above. Examples of arylamino moieties include, but are not limited to, phenylamino (anilido), naphthylamino, 2-, 3- and 4-pyridylamino and the like.

The term "aryl-fused cycloalkyl," alone or in combination, refers to a cycloalkyl moiety which shares two adjacent atoms with an aryl moiety, wherein the terms "cycloalkyl" and "aryl" are as defined above. An example of an aryl-fused cycloalkyl moiety is a benzofused cyclobutyl group.

The term "alkylcarbonylamino," alone or in combination, refers to a moiety of formula alkyl-CONH, wherein the term "alkyl" is as defined above.

The term "alkoxycarbonylamino," alone or in combination, refers to a moiety of formula alkyl-OCONH—, wherein the term "alkyl" is as defined above.

The term "alkylsulfonylamino," alone or in combination, refers to a moiety of forrnula alkyl-SO$_2$ NH—, wherein the term "alkyl" is as defined above.

The term "arylsulfonylamino," alone or in combination, refers to a moiety of formula aryl-SO$_2$NH—, wherein the term "aryl" is as defined above.

The term "N-alkylurea," alone or in combination, refers to a moiety of formula alkyl-NH—CO—NH—, wherein the term "alkyl" is as defined above.

The term "N-arylurea," alone or in combination, refers to a moiety of formula aryl-NH—CO—NH—, wherein the term "aryl" is as defined above.

The term "halogen" means fluorine, chlorine, bromine and iodine.

In view of the above definitions, other chemical terms used throughout this application can be easily understood by those of skill in the art. Terms may be used alone or combined to describe a combination of moieties according to accepted chemical nomenclature.

An agent of the invention can be synthesized using reagents and conditions well known to yield products having predictable moieties or characteristics. For example, peptides can be synthesized in large numbers at relatively low cost and they can be readily modified to exhibit diverse properties (see, for example, Rees et al., *Protein Engineering: A Practical Approach* (IRL Press 1992)). A peptide derepressor of an IAP-inhibited caspase can be synthesized using a modification of the solid phase peptide synthesis method (Merrifield (*J. Am. Chem. Soc.*, 85:2149 (1964); Houghten, U.S. Pat. No. 4,631,211, issued Dec. 23, 1986) or can be synthesized using standard solution methods well known in the art (see, for example, Bodanszky, M., *Principles of Peptide Synthesis* 2nd ed. (Springer-Verlag, 1988 and 1993, suppl.)). Peptides prepared by the method of Merrifield can be synthesized using an automated peptide synthesizer such as the Applied Biosystems 431A-01 Peptide Synthesizer (Mountain View, Calif.) or using a manual peptide synthesis method (Houghten, supra, 1986).

Furthermore, combinatorial methods such as those described below can be used to make an agent that derepresses an IAP-inhibited caspase. A library can be synthesized to have candidate agents with particular moieties such as those defined above or described in the Examples set forth below. Additionally, the synthetic conditions can be selected to produce a library of candidate compounds with particular characteristics inherent in one or more of the moieties described herein such as the characteristics described above for amino acid R groups. For example, a library can be synthesized to have characteristics of SMAC a naturally occurring IAP inhibitor. The N-terminal region of SMAC has been shown to mediate binding to and inhibition of IAPs (see Srinivasula et al., *Nature* 410:112–116 (2001), Wu et al., *Nature* 408:1008–1012 (2000), Liu et al., Nature 408: 1004–1008 (2000)). Accordingly, this N-terminal domain can be used to guide library synthesis such that reactants and conditions are chosen to selectively incorporate similar moieties and characteristics into the candidate agents in the library. Similar strategies can be employed using agents described herein or identified by the methods of the invention, wherein a library is made to selectively contain characteristics or moieties found in a particular agent or common to a plurality of agents. Such a design strategy increases the probability that an effective derepressor of an IAP-inhibited caspase will be identified.

An agent of the invention that is capable of derepressing an IAP-inhibited caspase can be identified in a screen or otherwise characterized according to any of a variety of functional properties described herein. In one embodiment a derepressor of an IAP-inhibited caspase is identified or otherwise characterized based on its ability to allow caspase activity in the presence of an IAP. For example, the effectiveness of a compound of the invention can be determined according to the ratio of caspase activity for an IAP-inhibited caspase in the presence and absence of an agent of the invention.

Using caspase derepression assays, several compounds have been disclosed herein that derepress an IAP-inhibited caspase. For example, the invention provides an isolated agent having a core structure selected from any of the structures shown in FIGS. 21-24, where the agent is selected from TPI 1349-1 through 1349-34; TPI 1396-1 through TPI 1396-36; TPI 1391-1 through TPI 1391-36; and TPI 1400-1 through TPI 1400-58 and where the agent derepresses an IAP-inhibited caspase.

A compound of the invention that derepress an IAP-inhibited caspase can be a member of a disclosed compound class, such as a polyphenylurea, diketopiperazine, bicyclic guanidine, N-acyl triamine, or a tetrapeptide. A summary of various activities observed for compound classes disclosed herein is presented in Table XII, below. This table shows average activities of representative compounds from the polyphenylurea, diketopiperazine, bicyclic guanidine, N-acyl triamine, and tetrapeptide classes in the caspase derepression assay, SMAC competition assay and the Jurkat cell cytotoxicity assay. Polyphenylurea and diketopiperazines were found to have activity in the enzyme derepression assay in the presence of either full length XIAP or XIAP BIR2 domain, as is described in Example VIII.

TABLE XII

IAP Antagonists
Families of Compounds

| Compound Class | Enzyme Derepress IC-50 (µM) | SMAC competition | Cell Activity IC-50 (µM) |
| --- | --- | --- | --- |
| Poly-phenylurea | 12 | No | 7 |
| Diketopiperazines | 32 | No | 8 |
| Bicyclic guanidines | 32 | N.T. | N.T. |
| N-Acyl triamines | 53 | N.T. | N.T. |
| Tetrapeptides-1 | 19 | No | 8 |
| Tetrapeptides-2 | 9 | Yes | 40 |

An exemplary assay for identifying a compound that derepresses an IAP-inhibited caspase is provided in Example I and use of the assay to identify such derepressor compounds is demonstrated in Examples I through VI. As described below in the Examples, a ratio of $V_{max}$ in the presence and absence of the agent for an IAP-inhibited caspase that is at least about 1.7, depending upon assay conditions, is indicative of an effective derepressor of an IAP-inhibited caspase. Those skilled in the art will understand that a value for this ratio that is indicative of effectiveness will depend upon the concentration of the agent used and the $IC_{50}$ of the agent. Accordingly, when higher concentrations of the agent are used the threshold value for the ratio of $V_{max}$ in the presence and absence of the agent can be at least about 2 at least about 2.5, at least about 3 or at least about 4 or higher. When lower concentrations of the agent are used this ratio can be as low as at least about 1.5, at least about 1.3 at least about 1 or lower. Thus, it can be appropriate to express the ratio in combination with the relative amount of agent to IAP present in the assay including, for example, 1 molar equivalent of agent per IAP, 2 molar equivalents of agent per IAP, 5 molar equivalents of agent per IAP, 10 molar equivalents of agent per IAP or 50 molar equivalents of agent per IAP or higher.

An agent that derepresses an IAP-inhibited caspase can also be identified by its affinity for an IAP or a caspase-binding fragment thereof, for example, in a binding assay. It will be understood that a functional fragment of an IAP, caspase or both can be used in a binding assay to identify a derepressor of an IAP-inhibited caspase. Affinity of an agent for an IAP determined using a binding assay can, if desired, be quantified by an equilibrium dissociation constant ($K_d$) or equilibrium association constant ($K_a$). An agent that derepresses an IAP-inhibited caspase can be identified as an agent that has a $K_d$ that is in the micromolar range including, for example, less than about $1 \times 10^{-6}$ M, $1 \times 10^{-7}$ M, or $1 \times 10^{-8}$ M. Higher affinity agents can also be identified including an agent having nanomolar range affinity such as a $K_d$ less than about $1 \times 10^{-9}$ M, $1 \times 10^{-10}$ M or $10 \times^{-11}$ M. An agent of the invention can also have picomolar affinity including, for example, a $K_d$ that is less than $1 \times 10^{-12}$ M.

Alternatively, the effectiveness of an agent at derepressing an IAP-inhibited caspase can be determined based on inhibition of the association between an IAP and caspase, for example, in an inhibition binding assay. It will be understood that a functional fragment of an IAP, caspase or both can be used in an inhibition binding assay. Alternatively, a derepressor of an IAP-inhibited caspase can be identified based on its ability to inhibit binding between IAP and another inhibitor such as SMAC. An exemplary assay for determining inhibition of IAP binding to SMAC is provided in Example VII. Inhibition can be quantified, if desired, by an equilibrium inhibition constant, such as $K_i$. Values for $K_i$ can be determined by performing derepression assays, such as those described herein, with increasing concentrations of the agent and a fixed concentration of each binding partner. Binding or inhibition can be analyzed to determine the equilibrium constants described above using well known kinetic analysis such as those described in Segel, *Enzyme Kinetics* John Wiley and Sons, New York (1975). An agent that derepresses an IAP-inhibited caspase can be identified as those having $K_i$ in the micromolar, nanomolar or picomolar ranges such as those ranges and values described above for $K_d$.

Accordingly, the invention provides a complex having an IAP bound to an agent, the agent having a core peptide or core structure of the invention including, for example, those core structures described above. The complex can be isolated from at least one other cellular component normally occurring with the IAP in nature. For example, the complex can be in a purified state being substantially free of other cellular components that normally occur with the IAP in nature. The complex can also occur in a recombinant cell that does not normally express the IAP.

The invention further provides conjugates including a moiety linked to an agent that derepresses an IAP-inhibited caspase. A conjugate of the invention can include a moiety useful for targeting the agent to a particular cell or for increasing the stability or biological half life of the agent that derepresses an IAP-inhibited caspase. For example, a moiety can be a particular antibody, functional fragment thereof, or other binding polypeptide that has specificity for a particular cell in which it is desired to promote apoptosis, such as a tumor cell. Any moiety capable of targeting the agent to a cell in which an IAP-inhibited caspase is to be derepressed can be used as a conjugate.

A conjugate of an agent that derepresses an IAP-inhibited caspase can also be a moiety capable of introducing the agent to the cytosol of a cell or otherwise facilitating passage of the agent through the cell membrane. An agent can be introduced into the cell by, for example, a heterologous targeting domain or using a lipid based carrier. Thus, the invention provides cytosolic delivery of an agent that derepresses an IAP-inhibited caspase.

A moiety can also be a drug delivery vehicle such as a chambered microdevice, a cell, a liposome or a virus that provides stability or properties otherwise advantageous for administration of the agent that derepresses an IAP-inhibited caspase. Generally, such microdevices, should be nontoxic and, if desired, biodegradable. Various moieties, including microcapsules, which can contain an agent, and methods for linking a moiety, including a chambered microdevice, to a therapeutic agent are well known in the art and commercially available (see, for example, "Remington's Pharmaceutical Sciences" 18th ed. (Mack Publishing Co. 1990), chapters 89–91; Harlow and Lane, *Antibodies: A laboratory manual* (Cold Spring Harbor Laboratory Press 1988); see, also, Hermanson, supra, 1996).

In addition, a derepressor of an IAP-inhibited caspase formulation can be incorporated into biodegradable polymers allowing for sustained release of the compound, the polymers being implanted in the vicinity of where drug delivery is desired, for example, at the site of a tumor or implanted so that the agent is released systemically over time. Osmotic minipumps also can be used to provide controlled delivery of specific concentrations of the derepressor of an IAP-inhibited caspase species and formulations through cannulae to the site of interest, such as directly into a tumor growth or into the vascular supply of a tumor. The biodegradable polymers and their use are described, for example, in detail in Brem et al., *J. Neurosurg.* 74:441–446 (1991).

A conjugate of the invention can include a moiety that is a label. A labeled agent that binds to an IAP and/or caspase can be used to identify the subcellular localization of the IAP and/or caspase or to identify a previously unidentified IAP or caspase. A labeled agent that binds to an IAP and/or caspase can also be used to identify other molecules that interact with an IAP and/or caspase. As described in further detail below, such a binding competition assay can be used to identify an agent that derepresses an IAP-inhibited caspase. A label that can be incorporated as a moiety includes, for example, a fluorophore, chromophore, paramagnetic spin label, radionuclide, or binding group having specificity for another molecule that can be detected.

A labeled agent of the invention can be useful for identifying cells within a tissue that are inhibited from apoptosis by an IAP-inhibited caspase. Thus, the labeled agent can be used in a diagnostic method to identify cells for which administration of a derepressor of an IAP-inhibited caspase will allow apoptosis to proceed. The method can include steps of administering a labeled agent of the invention to a tissue and identifying one or more cells that incorporate the labeled agent. The labeled agent can be administered using methods for in vivo delivery as described above. The diagnostic methods can be used at a variety of resolutions. For example, the method can be carried out to identify a tissue containing cells labeled by the agent. Alternatively, higher resolution methods can be used to identify a particular cell or cell type within a tissue that is labeled in the presence of an IAP-inhibited caspase. Because the diagnostic methods can be used to distinguish a cell for which administration of a derepressor of an IAP-inhibited caspase will allow apoptosis to proceed from non-labeled cells, the methods can be useful for guiding in the choice of targeting or delivery conjugate to use in a therapeutic method of the invention.

The diagnostic method can be performed in vitro in which case the labeled agent can be administered by injection or by soaking the tissue in a solution containing the labeled agent. Again the methods can be used at a resolution sufficient to distinguish within a tissue a cell having an IAP-inhibited caspase over those that are not inhibited from apoptosis in this way. Such resolution can be achieved for example, by use of a microscopic based technique. Further resolution can provide subcellular localization of an IAP-inhibited caspase. Subcellular localization can be used to determine an appropriate cytosolic delivery conjugate or to further identify the role of apoptosis in the particular tissue or cells under study.

The invention also provides a pharmaceutical composition containing a derepressor of an IAP-inhibited caspase and a pharmaceutical carrier. Such compositions can be used in the apoptosis promoting methods of the invention to inhibit, treat or reduce the severity of a pathological condition characterized by a pathologically reduced level of apoptosis. For example, a derepressor of an IAP-inhibited caspase can be administered as a solution or suspension together with a pharmaceutically acceptable medium.

The derepressor of an IAP-inhibited caspase formulations include those applicable for parenteral administration such as subcutaneous, intraperitoneal, intramuscular, intravenous, intradermal, intracranial, intratracheal, and epidural administration. As well as formulations applicable for oral, rectal, ophthalmic (including intravitreal or intracameral), nasal, topical (including buccal and sublingual), intrauterine, or vaginal administration. The derepressor of an IAP-inhibited caspase formulation can be presented in unit dosage form and can be prepared by pharmaceutical techniques well known to those skilled in the art. Such techniques include the step of bringing into association the active ingredient and a pharmaceutical carrier or excipient.

Formulations suitable for parenteral administration include aqueous and non-aqueous sterile injection solutions such as the pharmaceutically acceptable media described above. The solutions can additionally contain, for example, anti-oxidants, buffers, bacteriostats and solutes which render the formulation isotonic with the blood of the intended recipient. Other formulations include, for example, aqueous and non-aqueous sterile suspensions which can include suspending agents and thickening agents. The formulations can be presented in unit-dose or multi-dose containers, for example, sealed ampules and vials, and can be stored in a lyophilized condition requiring, for example, the addition of the sterile liquid carrier, immediately prior to use. Extemporaneous injection solutions and suspensions can be prepared from sterile powders, granules and tablets of the kind previously described.

A pharmaceutically acceptable medium can additionally contain physiologically acceptable compounds that act, for example, to stabilize the derepressor of an IAP-inhibited caspase agent. Such physiologically acceptable compounds include, for example, carbohydrates such as glucose, sucrose or dextrans; antioxidants such as ascorbic acid or glutathione; chelating agents such as EDTA, which disrupts microbial membranes; divalent metal ions such as calcium or magnesium; low molecular weight proteins; lipids or liposomes; or other stabilizers or excipients. As described previously, derepressor of an IAP-inhibited caspase formulation also can be formulated with a pharmaceutically acceptable medium such as a biodegradable polymer. All of the above-described pharmaceutical carriers and media can be what is termed in the art pharmaceutical grade which means that they are of sufficient purity and quality for use in humans and are distinguishable from comparable reagents in research grade formulations.

The invention also provides a composition including a derepressor of an IAP-inhibited caspase and a molecule having therapeutic activity. A molecule included with a derepressor of the invention can be a compound having activity against a condition characterized by a pathologically reduced level of apoptosis. For example, the compound can have activity against cancer. An exemplary compound that has activity against prostate cancer and that can be used in combination with a derepressor compound of the invention is VP-16 (etoposide). As demonstrated by the results of Example X, administration of VP-16 with either TPI 792-33 or TPI 792-35 had a more potent effect on killing cancer cells than any of these compounds alone.

Other anti-cancer drugs can also be used in a composition with a derepressor of an IAP-inhibited caspase including, but not limited to, an alkylating agent such as mechlorethamine, chlorambucil, cyclophosphamide, melphalan, ifosfamide; an antimetabolite such as methotrexate, 6-mercaptopurine, 5-fluorouracil or cytarabine; an antibody such as Rituxan, Herceptin, or MabThera; a plant alkaloid such as vinblastine or vincristine, or etoposide; an antibiotic such as doxorubicin, daunomycin, bleomycin, or mitomycin; a nitrosourea such as carmustine or lomustine; an inorganic ion such as cisplatin; a biological response modifier such as interferon; an enzyme such as aspariginase; or a hormone such as tamoxifen or flutamide. These and other anti-cancer compounds, including those described herein below with respect to practicing a therapeutic method of the invention in combination with another therapeutic method, are known in the art and formulations suitable for pharmaceutical use are known as described, for example, in The Merck Manual $16^{th}$ Ed., Merck Res. Labs., Rahway N.J. (1992). In addition, for treating a condition characterized by a pathologically reduced level of apoptosis, a compound of the invention can be administered in conjunction with a therapeutic antibody. Such a therapeutic antibody can be, for example, an antibody that modulates apoptosis, such as by binding to an apoptosis regulatory molecule and modulating its activity. As a non-limiting example, a compound of the invention can be administered in conjunction with an antibody that activates caspase 3, caspase 7, Trail-R1 or Trail R-2. Exemplary Trail-R1 and Trail-R2 monoclonal antibodies are available from Human Genome Sciences, Rockville, Md.

Figure 28:
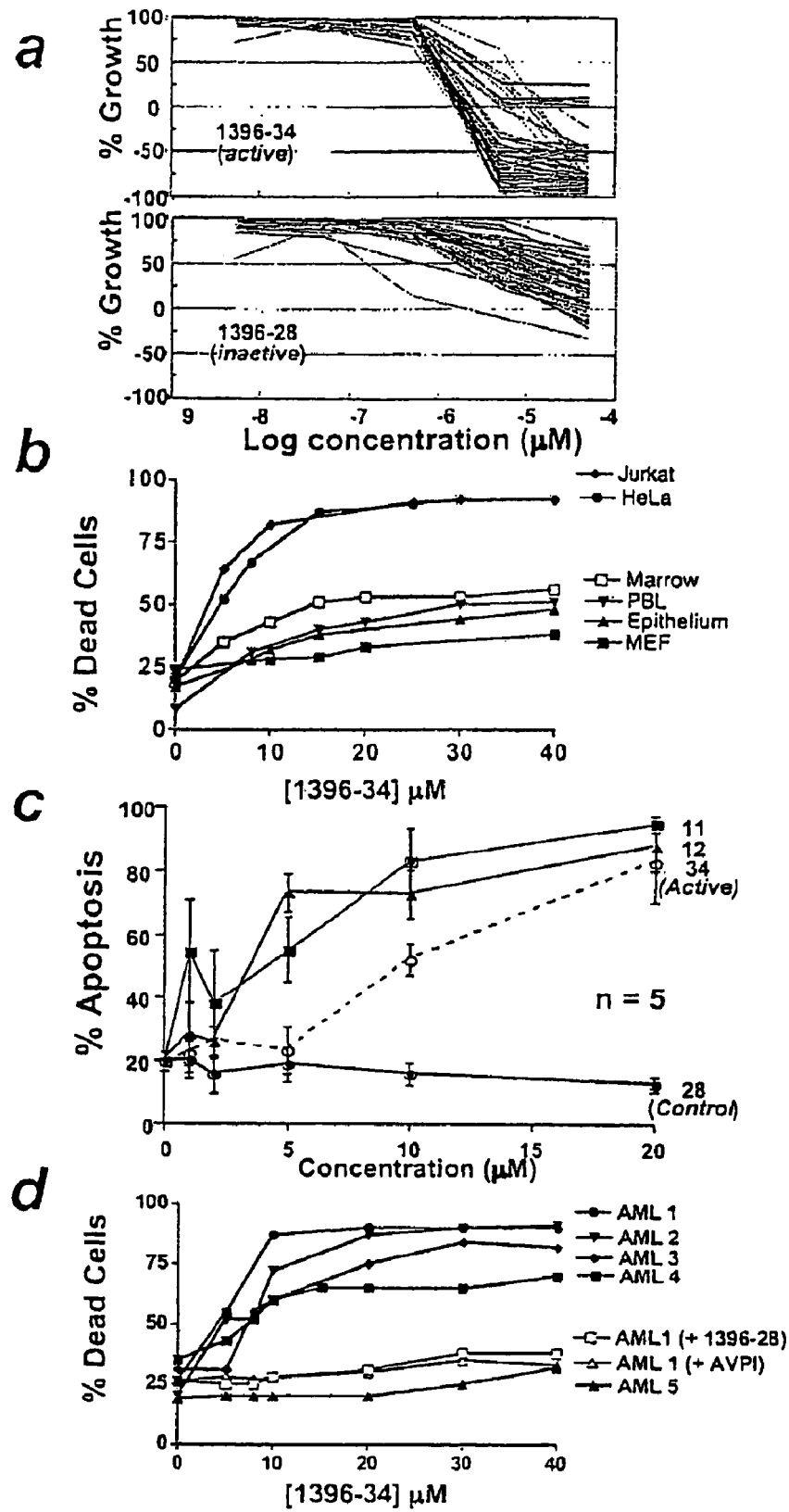
FIG. 28a, b, c and d show broad anti-tumor activity of TPI 1396-34.
FIG. 28b shows the effect of TPI 1396-34 on normal versus malignant cells.
FIG. 28c shows the mean (+/−standard deviation) percent apoptosis of CLL B-cells from five patients cultured with various poly-phenylurea compounds.
FIG. 28d shows cell death of AML cells isolated from 5 patients and cultured with various concentrations of TPI 1396-34. All samples were treated with active TPI 1396-34 and inactive TPI 1396-28 as well as AVPI peptide, but the complete data set is shown only for AML-1. Comparable results were obtained with the other samples.

The invention provides compounds that demonstrate broad anti-cancer activity alone or in combination with known anti-cancer agents. For example, polyphenylurea compound of the invention such as TPI 1396-34, TPI 1396-12, TPI 1396-22, and TPI 1396-11 significantly reduce tumor cell growth of sixty different tumor cell lines (see Example XIII and FIGS. 28 and 29). The concentration of polyphenylurea compound required to kill 50% of the cells (LD50) was comparable or better than that of known anti-cancer drugs. Toxicological analysis of mice treated with TPI 1396-12 at dosages effective to inhibit tumor growth indicated no toxic effects on a variety of parameters including white blood cell count, red blood cell count, platelet count, BUN, bilirubin, ALT and AST (see FIG. 41 and Example XXIII). In addition, as shown herein, normal cells were relatively resistant to polypheylurea compounds compared to tumor cell lines (see FIG. 28). Polyphenylurea compounds also were demonstrated to induce apoptosis in non-replicating malignant cells such as chronic lymphocytic leukemia (CLL) and acute myelogenous leukemia (AML) cells isolated from patients (see FIG. 28). Additional studies revealed that a polyphenylurea compound of the invention can enhance cytotoxicity of antigen-specific CTL (see FIG. 39).

Figure 30:
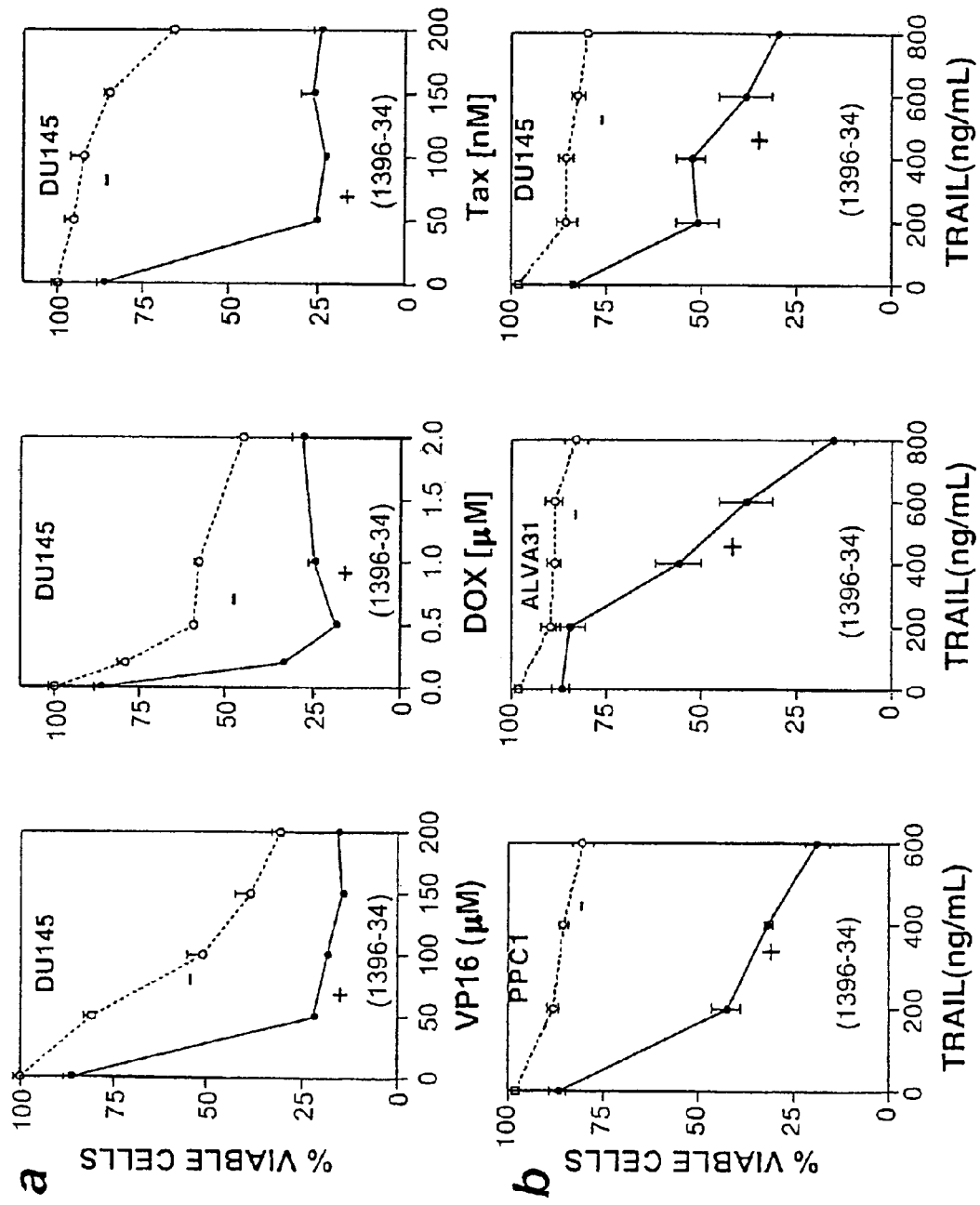
FIG. 30a and b show TPI 1396-34 sensitizes cancer cells to chemotherapy and TRAIL.
FIG. 30b shows viability of cancer cell lines treated with various concentrations of TRAIL alone or in combination with TPI 1396-34.

As further disclosed herein, polyphenylurea compounds can collaborate with conventional anticancer drugs to induce killing of tumor cells. For example, TPI 1396-34 significantly increases dose-dependent cytoxicity of etoposide (VP16), doxorubicin (DOX) or paclitaxel (TAXOL) in various cancer cell lines (see Example XIV and FIGS. 30 and 31). Similar effects on the induction of apoptosis were seen using polyphenylurea compounds and the biological agent TRAIL, which is an apoptosis inducing member of the Tumor Necrosis Factor (TNF) family (see FIG. 30).

Figure 32:
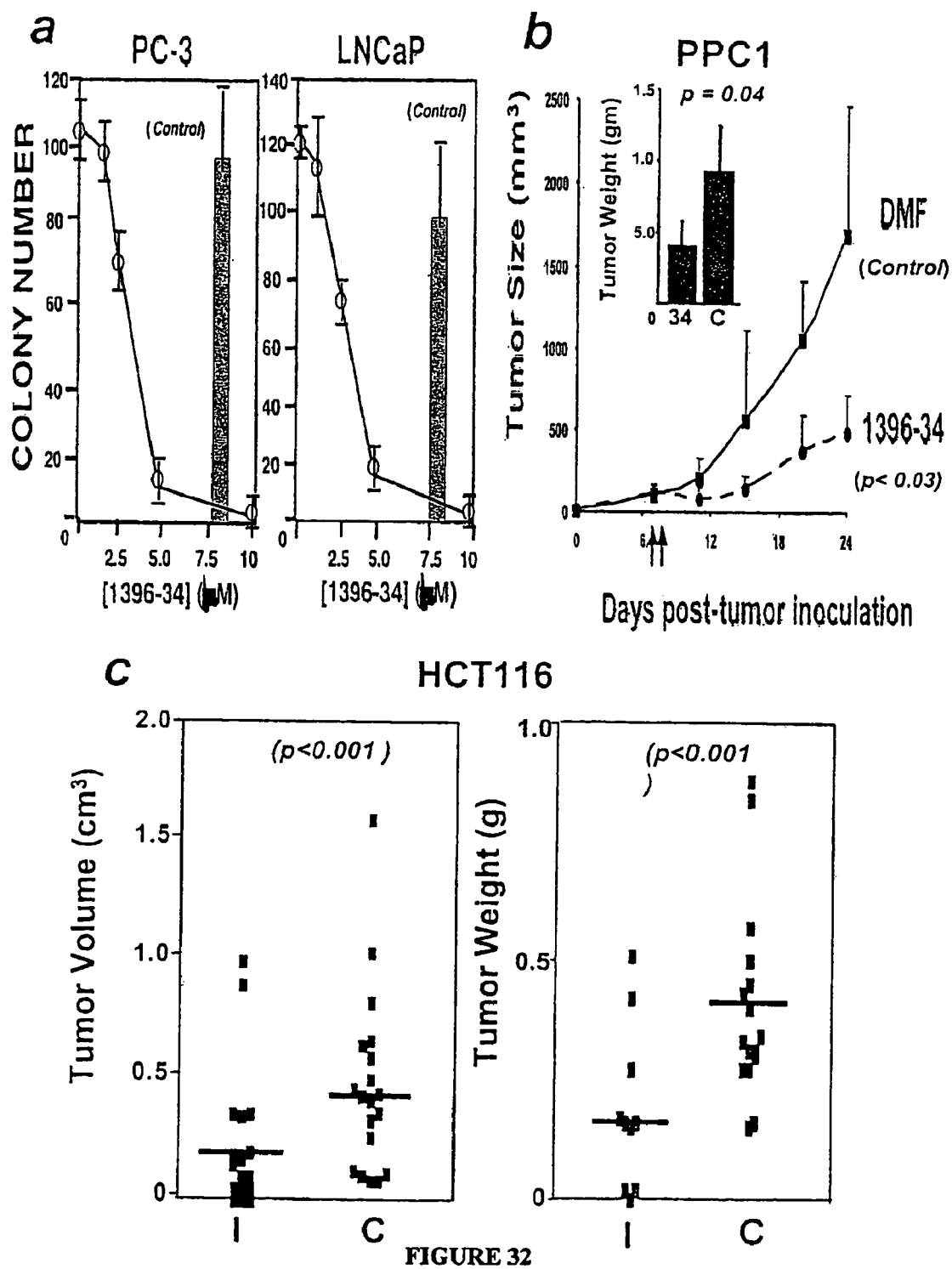
FIG. 32a, b and c show anti-tumor activity of TPI 1396-34 in clonogenic survival assays and tumor xenograft studies.
FIG. 32b shows tumor size in Balb/C nu–/nu– mice injected with PPC1 prostate cancer cells after treatment with TPI 1396-34. The inset shows tumor weight in mice sacrificed at 24 days after compound injections.
FIG. 32c shows tumor volume and tumor weight in Balb/C nu–/nu– mice injected with HCT116 colon cancer cells. On days 6, 7, and 8 mice were treated with TPI 1396-34 (1) or solvent control (C) and tumor volume was measured. On day 19, the mice were sacrificed and the tumors were weighed. Bars represent the median tumor size or weight.
Figure 33:
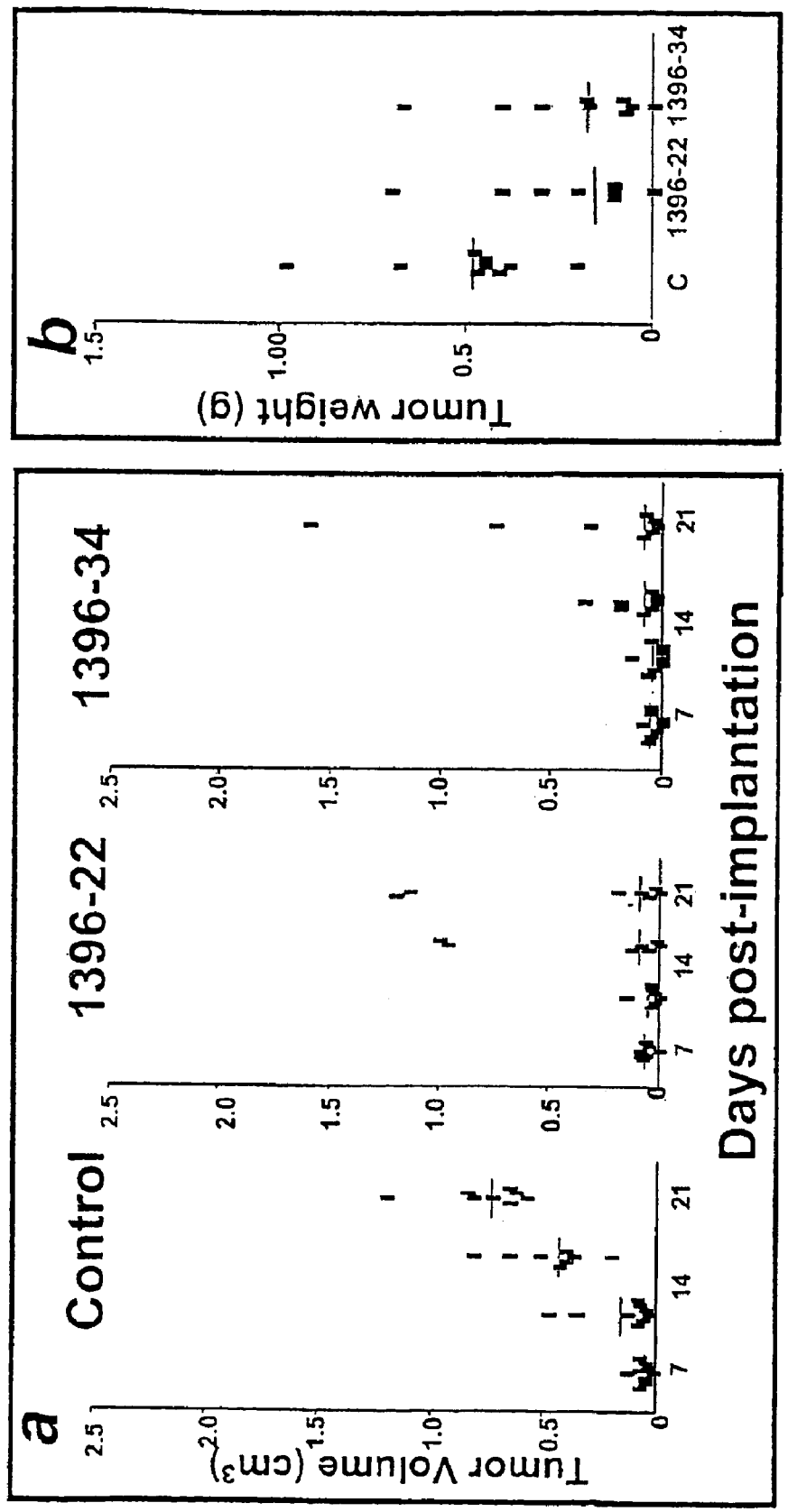
FIG. 33a and b show anti-tumor activity of poly-phenylurea compounds in a tumor xenograft model.
FIG. 33b shows tumor weight of mice sacrificed on day 19. Bars represent the median tumor size or weight.
Figure 38:
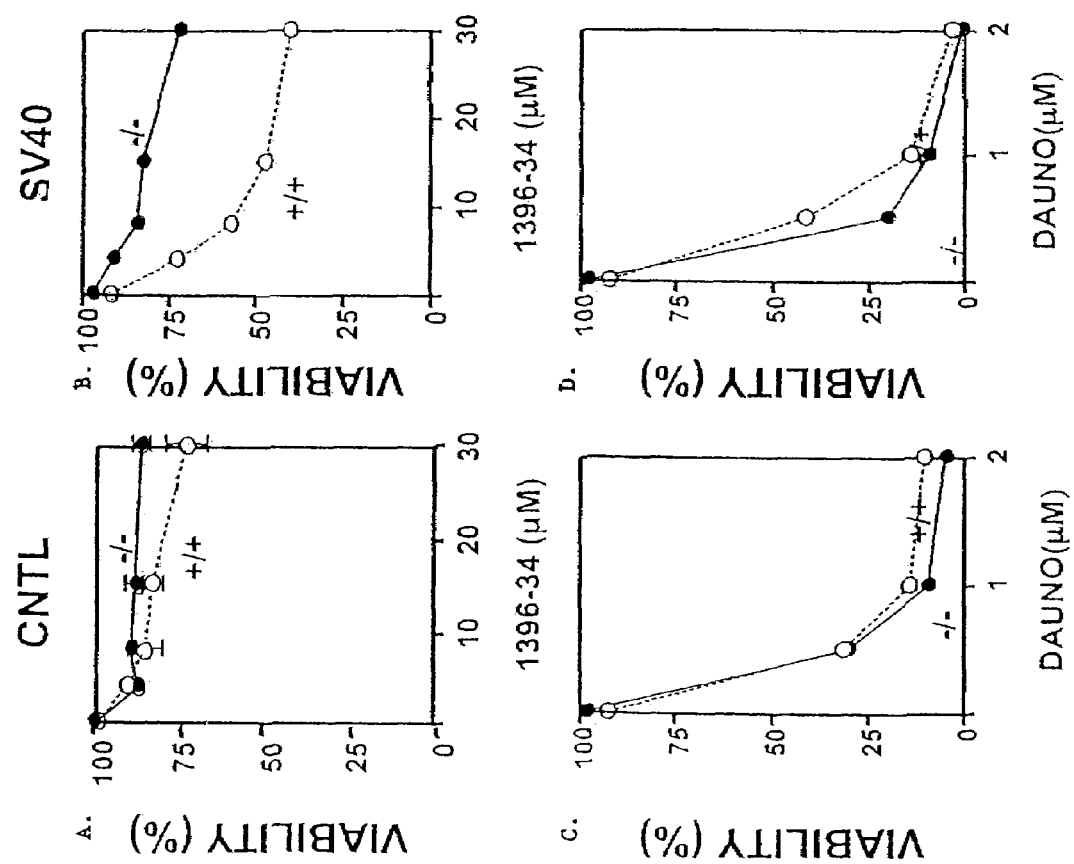
FIG. 38 shows that TPI 1396-34 functions by targeting XIAP protein. Cells from XIAP knock-out mice or wild type mice were treated with either TPI 1396-34 or daunorubicin and % viability was assessed. Cells used in these studies were either untransformed (FIG. 38 A and C) or transformed with a retrovirus encoding SC40 large T antigen (FIG. 38 B and D).
Figure 40:
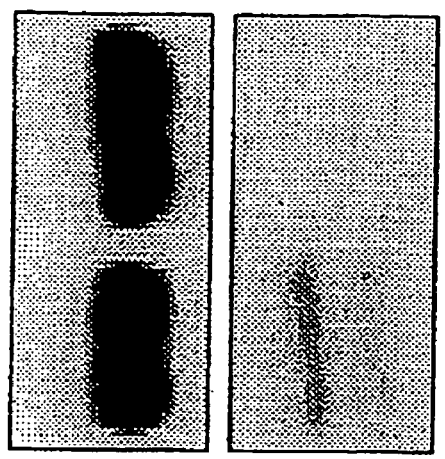
FIG. 40 shows that TPI 1396-12 effects in vivo activation of caspases.
Figure 40:
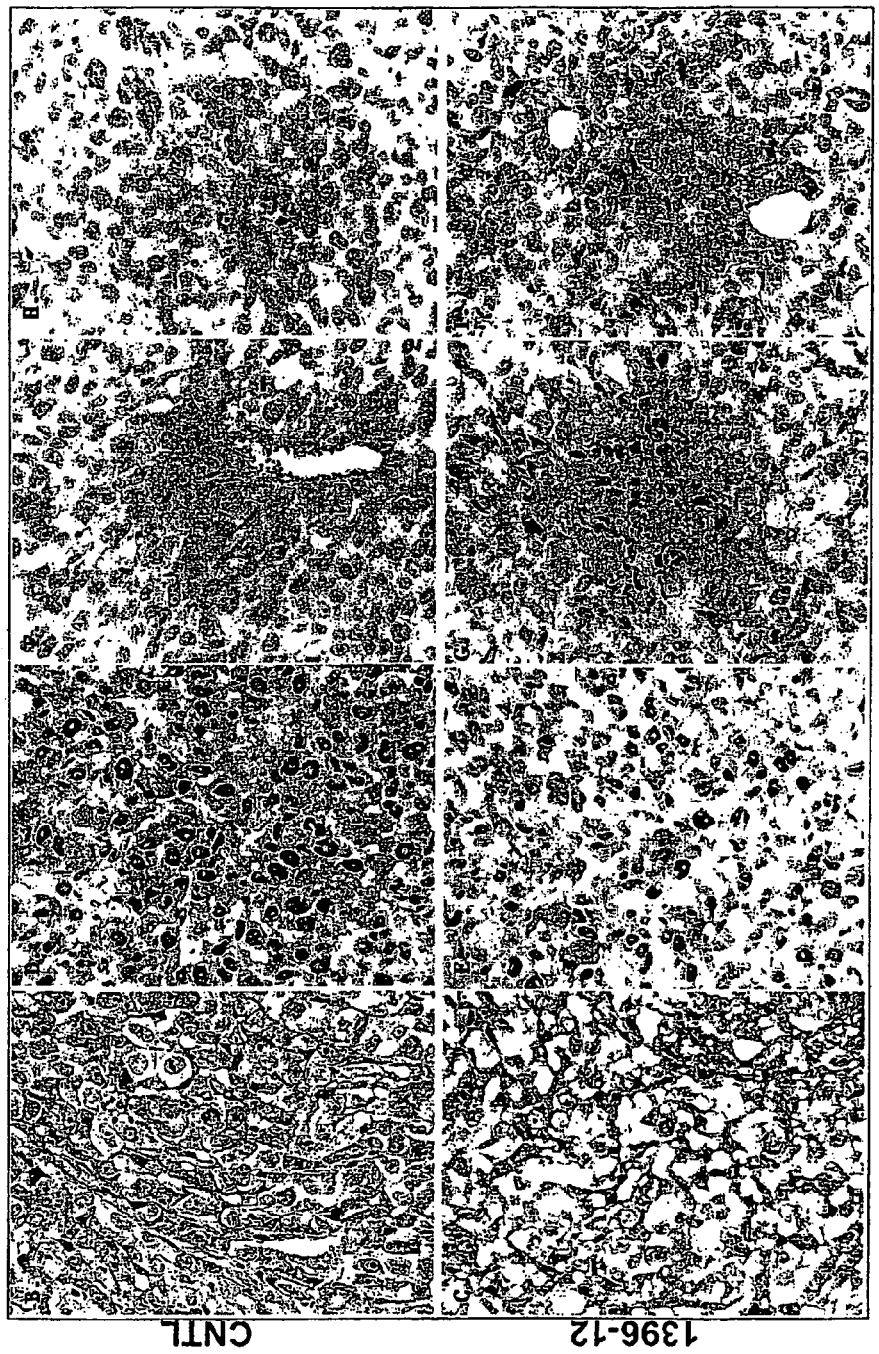

The invention also provides compounds that demonstrate anti-tumor activity in clonogenic survival assays and in vivo. For example, the polyphenylurea compound TPI 1396-34 decreased clonogenic survival of various cancer cell lines in a concentration dependent manner (see Example XV and FIG. 32). In addition, as disclosed herein, polyphenylurea compounds such as TPI 1396-34 and TPI 1396-22 have anti-tumor activity in vivo. For example, these compounds significantly reduced tumor size and tumor weight in human tumor xenografts grown in immunocompromised mice (see Example XV and FIG. 32 and 33). Additional studies confirmed that the polyphenylurea compounds of the invention function in vivo by modulating caspase activity (see FIG. 40), and that XIAP protein is indeed the target of these compounds in vivo (see FIG. 38).

The invention further provides a kit, including at least one compound of the invention that has activity as a derepressor of an IAP-inhibited caspase and a second compound having therapeutic activity. A compound of the invention that can be included in a kit includes, for example, a compound having a core peptide selected from the group consisting of Core peptides 4 through 39 and 42 through 55, or having a core structure selected from any of the structures shown in FIGS. 5, 9, 10, 12, 14B, 21–24, 34, 35, 36, 37 and 43, wherein the compound derepresses an IAP-inhibited caspase. Such kits are useful, for example, in the treatment of a condition characterized by a pathologically reduced level of apoptosis. For example, a kit including VP-16 with either TPI 792-33 or TPI 792-35 can be used to treat prostate cancer.

A suitable kit includes compounds as separately packaged formulations or in a mixed formulation, so long as the compounds are provided in an amount sufficient to have a therapeutic effect following at least one administration of each compound. The formulations can be any of those described above, or otherwise known to be appropriate for the particular compound and mode of administration.

The contents of a kit of the invention are housed in packaging material or other suitable physical structure, preferably to provide a sterile, contaminant-free environment. In addition, the packaging material contains instructions indicating how the materials within the kit can be administered for treatment of a condition characterized by a pathologically reduced level of apoptosis. The instructions for use typically include a tangible expression describing the route of administration or, if required, methods for preparing the formulation for administration. The instructions can also include identification of potential effects from use of the kit's contents or a warning regarding improper use of the contents of the kit.

The invention provides a method of identifying an agent that derepresses an IAP-inhibited caspase. The method includes the steps of (a) contacting an IAP and a caspase with an agent suspected of being able to derepress an IAP-inhibited caspase, wherein the caspase is an IAP-inhibited caspase that is inhibited by the IAP, wherein the contacting occurs under conditions that allow caspase activity in the absence of the IAP; and (b) detecting derepression of the IAP-inhibited caspase.

Derepression of the IAP-inhibited caspase can be detected as an increase in an IAP-inhibited caspase activity including, for example, proteolytic activity.

Proteolytic activity can be measured in an in vitro assay using a specific substrate. For example, a continuous fluorometric assay can be used to measure hydrolysis rates by following release of either 7-amino-4-trifluoromethyl-coumarin (AFC) from DEVD (SEQ ID NO:2) that is derivatized with a C-terminal aminomethylcoumarin, YVAD (SEQ ID NO:3) that is derivatized with a C-terminal aminomethylcoumarin (Tyr-Val-Ala-Asp-aminomethylcoumarin), or carbobenzoxy-Glu-Val-Asp-aminomethylcoumarin; or by following the release of p-nitroanilide (pNA) from similar peptides labeled with pNA, as described in U.S. Pat. No. 6,228,603 B1.

An immunoblot or other chromatography based assay can be used to detect proteolysis of a substrate by caspase according to altered molecular weight of the products compared to the substrate. For example, the proteolytic activity of an upstream initiator caspase, such as caspase-9, can be determined based on processing of a downstream effector pro-caspase, such as pro-caspase-3, to the mature form in an immunoblot assay as described in U.S. Pat. No. 6,228,603 B1. Comparison of the results of such an assay for an IAP-inhibited caspase in the presence and absence of an agent of the invention can be used to identify a derepressor of the IAP-inhibited caspase according to a relative increase in caspase activity in the presence of the agent.

Proteolytic activity of a caspase can also be determined by identifying morphological changes in a cell or a cell nucleus characteristic of apoptosis. Such changes that are characteristic of apoptosis include, for example, chromatin condensation, nuclear fragmentation, cell shrinkage, or cell blebbing leading to the eventual breakage into small membrane surrounded fragments termed apoptotic bodies. Thus, an agent that is a derepressor of an IAP-inhibited caspase can be identified according to the ability to cause a characteristic apoptotic change when added to a cell that is prevented from undergoing apoptosis by an IAP-inhibited caspase. A similar assay can be performed on a cell free extract derived from such a cell so long as an apoptotic change such as chromatin condensation or nuclear fragmentation can be distinguished in the presence and absence of the added agent.

Derepression of an IAP-inhibited caspase can also be detected as disassociation of an IAP-caspase species. An IAP-inhibited caspase can be identified as a caspase having an associated IAP using binding assays known in the art. Such a complex can be identified according to molecular weight or size using, for example, non-denaturing polyacrylamide gel electrophoresis, size exclusion chromatography, or analytical centrifugation. An IAP-caspase complex can also be identified using a co-precipitation technique. For example, an IAP-caspase complex can be identified due to the ability of an antibody to co-precipitate with both partners but not with one or the other partner alone. Similar, techniques can be used when either the IAP or caspase has been modified by a recombinant DNA method to incorporate an affinity tag such as glutathione-S-transferase (Amersham Pharmacia; Piscataway, N.J.), which can be precipitated with glutathione beads; polyhistidine tag (Qiagen; Chatsworth, Calif.), which can be precipitated with Nickel NTA sepharose; antibody epitopes such as the flag peptide (Sigma; St Louis, Mo.), which can be immunoprecipitated; or other known affinity tag. An agent that prevents IAP-caspase complex formation or otherwise causes dissociation of the complex can be identified in such an assay as a derepressor of an IAP-inhibited caspase.

The caspases are present in cells as precursor polypeptides referred to as procaspases. Caspase activation occurs due to proteolytic processing of the procaspase. For example, caspase-3 is a heterotetramer composed of approximately 17–20 kDa and 11 kDa polypeptides that are formed by proteolysis of a 32 kDa polypeptide precursor, pro-caspase-3. Cleavage of the pro-caspase-3 proceeds in two steps. The first cleavage results in production of a partially processed, subunit of about 11 kDa. In the second step, the pro-domain is cleaved from the partially processed large subunit, probably by an autocatalytic process, to produce the 17–20 kDa mature, fully processed large subunit of the caspase-3 enzyme. Removal of the pro-domain, however, is not necessary for protease activation, as the partially processed caspase also has caspase activity.

The methods of the invention for identifying an agent that derepresses an IAP-inhibited caspase can be used to identify a caspase that is prevented from being processed to a mature, fully proteolytically active form due to the presence of an IAP. For example, the methods can be used to identify an agent that prevents or suppresses an IAP from inhibiting processing of a procaspase to a caspase. Because processing of a procaspase to a caspase will coincide with an increase in caspase proteolytic activity, the methods described above for determining proteolytic activity can be used in a method for identifying an agent that prevents or suppresses an IAP from inhibiting processing of a procaspase to a caspase. Similarly, a binding assay, such as those described above, can be used to identify a procaspase-IAP complex according to the combined molecular weight of the partners. An agent that prevents complex formation or causes the complex to dissociate can be identified in such an assay as a derepressor of an IAP-inhibited caspase. A caspase that is prevented from being processed to a mature, fully proteolytically active form due to the presence of an IAP can also be identified according to differences in molecular weight or size of the mature and procaspase forms. Thus, an agent that, when contacted with a procaspase in the presence of an inhibitory IAP, causes a change in molecular weight or size indicative of the mature form can be identified as a derepressor of an IAP-inhibited caspase.

The methods of the invention can be used to identify a derepressor of an IAP-inhibited caspase that has specificity for a particular IAP or caspase or combination of a particular IAP and caspase. For example, the invention provides screening assays for identifing agents that alter the specific binding of a eukaryotic IAP such as XIAP, c-IAP-1 or c-IAP-2 and a caspase such as caspase-3, caspase-7 or caspase-9. Any IAP, including any eukaryotic IAP, can be used in a method of the invention in combination with the appropriate caspase. Other IAP proteins that are involved in regulating particular caspases can be identified using the methods disclosed herein, then the particular combination of caspase and IAP can be used in a screening assay to identify an agent that modulates the regulation of caspase activation by the IAP or that alters the specific association of the IAP and caspase.

As disclosed herein, invention core peptides were identified by screening combinatorial libraries having core tetrapeptide and hexapeptide structures. In view of the disclosed methods, the skilled artisan would recognize that combinatorial libraries of peptides having more than six amino acids or less than four amino acids also can be screened to identify other core peptides that derepress an IAP-inhibited caspase. Furthermore, while the disclosed methods can be used to initially identify core peptides that derepress an IAP-inhibited caspase, those skilled in the art would know that the methods can be used in an iterative fashion to optimize or to identify additional core peptides that derepress an IAP-inhibited caspase, as described below.

It is expected that those skilled in the art can use combinatorial synthetic methods coupled to rapid screening methods to optimize and identify additional derepressors with increased binding affinity for an IAP or increased activity in derepressing an IAP-inhibited caspase, thereby possessing enhanced therapeutic potential.

The iterative approach is well-known in the art and is set forth, in general, in Houghten et al., *Nature*, 354, 84–86

(1991); and Dooley et al., *Science,* 266, 2019–2022 (1994); both of which are incorporated herein by reference. In the iterative approach, for example, sublibraries of a molecule having three variable groups are made wherein the first variable is defined. Each of the compounds with the defined variable group is reacted with all of the other possibilities at the other two variable groups. These sub-libraries are each tested to define the identity of the second variable in the sub-library having the highest activity in the screen of choice. A new sub-library with the first two variable positions defined is reacted again with all the other possibilities at the remaining undefined variable position. As before, the identity of the third variable position in the sub-library having the highest activity is determined. If more variables exist, this process is repeated for all variables, yielding the compound with each variable contributing to the highest desired activity in the screening process. Promising compounds from this process can then be synthesized on larger scale in traditional single-compound synthetic methods for further biological investigation.

The positional-scanning approach has been described for various organic libraries and for various peptide libraries (see, for example, R. Houghten et al. PCT/US91/08694 and U.S. Pat. No. 5,556,762, both of which are incorporated herein by reference). In the positional scanning approach sublibraries are made defining only one variable with each set of sublibraries and all possible sublibraries with each single variable defined (and all other possibilities at all of the other variable positions) is made and tested. From the instant description one skilled in the art could synthesize libraries wherein 2 fixed positions are defined at a time. From the testing of each single-variable defined library, the optimum substituent at that position is determined, pointing to the optimum or at least a series of compounds having a maximum of the desired biological activity. Thus, the number of sublibraries for compounds with a single position defined will be the number of different substituents desired at that position, and the number of all the compounds in each sublibrary will be the product of the number of substituents at each of the other variables.

Phage display methods provide a means for expressing a diverse population of random or selectively randomized peptides. Various methods of phage display and methods for producing diverse populations of peptides are well known in the art. For example, Ladner et al. (U.S. Pat. No. 5,223,409, issued Jun. 29, 1993) describe methods for preparing diverse populations of binding domains on the surface of a phage. In particular, Ladner et al. describe phage vectors useful for producing a phage display library, as well as methods for selecting potential binding domains and producing randomly or selectively mutated binding domains.

An invention derepressor of an IAP-inhibited caspase that contains peptide moieties can be synthesized using amino acids, the active groups of which are protected as required using, for example, a t-butyloxycarbonyl (t-BOC) group or a fluorenylmethoxy carbonyl (FMOC) group. Amino acids and amino acid analogs can be purchased commercially (Sigma Chemical Co., St. Louis Mo.; Advanced Chemtec, Louisville Ky.) or synthesized using methods known in the art. Peptides synthesized using the solid phase method can be attached to a variety of resins, including, for example, 4-methylbenzhydrylamine (MBHA), 4-(oxymethyl)-phenylacetamido methyl and 4-(hydroxymethyl) phenoxymethyl-copoly(styrene-1% divinylbenzene (Wang resin), all of which are commercially available, or to p-nitrobenzophenone oxime polymer (oxime resin), which can be synthesized as described by De Grado and Kaiser, *J. Org. Chem.* 47:3258 (1982).

The choice of amino acids or amino acid analogs incorporated into an invention peptide will depend, in part, on the specific physical, chemical or biological characteristics required of the derepressor of an IAP-inhibited caspase. Such characteristics are determined by whether, for example, the peptide is to be used in vivo or in vitro, and, when used in vivo, by the route by which the invention peptide will be administered or the location in a subject to which it will be directed. For example, the derepressor of IAP-inhibited caspase core peptides exemplified herein can be synthesized using only L-amino acids. However, the skilled artisan would know that any or all of the amino acids in a peptide of the invention can be a naturally occurring L-amino acid, a non-naturally occurring D-amino acid or an amino acid analog, provided the peptide can derepress an IAP-inhibited caspase.

The choice of including an L-amino acid or a D-amino acid in the invention peptides depends, in part, on the desired characteristics of the peptide. For example, the incorporation of one or more D-amino acids can confer increased stability on the peptide in vitro or in vivo. The incorporation of one or more D-amino acids also can increase or decrease the activity, such as IAP binding affinity, of the peptide as determined, for example, using the assay described herein in Example VII or other well known methods for determining the binding affinity of a particular peptide to a particular protein.

As set forth above, invention peptides can be either linear, cyclic or multivalent, and the like, which conformations can be achieved using methods well-known in the art. As used herein a "cyclic" peptide refers to analogs of synthetic linear peptides that can be made by chemically converting the structures to cyclic forms. Cyclization of linear peptides can modulate bioactivity by increasing or decreasing the potency of binding to the target protein (Pelton, J. T., et al., *Proc. Natl. Acad. Sci. U.S.A.,* 82:236–239). Linear peptides are very flexible and tend to adopt many different conformations in solution. Cyclization acts to constrain the number of conformations available in solution, and thus, can favor a conformation having a higher affinity for IAP or more potent activity as a derepressor of an IAP-inhibited caspase.

Cyclization of linear peptides is accomplished either by forming a peptide bond between the free N-terminal and C-terminal ends (homodetic cyclopeptides) or by forming a new covalent bond between amino acid backbone and/or side chain groups located near the N- or C-terminal ends (heterodetic cyclopeptides) (Bodanszky, N., 1984, supra). The latter cyclizations use alternate chemical strategies to form covalent bonds, e.g. disulfides, lactones, ethers, or thioethers. Linear peptides of five or more amino acid residues, as described herein, can be cyclized relatively easily. The propensity of the peptide to form a beta-turn conformation in the central four residues facilitates the formation of both homo- and heterodetic cyclopeptides. The presence of proline or glycine residues at the N- or C-terminal ends also facilitates the formation of cyclopeptides, especially from linear peptides shorter than six residues in length.

An agent of the invention can be multivalent with respect to the number of derepressor IAP-inhibited caspase sequences or moieties are present per molecule. The sequences or moieties present in a multivalent agent can be either the same or different. Exemplary multivalent peptides can be produced using the well-known multiple antigen peptide system (MAPS; see, e.g., Briand et al., 1992, *J. Immunol Meth.*, 156(2):255–265; Schott et al., 1996, *Cell Immun.*, 174(2):199–209, and the like). An agent that is multivalent with respect to the number of derepressor IAP-inhibited caspase sequences or moieties present can be useful for interacting with an IAP having more than one BIR domain. For example, a single agent can be made to contain two or more sequences or moieties that interact with separate BIR domains on the same IAP. The presence of multiple interacting partners in the multivalent agent and IAP can increase affinity or specificity of the interaction.

In some cases, it can be desirable to allow a derepressor of an IAP-inhibited caspase to remain active for only a short period of time. In those cases, the incorporation of one or more L-amino acids in the agent can allow, for example, endogenous peptidases in a subject to digest the agent in vivo, thereby limiting the subject's exposure to the derepressor. In one embodiment, the agent, whether based on a peptide backbone or other structure, can include a peptide linkage through an L-aspartate moiety or residue. Degradation of the L-aspartate containing agent by the caspases that it derepresses can provide a feedback control mechanism minimizing the extent of apoptosis allowed by the agent. The skilled artisan can determine the desirable characteristics required of an invention agent by taking into consideration, for example, the age and general health of a subject, and the like. The half life in a subject of a peptide having, for example, one or more D-amino acids substituted for a corresponding L-amino acid can be determined using methods well known to those in the field of pharmacology.

Selective modification of the reactive groups in a peptide also can impart desirable characteristics to a derepressor of an IAP-inhibited caspase. An invention peptide can be manipulated while still attached to the resin to obtain, for example, an N-terminal modified peptide such as an N-acetylated peptide. Alternatively, the peptide can be removed from the resin using hydrogen fluoride or an equivalent cleaving reagent and then modified. Agents synthesized containing the C-terminal carboxy group (Wang resin) can be modified after cleavage from the resin or, in some cases, prior to solution phase synthesis. Methods for modifying the N-terminus or C-terminus of a peptide are well known in the art and include, for example, methods for acetylation of the N-terminus and methods for amidation of the C-terminus.

Also encompassed within the scope of invention peptides are peptide analogs. As used herein, the term "peptide analog" includes any peptide having an amino acid sequence substantially the same as a sequence specifically shown herein, such as Core peptides 1 through 55, in which one or more residues have been conservatively substituted with a functionally similar residue and which displays the ability to functionally mimic an invention lectin-binding peptide as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another.

As used herein the phrase "conservative substitution" also includes the use of a chemically derivatized residue in place of a non-derivatized residue, provided that such peptide displays the required IAP binding or inhibiting activity. A chemical derivative can include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Peptides of the present invention also include any peptide having one or more additions, deletions or combination of additions and deletions of residues, relative to the sequence of a peptide whose sequence is shown herein, so long as the required IAP binding or inhibiting activity is maintained.

Those skilled in the art will recognize from the guidance provided herein that an agent of the invention can include a core peptide or core structure that is modified, derivatized, or substituted with an analogs or derivative so long as the agent is capable of derepressing an IAP-inhibited caspase. Such alterations in a core peptide or core structure can be made by well known synthetic methods such as those described herein. An agent so altered can be tested for activity using the methods described herein such as the derepression assay described in Example I or the polarization binding assay described in Example VII.

An agent identified as a derepressor of an IAP-inhibited caspase can be tested using an assay for determining caspase proteolytic activity or binding of IAP and caspase in the presence or absence of the agent including, for example, the assays described above. An agent that is identified as capable of derepressing an IAP-inhibited caspase using such assays can be further combinatorialized at one or more positions using the iteration approach described above. Alternatively, an identified derepressor or plurality of derepressors can be used as a basis for the rational design of second generation agents. For example, common structural features between a plurality of validated agents can be used to guide the synthesis of a generalized structure incorporating those shared features. Structural information regarding an agent when bound to an IAP or caspase can also be used to design a second generation agent that retains or improves upon moieties identified as providing favorable interactions while removing moieties that lead to unfavorable interactions with the caspase or IAP.

The invention provides structure activity relationship (SAR) information of polyphenylurea compounds which is used in designing optimized second generation agents (see Example XVI and Table X and XI). A series of compounds, shown in FIG. 34 (TPI 1509), were synthesized based on the TPI 1396 polyphenylurea compounds. All of these compounds were active in the XIAP derepression assay. Therefore, the invention provides an isolated agent having a core structure selected from any of the structures shown in FIG. 34 where the agent derepresses an IAP-inhibited caspase. In addition, modifications of R groups of a compound from the TPI 1509 series are provided herein in Example XVII (see also FIG. 35). As understood by one skilled in the art, these types of R group modifications can be used for other polyphenylurea compounds such as those in the TPI 1396 library.

The invention provides a method of identifying an agent that derepresses an IAP-inhibited caspase. The method includes the steps of (a) detecting a labeled derepressor of an IAP-inhibited caspase bound to an IAP or caspase; (b) contacting the bound IAP or caspase with a candidate agent, the candidate agent suspected of being able to derepress an IAP-inhibited caspase; and (c) detecting dissociation of the labeled derepressor of an IAP-inhibited caspase from the IAP or caspase, whereby the candidate agent is identified as an agent that derepresses an IAP-inhibited caspase. A labeled derepressor of an IAP-inhibited caspase used in the method can have a core motif selected from a core peptide of the invention such as Core peptides 4 through 39 and 42 through 55 or a core structure selected from TPI 759, TPI 882, TPI 914, TPI 927, or a compound having a structure selected from TPI 1391, TPI 1349, TPI 1400, TPI 1396, TPI 1509, TPI 1540, TPI 1577, TPI 1567, TPI 1572, TPI 792 and TPI 1332. The methods can be used to identify a better derepressor of an IAP-inhibited caspase in a screening format as described above and in the Examples.

Figure 26:
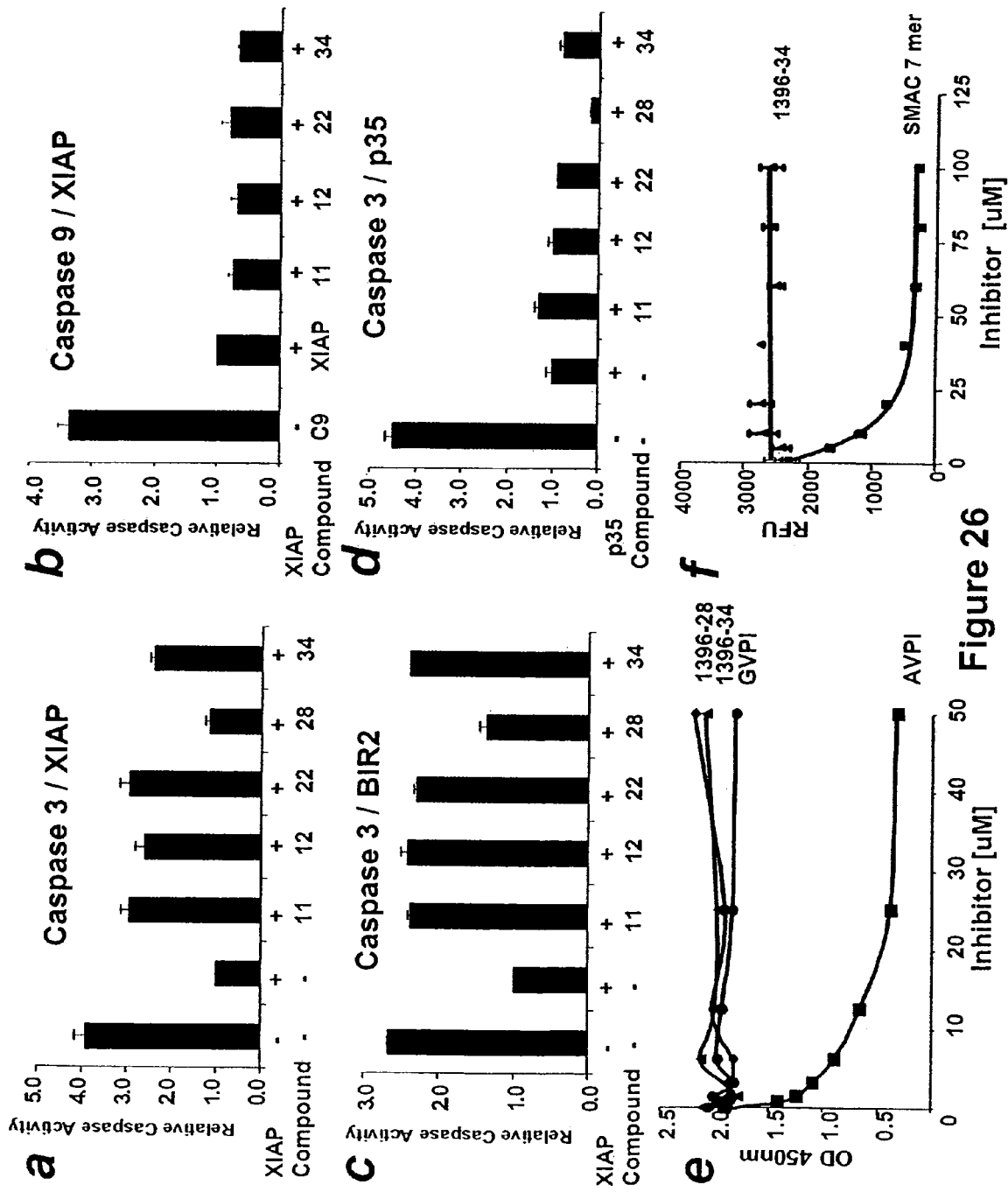
FIG. 26a, b, c, d, e, and f show characterization of the biochemical mechanism of poly-phenylurea compounds.
FIG. 26e shows a binding assay where biotinylated SMAC (7-mer) was adsorbed to Neutravidin-coated plates then GST-XIAP was added with or without compounds. Bound GST-XIAP was detected with an anti-GST antibody.
FIG. 26f shows a binding assay where GST-XIAP was adsorbed to plates and then incubated with biotinylated-SMAC (7-mer) with or without compounds. Bound biotinylated-SMAC peptide was detecting by a streptavidin-europium-based fluorescence method.
Figure 42:
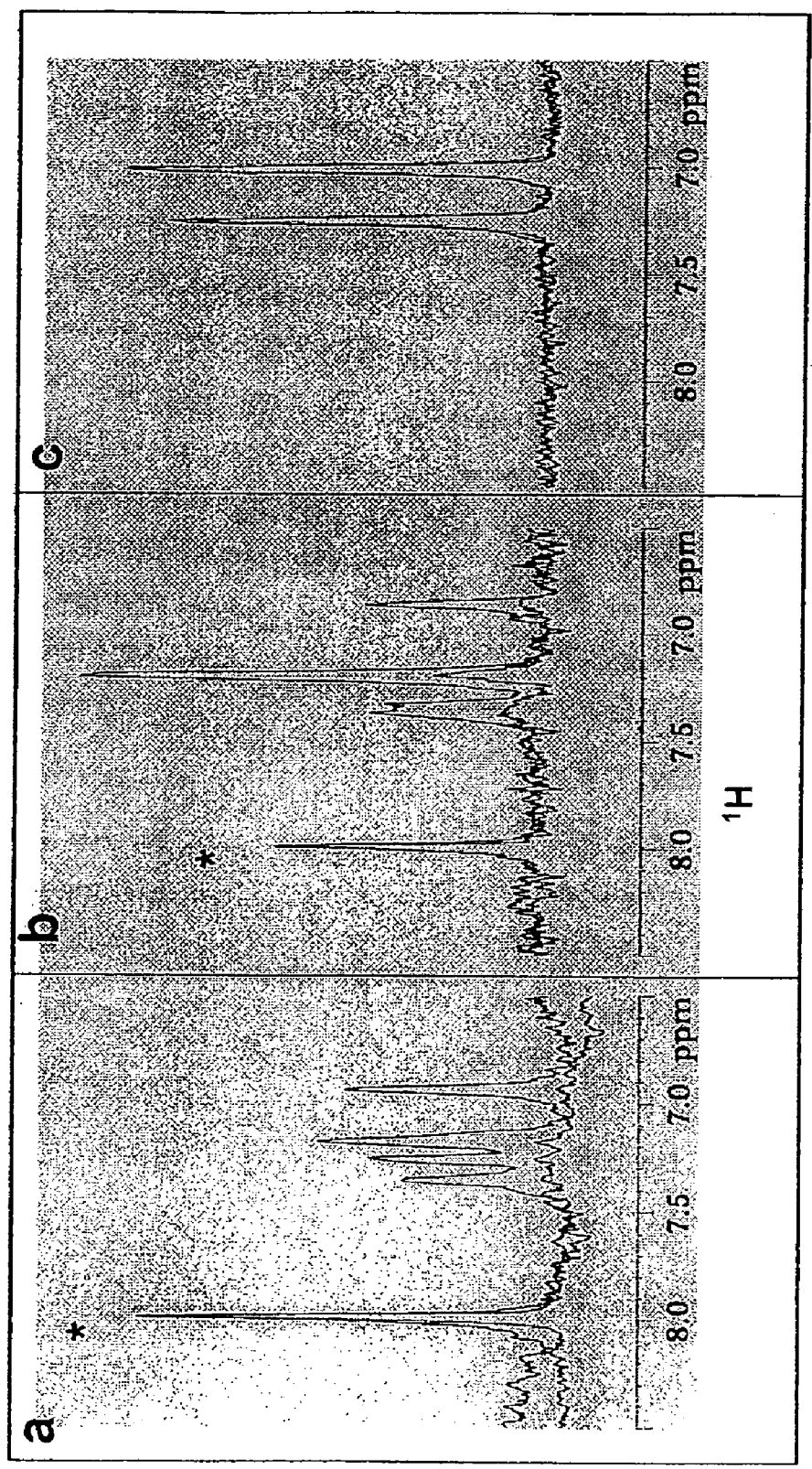
FIG. 42 shows that both TPI 1540-14 (a) and TPI 1540-15 (b) selectively binds to the BIR2 domain of XIAP, while inactive compound TPI 1540-20 does not (c).
Figure 45:
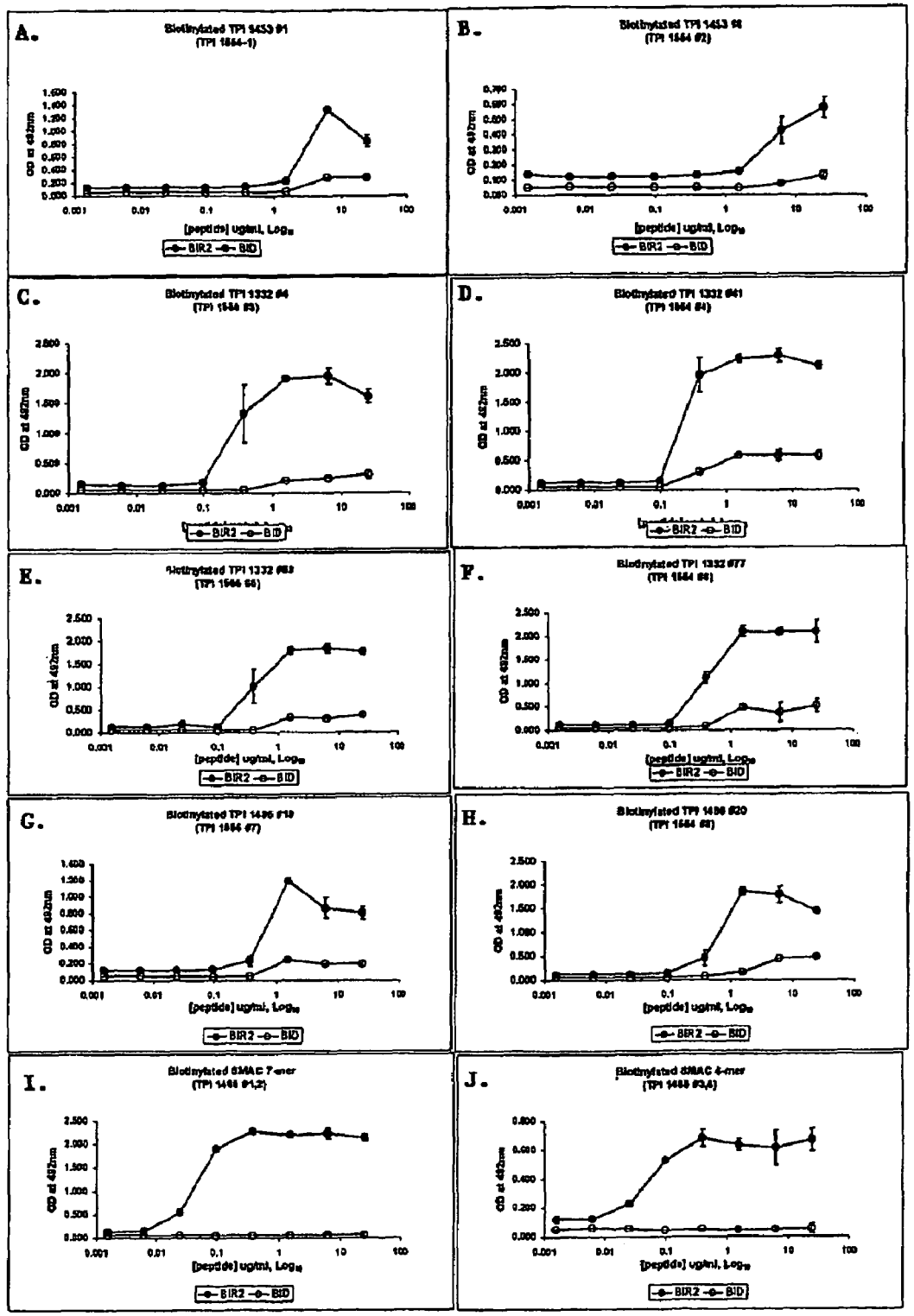
FIGS. 45A–J show binding of BID and XIAP-BIR2 to biotinylated peptides as follows: (A) TPI 1453-1 (TPI 1554-1); (B) TPI 1453-6 (TPI 1554-2); (C) TPI 1332-4 (TPI 1554-3);(D) TPI 1332-41 (TPI 1554-4); (E) TPI 1332-69 (TPI 1554-5); (F) TPI 1332-77 (TPI 1554-6);(G) TPI 1495-19 (TPI 1554-7); (H) TPI 1495-20 (TPI 1554-8); (I) SMAC 7-mer (TPI 1465-1, -2);and (J) SMAC 4-mer (TPI 1465-3, -4).
Figure 46:
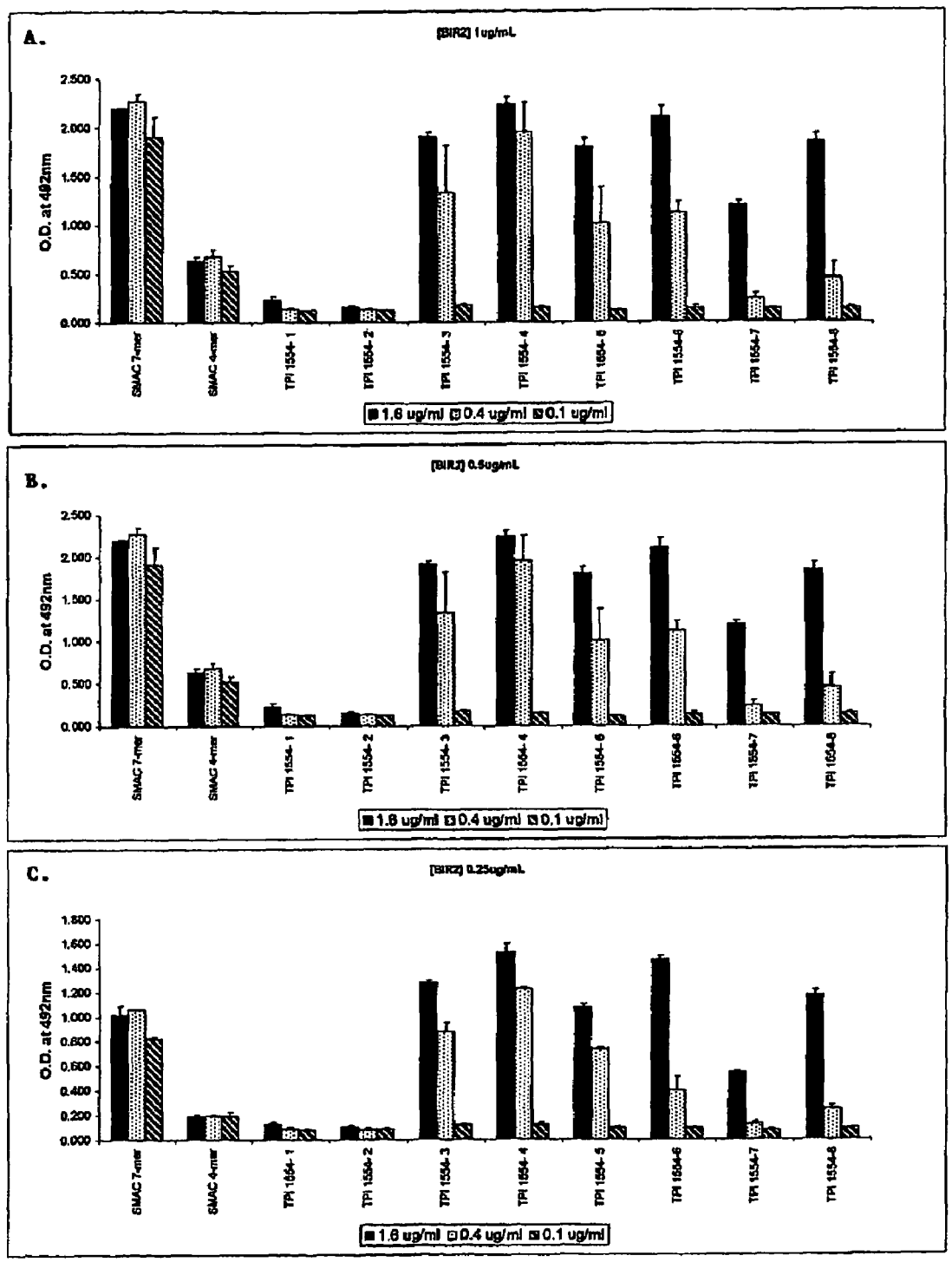
FIGS. 46A–C show binding of three concentrations of XIAP-BIR2 to biotinylated tetrapeptides, with FIG. 46A showing results using 1μg/ml XIAP BIR2.
Figure 47:
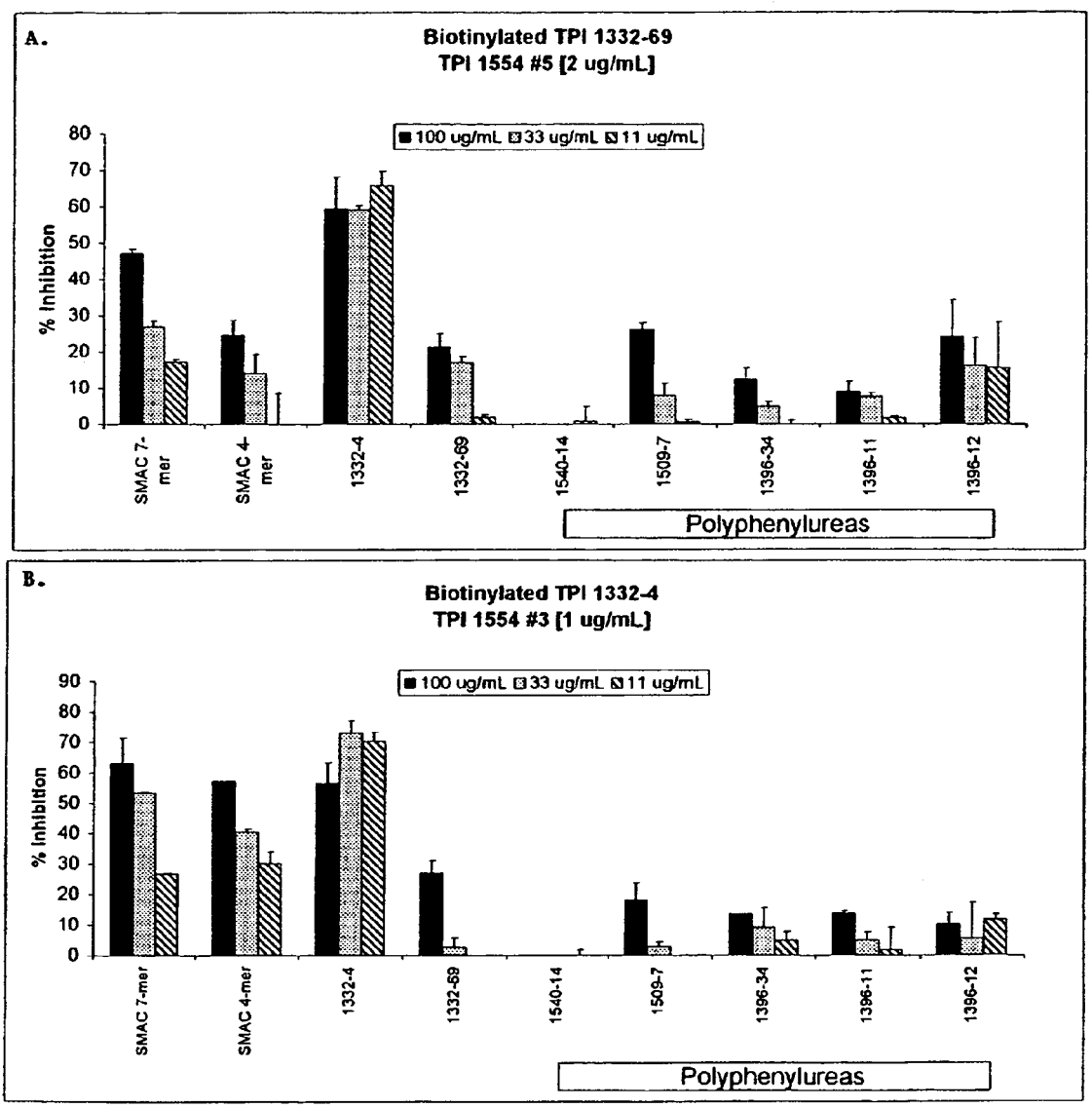
FIG. 47 shows competition of the binding of biotinylated tetrapeptides with XIAP-BIR2, using (A) biotinylated TPI 1332-69, which is a non-SMAC mimic; and (B) biotinylated TPI 1332-4, which is a SMAC mimic.
Figure 48:
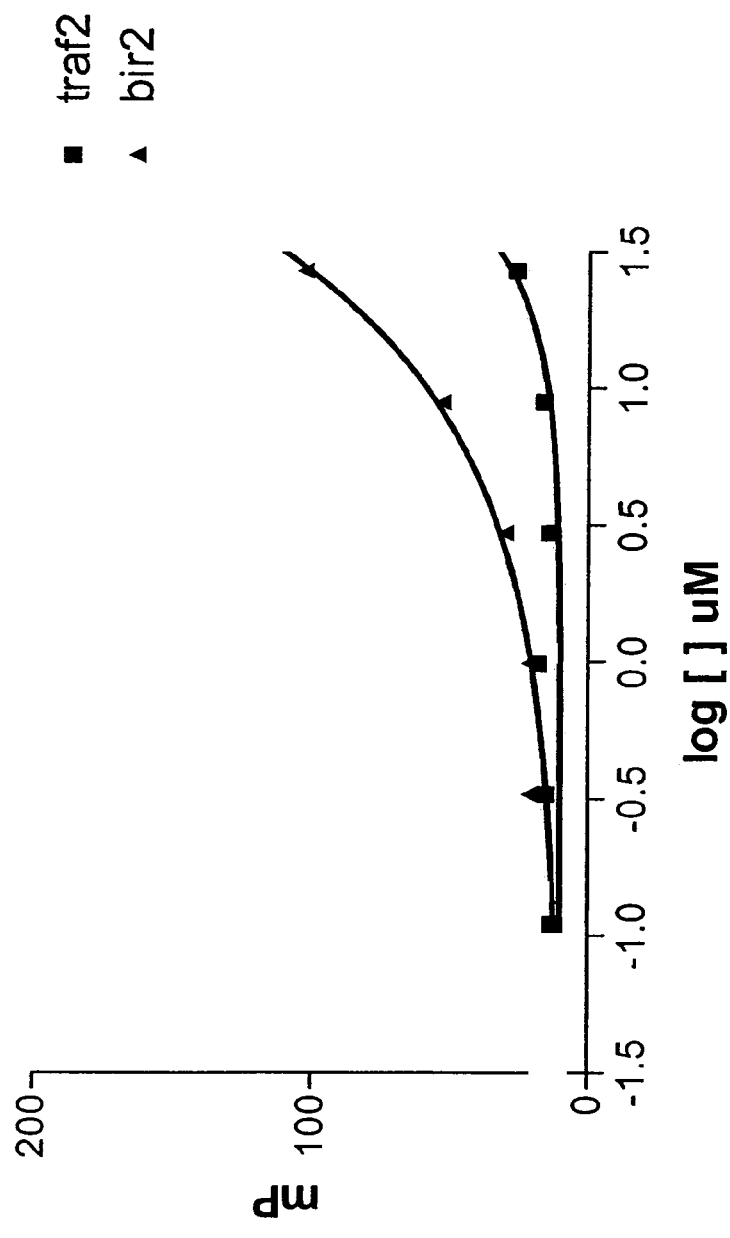
FIG. 48 shows binding of rhodamine labeled TPI-1332-4 (1566-11) to His-BIR2 of XIAP and His-Traf2 (negative protein control). Rhodamine labeled TPI 1332-4 was present at 2.4 μM in 50 mM KPi (potassium phosphate) at pH 7.4/50 mM NaCl. His-BIR2 of XIAP and His-Traf2 were present at 0, 0.11, 0.33, 0.99, 2.96, 8.89, 26,67 and 80 μM. Plates were incubated for 1 hour at room temperature and read in an LJL Analyst HT in fluorescence polarization mode with rhodamine filters (excitation 530 nm; emission 580 nm) and a rhodamine dichroic mirror at 565 nm. Data was fit in Prism™ by non-linear regression for a sigmoidal dose-response curve with variable slope.

The invention also provides a novel negative regulatory binding site on an IAP. The novel negative regulatory binding site identified herein does not bind to the SMAC peptide (also known as DIABLO). The SMAC peptide is known to bind to IAPs such as XIAP through the BIR3 domain of the IAP (Liu et al, Nature 408:1004–1008 (2000)). As disclosed herein in FIG. 26, an active polyphenylurea compound such as TPI 1396-34 does not compete with biotin-SMAC 7-mer peptide AVPIAQK (SEQ ID NO: 5) for binding to XIAP. As further disclosed herein in Example XVII and FIG. 36, an active tetrapeptide compound such as TPI 1332-69 or TPI 1332-4 does not compete with biotin-SMAC 7-mer peptide AVPIAQK (SEQ ID NO: 5) for binding to XIAP. Therefore, disclosed herein are compounds that act through a non-SMAC binding site on an IAP such as XIAP. As is further disclosed herein, the non-SMAC binding site of XIAP has been identified to be the BIR2 domain. The ability of polyphenylurea compounds of the invention to derepress XIAP BIR2 domain-inhibited caspase is disclosed herein, for example, in FIGS. 21C, 22E, 23E and 24G. In addition, the ability of polyphenylurea compounds of the invention to bind directly to BIR2 is shown in FIG. 42 and described in Example XXIV.

These results indicate that agent that derepresses an IAP-inhibited caspase can function by binding to a BIR domain of the IAP and thereby reducing the ability of the BIR domain to block caspase-IAP function. Therefore, the invention provides a method of identifying an agent that derepresses an XIAP-inhibited caspase that involves (a) contacting a caspase and an BIR domain, wherein the BIR domain is capable of inhibiting the caspase, under conditions that allow caspase activity in the absence of the BIR domain, with a candidate agent, and (b) detecting caspase activity, wherein an increase in the activity of the inhibited caspase identifies an agent that derepresses an IAP-inhibited caspase.

The method of the invention for identifying an agent that derepresses an IAP-inhibited caspase involves contacting a caspase with a BIR domain that is capable of inhibiting the caspase. Any BIR domain that is capable of inhibiting a caspase can be used in the methods of the invention. The ability of a BIR domain to inhibit caspase activity can be determined using a variety of well known methods, for example, by determining a lower level of hydrolysis of a specific substrate by the caspase in the presence of the BIR domain as compared to the activity in the absence of the BIR domain. Given the role of caspases in apoptosis, it will be recognized by those skilled in the art that caspase activity can be identified directly, for example, by examining proteolysis (hydrolysis) of a specific substrate or indirectly, for example, by identifying morphological changes in a cell or cell nucleus characteristic of apoptosis. Exemplary assays for detecting caspase activity are described herein above and in Example I. An example of a BIR domain capable of inhibiting caspase-3 is the BIR2 domain of XIAP (see Example VIII).

The invention further provides a method of identifying an agent that derepresses an IAP-inhibited caspase by (a) detecting a labeled derepressor of an IAP-inhibited caspase bound to a non-SMAC binding site on the IAP; (b) contacting the bound IAP or caspase with a candidate agent, the candidate agent suspected of being able to derepress an IAP-inhibited caspase; and (c) detecting dissociation of the labeled derepressor of an IAP-inhibited caspase from the IAP or caspase, whereby the candidate agent is identified as an agent that derepresses an IAP-inhibited caspase. In one embodiment, the labeled derepressor is based on a core structure from the TPI 1332 or TPI 1396 library. In another embodiment, the non-SMAC binding site on the IAP is a site bound by TPI 1332-69 or TPI 1332-4.

In a further embodiment, the non-SMAC binding the on IAP is a BIR domain. Therefore, the method can be practiced by (a) detecting a labeled derepressor of a BIR domain-inhibited caspase, the derepressor bound to the BIR domain of a BIR domain-caspase complex; (b) contacting the BIR domain-caspase complex with a candidate agent, the candidate agent suspected of being able to derepress a BIR domain-inhibited caspase, and (c) detecting dissociation of the labeled derepressor of the BIR domain-inhibited caspase from the complex, wherein the derepressor is selected from an isolated agent comprising a core structure selected from TPI 1391, TPI 1349, TPI 1396, TPI 1509, TPI 1540, TPI 1400, TPI 792 and TPI 1332, whereby the candidate agent is identified as an agent that derepresses an IAP-inhibited caspase.

As is described in Example XXIV, a compound of the invention that derepresses an XIAP-inhibited caspases can bind directly to the BIR2 domain of XIAP. It is recognized that an agent capable of competing with a compound of the invention that binds to a BIR2 domain will also bind to the BIR2 domain at a site important for derepression activity. Therefore, the invention provides a method for identifying an agent that derepresses an IAP-inhibited caspase based on the ability of the agent to compete with a compound of the invention for binding to a BIR2 domain. The method involves (a) contacting a BIR2 domain with a candidate agent in the presence of a derepressor of an IAP-inhibited caspase, under conditions wherein the BIR2 domain binds to the derepressor, and (b) detecting dissociation of the derepressor from the BIR2 domain, whereby the candidate agent is identified as an agent that derepresses an IAP-inhibited caspase, wherein the derepressor is selected from an isolated agent comprising a core structure selected from TPI 1391, TPI 1349, TPI 1396, TPI 1509, TPI 1540, TPI 1400, TPI 792 and TPI 1332.

A variety of assays are well known in the art that can be used to identify an agent that derepresses an IAP-inhibited caspase. Such methods include binding assays where candidate agents are added to a complex that contains a derepressor and an IAP such as XIAP. The derepressor or IAP can be immobilized, for example to a latex bead or plate or can be free in solution. The derepressor, IAP or candidate agent can be conjugated to a radiolabel, fluorescent label or enzyme label such as alkaline phosphatase, horse radish peroxidase or luciferase. For example, a candidate agent can be added to a complex which contains an IAP and a labeled derepressor, for example, where the IAP is immobilized on a solid support such as a latex bead. The amount of labeled derepressor that is displaced by the candidate agent can then be determined. Alternatively, this assay can be performed where the IAP is not bound to a solid support but is free in solution. In addition, fluorescently labeled candidate compounds can also be added to a complex that contains a derepressor and IAP and bound complexes that contain the labeled candidate agent can be detected, for example, using a fluorescence polarization assay (Degterev et al., *Nature Cell Biology* 3:173–182 (2001)).

One skilled in the art understands that a variety of additional means can be used to determine whether a candidate agent is an agent that derepresses an IAP-inhibited caspase or whether the candidate agent can displace a derepressor bound to an IAP. For example, a scintillation proximity assay (Alouani, *Methods Mol. Biol.* 138:135–41 (2000)) can be used. Scintillation proximity assays involve the use of a fluomicrosphere coated with an acceptor molecule, such as an antibody, to which an antigen will bind selectively in a reversible manner. For example, an IAP-derepressor complex can be bound to a fluomicrosphere using an antibody that specifically binds to the IAP, and contacted with a $^3$H or $^{125}$I labeled FP candidate agent. If the labeled candidate agent specifically binds to the IAP, the radiation energy from the labeled candidate agent is absorbed by the fluomicrosphere, thereby producing light which is easily measured.

Additional assays suitable for identifying an agent that derepresses an IAP-inhibited caspase and for determining specific binding of a candidate agent to an XIAP after displacing a derepressor can include, without limitation, UV or chemical cross-linking assays (Fancy, *Curr. Opin. Chem. Biol.* 4:28–33 (2000)) and biomolecular interaction analyses (Weinberger et al., *Pharmacogenomics* 1:395–416 (2000)). Specific binding of a candidate agent to an IAP can be determined by cross-linking these two components, if they are in contact with each other, using UV or a chemical cross-linking agent. In addition, a biomolecular interaction analysis (BIA) can detect whether two components are in contact with each other. In such an assay, one component, such as an IAP-derepressor complex is bound to a BIA chip, and a second component such as a candidate agent is passed over the chip. If the candidate agent displaces the derepressor and binds to the IAP, the contact results in an electrical signal, which is readily detected.

Further assays suitable for identifying an agent that derepresses an IAP-inhibited caspase include those based on NMR methods. Such methods take advantage of the significant perturbations that can be observed in NMR-sensitive parameters of a candidate agent or its target, such as an IAP or domain thereof, that occur upon complex formation between the agent and target. These perturbations can be used to detect binding between a candidate agent and IAP, as well as to assess the strength of the binding interaction. In addition, some NMR techniques allow the identification of the agent binding site or which part of the agent is responsible for interacting with the target. Exemplary NMR methods useful for identifying an agent that derepresses an IAP-inhibited caspase include "SAR by NMR," which is described, for example, in Shuker et al. Science, 274, 1531–1534 (1996), and a variety of NMR-based screening assays, including SHAPES screening, fragment-based approaches for lead optimization using NMR, and fluorine-NMR competition binding experiments, all of which are described, for example, in *Combinatorial Chemistry & High Throughput Screening*, Vol. 5, No. 8 (2002) and in Hajduk et al., *Quarterly Reviews of Biophysics* 32(3):211–240 (1999).

Fluorescence-based assays are also suitable for identifying an agent that derepresses an IAP-inhibited caspase. Examples of fluorescence methods applicable to determining an interaction between an agent that derepresses an IAP-inhibited caspase and its corresponding target, such as an IAP or caspase, include observations fluorescence intensity changes resulting from an alteration in interaction between agent and target; fluorescence resonance energy transfer (FRET), which is useful for determining change in fluorescence intensity based on distance between agent and target; fluorescence polarization changes resulting a change in size of an observed binding partner when associated or dissociated from the another binding partner; fluorescence lifetime changes, and fluorescence correlation spectroscopy, which is based on translation diffusion, a parameter related to the size of an observed binding partner. Such methods can involve employing a fluorescently labeled agent or binding partner. For example, a fluorophore can be detected based on the excitation or emission wavelengths of the fluorophore, fluorescence polarization of the fluorophore, or intensity of fluorescence emitted from the fluorophore. Alternatively, detection can be based on a difference in a measurable property of the label for the bound and unbound state. For example, as demonstrated in Example VII, difference in fluorescence polarization due to the slower rotation of a substrate bound to an IAP compared to the unbound substrate can be used to detect association. Other measurable differences that can be used to determine association of a fluorophore-labeled agent with an IAP or caspase include, for example, different emission intensity due to the presence or absence of a quenching agent, difference in emission wavelength due to the presence or absence of a fluorescence resonance energy transfer (FRET) donor or acceptor, or difference in emission wavelength due to differences in fluorophore conformation or environment. A derepressor of an IAP-inhibited caspase used in a method of the invention can be labeled with any of a variety of labels including, for example, those described above. A labeled derepressor that is bound to an IAP or caspase can be detected according to a known measurable property of the label.

Dissociation of the labeled derepressor of an IAP-inhibited caspase from the IAP or caspase can be detected as absence or reduction in the amount of label from the IAP or caspase in the presence of a competitive binding candidate agent or as a reversal of a change that occurs upon association of the labeled agent with a caspase or IAP in the presence of a competitive binding candidate agent. Thus, dissociation can be detected in the presence of a non-labeled candidate agent as a reduction or loss of radioactivity of the IAP or caspase in the presence of a radionuclide labeled derepressor, reduction or loss of electromagnetic absorbance at a specified wavelength for the IAP or caspase in the presence of a chromophore labeled derepressor, reduction or loss of magnetic signal at a specified field strength or radio frequency for the IAP or caspase in the presence of a paramagnetic spin labeled derepressor or reduction or loss of a secondary label associated with the IAP or caspase in the presence of a derepressor that is labeled with a binding group for the secondary label. An example of dissociation measured by the reversal of a change occurring upon association is provided in Example VII, where a difference in polarization due to the faster rotation of a dissociated substrate compared to the IAP-bound substrate is used to detect dissociation.

Other changes in a property of a label that can be detected to determine association or dissociation of an appropriately labeled derepressor and IAP or caspase include, for example, absorption and emission of heat, absorption and emission of electromagnetic radiation, affinity for a receptor, molecular weight, density, mass, electric charge, conductivity, magnetic moment of nuclei, spin state of electrons, polarity, molecular shape, or molecular size. Properties of the surrounding environment that can change upon association or dissociation of an appropriately labeled derepressor and IAP or caspase include, for example, temperature and refractive index of surrounding solvent. Association and dissociation of a derepressor from an IAP or caspase can be measured based on any of a variety of properties of a labeled derepressor or of the complex between a derepressor and IAP or caspase using well known methods including, for example, equilibrium binding analysis, competition assays, and kinetic assays as described in Segel, *Enzyme Kinetics* John Wiley and Sons, New York (1975), and Kyte, *Mechanism in Protein Chemistry* Garland Pub. (1995).

In addition, virtual computational methods and the like can be used to identify compounds that can displace a derepressor in a screening method of the invention. Exemplary virtual computational methodology involves virtual docking of small-molecule agents on a virtual representation of an IAP or IAP-derepressor complex structure in order to determine or predict specific binding. See, for example, Shukur et al., supra, 1996; Lengauer et al., *Current Opinions in Structural Biology* 6:402–406 (1996); Choichet et al., *Journal of Molecular Biology* 221:327–346 (1991); Cherfils et al., *Proteins* 11:271–280 (1991); Palma et al., *Proteins* 39:372–384 (2000); Eckert et al., *Cell* 99:103–115 (1999); Loo et al., *Med. Res. Rev.* 19:307–319 (1999); Kramer et al., *J. Biol. Chem.* (2000).

The methods of the invention for identifying an agent that derepresses an IAP-inhibited caspase can be performed using low throughput or high throughput assay formats. Screening can be carried out in all plate formats, including for example, 96, 384 and 1536 well formats. In addition, assays such as those described above can be performed in kinetic-based or end point-based formats. To increase screening throughout, more than one candidate agent or caspase can be present in an assay sample. The number of different candidate agents to test in the methods of the invention will depend on the application of the method. For example, one or a small number of candidate agents can be screened using manual screening procedures, or when it is desired to compare efficacy among several candidate agents. However, it will be appreciate that the larger the number of candidate agents, the greater the likelihood of identifying a n agent having the desired activity in a screening assay. Additional, large numbers of candidate agents can be processed in high-throughput automated screening methods.

The invention further provides a method for identifying a derepressor of an IAP-inhibited caspase in a database. A database of molecules such as peptides or small molecules can be queried with the structure of a derepressor of an IAP-inhibited caspase to identify candidate agents having a moiety identical or similar to the query structure. A candidate agent identified in a database search can be synthesized, isolated or otherwise obtained using known methods and then tested for its level of activity as a derepressor of an IAP-inhibited caspase using the assays described above and in the Examples.

For peptide based derepressors, a query can be made to a database based on amino acid sequence (primary structure) or three dimensional structure (tertiary structure) or a combination of both to identify peptides or proteins having identical or substantially similar structures. Methods for comparing primary sequence structure which can be used to determine that two sequences are substantially the same are well known in the art as are databases including, for example, SwissProt and GenPept. For example, one method for determining if two sequences are substantially the same is BLAST, Basic Local Alignment Search Tool, which can be used according to default parameters as described by Tatiana et al., *FEMS Microbial Lett.* 174:247–250 (1999) or on the National Center for Biotechnology Information web page. BLAST is a set of similarity search programs designed to examine all available sequence databases and can function to search for similarities in amino acid or nucleic acid sequences. A BLAST search provides search scores that have a well-defined statistical interpretation. Furthermore, BLAST uses a heuristic algorithm that seeks local alignments and is therefore able to detect relationships among sequences which share only isolated regions of similarity including, for example, protein domains (Altschul et al., *J. Mol. Biol.* 215:403–410 (1990)).

In addition to the originally described BLAST (Altschul et al., supra, 1990), modifications to the algorithm have been made (Altschul et al., *Nucleic Acids Res.* 25:3389–3402 (1997)). One modification is Gapped BLAST, which allows gaps, either insertions or deletions, to be introduced into alignments. Allowing gaps in alignments tends to reflect biologic relationships more closely. For example, gapped BLAST can be used to identify sequence identity within similar domains of two or more polypeptides. A second modification is PSI-BLAST, which is a sensitive way to search for sequence homologs. PSI-BLAST performs an initial Gapped BLAST search and uses information from any significant alignments to construct a position-specific score matrix, which replaces the query sequence for the next round of database searching. A PSI-BLAST search is often more sensitive to weak but biologically relevant sequence similarities.

A second resource that can be used to determine if two sequences are substantially the same is PROSITE, available on the world wide web at ExPASy. PROSITE is a method of determining the function of uncharacterized polypeptides translated from genomic or cDNA sequences (Bairoch et al., *Nucleic Acids Res.* 25:217–221 (1997)). PROSITE consists of a database of biologically significant sites and patterns that can be used to identify which known family of polypeptides, if any, the new sequence belongs. Using this or a similar algorithm, a polypeptide that is substantially the same as another polypeptide can be identified by the occurrence in its sequence of a particular cluster of amino acid residues, which can be called a pattern, motif, signature or fingerprint, that is substantially the same as a particular cluster of amino acid residues in a reference polypeptide including, for example, those found in similar domains. PROSITE uses a computer algorithm to search for motifs that identify polypeptides as family members. PROSITE also maintains a compilation of previously identified motifs, which can be used to determine if a newly identified polypeptide is a member of a known family.

Tertiary structure of a derepressor of an IAP-inhibited caspase can be determined by a theoretical method such as ab initio protein folding using algorithms known in the art or by an empirical method such as X-ray crystallographic or nuclear magnetic resonance based structure determination. A structural model of a derepressor can be used in an algorithm that compares polypeptide structure including, for example, SCOP, CATH, or FSSP which are reviewed in Hadley and Jones, *Structure* 7:1099–1112 (1999) and regions having a particular fold or conformation used as a region for sequence comparison to a second polypeptide to identify substantially similar regions.

Similar database searching methods can be used for non-peptide based derepressors or to query a database of non-peptide based candidate agents based on structure. A database can be searched, for example, by querying based on chemical property information or on structural information. In the latter approach, an algorithm based on finding a match to a template can be used as described, for example, in Martin, "Database Searching in Drug Design," *J. Med. Chem.* 35:2145–2154 (1992).

A derepressor of an IAP-inhibited caspase can also be identified in a database using the results of a positional scanning synthetic combinatorial library as a query. Such results can be represented as a motif and the motif used to search a database for a derepressor of an IAP-inhibited caspase. Motif searches are generated from screening results of positional scanning synthetic combinatorial libraries, and contained in each position are amino acids corresponding to mixtures having an activity threshold greater than a specified value. An example of an activity threshold is the ratio of $V_{max}$ for caspase activity in the presence and absence of a candidate agent as described in Example I. Motif based database searching is known in the art as described, for example, in Hemmer et al., *Nat. Med.* 5:1375–1382 (1999), Hemmer et al., *J. Exp. Med.* 185:1651–1659 (1997) and Hemmer et al., *Immunol Today* 19:163–168 (1998).

Alternatively, results from a positional scanning synthetic combinatorial library can be represented as a score matrix and the score matrix used to query for other derepressors of an IAP-inhibited caspase in a sequence database. Methods for identifying candidate peptides or proteins based on score-matrix based searches of a databases are described in Zhao et al., *J. Immunol.* 167:2130–2141 (2001). Briefly, a matrix is constructed in which columns represent positions, rows represent the 20 amino acids and each is correlated with a score. The score for a particular position and amino acid is based on assay results for the mixture of a positional scanning synthetic combinatorial library corresponding to that amino acid defined at that position. For example, each score can correspond to the ratio of $V_{max}$ for caspase activity in the presence and absence of the mixture corresponding to the amino acid defined at the particular position. The scoring matrix is then used to search for candidate derepressors of an IAP-inhibited caspase by moving the scoring matrix across database entries in 1 amino acid increments. A score is calculated for the database entries searched and each is ranked. Those having a score above a predetermined cutoff are identified as candidate derepressors of an IAP-inhibited caspase.

The invention provides a method of derepressing an IAP-inhibited caspase, by contacting an IAP-inhibited caspase with an effective amount of an agent to derepress an IAP-inhibited caspase, the agent having a core motif selected from a core peptide of the invention, such as core peptides 4 through 39 and 42 through 55, or a core structure of the invention such as TPI 759, TPI 882, TPI 914 or TPI 927.

For inhibiting a caspase inhibitory activity of an inhibitor of apoptosis protein (IAP), the IAP-inhibited caspase is contacted with an amount of derepressor effective to derepress the IAP-inhibited caspase. Thus, an effective amount of the agent is an amount that is sufficient to yield an increase in caspase proteolytic activity from the derepressed IAP-inhibited caspase compared to the caspase activity for an IAP-inhibited caspase. An increase in proteolytic activity from a derepressed IAP-inhibited caspase can be determined using any of the methods described above in reference to a method for identifying a derepressor of an IAP-inhibited caspase.

An agent of the invention can be contacted with an IAP-inhibited caspase under conditions suitable for caspase activity to occur once an IAP is inhibited from inhibiting the caspase. Such conditions include those described in Example I. The agent that is contacted with the IAP-inhibited caspase can be present in a mixture of compounds, in an isolated form or in substantially pure form. As described above, a mixture of compounds can be contacted with an IAP-inhibited caspase in a screening method employing positional scanning or iteration. Such a mixture can be identified as having the ability to derepress an IAP-inhibited caspase. The mixture can be used in the methods of the invention to derepress an IAP inhibited caspase. Alternatively, a particular species in the mixture having such activity can be further defined by isolating individual species in the mixture and repeating the derepression assay or performing a second assay for derepression of an IAP-inhibited caspase. An agent that derepresses an IAP-inhibited caspase can be contacted with the IAP-inhibited caspase in a substantially pure form, as a conjugate or in a formulation as described above.

In a further embodiment of the invention an IAP-inhibited caspase can be contacted with an agent of the invention in a cell. Accordingly, the invention provides a method of promoting apoptosis in a cell, by contacting the cell with an effective amount of an agent to derepress an IAP-inhibited caspase, the agent having a core motif selected from a core peptide of the invention, such as Core peptides 4 through 39 and 42 through 55, or a core structure of the invention such as TPI 759, TPI 882, TPI 914 or TPI 927.

Methods described herein for cytosolic delivery of an IAP-inhibited caspase, such as attachment of a moiety of conjugate, can be used in a method of promoting apoptosis in a cell. An effective amount of the agent can be identified as an amount sufficient to allow apoptosis to occur in the cell. Methods of determining morphological changes in a cell or nucleus that are characteristic of apoptosis, such as those described above in relation to identifying a derepressor of an IAP-inhibited caspase, can be used to monitor apoptosis while performing a method of promoting apoptosis in a cell.

The invention also provides a method for reducing the ability of a population of cells to survive ex vivo. The method can include the steps of contacting the cells with an agent of the invention, wherein the agent derepresses an IAP-inhibited caspase. The cells can be contacted with the agent using the methods described above for promoting apoptosis in a cell. The methods can be used to remove a particular subpopulation of cells in a sample using the targeting methods described above, such as the attachment of a targeting moiety to the agent.

The methods of the invention can be carried out in a cell from any organism in which apoptosis can occur when an IAP-inhibited caspase is derepressed including, for example, a eukaryotic cell, such as a mammalian cell, human cell, non human-primate cell, mouse cell, hamster cell, or other animal cell; an invertebrate cell such as a fly or nematode cell or a yeast cell. Various cell types can be used in the methods of the invention including, for example, a tumor cell, stem cell, neural cell, fat cell, hematopoietic cell, liver cell or muscle cell. In particular the methods are useful for inducing apoptosis in aberrantly regulated cells including, for example, cells that exhibit uncontrolled cell proliferation as well as cells that exhibit dysfunction in specific phases of the cell cycle, leading to altered proliferative characteristics or morphological phenotypes. Specific examples of aberrantly regulated cell types include neoplastic cells such as cancer and hyperplastic cells characteristic of tissue hyperplasia. Another specific example includes immune cells that become aberrantly activated or fail to down regulate following stimulation. Autoimmune diseases are mediated by such aberrantly regulated immune cells. Aberrantly regulated cells also include cells that are biochemically or physiologically dysfunctional. Other types of aberrant regulation of cell function or proliferation are known to those skilled in the art and are similarly target cells of the invention applicable for apoptotic destruction using the methods of the invention.

Because a number of characteristic changes associated with apoptosis of a cell are due to the proteolytic activity of caspases, the methods can be used to induce characteristic changes of apoptosis. For example, caspase induced proteolysis of lamin B, which is involved in attachment of chromatin to the nuclear envelope, can be responsible for collapse of the chromatin associated with apoptosis (Martin and Green, supra, 1995). Caspase induced proteolysis of the 45 kDa subunit of DNA fragmentation factor (DFF-45) activates a pathway leading to fragmentation of genomic DNA into nucleosomal fragments (Liu et al., Cell 89:175–184 (1997)). In addition, caspase induced proteolysis of PARP can prevent the ability of PARP to repair DNA damage, further contributing to the morphologic changes associated with apoptosis. Thus, the methods of the invention can be used to induce collapse of the chromatin and fragmentation of genomic DNA associated with apoptosis. Other caspase target proteins include sterol regulatory element binding proteins; retinoblastoma (RB) protein; DNA-dependent kinase; U1 70-K kinase; and the large subunit of the DNA replication complex (Wang et al., EMBO J. 15:1012–1020 (1996); Takahashi et al., Proc. Natl. Acad. Sci., USA 93:8395–8400 (1996); Casciola-Rosen et al., J. Exp. Med. 183:1957–1964 (1996); and Ubeda and Habener, J. Biol. Chem. 272:19562–19568 (1997)) each of which can be induced to be proteolyzed by the methods of the invention.

In mammalian cells, activation of caspases is achieved through at least two independent mechanisms, which are initiated by distinct caspases but result in activation of common "executioner" caspases. Apoptosis initiated by ligand binding to the Fas receptor is one well described cell death pathway. In this pathway, binding of a ligand to Fas allows the intracellular domain of Fas to bind the intracellular MORT1 (FADD) protein, which, in turn, binds to caspase-8 (MACH; FLICE; Mch5; see Boldin et al., Cell 85:803–815 (1996); Muzio et al., Cell 85:817–827 (1996)). These results define caspase-8 as an upstream caspase involved in the Fas cell death pathway. In addition, caspase-3 is activated in the Fas cell death pathway, suggesting that an upstream protease such as caspase-8 or a protease activated by caspase-8 is involved in caspase-3 activation. Accordingly, the methods of the invention can be used to directly derepress IAP inhibited-caspase-8 thereby effectively derepressing the downstream caspase-3 protease.

Caspase activation also can involve cytochrome c, which in mammalian cells is often released from mitochondria into the cytosol during apoptosis (Liu et al., Cell 86:147–157 (1996); Kharbanda et al., Proc. Natl. Acad. Sci., USA 94:6939–6942 (1997); Kluck et al., Science 275:1132–1136 (1997); and Yang et al., Science 275:1129–1132 (1997)). Upon entering the cytosol, cytochrome c induces the ATP- or dATP-dependent formation of a complex of proteins that results in proteolytic activation of pro-caspase-3 and apoptotic destruction of nuclei (Liu et al., supra, 1996). Among the members of this complex are the CED-4 homolog Apaf-1, and caspase-9 (Apaf-3; Liu et al., supra, 1996; Li et al., Cell 91:479–489 (1997); Zou et al., Cell 90:405–413 (1997)). XIAP, c-IAP-1 and c-IAP-2 suppress apoptosis induced by stimuli known to cause release of cytochrome c from mitochondria and can inhibit caspase activation induced by cytochrome c in vitro. Thus, the agents and methods of the invention can be used to allow apoptosis to occur in response to release of cytochrome c from mitochondria by suppressing inhibition of a caspase by XIAP, c-IAP-1 or c-IAP-2.

The invention further provides a method of reducing the severity of a pathologic condition in an individual, by administering to an individual having a pathologic condition characterized by a pathologically reduced level of apoptosis, an effective amount of an agent to derepress an IAP-inhibited caspase. Examples of conditions characterized by pathologically reduced levels of apoptosis that can be treated in a method of the invention include, but are not limited to, restenosis; autoimmune disease such as lupus or Rheumatoid Arthritis; allograft rejection, proliferative lesions of the skin such as Eczema; or benign prostate hypertrophy The agent can have a core motif selected from a core peptide of the invention, such as Core peptides 4 through 39 and 42 through 55, or a core structure of the invention such as TPI 759, TPI 882, TPI 914, TPI 927 or a compound comprising a core structure selected from TPI 1391, TPI 1349, TPI 1396, TPI 1509, TPI 1540, TPI 1400, TPI 792 and TPI 1332.

An effective amount of an agent that derepresses an IAP-inhibited caspase when used to treat a pathological condition is an amount required to allow an increase in apoptosis when administered to an individual. The dosage of an agent of the invention required to be therapeutically effective will depend, for example, on the pathological condition to be treated, the route and form of administration, the weight and condition of the individual, and previous or concurrent therapies. The appropriate amount considered to be an effective dose for a particular application of the method can be determined by those skilled in the art, using the guidance provided herein. For example, the amount can be extrapolated from in vitro or in vivo assays as described previously. One skilled in the art will recognize that the condition of the patient can be monitored throughout the course of therapy and that the amount of the agent that is administered can be adjusted accordingly.

For treating or reducing the severity of a pathological condition, an effective amount is an efficacious amount of the agent capable of increasing apoptosis that is pathologically reduced. An effective amount can be, for example, between about 10 µg/kg to 500 mg/kg body weight, for example, between about 0.1 mg/kg to 100 mg/kg, or preferably between about 1 mg/kg to 50 mg/kg, depending on the treatment regimen. For example, if an agent or formulation containing the agent is administered from one to several times a day, then a lower dose would be needed than if a formulation were administered weekly, or monthly or less frequently. Similarly, formulations that allow for timed-release of the agent, such as those described above, would provide for the continuous release of a smaller amount of derepressor of apoptosis than would be administered as a single bolus dose. For example, an agent of the invention can be administered at between about 1–5 mg/kg/week.

Formulations of a derepressor of an IAP-inhibited caspase, variants and combinations thereof can also be delivered in an alternating administrations so as to combine their apoptosis increasing effects over time. For example, an agent having a core peptide or structure of the invention can be administered in a single bolus dose followed by multiple administrations of one or more such agents species or variant alone, or in combination with a different formulation of such an agent or formulation of a different agent. Whether simultaneous or alternating delivery of the agent formulation, variant or combination thereof, the mode of administration can be any of those types of administrations described previously and will depend on the particular therapeutic need and efficacy of the derepressor of an IAP-inhibited caspase selected for the purpose. Determining which agent, formulation, species and variants to combine in a temporally administered regime, will depend on the pathological condition to be treated and the specific physical characteristics of the individual affected with the disease. Those skilled in the art will know or can determine a specific regime of administration which is effective for a particular application using the teachings and guidance provided herein together with diagnostic and clinical criteria known within the field of art of the particular pathological condition.

The methods of treating a pathological condition characterized by pathologically reduced apoptosis additionally can be practiced in conjunction with other therapies. For example, for treating cancer, the methods of the invention can be practiced prior to, during, or subsequent to conventional cancer treatments such as surgery, chemotherapy, including administration of cytokines and growth factors, radiation or other methods known in the art.

Such treatments can act in a synergistic manner, with the reduction in tumor mass caused by the conventional therapy increasing the effectiveness of a compound of the invention, and vice versa. Non-limiting examples of anti-cancer drugs that are suitable for co-administration with a compound of the invention are well known to those skilled in the art of cancer therapy and include aminoglutethimide, amsacrine (m-AMSA), azacitidine, asparaginase, bleomycin, busulfan, carboplatin, carmustine (BCNU), chlorambucil, cisplatin (cis-DDP), cyclophosphamide, cytarabine HCl, dacarbazine, dactinomycin, daunorubicin HCl, doxorubicin HCl, erythropoietin, estramustine phosphate sodium, etoposide (V16-213), floxuridine, fluorouracil (5-FU), flutamide, hexamethylmelamine (HMM), hydroxyurea (hydroxycarbamide), ifosfamide, interferon alpha, interleukin 2, leuprolide acetate (LHRH-releasing factor analogue), lomustine (CCNU), mechlorethamine HCl (nitrogen mustard), melphalan, mercaptopurine, mesna, methotrexate (MTX), mitoguazone (methyl-GAQ methyl glyoxal bis-guanylhydrazone, MGBG), mitomycin, mitotane (o. p'-DDD), mitoxantrone HCl, octreotide, pentostatin, plicamycin, procarbazine HCl, semustine (methyl-CCNU), streptozocin, tamoxifen citrate, teniposide (VM-26), thioguanine, thiotepa, vinblastine sulfate, vincristine sulfate, vindesine sulfate, Herceptin, and MabThera. As set forth above and demonstrated by the results of Example X, TPI 792-33 or TPI 792-35 can be administered in conjunction with VP-16 to treat cancer. Similarly, as demonstrated by the results of Example XIV, TPI 1396-34 also can be administered in conjunction with an anti-cancer drug to treat cancer. Those skilled in the art will appreciate that similar effects are expected for any active polyphenylurea compound of the invention.

Similarly, for treating pathological conditions which include infectious disease, the methods of the invention can be practiced prior to, during, or subsequent to conventional treatments, such as antibiotic administration, against infectious agents or other methods known in the art. Treatment of pathological conditions of autoimmune disorders also can be accomplished by combining the methods of the invention for derepressing an IAP-inhibited caspase with conventional treatments for the particular autoimmune diseases. Conventional treatments include, for example, chemotherapy, steroid therapy, insulin and other growth factor and cytokine therapy, passive immunity, inhibitors of T cell receptor binding and T cell receptor vaccination.

The methods of the invention can be administered in conjunction with these or other methods known in the art and at various times prior, during or subsequent to initiation of conventional treatments. For a description of treatments for pathological conditions characterized by aberrant cell growth see, for example, *The Merck Manual*, Sixteenth Ed, (Berkow, R., Editor) Rahway, N.J., 1992. Furthermore, anti-cancer drugs including, for example, any of those set forth above with regard to combination compositions, can be administered prior to, during, or subsequent to administration of a derepressor of an IAP-inhibited caspase in a method of treatment.

As described above, administration of a formulation of an agent that derepresses an IAP-inhibited caspase can be, for example, simultaneous with or delivered in alternative administrations with the conventional therapy, including multiple administrations. Simultaneous administration can be, for example, together in the same formulation or in different formulations delivered at about the same time or immediately in sequence. Alternating administrations can be, for example, delivering an agent of the invention and a conventional therapeutic treatment in temporally separate administrations. As described previously, the temporally separate administrations of an agent of the invention and conventional therapy can similarly use different modes of delivery and routes.

A condition characterized by a pathologically reduced level of apoptosis that can be treated using the agents and methods of the invention include, for example, cancer, hyperplasia, autoimmune disease and restenosis. A growing number of human diseases have been classified as autoimmune and include, for example, rheumatoid arthritis, myasthenia gravis, multiple sclerosis, psoriasis, systemic lupus erythematosus, autoimmune thyroiditis, Graves disease, inflammatory bowel disease, autoimmune uveoretinitis, polymyositis and diabetes. Animal models for many conditions characterized by a pathologically reduced level of apoptosis have been developed and can be employed for predictive assessment of therapeutic treatments employing an agent that derepresses an IAP-inhibited caspase. Moreover, pharmaceutical compositions of a derepressor of IAP-inhibited caspase can be reliably extrapolated for the treatment of these conditions from such animal models.

Those skilled in the art will know how to determine efficacy or amounts of an agent of the invention to administer based on the results of routine tests in a relevant animal model. The amount of an agent to be administered can be determined in a clinical setting as well based on the response in a treated individual. Modulation of efficacy, will depend on the pathological condition and the extent to which progression of apoptosis is desired for treatment or reduction in the severity of the pathological condition. Modulation can be accomplished by adjusting the particular agent used to derepress an IAP-inhibited caspase, formulation, or dosing strategy. Based on the guidance provided herein, those skilled in the art will be able to modulate efficacy in response to well known indicators of the severity of the particular condition being treated. For a description of indicators for the various pathological conditions described herein or otherwise known to be characterized by a pathologically reduced level of apoptosis see, for example, *The Merck Manual*, Sixteenth Ed, (Berkow, R., Editor) Rahway, N.J., 1992.

The following examples are intended to illustrate but not limit the present invention.

EXAMPLE I

Identification of Derepressors of an IAP-Inhibited Caspase from Hexapeptide Libraries This example demonstrates an IAP derepression assay. This Example. further demonstrates a positional-scanning approach to identifying agents that are capable of derepressing an IAP-inhibited caspase.

The DCR390 library consisting of 120 mixtures of hexapeptides was synthesized using methods known in the art as described in R. Houghten et al. PCT/US91/08694 and U.S. Pat. No. 5,556,762. Each mixture was made up of a population of hexapeptides all of which had the same amino acid at a defined position and any combination of the 20 essential amino acids at the remaining 5 positions. Each mixture is identified by the position number where the defined amino acid occurs (numbered from 1 to 6 going from the amino-terminus to carboxy-terminus of the hexapeptide) and the identity of the defined amino acid. Thus, as shown in the first column of Table I, the mixture having a tryptophan at position 1 and all combinations of the 20 amino acids at positions 2 through 5 is identified as "position 1, W."

The DCR390 library was screened using the assay set forth below. Based on the mixtures identified from the DCR390 library screen as being capable of derepressing an IAP-inhibited caspase, additional defined positions were incorporated into the TPI 1239 and TPI 1328 sublibraries, and the sublibraries screened using the same assay.

Caspase activity was assayed by release of 7-amino-4-trifluoromethyl-coumarin (AFC) from Ac-DEVD-AFC synthetic peptide using a Molecular Devices Spectromax 340 (see Zhou et al., *J. Biol. Chem.* 272:7797–7800 (1997)). Candidate mixtures were screened for the ability to derepress an IAP-inhibited caspase by measuring AFC hydrolysis rates for mixtures containing purified recombinant caspase-3, Ac-DEVD-AFC, and GST-XIAP in the presence and absence of the candidate agent. The ratio of $V_{max}$ for hydrolysis of Ac-DEVD-AFC in the presence and absence of the candidate mixture was calculated and used to identify those that contain an agent that derepresses an IAP-inhibited caspase. The ratio=($V_{max}$ when candidate mixture, caspase 3 and XIAP are present)/($V_{max}$ when caspase 3 and XIAP are present).

Screening of each mixture from the DCR390, TPI 1239 or TPI 1328 library, respectively, using the above described assay was carried out as follows. Each mixture was aliquoted in a 25 microliter volume and in duplicate to a well of a 96 well microtiter plate. Into the first set of duplicate wells was added 25 microliters of caspase assay buffer (50 mM HEPES, pH 7.4, 100 mM NaCi, 10% sucrose, 10 mM DTT, 1 mM EDTA and 0.1% CHAPS) and into the second set of wells was added 25 microliters of a stock solution of 40 nM XIAP in caspase assay buffer. Each microtiter plate also had the following controls: (1) a buffer blank well to which was added 25 microliters of caspase assay buffer and 25 microliters of peptide carrier solvent, (2) an XIAP control well to which was added 25 microliters of peptide carrier solvent and 25 microliters of a stock solution of 40 nM XIAP in caspase assay buffer, and (3) a SMAC control well to which was added 25 microliters of a stock solution of 40 nM XIAP in caspase assay buffer, and 2.5 microliters of 4 µM SMAC peptide (H-Ala-Val-Pro-Ile-Ala-Gln-Lys-NH$_2$, SEQ ID NO:5). Into each of the sample and control wells was added 25 microliters of 0.64 nM caspase-3 solution followed by 25 microliters of 400 µM Ac-DEVD-AFC substrate. Fluorescence of liberated AFC was immediately detected from each well for 30 minutes at 30 second intervals. The $V_{max}$ for hydrolysis of AC-DEVD-AFC from each well was measured using the softmax software package. Results of the screen for the DCR390 library are shown in Table I. Sets of mixtures having the same position fixed with different respective amino acids are arranged in 6 sections identified with the position number. Within each of the six sections are 3 columns showing (1) the identify of the fixed amino acid, (2) the apparent velocity of the reaction when candidate mixture, caspase 3 and XIAP are present, and (3) the apparent velocity of the reaction when canidate mixture, and caspase 3 are present. Also shown in each section are results for the XIAP control reaction. The mixture in each section are arranged in descending order according to apparent velocity in the second column. Those mixtures having significantly higher apparent velocity compared to the XIAP control reaction are listed above the horizontal line and are thereby identified as containing an agent capable of derepressing an XIAP-inhibited caspase.

TABLE I

| Amino Acid | DCR 390 | |
|---|---|---|
| | XIAP + Mixtures | Mixtures |
| Position 1 | | |
| W | 43 | 63 |
| A | 35 | 67 |
| Y | 35 | 63 |
| F | 34 | 61 |
| C | 30 | 62 |
| L | 26 | 63 |
| I | 23 | 64 |
| E | 22 | 64 |
| T | 22 | 62 |
| V | 20 | 60 |
| M | 19 | 65 |
| G | 17 | 65 |
| P | 17 | 64 |
| Q | 17 | 66 |
| XIAP | 16 | 64 |
| R | 16 | 65 |
| XIAP | 15 | 64 |
| H | 15 | 63 |
| K | 15 | 65 |
| S | 15 | 65 |
| D | 14 | 67 |
| N | 13 | 63 |
| XIAPX1.5 | 24 | |
| Position 2 | | |
| W | 57 | 58 |
| F | 44 | 58 |
| L | 38 | 61 |
| C | 36 | 64 |
| I | 32 | 61 |

TABLE I-continued

DCR 390

| Amino Acid | XIAP + Mixtures | Mixtures |
|---|---|---|
| V | 30 | 59 |
| Y | 30 | 61 |
| A | 20 | 62 |
| D | 20 | 67 |
| P | 20 | 60 |
| R | 20 | 58 |
| XIAP | 19 | 63 |
| XIAP | 19 | 63 |
| G | 19 | 58 |
| H | 19 | 58 |
| M | 19 | 60 |
| E | 18 | 67 |
| N | 18 | 64 |
| T | 18 | 59 |
| Q | 17 | 59 |
| S | 17 | 59 |
| K | 16 | 61 |
| XIAPX1.5 | 29 | |

Position 3

| Amino Acid | XIAP + Mixtures | Mixtures |
|---|---|---|
| F | 50 | 64 |
| I | 36 | 65 |
| W | 34 | 65 |
| L | 26 | 65 |
| C | 20 | 64 |
| V | 19 | 62 |
| A | 16 | 67 |
| H | 16 | 70 |
| K | 15 | 67 |
| Y | 14 | 63 |
| XIAP | 13 | 64 |
| XIAP | 13 | 64 |
| D | 13 | 66 |
| T | 13 | 62 |
| M | 12 | 67 |
| N | 12 | 64 |
| R | 12 | 67 |
| E | 11 | 63 |
| G | 11 | 63 |
| P | 11 | 67 |
| S | 11 | 68 |
| Q | 10 | 63 |
| XIAPX1.5 | 20 | |

Position 4

| Amino Acid | XIAP + Mixtures | Mixtures |
|---|---|---|
| W | 52 | 63 |
| F | 37 | 61 |
| L | 23 | 61 |
| Y | 17 | 64 |
| C | 15 | 60 |
| I | 15 | 60 |
| V | 13 | 63 |
| XIAP | 12 | 61 |
| M | 12 | 64 |
| N | 12 | 63 |
| A | 11 | 64 |
| XIAP | 10 | 61 |
| D | 10 | 63 |
| E | 10 | 59 |
| G | 10 | 60 |
| H | 10 | 59 |
| P | 10 | 66 |
| Q | 10 | 64 |
| S | 10 | 62 |
| K | 9 | 60 |
| R | 9 | 62 |
| T | 9 | 62 |
| XIAPX1.5 | 18 | |

Position 5

| Amino Acid | XIAP + Mixtures | Mixtures |
|---|---|---|
| W | 44 | 56 |
| Y | 23 | 57 |
| V | 15 | 57 |
| I | 14 | 57 |
| L | 14 | 52 |
| A | 13 | 57 |
| C | 12 | 54 |
| F | 12 | 53 |
| XIAP | 11 | 52 |
| XIAP | 11 | 52 |
| H | 11 | 57 |
| K | 11 | 55 |
| S | 11 | 57 |
| T | 11 | 56 |
| D | 10 | 54 |
| E | 10 | 53 |
| M | 10 | 49 |
| P | 10 | 54 |
| G | 9 | 57 |
| N | 9 | 52 |
| Q | 9 | 54 |
| R | 9 | 52 |
| XIAP1.5 | 17 | |

Position 6

| Amino Acid | XIAP + Mixtures | Mixtures |
|---|---|---|
| W | 23 | 51 |
| R | 22 | 52 |
| A | 13 | 53 |
| C | 12 | 51 |
| G | 12 | 51 |
| K | 12 | 53 |
| Q | 11 | 50 |
| XIAP | 10 | 51 |
| XIAP | 10 | 51 |
| S | 10 | 53 |
| Y | 10 | 51 |
| D | 9 | 50 |
| E | 9 | 49 |
| L | 9 | 53 |
| M | 9 | 51 |
| N | 9 | 50 |
| T | 9 | 53 |
| V | 9 | 51 |
| F | 8 | 50 |
| H | 8 | 51 |
| I | 8 | 53 |
| P | 8 | 49 |
| XIAPX1.5 | 15 | |

Based on the results of the DCR390 screen, the TPI 1239 library was synthesized and screened using the above-described caspase assay. In particular mixtures were synthesized having positions 5 and 6 defined as tryptophan, positions 3 and/or 4 defined variously, and the remaining positions randomized with the 20 essential amino acids as set forth in Table II. As shown in Table II, in the absence of XIAP the mixtures had an insignificant effect on caspase activity. Mixtures having ratios of 1.9 or higher in the presence of XIAP were identified as containing an agent capable of derepressing an IAP-inhibited caspase.

TABLE II

TPI 1239

| Mixture | $\frac{V_{max}(mix + casp3)}{V_{max}(casp3)}$ | $\frac{V_{max}(mis + casp3 + XIAP)}{V_{max}(casp3 + XIAP)}$ |
|---|---|---|
| caspase 3 | 1.0 ± 0.0 | 5.1 ± 2.3 |
| Xiap + caspase3 | 0.2 ± 0.1 | 1.0 ± 0.0 |
| SMAC | 0.8 ± 0.0 | 3.8 ± 1.7 |
| XXFWWW SEQ ID NO: 11 | 0.9 ± 0.0 | 0.8 ± 0.1 |
| XXLWWW SEQ ID NO: 12 | 0.9 ± 0.0 | 0.7 ± 0.1 |
| XXWLWW SEQ ID NO: 13 | 0.9 ± 0.0 | 0.7 ± 0.1 |
| XXWWWW SEQ ID NO: 14 | 0.9 ± 0.0 | 0.8 ± 0.1 |
| XXXTWW | 0.8 ± 0.0 | 4.2 ± 1.6 |
| XXXAWW | 0.9 ± 0.0 | 3.7 ± 1.6 |
| XXXSWW | 0.8 ± 0.0 | 3.4 ± 1.1 |
| XXXQWW | 0.8 ± 0.0 | 2.4 ± 0.4 |
| XXXKWW | 0.9 ± 0.0 | 2.3 ± 1.0 |
| XXXVWW | 0.9 ± 0.0 | 2.2 ± 0.5 |
| XXXRWW | 0.9 ± 0.0 | 2.1 ± 0.2 |
| XXXHWW | 0.9 ± 0.0 | 2.1 ± 0.6 |
| XXXNWW | 0.9 ± 0.0 | 1.9 ± 0.6 |
| XXXPWW | 0.9 ± 0.0 | 1.5 ± 0.2 |
| XXXYWW | 0.9 ± 0.0 | 1.2 ± 0.3 |
| XXXDWW | 0.9 ± 0.0 | 1.1 ± 0.2 |
| XXXIWW | 0.9 ± 0.0 | 0.9 ± 0.1 |
| XXXLWW | 0.9 ± 0.0 | 0.9 ± 0.1 |
| XXXCWW | 0.9 ± 0.0 | 0.8 ± 0.2 |
| XXXEWW | 0.9 ± 0.0 | 0.8 ± 0.2 |
| XXXGWW | 0.9 ± 0.0 | 0.7 ± 0.1 |
| XXXMWW | 0.9 ± 0.0 | 0.6 ± 0.2 |
| XXXFWW | 0.9 ± 0.0 | 0.6 ± 0.1 |
| XXXWWW | 0.8 ± 0.0 | not determined |
| XXXXWW | 1.0 ± 0.0 | 2.0 ± 0.3 |

The mixtures identified from the TPI 1239 library as containing an agent capable of derepressing an IAP-inhibited caspase were further analyzed for dose response. The dose response data is provided in FIG. 11 which shows that the mixtures had no effect on caspase activity. The most active mixtures were found to have alanine, lysine or threonine at position 4, tryptophan at positions 5 and 6 and mixtures at positions 1 through 3.

Based on the results of the DCR390 and TPI 1239 library screens, the TPI 1328 library was synthesized and screened using the above-described caspase assay. For each mixture in the TPI 1328 library, 3 to 4 positions were defined and the remaining positions were combinatorialized with all 20 of the essential amino acids including Ala, Asp, Glu, Phe, Gly, His, Ile, Lys, Leu, Met, Asn, Pro, Gln, Arg, Ser, Thr, Val, Trp, Cys or Tyr. Position 4 was defined with Ala, Lys or a mixture of Ala, Lys and Thr (the mixture is referred to as "3X" or "A,K,T").

Various TPI 1328 sublibraries that were screened and values obtained for the ratio of $V_{max}$ for hydrolysis of Ac-DEVD-AFC in the presence and absence of each mixture are plotted in FIG. 1. In FIG. 1 and Table III, "X" represents a mixture of all 20 essential amino acids and "O" represents the location of the defined position, the identity of the amino acid at the defined position being plotted on the x axis. Candidates having a ratio over 1.7 were identified as being derepressors of XIAP-inhibited caspase-3. A list of derepressors of XIAP-inhibited caspase-3 identified from the TPI 1328 library is provided in Table III.

TABLE III

| Pos 1 | Pos 2 | Pos 3 | Pos 4 | Pos 5 | Pos 6 | SEQ ID NO: |
|---|---|---|---|---|---|---|
| X | X | Ala | Ala | Trp | Trp | 7 |
| X | X | Gly | Ala | Trp | Trp | 8 |
| X | X | Arg | Ala | Trp | Trp | 9 |
| X | X | X | Ala | Trp | Trp | |
| X | X | Cys | Lys | Trp | Trp | 10 |
| X | X | Leu | Lys | Trp | Trp | 15 |
| X | X | Gly | 3X | Trp | Trp | |
| X | X | Arg | 3X | Trp | Trp | |
| X | X | Thr | 3X | Trp | Trp | |
| X | X | Val | 3X | Trp | Trp | |
| X | Thr | X | 3X | Trp | Trp | |
| X | Tyr | X | 3X | Trp | Trp | |
| Ala | X | X | 3X | Trp | Trp | |
| Cys | X | X | 3X | Trp | Trp | |
| Phe | X | X | 3X | Trp | Trp | |
| Lys | X | X | 3X | Trp | Trp | |

EXAMPLE II

Identification of Derepressors of an IAP-Inhibited Caspase from the TPI 1332 and TPI 1352 Individual Tetrapeptide Libraries This Example demonstrates identification of agents from the TPI 1332 and TPI 1352 tetrapeptide libraries that are capable of derepressing an XIAP-inhibited caspase-3.

The TPI 1332 and TPI 1352 tetrapeptide libraries were synthesized identically with the exception that the formyl protecting groups on tryptophan were removed by different procedures. The deprotection step used for the TPI 1332 library was less complete leaving the possibility that some of the tryptophan residues present on candidate compounds used in the screen retained formyl protecting groups. The deprotecting chemistry used for the TPI 1352 library was substantially complete, however resulted in the formation of polymeric structures for a subset of the species in the library.

Candidates from the TPI 1332 and TPI 1352 libraries were screened using the derepression assay described in Example I. The ratios of $V_{max}$ for hydrolysis of Ac-DEVD-AFC in the presence and absence of each species of the TPI 1332 and TPI 1352 libraries were determined and those having values greater than 2.4 were identified as derepressors of an IAP-inhibited caspase.

A list of derepressors of XIAP-inhibited caspase-3 identified from the TPI 1332 and TPI 1352 tetrapeptide libraries is provided in Table IV. Agents identified in both libraries are indicted as "1332/1352".

TABLE IV

| Agent | Position 1 | Position 2 | Position 3 | Position 4 |
|---|---|---|---|---|
| 1332/1352-1 | L-Ala | L-Trp | L-Trp | L-ThiAla |
| 1332/1352-2 | L-Ala | L-Trp | L-Trp | L-pClPhe |
| 1332/1352-47 | L-Ala | D-Trp | L-Trp | L-ThiAla |
| 1332-13 | L-Ala | D-Nal | L-Trp | L-Nal |
| 1332-24 | D-Trp | D-Trp | L-Trp | D-Nal |
| 1332-41 | L-Cha | D-Nal | L-Trp | L-ThiAla |
| 1352-5 | L-Ala | L-Trp | L-Trp | L-3I-Tyr |
| 1352-6 | L-Ala | D-Trp | L-Trp | L-ThiAla |
| 1352-32 | L-Cha | L-Trp | L-Trp | L-pClPhe |
| 1352-46 | L-Ala | D-Trp | L-Trp | D-Trp |
| 1352-48 | L-Ala | D-Trp | D-Phe | D-Trp |
| 1352-64 | L-Nal | D-Trp | D-Phe | D-Trp |
| 1352-66 | L-Nal | D-Cha | L-Trp | D-Trp |
| 1352-72 | L-Nal | D-ThiAla | D-Phe | D-Trp |

Structures of TPI 1332 library compounds are shown in FIG. 36A; structure of related compounds of the TPI 1495 series are shown in FIG. 37.

EXAMPLE III

Identification of Individual Peptide Derepressors of an IAP-Inhibited Caspase from the TPI 792 Library This Example demonstrates identification of agents from the TPI 792 library that are capable of derepressing an XIAP-inhibited caspase-3.

The TPI 792 library is based on a tetrapeptide backbone. The species of the TPI 792 library were screened in the derepression assay described in Example I. A list of derepressors of XIAP-inhibited caspase-3 identified from the TPI 792 library is provided in Table V. Structures for the TPI 792 core peptides that were tested are shown in FIG. 20.

TABLE V

| Agent | Pos 1 | Pos 2 | Pos 3 | Pos 4 | LC µg/ml |
|---|---|---|---|---|---|
| 792-3 | D-Nal | Lys-εFmoc | L-pClPhe | Lys-εFmoc | 2 |
| 792-9 | D-Nal | D-pClPhe | L-pClPhe | Lys-εFmoc | 10 |
| 792-15 | D-Nal | L-Nal | L-pClPhe | D-Lys-εFmoc | 2 |
| 792-17 | D-Nal | L-Nal | D-Lys(Fm) | Lys-εFmoc | 2 |
| 792-19 | L-ThiAla | Lys-εFmoc | D-Nal | Lys-εFmoc | 2 |
| 792-22 | L-ThiAla | Lys-εFmoc | L-pClPhe | D-pFPhe | 2 |
| 792-27 | L-ThiAla | D-pClPhe | L-pClPhe | Lys-εFmoc | 2 |
| 792-33 | L-ThiAla | L-Nal | L-pClPhe | Lys-εFmoc | 0.4 |
| 792-35 | L-ThiAla | L-Nal | D-Lys(Fm) | D-Lys-εFmoc | 2 |

The dose response of the agents identified from the TPI 792 library were determined by repeating the derepression assay with variable concentrations of the agent. Four concentrations were chosen: 0.4, 2, 10 and 50 micrograms per milliliter. From this data the lowest concentration with a ratio of 2 or higher in the derepression assay (LC) was determined and shown in Table V. The lowest LC value determined from the TPI 792 library was 0.4 micrograms per milliliter for TPI792-33.

EXAMPLE IV

Identification of Derepressors of an IAP-Inhibited Caspase from the TPI 1313 Library This Example demonstrates identification of agents from the TPI 1313 library that are capable of derepressing an XIAP-inhibited caspase-3.

The TPI 1313 library is based on a tetrapeptide backbone. The species of the TPI 1313 library, listed in FIG. 2 and shown in FIG. 3, were screened in the derepression assay described in Example I. A list of derepressors of XIAP-inhibited caspase-3 identified from the TPI 1313 library is provided in Table VI.

TABLE VI

| Agent | Pos 1 | Pos 2 | Pos 3 | Pos 4 |
|---|---|---|---|---|
| 1313-4 | L-ThiAla | D-pCL-Phe | D-Nal | D-pCL-Phe |
| 1313-5 | L-ThiAla | D-pCL-Phe | D-Nal | D-pNO$_2$Phe |
| 1313-7 | L-ThiAla | D-OEt-Tyr | D-OEt-Tyr | D-pCL-Phe |
| 1313-40 | Phe | D-pCL-Phe | D-Nal | D-pCL-Phe |

The dose response of the agents identified from the TPI 1313 library were determined by repeating the derepression assay with variable concentrations of the agent. Four concentrations were chosen: 0.4, 2, 10 and 50 micrograms per milliliter. From this data the apparent IC$_{50}$ was determined. The lowest IC$_{50}$ value determined from the TPI 1313 library range from 3.9 to 6.3 micrograms per milliliter for TPI 1313-7.

EXAMPLE V

Identification of Derepressors of an IAP-inhibited Caspase from the TPI 1325 Library This Example demonstrates identification of agents from the TPI 1325 library that are capable of derepressing an XIAP-inhibited caspase-3.

The TPI 1325 library was screened in the derepression assay described in Example 1. For each species aliquoted in the assay 1 position was fixed (i.e. having a single known amino acid R group) and three positions were combinatorialized. Thus, each "mixture" identified from the TPI 1325 library represents a mixture of compounds where $X_1$ and $X_2$ are selected from Ala, Asp, Glu, Phe, Gly, His, Ile, Lys, Leu, Met, Asn, Pro, Gln, Arg, Ser, Thr, Val, Trp and Tyr and $X_3$ includes any one of Ala, Lys and Thr.

A list of derepressors of XIAP-inhibited caspase-3 identified from the TPI 1325 library is provided in Table VII.

TABLE VII

| Mixture | Pos 1 | Pos 2 | Pos 3 | Pos 4 |
| --- | --- | --- | --- | --- |
| 1325-10 | L-Ala | L-Met | $X_1$ | $X_2$ |
| 1325-15 | L-Ala | L-Ser | $X_1$ | $X_2$ |
| 1325-16 | L-Ala | L-Thr | $X_1$ | $X_2$ |
| 1325-18 | L-Ala | L-Trp | $X_1$ | $X_2$ |
| 1325-44 | L-Ala | L-ThiAla | $X_1$ | $X_2$ |
| 1325-61 | L-Ala | $X_1$ | $X_2$ | $X_3$ |
| 1325-64 | $X_1$ | $X_2$ | L-Trp | D-Trp |

The dose response of the agents identified from the TPI 1325 library were determined by repeating the derepression assay with variable concentrations of the agent. Four concentrations were chosen: 0.4, 2, 10 and 50 micrograms per milliliter. From this data the apparent $IC_{50}$ was determined. The lowest $IC_{50}$ value determined from the TPI 1325 library was 12 micrograms per milliliter for TPI 1325-15.

EXAMPLE VI

Identification of Derepressors of an IAP-Inhibited Caspase from the TPI 914, TPI 927, TPI 759 and TPI 882 Libraries This Example demonstrates identification of agents, from non-peptide based libraries, that are capable of derepressing an XIAP-inhibited caspase-3.

The TPI 914, TPI 927, TPI 759 and TPI 882 libraries were screened using positional scanning (as described in U.S. Pat. No. 5,556,762) in combination with the derepression assay described in Example I.

Analysis was started with combinatorial libraries in which at least one position was defined. Hits were identified as those mixtures producing a mixture/XIAP ratio that was greater than or equal to 2. Following analysis of the first library; libraries of increasing definition were screened until a discrete library was prepared in which all positions were defined. Hits from this defined library were then checked for a dose response which yielded the IC50 values listed below.

Figure 21B:
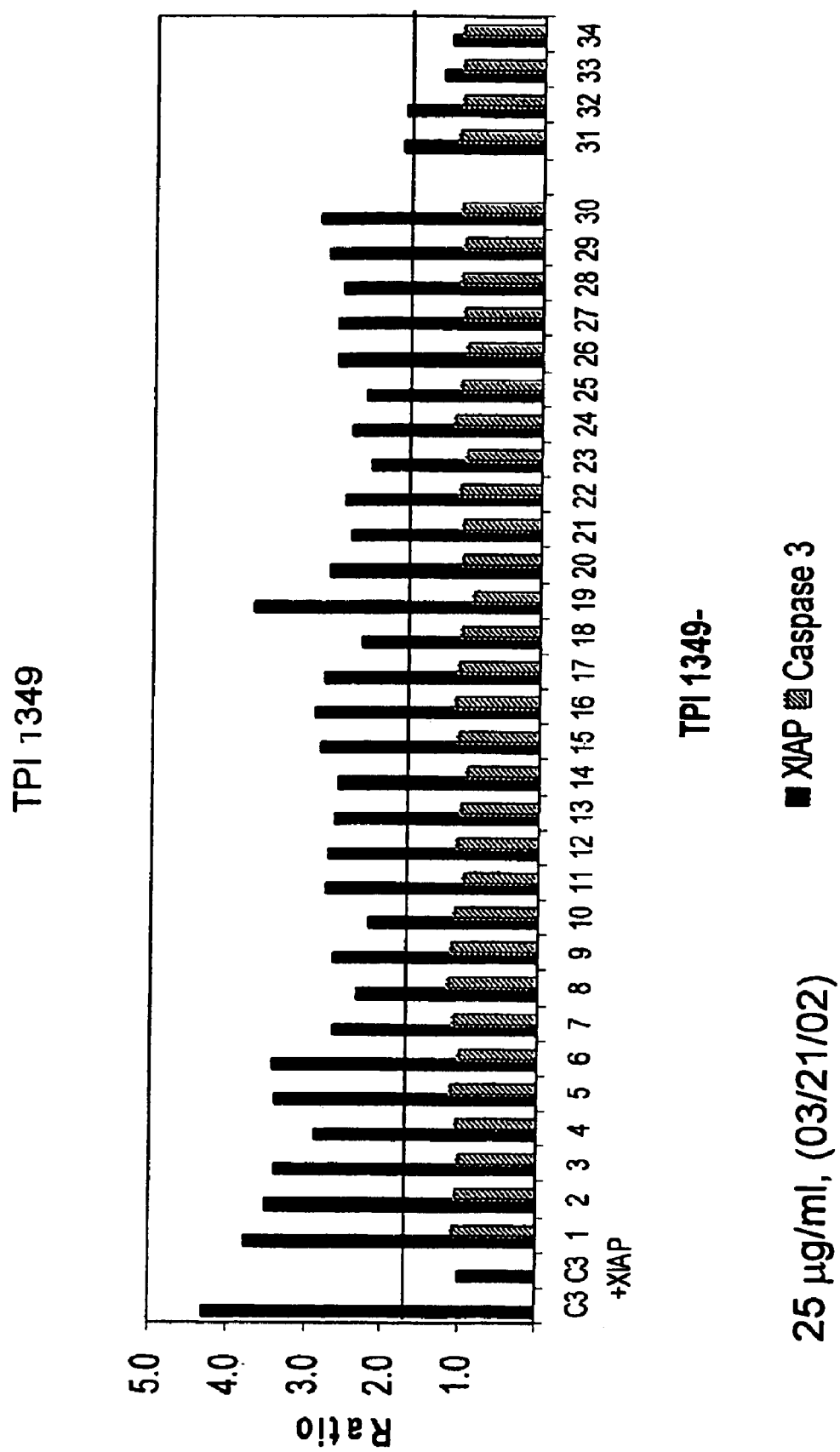
FIG. 21B shows the activity of TPI 1349-1 through TPI 1349-34 in the derepression assay using full length XIAP.
Figure 21C:
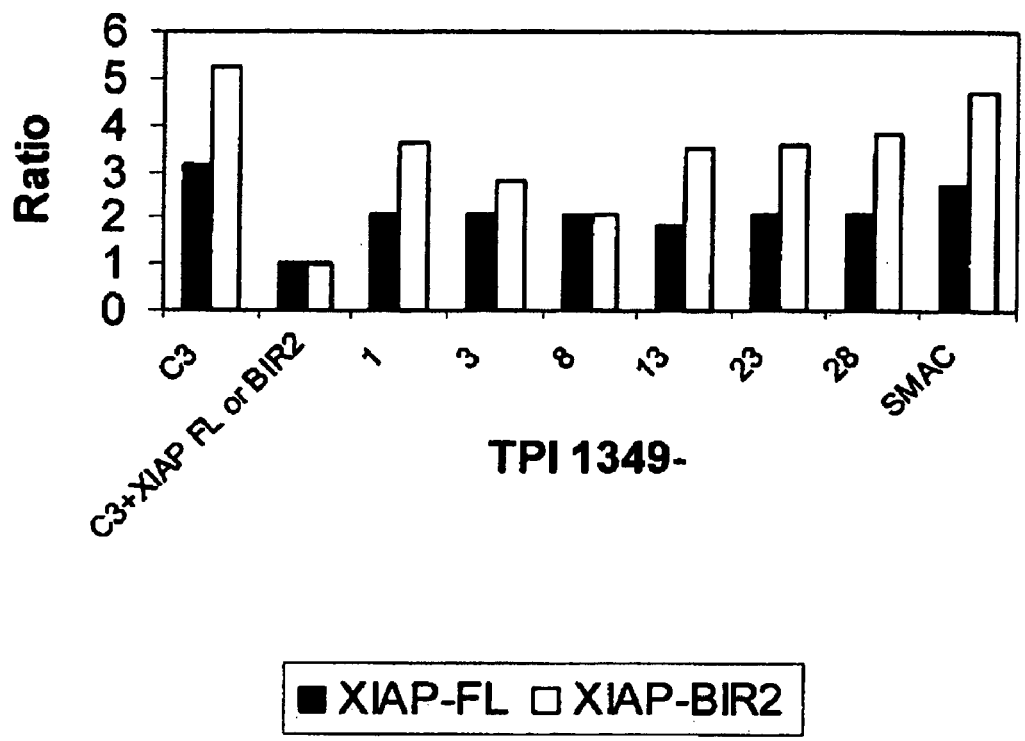
FIG. 21C shows the activity of TPI 1349-1, -3, -8, -13, -23, and -28 using both full length XIAP and XIAP BIR2 domain.
Figure 21D:
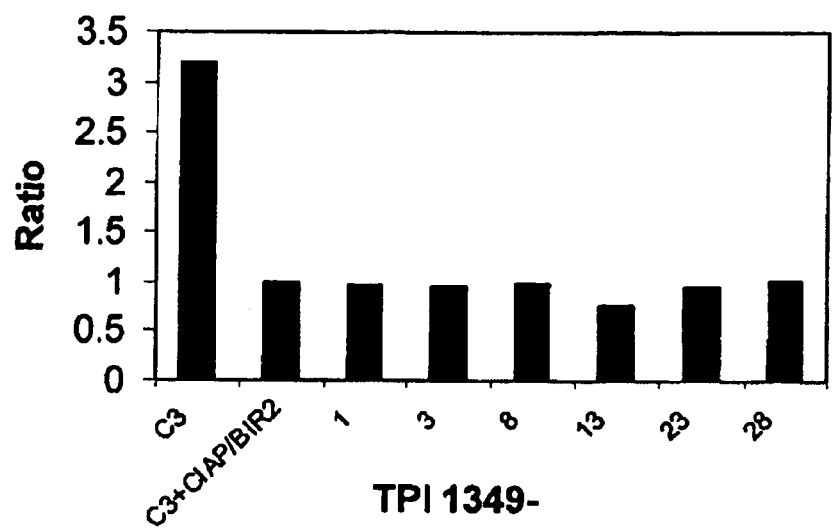
FIG. 21D shows the activity of TPI 1349-1, -3, -8, -13, -23, and -28 using cIAP BIR2 domain.

The TPI 914 N-acyltriamine library included 50 amino acid R groups at position R1, 50 amino acid R groups at position R2 and 50 acid derivatives at position R3 for a total diversity of 125,000 species. Mixtures having a defined functionality at one of the R positions and identified by positional scanning of the TPI 914 library as having a peptide/XIAP ratio greater than or equal to about 1.8 when present at 25 micrograms per milliliter in the derepression assay were identified and are shown in FIG. 4. Control agents having a peptide/XIAP ratio greater than or equal to about 1.8 when present at 6.25 micrograms per milliliter or 12.5 micrograms per milliliter in the derepression assay were identified and are shown in FIG. 5. Additional compounds designed based on this screening are shown in FIG. 21A as TPI 1349-1 through TPI 1349-34. The activity of these compounds is shown in FIGS. 21B–D.

The TPI 927 polyphenylurea library included 48 amino acid R groups at position R1, 48 amino acid R groups at position R2 and 39 acid derivatives at position R3 for a total diversity of 89,856 species. Mixtures having a defined functionality at one of the R positions and identified by positional scanning of the TPI 927 library as having a peptide/XIAP ratio greater than or equal to about 1.8 when present at 4 micrograms per milliliter in the derepression assay were identified and are shown in FIG. 6. Control agents having a peptide/XIAP ratio greater than or equal to about 1.8 when present at 25 micrograms per milliliter in the derepression assay were identified and are shown in FIG. 9.

Figure 25:
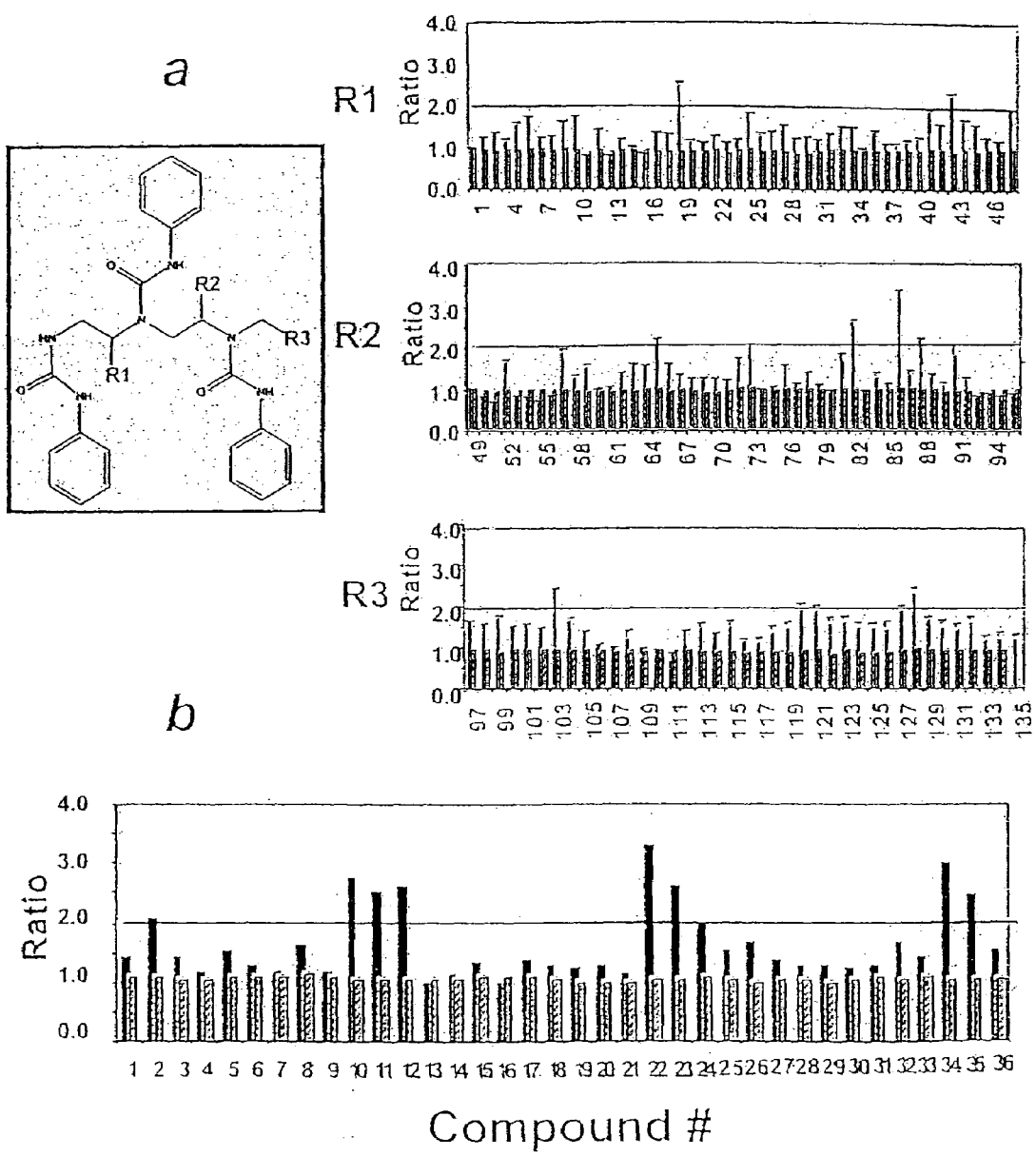

In particular, as shown in FIG. 25a, aliquots of the mixture-based combinatorial library of poly-phenylureas based on TPI 927 described above were added to microtiter plates containing XIAP and caspase-3 (black bars) or, as a control, caspase-3 alone (gray bars). Caspase-3 activity was measured by monitoring cleavage of the fluorogenic substrate Ac-DEVD-AFC as described herein. Briefly, recombinant proteins were produced in bacteria and purified as described, for example, in Deveraux et al., Nature 388: 300–304(1997). GST-XIAP (46 nM) was added to active caspase-3-His6 (0.36 nM) in 100 µl of 50 mM HEPES pH 7.4, 10% sucrose, 1 mM EDTA, 0.1% CHAPS, 100 mM NaCl, and 10 mM DTT to achieve approximately 75% inhibition of protease activity. Activity of caspase-3 was measured by monitoring cleavage of the fluorogenic tetrapeptide substrate acetyl-DEVD-AFC (BIOMOL, Plymouth, Pa.) at 100 µM. Generation of fluorogenic AFC (7-amino-4-trifluoromethyl coumarin) product was measured with a spectrofluorometric plate reader in kinetic mode for 30 minutes at 37° C. using excitation and emission wavelengths of 405 nm and 510 nm, respectively. Chemical compounds were screened at 6.25, 12.5 and 25.0 µg/ml to identify compounds that increase caspase-3 induced cleavage of Ac-DEVD-AFC. Control reactions lacked XIAP, and all assays were conducted in the linear range of substrate hydrolysis to avoid substrate depletion artifacts.

A representative screen of the positional scanning combinatorial library (final concentration 25 mg/ml) is shown in FIG. 25a. In FIG. 25a, hits were defined as compounds that increased caspase-3 activity greater than or equal to 2 fold in XIAP-inhibited reactions without affecting caspase-3 alone. Caspase activity is presented as the fold increase in enzyme velocity after the addition of the compound. The positive compound mixtures were deconvoluted by standard methods yielding 36 individual compounds which were screened in the same caspase derepression assay as described below.

The 36 individual compounds (TPI 1396-1 through TPI 1396-36) were synthesized based on deconvolution of the polyphenylurea library. The individual compounds result from the combination of the defined functionalities of the most active mixtures of the positional scanning combinatorial library. The number of functionalities used were 3, 4, and 3 at R1, R2 and R3, respectively. As shown in FIG. 25b, each of the 36 individual compounds was tested at 25 mg/ml using the caspase derepression assay for their ability to increase caspase-3 activity in the presence (black bars) or absence (gray bars) of XIAP, using a 2-fold elevation in the enzyme velocity as the cut-off for positivity. Other cut-offs for positivity can include, for example, 1.5 fold and higher, or 1.8 fold and higher.

Figure 23B:
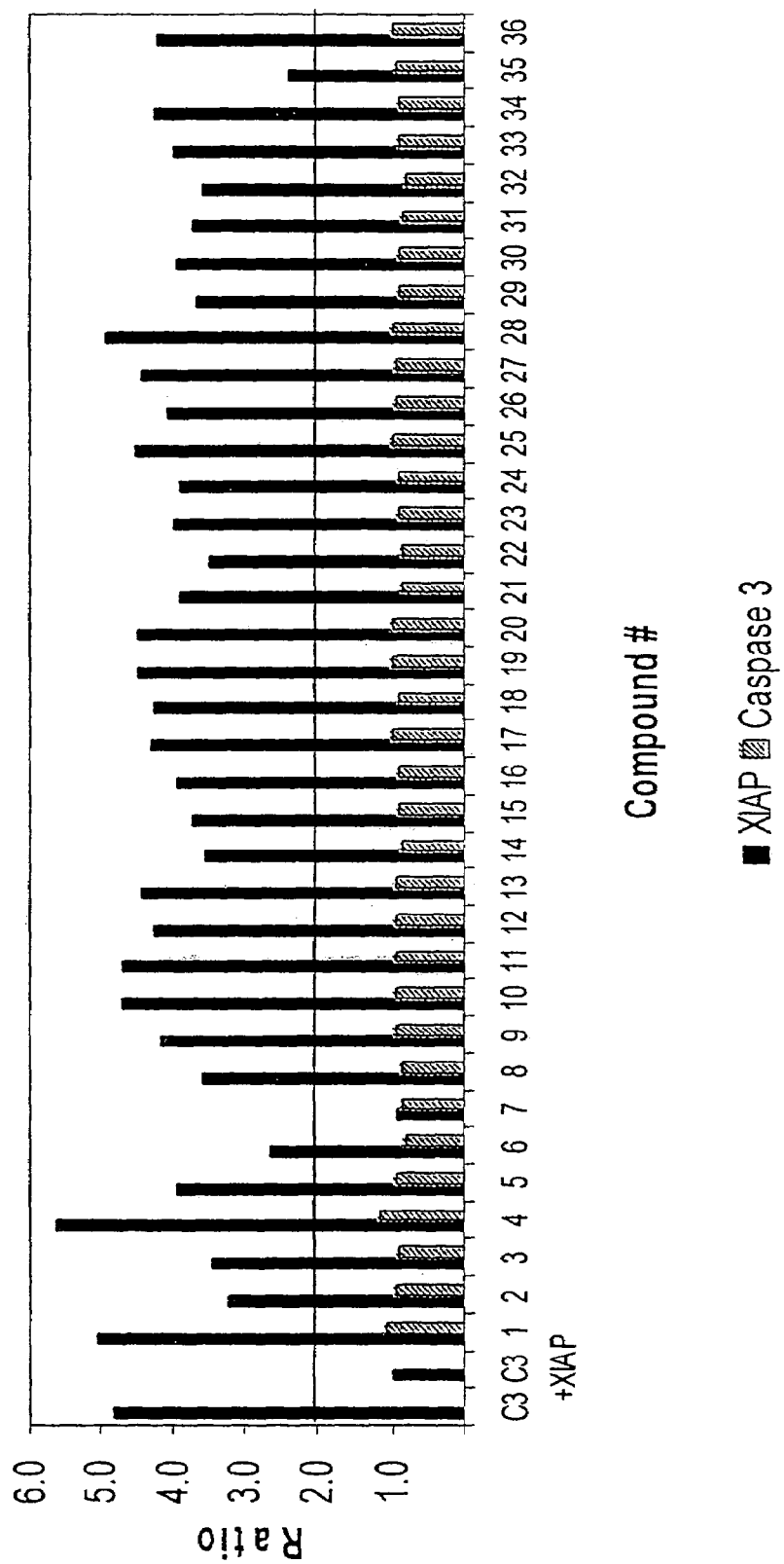
FIG. 23B shows the activity of TPI 1391-1 through TPI 1391-36 at 100 µg/ml in the derepression assay using full length XIAP.

The TPI 759 N-benzyl-1,4,5-trisusbstituted-2,3-diketopiperazine library included 29 amino acid R groups at position R1, 27 amino acid R groups at position R2 and 40 acid derivatives at position R3 for a total diversity of 31,320 species. Mixtures having a defined functionality at one of the R positions and identified by positional scanning of the TPI 759 library as having a peptide/XIAP ratio greater than or equal to about 2.0 (or in the case of the sublibrary where R3 was fixed, a ratio of 1.9 or higher) when present at 25 micrograms per milliliter in the derepression assay were identified and are shown in FIG. 8. Additional compounds designed based on these functionalities are shown in FIG. 23A as TPI 1391-1 through TPI 1391-36. The activity of these compounds is shown in FIGS. 23B–F.

Figure 24B:
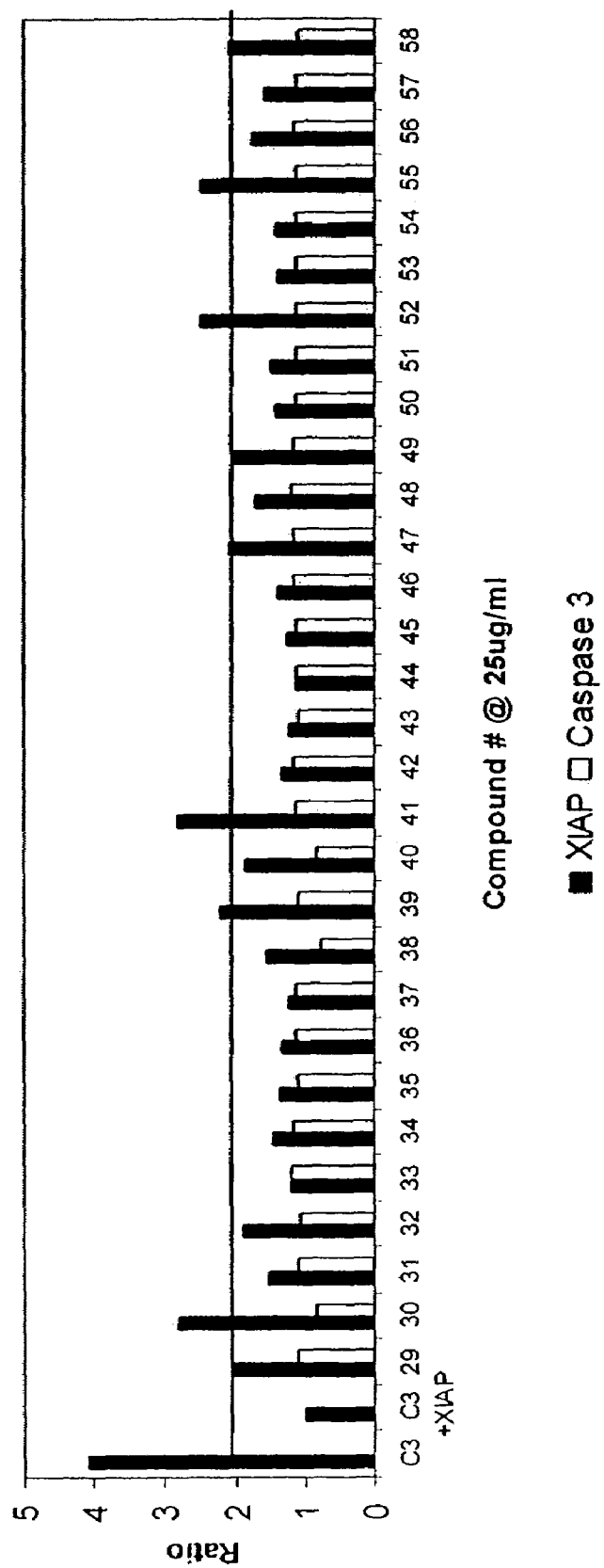
FIG. 24B shows the activity of TPI 1400-1 through TPI 1400-28 at 25 µg/ml in the derepression assay using full length XIAP.

The TPI 882 C-6-acylamino bicyclic guanidine library included 43 amino acid R groups at position R1, 41 acid derivatives at R2 and 41 acid derivatives at R3 for a total diversity of 72,283 species. Mixtures having a defined functionality at one of the R positions and identified by positional scanning of the TPI 882 library as having a peptide/XIAP ratio greater than or equal to about 1.9 when present at 5 micrograms per milliliter in the derepression assay were identified and are shown in FIG. 7. Control agents having a peptide/XIAP ratio greater than or equal to about 2.0 when present at 8 micrograms per milliliter in the derepression assay were identified and are shown in FIG. 10. Additional compounds designed based on these functionalities are shown in FIG. 24A as TPI 1400-1 through TPI 1400-58. The activity of these compounds is shown in FIGS. 24B–H.

EXAMPLE VII

SMAC Competition Assay

This Example describes an assay useful for determining the binding affinity of a derepressor of an IAP-inhibited caspase for an IAP, or functional fragment thereof.

A polarization based binding assay was used to detect binding between rhodamine labeled SMAC (rhodamine-SMAC) and the XIAP fragments BIR2 or BIR3RING. The assay is based on the decrease in mobility that occurs for rhodamine-SMAC when associated with XIAP or functional fragments thereof which is detected as a reduction in polarization for bound rhodamine-SMAC compared to free (unbound) rhodamine-SMAC.

Binding affinity of rhodamine-SMAC for a glutathione-S-transferase-BIR2 fusion protein (GST-BIR2) or BIR3RING was determined as follows. Assays were run in 50 mM Tris @ pH 7.2/100 mM NaCl/0.1% BSA. Rhodamine labeled SMAC was present at 400 nM. GST-BIR2 ranged from 0.05 to 20 µM while GST-BIR3RING ranged from 0.02 to 6 µM. Plates (proxi from Packard) were read in fluorescence polarization mode after 1 hr at 28° C. in a Victor from Perkin-Elmer with excitation at 531 nm and emission at 595 nm. Data was plotted as a function of millipolars vs. protein concentration. Rhodamine-SMAC had a $K_d$ of 20 µM for GST-BIR2 and 280 nM for GST-BIR3RING Unlabelled SMAC was titrated against a solution containing 400 nM rhodamine-SMAC and 10 µM GST-BIR2 or 1 µM GST-BIR3RING. Plates (proxi from Packard) were read in fluorescence polarization mode after 1 hr at 28° C. in a Victor from Perkin-Elmer with excitation at 531 nm and emission at 595 nm. Unlabeled SMAC was titrated in the range of 0 to 50 µM Data was plotted as a function of millipolars vs SMAC concentration and $IC_{50}$ values determined. The $IC_{50}$ value of the SMAC titration was 21 µM for GST-BIR3RING. Competition with unlabeled SMAC was also seen for GST-BIR2 but was not sufficient to allow calculation of an $IC_{50}$.

Candidate agents from a library are added to a solution containing 400 nM rhodamine-SMAC and 10 µM GST-BIR2. Fluorescence polarization is determined for each sample and those candidates that show a decrease in polarization compared to a control reaction containing 400 nM rhodamine-SMAC and 10 µM GST-BIR2 are identified as derepressors of an IAP-inhibited caspase. As a control, fluorescence polarization is also determined for the library sample in the absence of GST-BIR2.

An agent identified as a derepressor of an IAP-inhibited caspase is titrated against a solution of rhodamine-SMAC and GST-BIR2. Polarization is determined at each concentration of the agent as described above. Data is plotted as a function of millipolars vs. agent concentration and binding constants determined also as described above.

EXAMPLE VIII

Screening of Individual Compounds from Various Libraries

This example describes screening of individual agents derived from TPI 914, TPI 927, TPI 759 and TPI 882 libraries and identification of individual agents that Derepress an IAP-Inhibited Caspase.

Individual agents were synthesized based on the active agents identified in Example VI. Selected agents based on the TPI 914 derepressors shown in FIG. 5 were synthesized and are identified as agents TPI 1349-1 through TPI 1349-34 in FIG. 21. Selected agents based on the TPI 927 derepressors shown in FIG. 9 were synthesized and are identified as agents TPI 1396-1 through TPI 1396-65 in FIG. 22. Selected agents based on the TPI 759 derepressors shown in FIG. 8 were synthesized and are identified as agents TPI 1391-1 through TPI 1391-36 in FIG. 23. Selected agents based on the TPI 882 derepressors shown in FIG. 10 were synthesized and are identified as agents TPI 1400-1 through TPI 1400-58 in FIG. 24.

The caspase derepression assay was used to evaluate the agents shown in FIGS. 21–24. Each compound was tested using the caspase derepression assay for its ability to increase caspase-3 activity. The structures for TPI 1349-1 through TPI 1349-34 along with respective molecular weights and masses are shown in FIG. 21A. The activity of TPI 1349-1 through TPI 1349-34 in a caspase derepression assay using full length XIAP is shown in FIG. 21B. The activity of TPI 1349-1, -3, -8, -13, -23, and -28 using both full length XIAP and XIAP BIR2 domain is shown in FIG. 21C. The activity of TPI 1349-1, -3, -8, -13, -23, and -28 using cIAP-1 BIR2 domain is shown in FIG. 21D. These data indicate that the TPI 1349 compounds are active in derepressing caspase inhibited by either XIAP or the BIR2 domain of XIAP, but do not overcome cIAP1-mediated suppression of caspase-3. It is important to note that the lack of activity observed for various compounds can be the result of the compounds being present at a two fold excess over cIAP1.

Figure 22A:
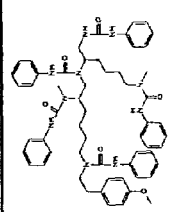
FIG. 22A shows structures of TPI 1396-1 through TPI 1396-65 along with respective molecular weights, masses and lowest concentration of each agent having a ratio of 1.8 or higher in SMAC competition assays.
Figure 22B:
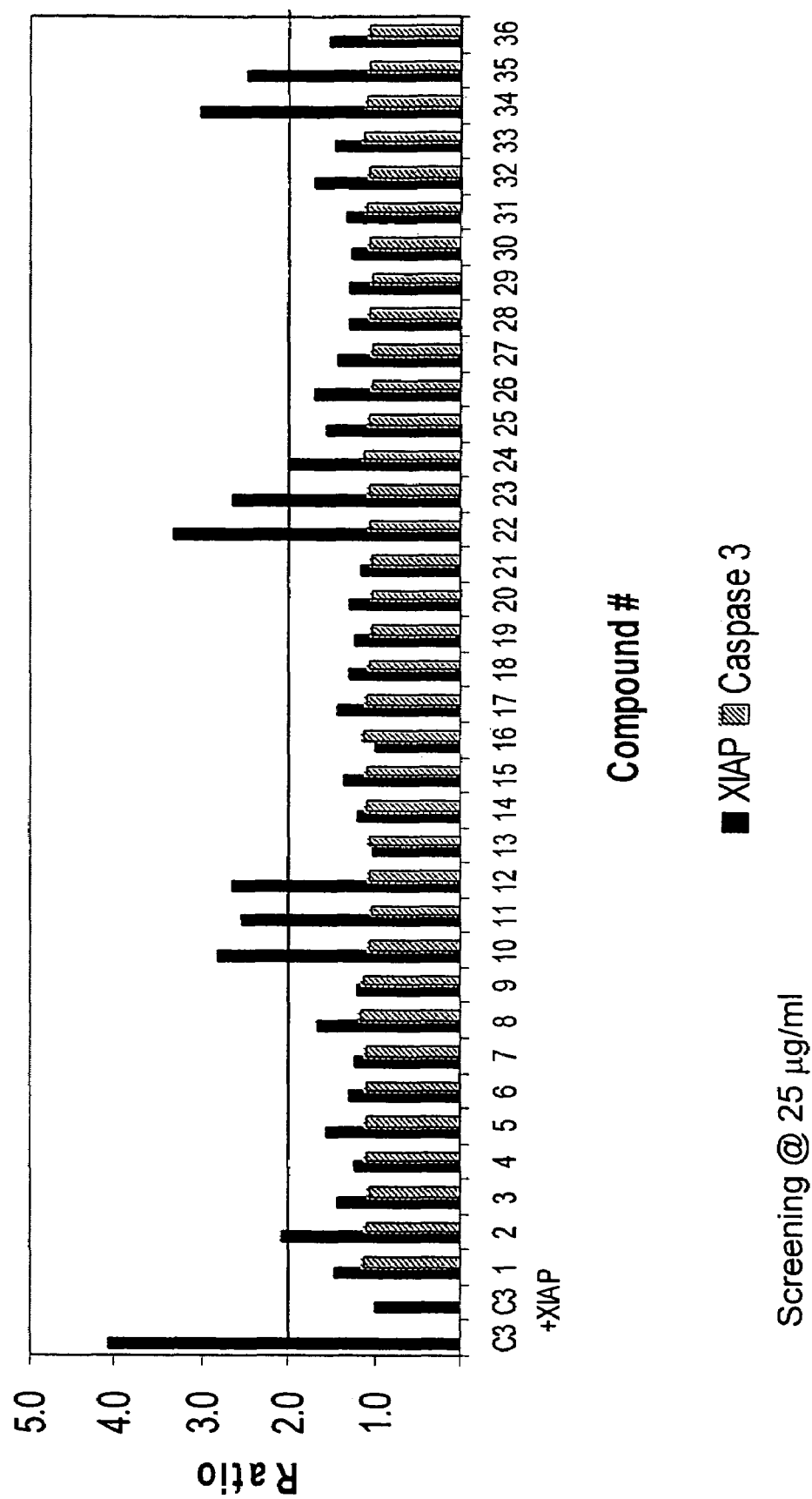
FIG. 22B shows the activity of TPI 1396-1 through TPI 1396-36 in the derepression assay using full length XIAP.
Figure 22C:
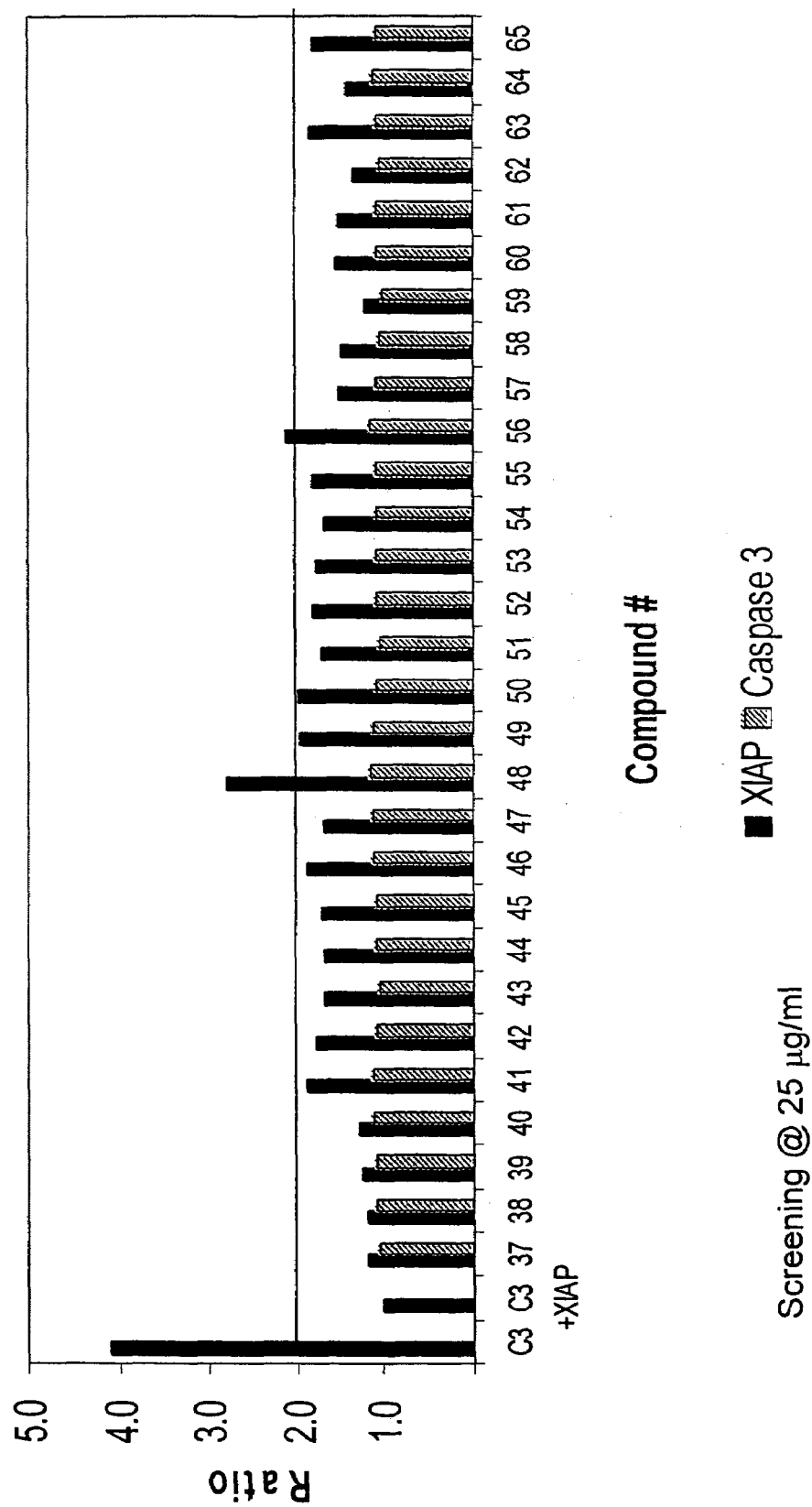
FIG. 22C shows the activity of TPI 1396-37 through TPI 1396-65 in the derepression assay using full length XIAP.
Figure 22E:
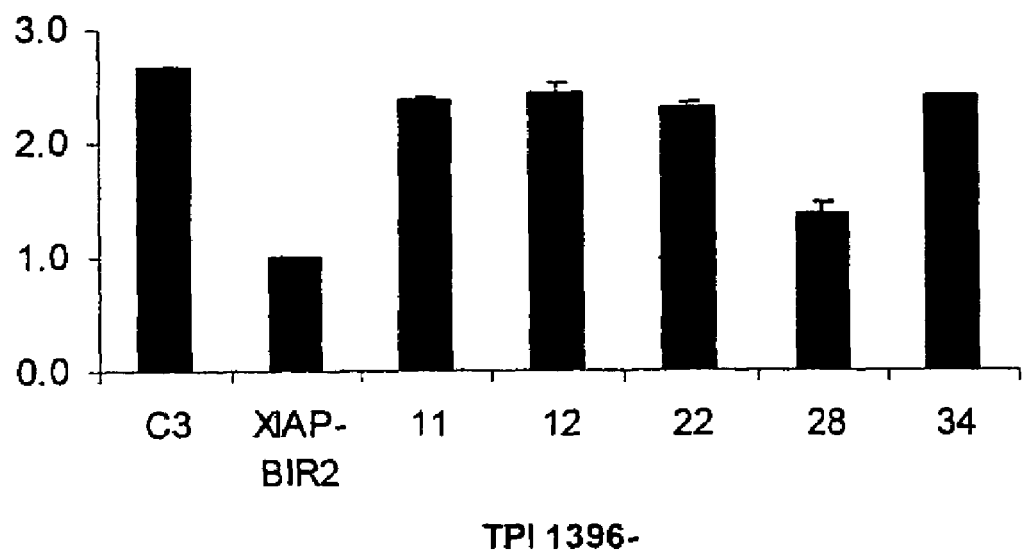
FIG. 22E shows the activity of TPI 1396-11, -12, -22, -28, and -34 at 50 µg/ml using XIAP BIR2 domain.
Figure 22F:
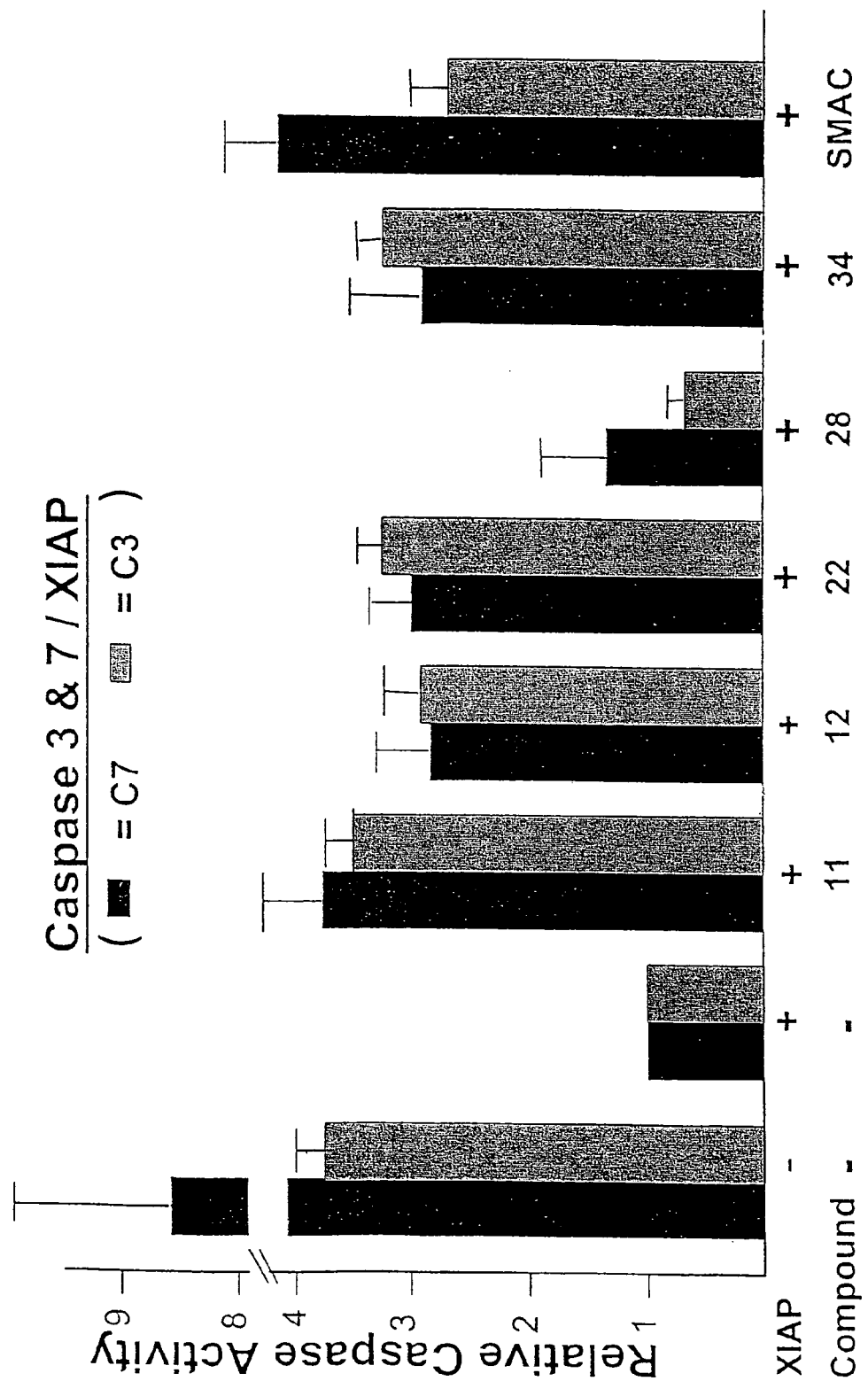
FIG. 22F shows the activity of TPI 1396-11, -12, -22, -28, and -34 at 100 µg/ml using full length XIAP and Caspase 3 or 7.
Figure 22G:
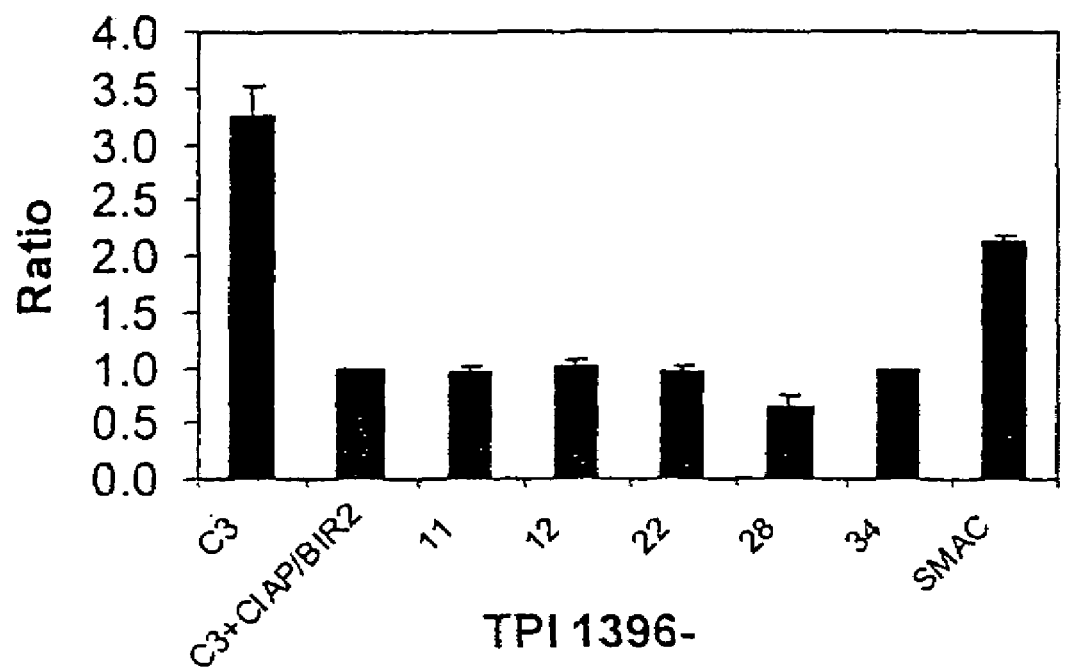
FIG. 22G shows the activity of TPI 1396-11, -12, -22, -28, and -34 at 100 µg/ml using cIAP BIR2 domain.

The structures of TPI 1396-1 through TPI 1396-65 along with respective molecular weights and masses are shown in FIG. 22A. The activity of TPI 1396-1 through TPI 1396-36 in a caspase derepression assay using full length XIAP is shown in FIG. 22B. The activity of TPI 1396-37 through TPI 1396-65 in the derepression assay using full length XIAP is shown in FIG. 22C. A table indicating the activities of TPI 1396-11, -12, -22, -28, and -34 in the derepression assay using full length XIAP and the XIAP BIR2 domain is shown in FIG. 22D. The activity of TPI 1396-11, -12, -22, -28, and -34 at 50 µg/ml using XIAP BIR2 domain is shown in FIG. 22E. Additional representative data for the activity of TPI 1396-11, -12, -22, -28, and -34 at 100 µg/ml using full length XIAP and Caspase 3 or 7 is shown in FIG. 22F. The activity of TPI 1396-11, -12, -22, -28, and -34 at 100 µg/ml using cIAP-1 BIR2 domain is shown in FIG. 22G These data indicate that TPI 1396 compounds are active in derepressing caspase inhibited by either XIAP or the BIR2 domain of XIAP, but do not overcome cIAP1-mediated suppression of caspase-3. It is important to note that the lack of activity observed for various compounds can be the result of the compounds being present at a two fold excess over cIAP1.

Figure 23C:
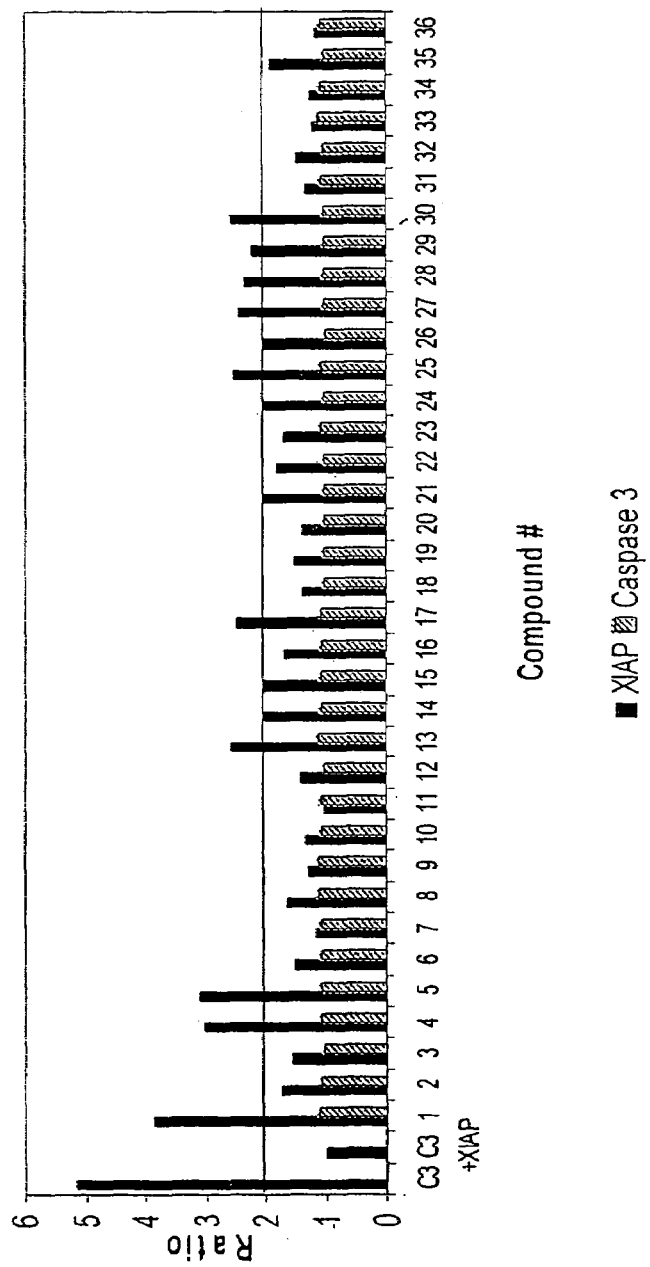
FIG. 23C shows the activity of TPI 1391-1 through TPI 1391-36 at 25 µg/ml in the derepression assay using full length XIAP.
Figure 23E:
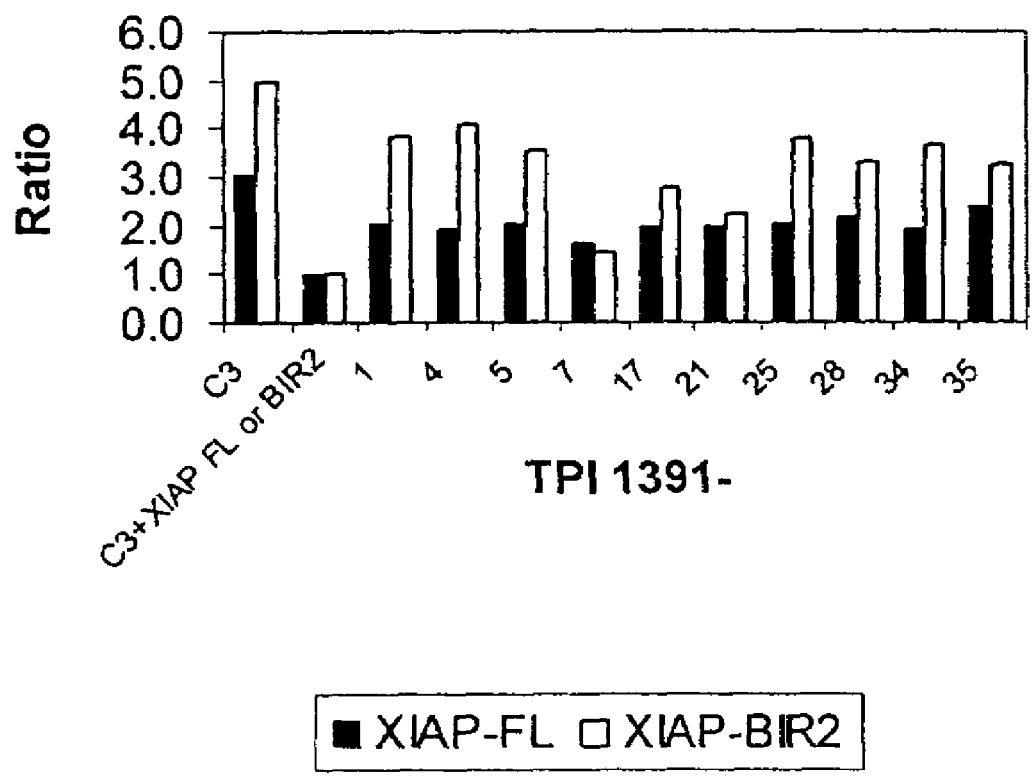
FIG. 23E shows a comparison of the activities of TPI 1391-1, -4, -5, 7, -17, -21, -25, -28, -34 and -35 in the derepression assay using full length XIAP or XIAP BIR2 domain.
Figure 23F:
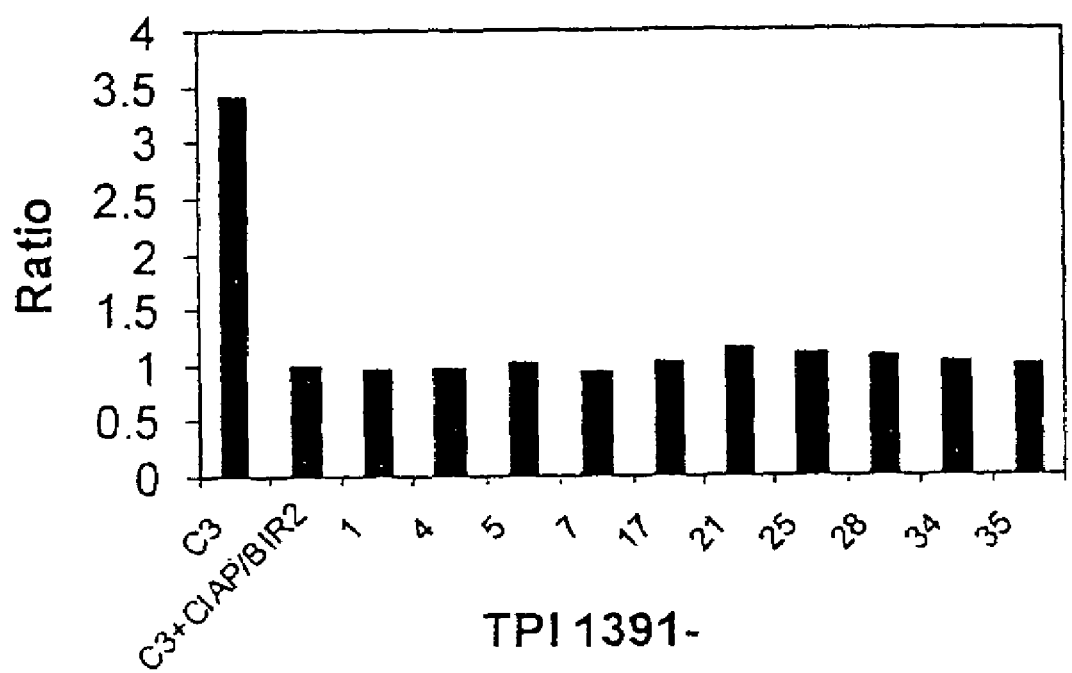
FIG. 23F shows the activity of TPI 1391-1, -4, -5, 7, -17, -21, -25, -28, -34 and -35 using cIAP BIR2 domain.

The structures of TPI 1391-1 through TPI 1391-36 along with respective molecular weights and masses are shown in FIG. 23A. The activity of TPI 1391-1 through TPI 1391-36 at 100 µg/ml in a caspase derepression assay using full length XIAP is shown in FIG. 23B. The activity of TPI 1391-1 through TPI 1391-36 at 25 µg/ml in the derepression assay using full length XIAP is shown in FIG. 23C. A table indicating the activities of TPI 1391-1, -4, -5, 7, -17, -21, -25, -28, -34 and -35 in the derepression assay using full length XIAP is shown in FIG. 23D. A comparison of the activities of TPI 1391-1, -4, -5, 7, -17, -21, -25, -28, -34 and -35 in the derepression assay using full length XIAP or XIAP BIR2 domain is shown in FIG. 23E. The activity of TPI 1391-1, -4, -5, 7, -17, -21, -25, -28, -34 and -35 using cIAP-1 BIR2 domain is shown in FIG. 23F. These data indicate that TPI 1391 compounds are active in derepressing caspase inhibited by either XIAP or the BIR2 domain of XIAP, but do not overcome cIAP1-mediated suppression of caspase-3. It is important to note that the lack of activity observed for various compounds can be the result of the compounds being present at a two fold excess over cIAP1.

Figure 24C:
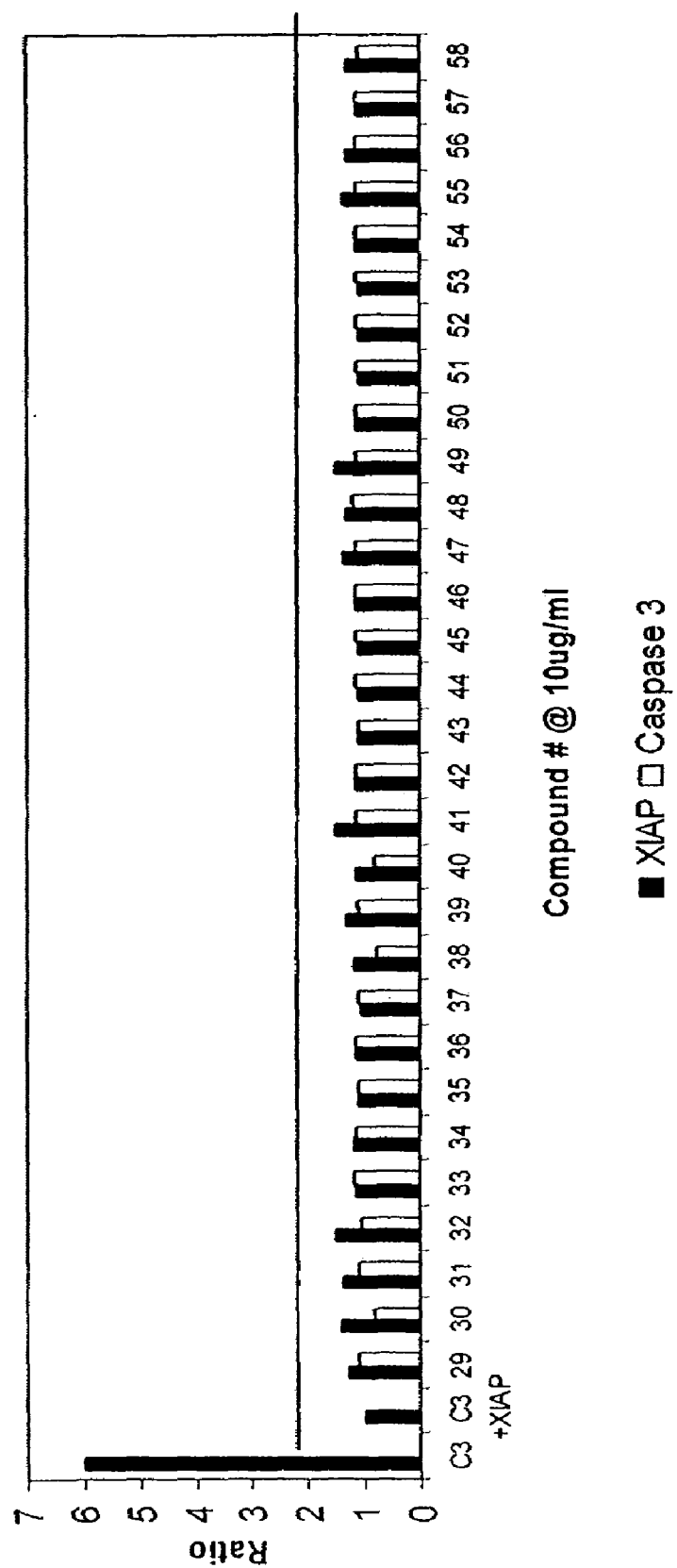
FIG. 24C shows the activity of TPI 1400-1 through TPI 1400-28 at 10 µg/ml in the derepression assay using full length XIAP.
Figure 24D:
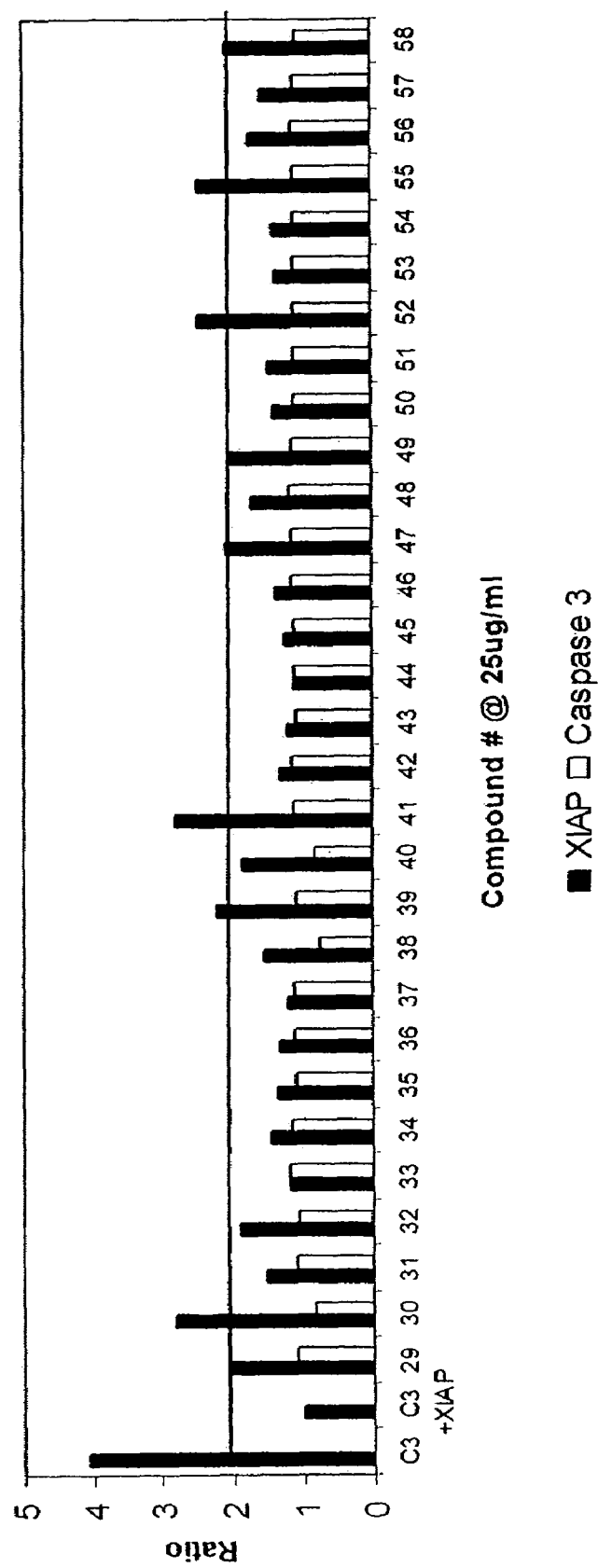
FIG. 24D shows the activity of TPI 1400-29 through TPI 1400-58 at 25 µg/ml in the derepression assay using full length XIAP.
Figure 24E:
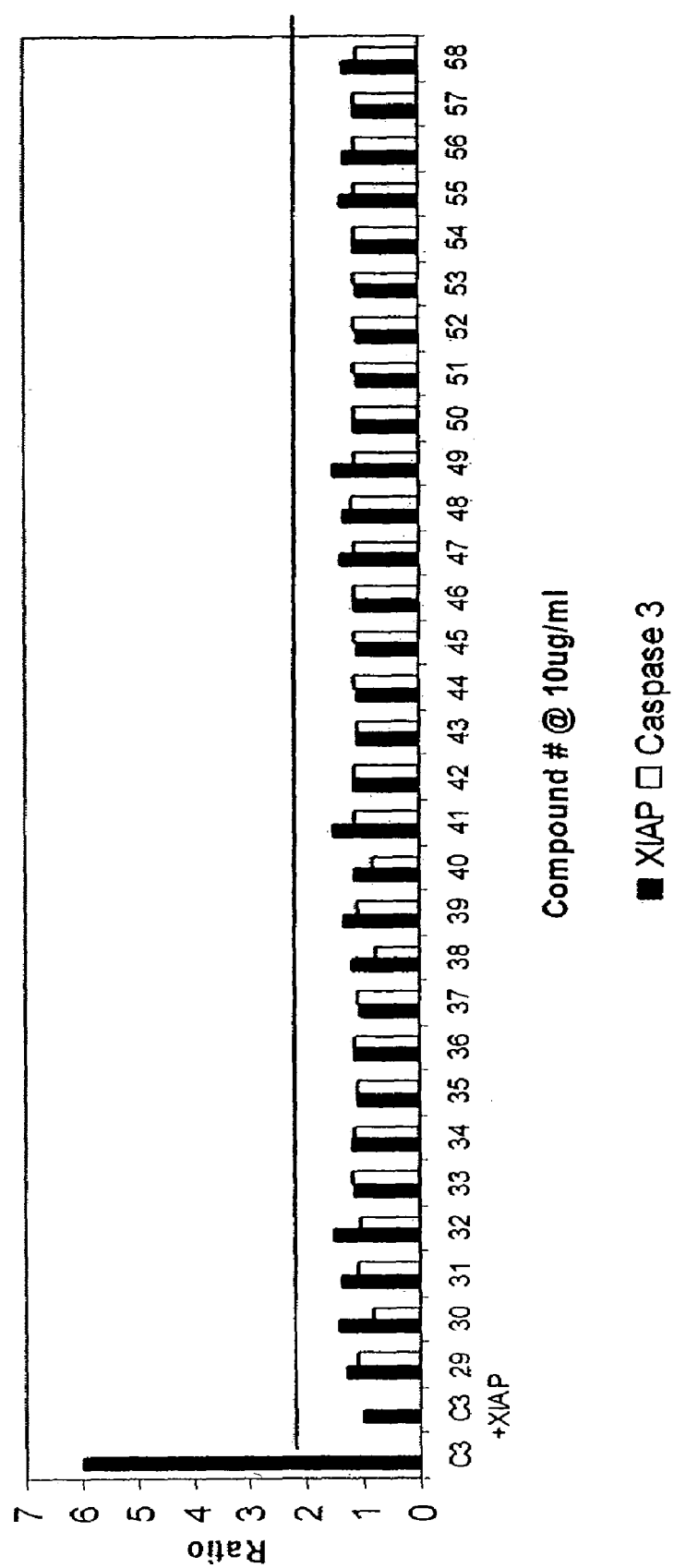
FIG. 24E shows the activity of TPI 1400-29 through TPI 1400-58 at 10 µg/ml in the derepression assay using full length XIAP.
Figure 24G:
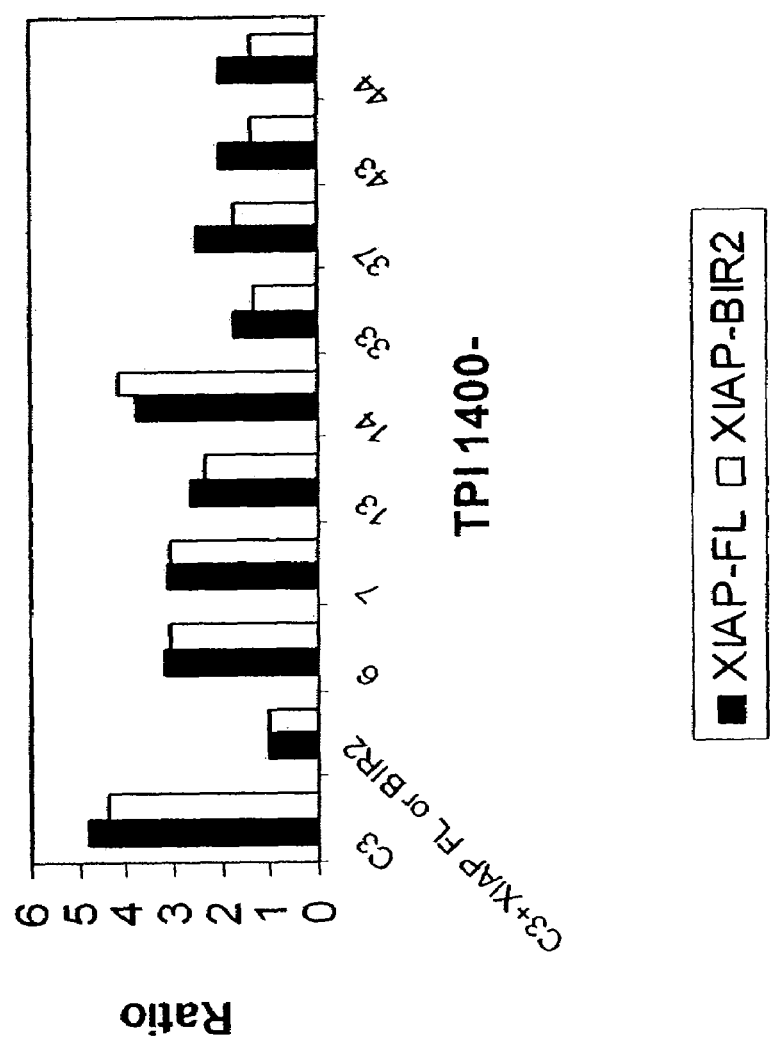
FIG. 24G shows a comparison of the activities of TPI 1400-6, -7, 13, -14, -33, -37, -43, -44 in the derepression assay using full length XIAP or XIAP BIR2 domain.
Figure 24H:
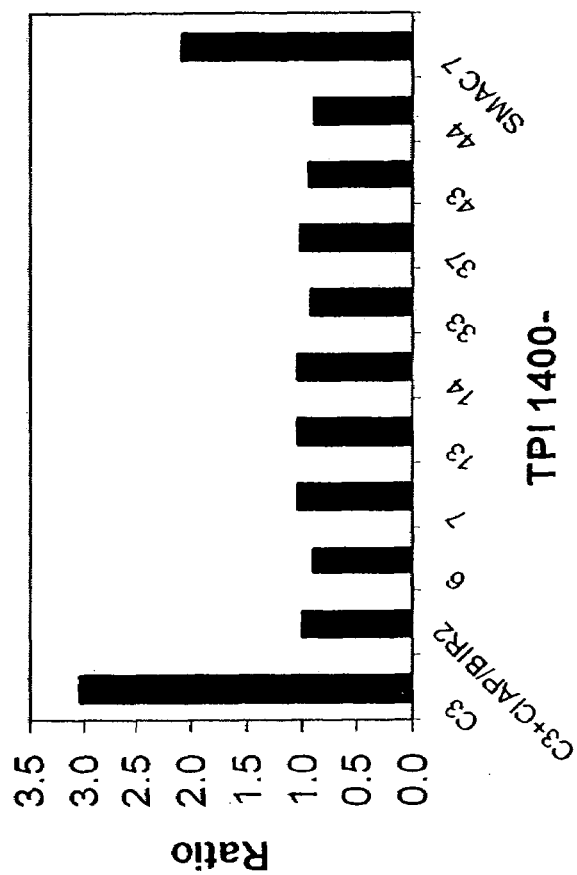
FIG. 24H shows the activity of TPI 1400-6, -7, 13, -14, -33, -37, -43, -44 using cIAP BIR2 domain.

The structures of TPI 1400-1 through TPI 1400-58 along with respective molecular weights and masses are shown in FIG. 24A. The activity of TPI 1400-1 through TPI 1400-28 at 25 µg/ml in a caspase derepression assay using full length XIAP is shown in FIG. 24B. The activity of TPI 1400-1 through TPI 1400-28 at 10 µg/ml in the derepression assay using full length XIAP is shown in FIG. 24C. The activity of TPI 1400-29 through TPI 1400-58 at 25 µg/ml in the derepression assay using full length XIAP is shown in FIG. 24D. The activity of TPI 1400-29 through TPI 1400-58 at 10 µg/ml in the derepression assay using full length XIAP is shown in FIG. 24E. A table indicating the activities of TPI 1400-6, -7, 13, -14, -33, -37, -43, -44 in the derepression assay using full length XIAP is shown in FIG. 24F. A comparison of the activities of TPI 1400-6, -7, 13, -14, -33, -37, -43, -44 in the derepression assay using full length XIAP or XIAP BIR2 domain is shown in FIG. 24G The activity of TPI 1400-6, -7, 13, -14, -33, -37, -43, -44 using cIAP BIR2 domain is shown in FIG. 24H. These data indicate that TPI 1400 compounds are active in derepressing caspase inhibited by either XIAP or the BIR2 domain of XIAP, but do not overcome cIAP1-mediated suppression of caspase-3. It is important to note that the lack of activity observed for various compounds can be the result of the compounds being present at a two fold excess over cIAP1.

EXAMPLE IX

Peptidyl and Non-Peptidyl Compounds Restore Caspase Activity of IAP-Inhibited Caspase In Vitro This example demonstrates an assay for determining potency of peptidyl and non-peptidyl derepressors of IAP-inhibited caspases in vitro. This example also identifies peptidyl and non-peptidyl compounds having potency at restoring caspase activity of IAP-inhibited caspase in vitro.

The caspase derepression assay was used to evaluate peptidyl IAP antagonists identified from screens of the TPI 792 library and non-peptidyl IAP antagonists identified from screens of the TPI 1391 and TPI 1396 libraries. Each compound was titrated against a solution of rhodamine labeled SMAC tetrapeptide, AVPI (SEQ ID NO:4), and full length XIAP under the conditions described in Example VII. Polarization was determined at each concentration of the IAP antagonist, data was plotted as a function of millipolars vs. compound concentration, and the EC50 binding constants were determined from the plots. As a control unlabeled SMAC tetrapeptide, AVPI (SEQ ID NO:4) was also assayed.

For several compounds of the TPI 1396 library (TPI 1396-11, -12, -22 -28, and -34), the caspase derepression assay was carried out in the presence of caspase-3 or caspase-7. These studies, representative results of which are shown in FIG. 22F, polyphenylureas reversed XIAP-mediated suppression of caspases 3 and 7. For these experiments, GST-XIAP was added to active caspase-3 (0.69 nM) or caspase 7 (3.2 nM) and 75 µM compounds with 100 µM DEVD-AFC in a 100 µl of buffer. Generation of AFC was measured in a spectrofluorimeter with 405 nm excitation and 510 nm emission at 37° C. for 30 minutes. The data shown in FIG. 22F represent caspase activity, compared to XIAP-inhibited reactions (=1.0) and are mean±standard deviation of three determinations. As a control unlabeled SMAC heptapeptide, AVPIAQK was also assayed.

Table VIII summarizes the results of the SMAC competition assay for IAP antagonists identified from the TPI 792, TPI 1391 and TPI 1396 libraries. The EC50 was determined, by calculating the amount of compound necessary to restore caspase-3 activity to 50% of maximum velocity (Vmax). Two of the most potent tetramer peptides were TPI 792-33 and TPI 792-35 which displayed enzyme derepression activities in vitro that were 5.2 to 2.5 fold better than SMAC peptide, respectively. The most potent diketopiperazine based compounds included TPI 1391-21, TPI 1391-28 and TPI 1391-34 which exhibited potencies 3.3 to 5.0 fold more active than SMAC peptide. The most potent phenyl-urea compounds included TPI 1396-22, TPI 1396-34 and TPI 1396-28 which exhibited potencies that were 1.6 to 2.8 fold more active than SMAC peptide.

The caspase derepression assay was used to evaluate non-peptidyl IAP antagonists identified from screens of the TPI 1396 library in the presence of the cIAP1 BIR2 domain. Each compound was present at a 100 µM with caspase-3 at 8.5 nM, cIAP BIR2 at 37 µM and 100 µM Ac-DEVD-AFC. Assays were initiated upon addition of DEVD substrate and release of fluorogenic product was followed in the kinetic mode for 30 minutes at 37 ° C. Assays were performed in a Molecular Devices FMAX spectrofluorimeter. Ratios are relative to assay with cIAP BIR2 in the absence of compound. FIGS. 22B and 22C show relative caspase activity in the presence of various TPI 1396 library compounds. As is shown in FIG. 22G, polyphenylurea compounds inhibit XIAP but do not inhibit cIAP1, as assayed using the cIAP1 BIR2 domain. Compounds TPI 1396-11, TPI 1396-12, TPI 1396-22 and TPI 1396-34 represent active XIAP inhibitors, while TPI 1396-28 is an inactive analog.

TABLE VIII

|  | EC50 (µM) | Relative Potency |
|---|---|---|
| Natural peptides |  |  |
| SMAC AVPI tetrapeptide (SEQ ID NO: 4) | 125 | 1.0 |
| Un-natural peptides |  |  |
| TPI 792-33 | 24 | 5.2 |
| TPI 792-35 | 51 | 2.5 |

TABLE VIII-continued

| | EC50 (µM) | Relative Potency |
|---|---|---|
| Diketopiperazines | | |
| TPI 1391-21 | 33.6 | 3.7 |
| TPI 1391-28 | 25.1 | 5 |
| TPI 1391-34 | 39.4 | 3.3 |
| Diphenyl and Triphenyl Ureas | | |
| TPI 1396-22 | 45.3 | 2.8 |
| TPI 1396-34 | 77.1 | 1.6 |
| TPI 1396-28 | >134 | N/A |

These results demonstrate that peptidyl compounds TPI 792-33 and TPI 792-35; diketopiperazine based compounds TPI 1391-21, TPI 1391-28 and TPI 1391-34; and phenyl-urea compounds TPI 1396-22 and TPI 1396-34 derepressed XIAP inhibited caspase in vitro and did so with more potency than the SMAC AVPI tetrapeptide (SEQ ID NO:4).

EXAMPLE X

Peptidyl Compounds TPI 792-33 and TPI 792-35 Kill Tumor Cells

This example demonstrates an assay for determining potency of derepressors of IAP-inhibited caspases in cell cultures. This example also demonstrates that TPI 792-33 and TPI 792-35 reduce the viability of tumor cells in culture.

The TPI 792-33 and TPI 792-35 compounds were assayed to determine their effects on tumor cell viability. As shown in FIG. 12, TPI 792-33 and TPI 792-35 are tetrapeptides composed of unnatural amino acids that differ in their amino acid sequence at the third position. The TPI 792-33 and TPI 792-35 compounds both have L-3-(2-thienyl)-alanyl, L-(2-naphthyl)-alanyl, and L-(e-fluorenylmethyloxycarbonyl)-lysine moieties at positions 1 (N-terminus), 2 and 4, respectively, but differ at position 3 where TPI 792-33 has L-p-chloro-phenylalanyl and TPI 792-35 has a D-(e-fluorenylmethyloxycarbonyl)-lysyl moiety.

Cells from the prostate cancer cell line, ALVA31 express XIAP, as well as other IAP-family proteins. The in vivo effects of TPI 792-33 or TPI 792-35, either individually or in combination with the cytotoxic anticancer drug VP-16 (etoposide), on derepression of XIAP-inhibited caspase and viability of ALVA31 cells was determined as follows. ALVA31 prostate cancer cells were seeded onto 96 well plates ($10^4$ cells/well) in 100 µL RPMI containing 2.5% fetal bovine serum (FBS). After 24 hours, the IAP antagonists TPI 792-33, TPI 792-35 or the SMAC AVPI tetrapeptide (SEQ ID NO:4) was added at a final concentration of 40 µM with or without VP-16 (100 µM final concentration). After another 24 hrs incubation, cell viability was measured by the XTT dye-reduction assay (Roche, Molecular Biochemicals; Indianapolis, Ind.) and trypan blue dye exclusion assay.

Figure 13:
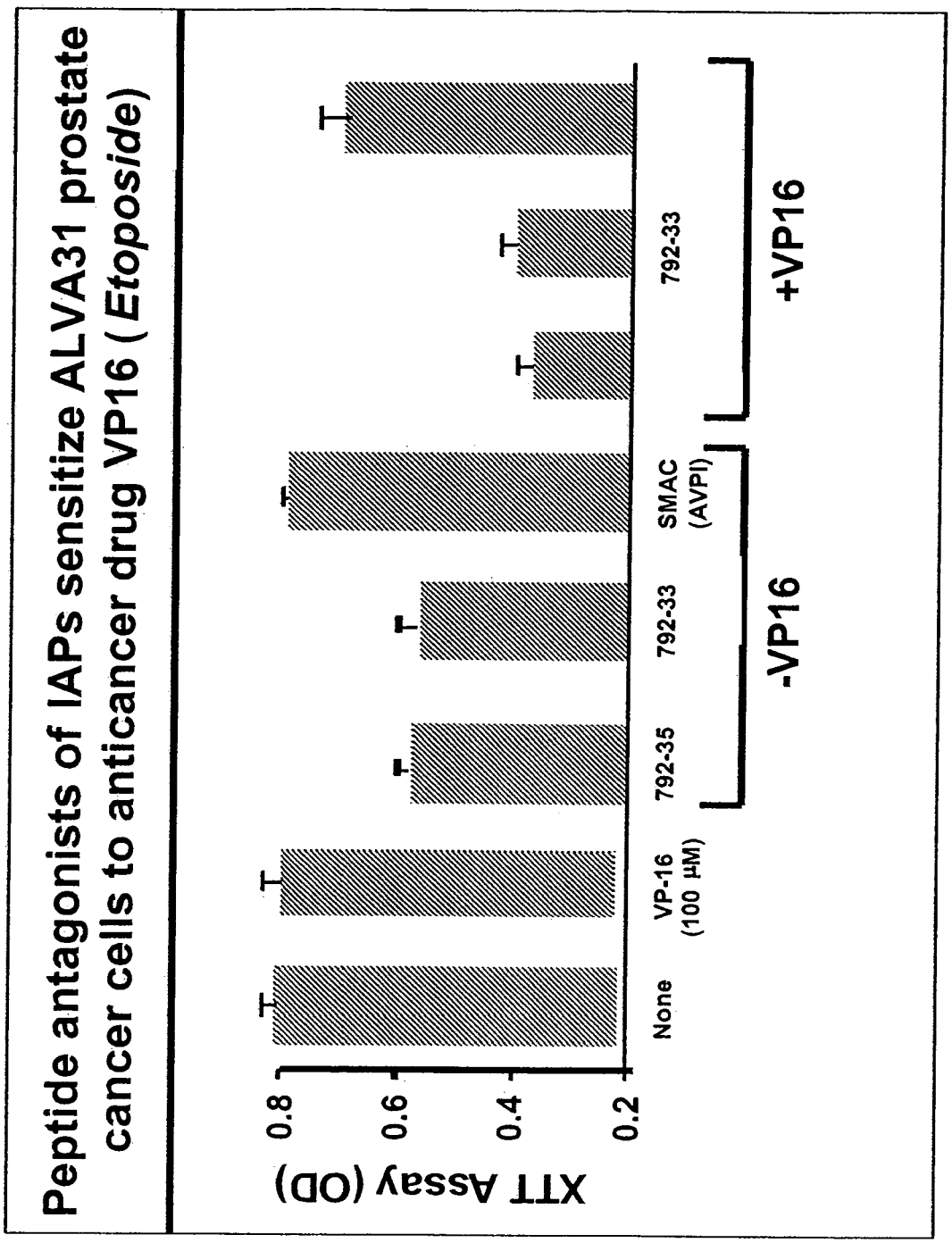
FIG. 13 shows the effects of VP-16 (etoposide), TPI792-35, TPI792-33 and the SMAC AVPI tetrapeptide (SEQ ID NO:4) on prostate cancer cell viability.

Anti-cancer drug VP-16 (etoposide), when administered alone to ALVA31 cells, had essentially no effect on the viability of the cells in the XTT dye-reduction assay (FIG. 13) and trypan blue dye exclusion assay. The SMAC AVPI tetrapeptide (SEQ ID NO:4), when administered alone to the ALVA31 cells, also had no effect on cell viability. In contrast, the TPI 792-33 and TPI 792-35 peptides reduced viability of these prostate cancer cells by nearly half. Moreover, the combination of VP-16 with these peptides resulted in more potent tumor cell killing compared to VP-16 alone. By comparison, the SMAC peptide was inactive, failing to significantly reduce the relative number of viable tumor cells under the same culture conditions.

These results demonstrate that TPI 792-33 and TPI 792-35 display markedly improved cellular activity compared to wild-type AVPI peptide from SMAC (SEQ ID NO:4). Furthermore, these results indicate that TPI 792-33 and TPI 792-35 have the effect of increasing apoptosis in tumor cells by derepressing IAP-inhibited caspase. These results also demonstrate that TPI 792-33 and TPI 792-35 sensitize prostrate cancer cells to the anticancer drug VP-16.

EXAMPLE XI

Non-Peptidyl Compounds TPI 1396-34 and TPI 1391-28 Kill Tumor Cells

This example demonstrates that phenyl urea compounds (also called polyphenylurea compounds) identified from the TPI 1396 library and diketopiperazine compounds identified from the TPI 1391 library reduce the viability of tumor cells in culture. This example further demonstrates that cell killing activity for TPI 1396-34 and TPI 1391-28 is specific for tumor cells.

The following assay was used to test the ability of individual compounds from the TPI 1396 and TPI 1391 libraries to induce apoptosis of cultured tumor cell lines. Each of the compounds listed in Table IX was individually added to Jurkat leukemia cells ($6.25 \times 10^5$ cells/mL) in RPMI containing 2.5% FBS at various concentrations for 20 hours. After incubation, cells were washed and stained with FITC-conjugated Annexin V antibody and propidium iodide (Biovision; Mountain View, Calif.). Cells were incubated for 20 minutes at room temperature in the dark and fluorescence was measured by flow cytometry (FACScan, Immunocytometry system; Becton-Dickinson; San Jose, Calif.). Cells staining positive for Annexin V were deemed non-viable.

Figure 27:
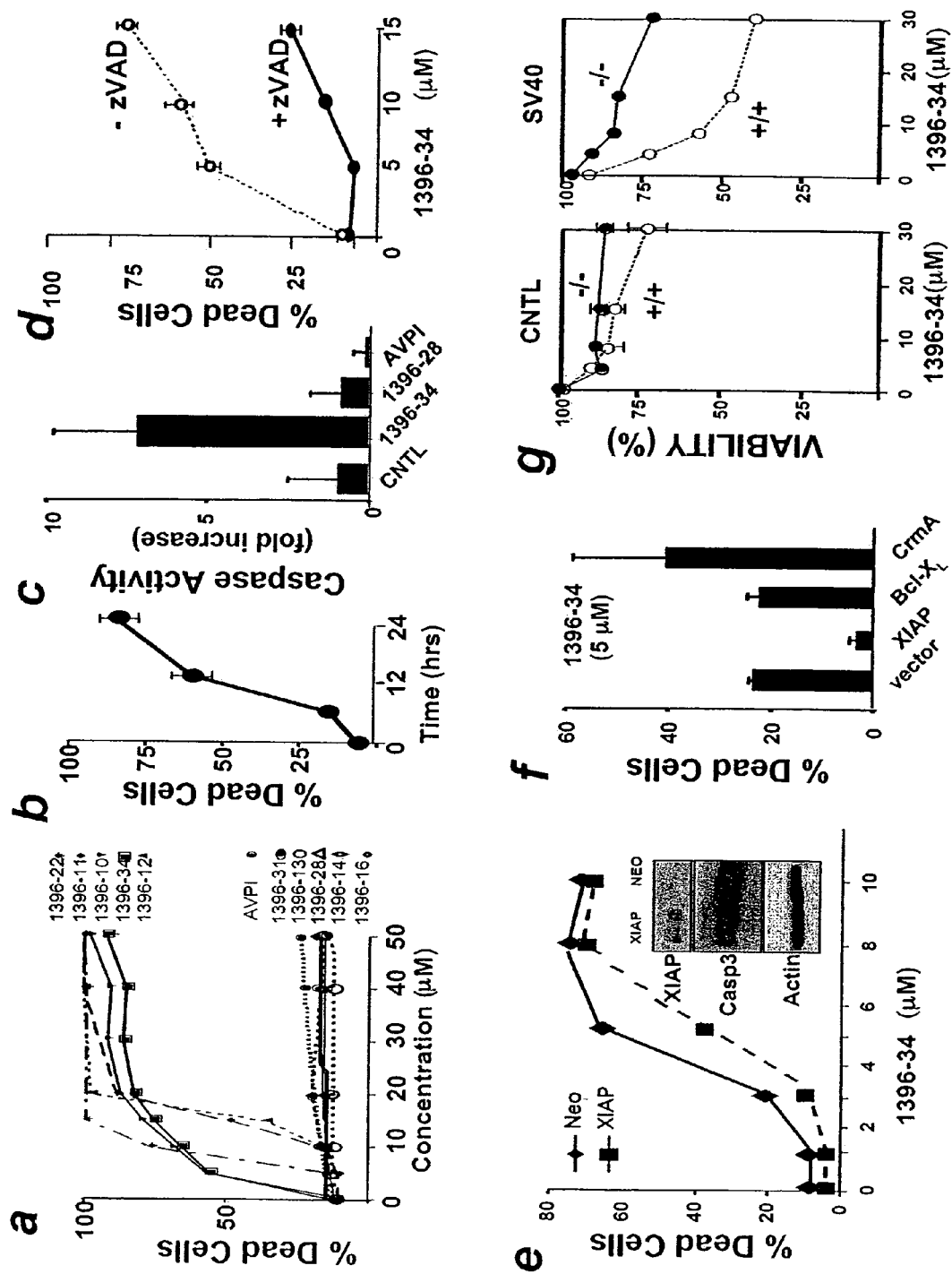
FIG. 27a, b, c, d, e, and f show characterization of cellular activity of poly-phenylurea compounds.
FIG. 27c shows Caspase3/7 activity after incubation of Jurkat cells with various compounds.
FIG. 27d shows cell death in Jurkat cells cultured with various concentrations of TPI 1396-34 with or without zVAD-fmk.
FIG. 27e shows cell death after incubation of U937 cells that stably over-express XIAP or neomycin with TPI 1396-34. Inset shows immunoblot analysis of lysates prepared from the U937 cells.
FIG. 27f shows cell death of HeLa cells transfected with XIAP, Bcl-XL or CrmA and incubated with TPI 1396-34.
FIG. 27g shows viability of control and SV40-transfected cells treated with TPI 1396-34.

As shown in Table IX, these compounds were able to induce cell death in a concentration dependent manner. Although SMAC was able to reduce cell viability by about 16% when present at 50 µM, several TPI 1396-34 and TPI 1391-28 compounds reduce cell viability by about 85 to 94%. Thus, compounds identified from the TPI 1396-34 and TPI 1391-28 libraries were about 5 to 6 fold more potent than SMAC at inducing apoptosis in tumor cells. A representative experiment testing additional compounds is shown in FIG. 27a.

TABLE IX

| | Concentration µM | | | | | | |
|---|---|---|---|---|---|---|---|
| | 100 | 50 | 25 | 10 | 5 | 5 | 1 |
| TPI 1391% nonviable cells | | | | | | | |
| 1391-28 | | 91 | 87 | 55 | 12 | 28 | 19 |
| 1391-21 | | 94 | 91 | 44 | 11 | 18 | 16 |
| 1391-25 | | 87 | 90 | 60 | 22 | 49 | 16 |
| 1391-17 | | 91 | 88 | 45 | N.T. | 25 | 13 |
| 1391-5 | | 88 | 88 | 36 | N.T. | | 17 |
| 1391-1 | | 91 | 69 | 20 | N.T. | | 18 |
| 1391-4 | | 86 | 90 | 48 | 12 | 18 | 20 |
| TPI 1396% nonviable cells | | | | | | | |
| 1396-34 | | 85 | 83 | 62 | 73 | 51 | 13 |
| 1396-12 | | 85 | 89 | 89 | 95 | 95 | 15 |
| 1396-11 | | 90 | 90 | 90 | 97 | 95 | 14 |
| 1396-28 | | 13 | 14 | 13 | | | 13 |
| SMAC | 15 | 16 | 16 | | 12 | | |

The TPI 1396-34 and TPI 1391-28 compounds were further tested as set forth below. FIG. 14 (Panel B) shows the structures for phenyl urea TPI 1396-34 and diketopiperazine TPI 1391-28. Both of these compounds were shown to induce apoptosis of cultured tumor cell lines in a concentration-dependent manner using the assay described above, except that compounds were added in the range of 0 to 20 µM.

Figure 15:
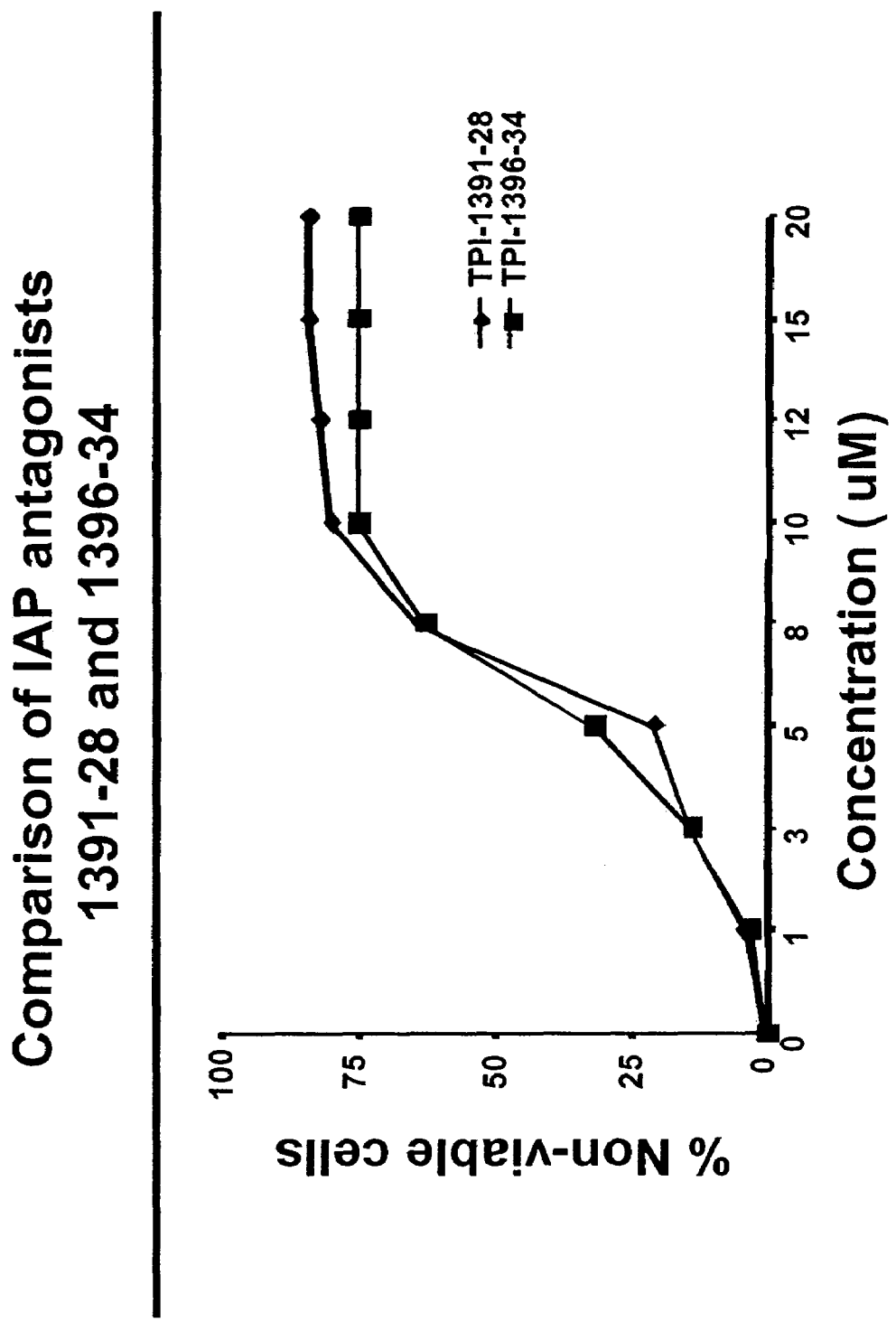
FIG. 15 shows concentration-dependent killing of Jurkat leukemia cells by TPI 1391-28 and TPI 1396-34.

As shown in FIG. 15, TPI 1396-34 and TPI 1391-28 killed Jurkat leukemia cells with $EC_{50}$ values of about 6.5 µM following a one-day exposure. Control compounds having the same core pharmacophore structure but with different substituents at the R group which prevent binding to XIAP, did not significantly reduce the viability of Jurkat leukemia cells under the assay conditions.

Figure 16:
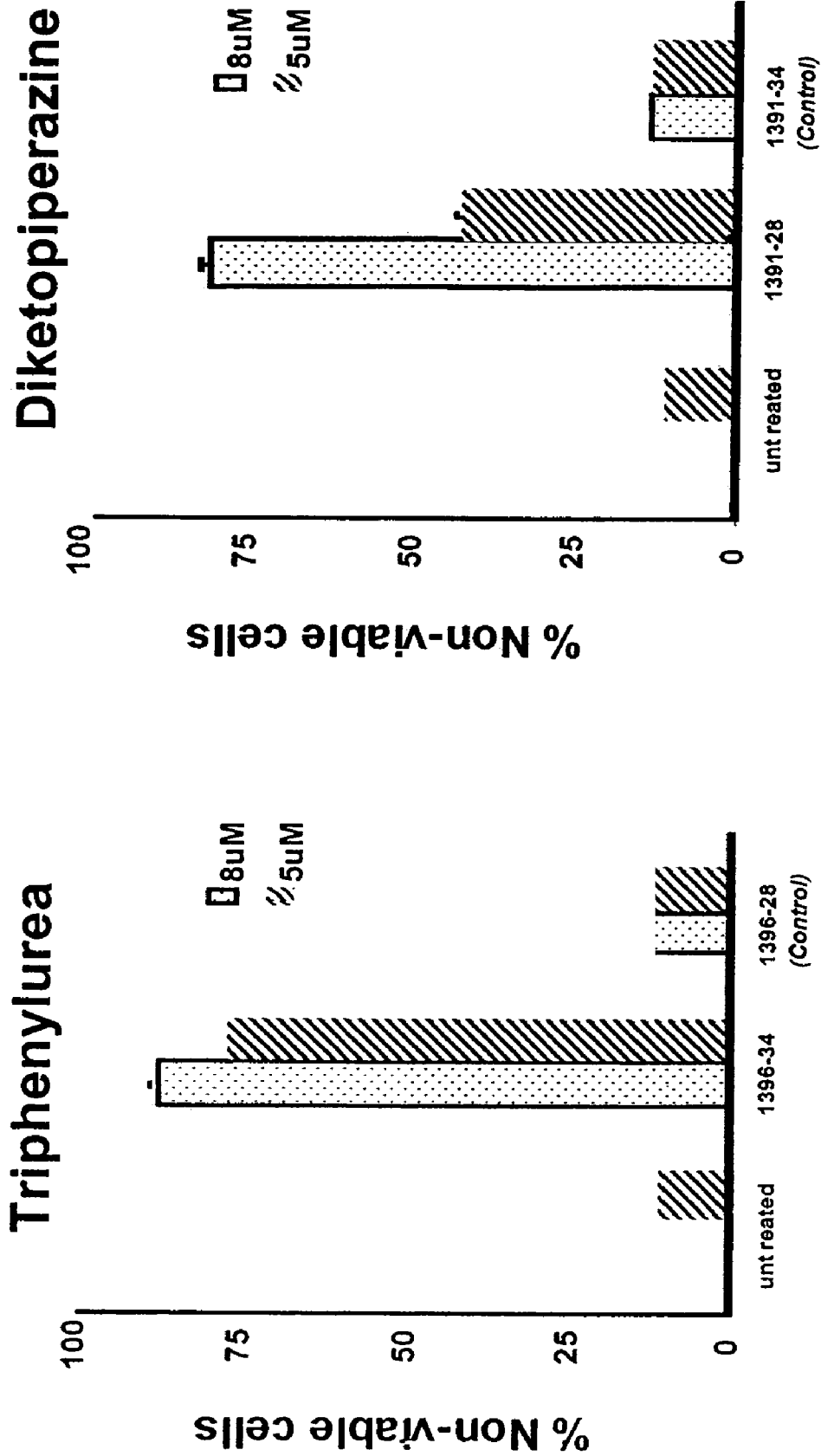
FIG. 16 shows killing of Jurkat leukemia cells by TPI 1391-28 and TPI 1396-34 compared to control compounds having similar core pharmacophores, respectively, but different R groups.

Comparison of cell killing by TPI 1396-34 and TPI 1391-28 to the respective control compounds is shown in FIG. 16. One day treatment of Jurkat leukemia cells with 5 µM or 8 µM of TPI 1396-34, killed about 75% and 85% of cells, respectively. One day treatment of Jurkat leukemia cells with 5 µM or 8 µM of TPI 1391-28, killed about 45% and 80% of cells, respectively. In contrast, the control compounds had no significant effect on the viability of these leukemia cells compared to untreated cells, indicating that the cytotoxic activity of these compounds is specific. Under the same assay conditions, 5 or 8 µM of the SMAC AVPI tetrapeptide (SEQ ID NO:4) had no significant effect on the viability of these leukemia cells, confirming that TPI 1396-34 and TPI 1391-28 had far greater potency than SMAC. FIG. 27b shows a representative assay as described above where Jurkat cells were cultured with 10 µM 1396-34 for various times before measuring percent cell death by annexin-V staining. As can be seen in FIG. 27b, the kinetics of apoptosis induction of Jurkat cells by TPI 1396-34 was rapid, with half-maximal killing achieved at approximately 12 hours and maximum killing at about 24 hours.

Jurkat cells were also cultured with TPI 1396-34, a structurally related compound TPI 1396-28, or SMAC 4-mer peptide AVPI (SEQ ID NO: 4) at final concentrations of 8 µM for 20 hours. After incubation, caspase-3 and caspase-7 activity was measured in whole cells using a cell permeable substrate. As expected, TPI 1396-34 induced caspase activation, while TPI 1396-28 (which differs from TPI 1396-34 only at R2) did not induce caspase activation (see FIG. 27c).

In addition, Jurkat cells were cultured with various concentrations of TPI 1396-34 with or without 100 µM zVAD-fmk, which is a broad spectrum caspase inhibitor. The percentage of cell death was measured 20 hours later by annexin-V staining. Apoptosis induced by TPI 1396-34 was suppressible by co-culturing the cells with zVAD-fmk, (see FIG. 27d).

A comparison of the effects of TPI 1396-34 on normal bone marrow cells versus Jurkat leukemia cells was performed as follows. TPI 1396-34 (5 µM) was incubated with Jurkat cells or normal bone marrow mononuclear cells ($6.25 \times 10^5$/mL) in RPMI and 2.5% FBS for 20 hours. After incubation, cells were washed, stained with FITC-conjugated Annexin V antibody and propidium iodide, and fluorescence measured by flow cytometry as described above.

Figure 17:
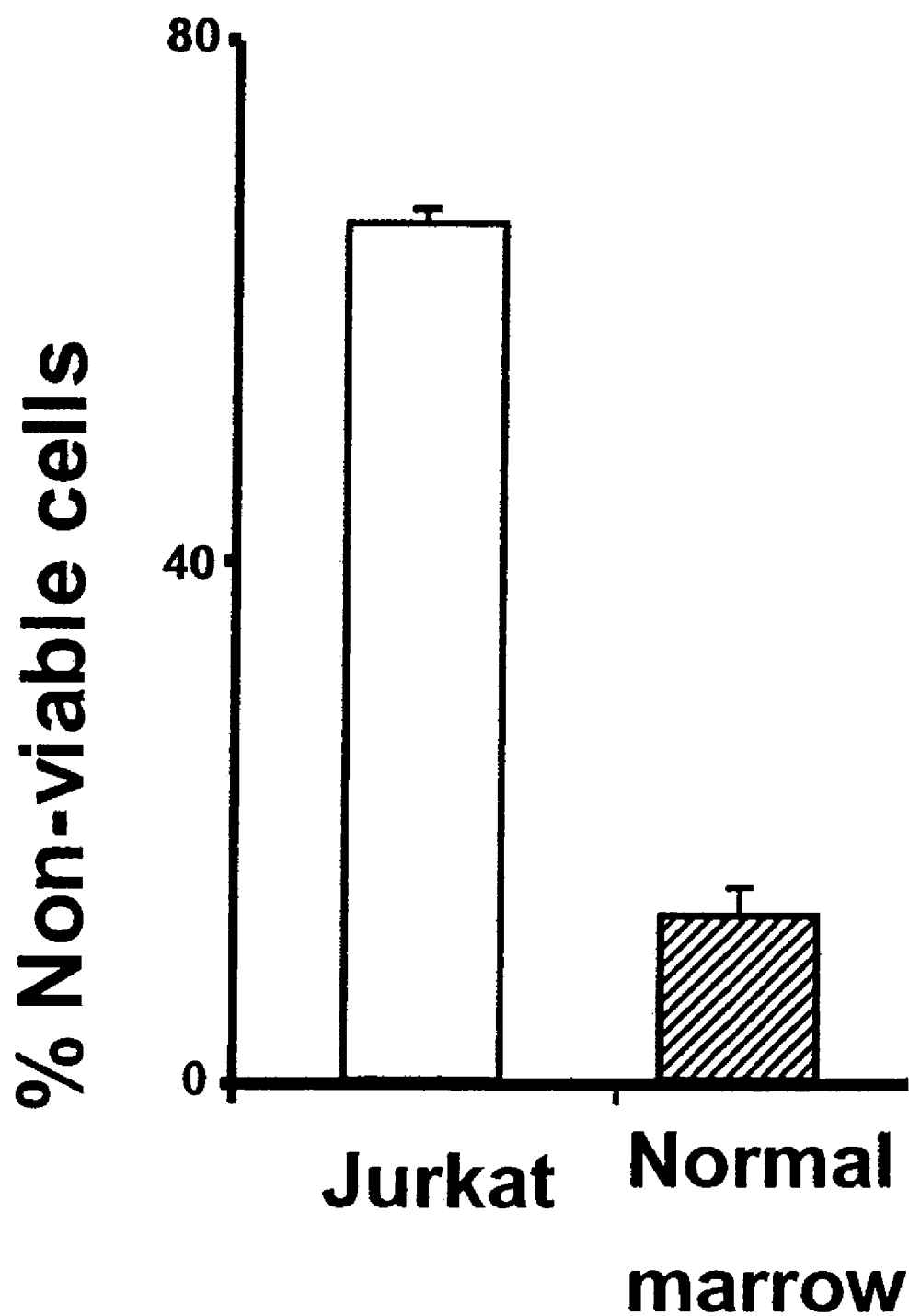
FIG. 17 shows a comparison of the effects of TPI 1396-34 and TPI 1391-28 on normal bone marrow cells versus Jurkat leukemia cells.

As shown in FIG. 17, TPI 1396-34 and TPI 1391-28 caused little toxicity to normal bone marrow cells under the same culture conditions where robust killing of the leukemia cells was observed. These results demonstrate that the TPI 1396-34 and TPI 1391-28 selectively kill tumor cells compared to normal cells.

EXAMPLE XII

Killing of Tumor Cells by TPI 1396-34 is Mediated by XIAP

This Example describes the effects of over-expressing wild type and mutant XIAP on tumor cell killing by TPI 1396-34.

U937 leukemia cells ($6.25 \times 10^5$ cells/mL) that had been stably transfected with either a Neo-control plasmid (U937-Neo cells) or a plasmid encoding XIAP (U937-XIAP cells) were treated with 5 or 8 µM of TPI 1396-34 in RPMI and 2.5% FBS for 20 hours. After incubation, cells were washed, stained with FITC-conjugated Annexin V antibody and propidium iodide, and fluorescence measured by flow cytometry as described in Example XI.

Figure 18:
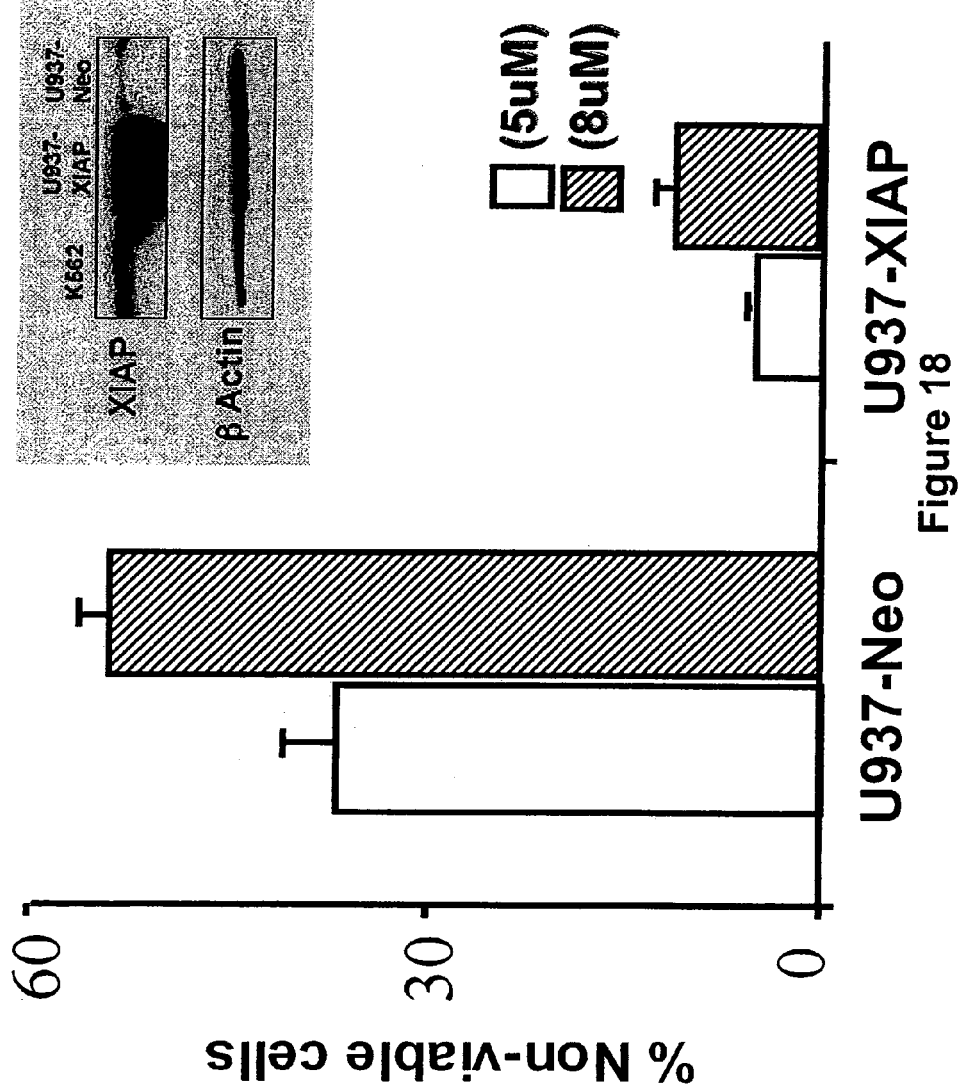
FIG. 18 shows the effects of over-expression of wild-type XIAP on the apoptogenic activity of TPI 1396-34.

As shown in FIG. 18 and FIG. 27e, over-expression of XIAP rendered U937 cells resistant to TPI 1396-34. Comparisons of the effects of TPI 1396-34 on U937-Neo and U937-XIAP cells demonstrated that over-expression of XIAP correlated with resistance to apoptosis induction by this agent. The increased resistance of tumor cells to the apoptogenic effects of TPI 1396-34 when the cells over-express XIAP indicates that TPI 1396-34 induces apoptosis by binding to XIAP.

Over-expression of XIAP in the U937-XIAP cells compared to vector transfected control cells was confirmed by immunoblotting (FIG. 18, upper right panel). Expression of XIAP in K562 cells was included as a control, as these cells are known to express XIAP endogenously. Equal amounts of protein were subjected to SDS-PAGE (4–20% gradient gels from ISC BioExpress, Kaysville, Utah.), followed by transfer to nitrocellulose membranes. Membranes were probed with monoclonal mouse-anti human XIAP (0.25 mg/mL) (Transduction Laboratories, Lexington, Ky.) or monoclonal mouse-anti b-actin (1:3000 v/v) (Sigma Inc, Milwaukee, Wis.). Secondary antibodies consisted of horseradish peroxidase (HRP)-conjugated goat anti-mouse IgG (Bio-Rad, Hercules, Calif.). Detection was performed by the enhanced chemiluminescence (ECL) method. In FIG. 27e, U937 cells stably over-expressing XIAP or neomycin control transfectants were cultured with various concentrations of TPI 1396-34 for 20 hours and the percentage of cell death was measured by annexin-V staining. Lysates were prepared from the cells, normalized for total protein content and analyzed by SDS-PAGE immunoblotting using antibodies specific for XIAP, caspase-3, and β-actin.

In addition to transfecting the cells with full-length XIAP, analogous assays were performed with HeLa cells transfected with plasmids over-expressing various XIAP mutants. HeLa cells were transiently transfected with plasmids encoding full-length, wild-type XIAP versus deletion mutants having only the BIR2 (caspase-3/7 suppressing) domain, BIR3 (caspase-9 suppressing) domain, or a mutant in which both of the putative SMAC-binding pockets in BIR2 and BIR3 had been mutated to no longer bind caspases. The mutant was produced by site-directed mutagenesis to modify positions 148, 219, 223, 314 and 323 to contain alanine. HeLa cells were also transiently transfected with plasmids encoding Bcl-XL, an anti-apoptotic protein that operates upstream of caspases to suppress Cytochrome C release from mitochondria. HeLa cells ($2.5 \times 10^5$) were seeded onto six well plates in 2 mL DMEM H21 with 5% FBS. After 24 hrs, cells were transfected (Gene Porter) with plasmids. At 48 hrs after transfection, cells were treated with 5 µM of TPI 1396-34 for 20 hours. Both floating and adherent cells were then recovered from cultures, washed, and apoptosis was determined by Annexin V staining using flow cytometry.

Figure 19:
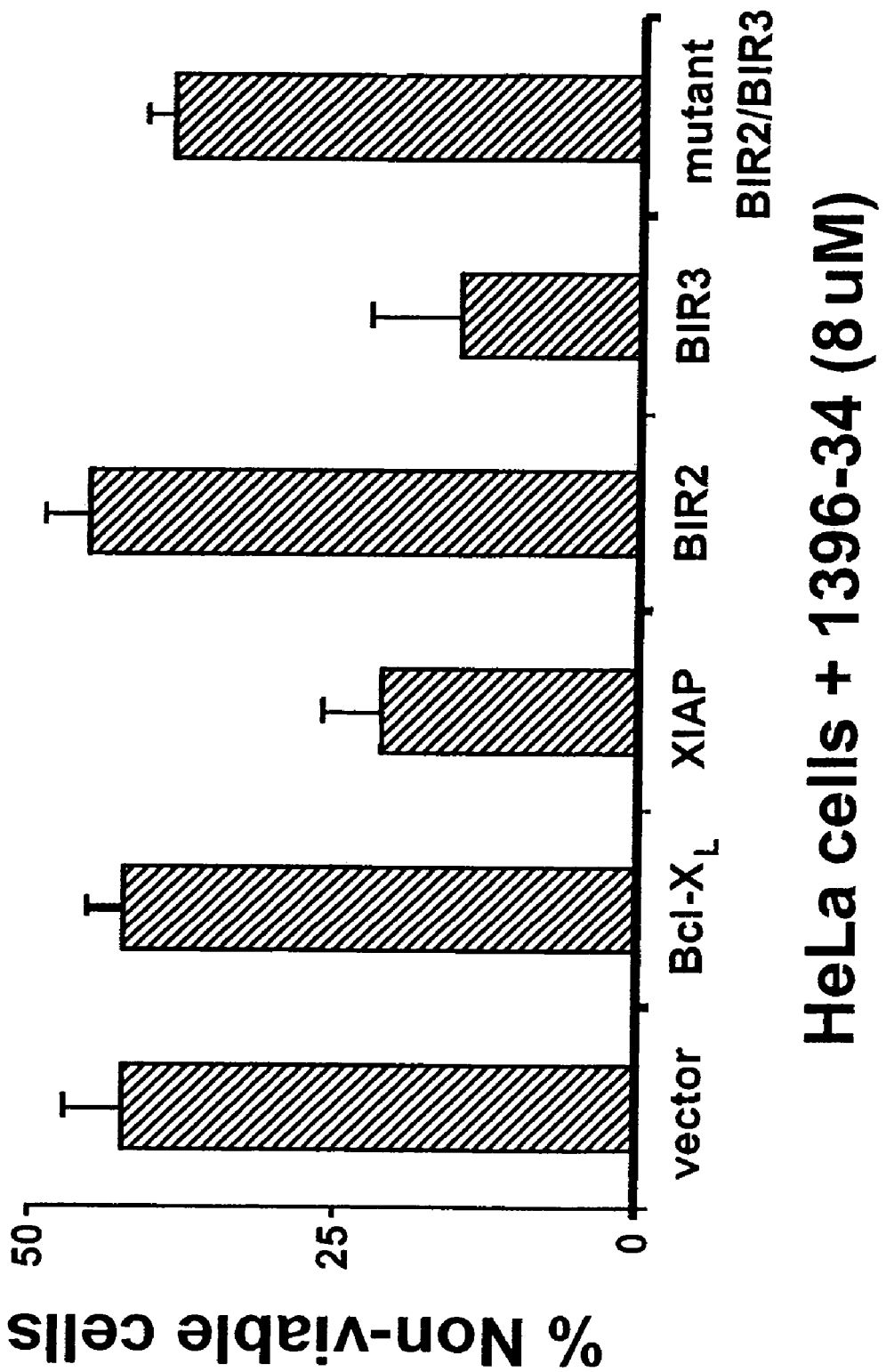
FIG. 19 shows the effects of over-expression of wild-type XIAP on the apoptogenic activity of TPI1396-34.

As shown in FIG. 19, TPI 1396-34 induced apoptosis in HeLa cells transfected with a control vector. Apoptosis induced by TPI 1396-34 was not blocked by over-expressing Bcl-XL, consistent with the fact that Bcl-XL operates upstream of XIAP. In contrast, HeLa cells over-expressing full-length XIAP were protected from TPI 1396-34. In addition, cells expressing a mutant of XIAP in which the SMAC-binding pocket of XIAP was mutated were not protected from the chemical compound nor were cells expressing a mutant comprised of only the BIR2 domain. Cells expressing the BIR3 domain were protected from the apoptogenic activity of TPI-1396-34. Taken together, these results indicate that TPI 1396-34 induces apoptosis of tumor cell lines in culture by targeting XIAP.

As shown in FIG. 27f, HeLa cells were transfected with plasmids encoding XIAP, Bcl-X, CrmA, or empty vector. At 2 days after transfection, cells were treated with TPI 1396-34 (5 µM) for 20 hours and the percentage of dead cells was measured by annexin-V staining. Consistent with IAPs representing a target of the polyphenylurea compounds disclosed herein, transient or stable over-expression of XIAP rendered tumor cell lines more resistant to apoptosis induction by active compound, shifting the dose-response curve to the right, so that higher concentrations of compound were required (FIG. 27e and 27f). In contrast, over-expressing anti-apoptotic proteins Bcl-XL or CrmA did not alter sensitivity of tumor cell lines to TPI 1396-34, demonstrating a specific effect (see FIG. 27f). Bcl-XL over-expression did afford resistance to traditional anticancer drugs such as etoposide and CrmA (a caspase-8 inhibitor), and protected cells from apoptosis induced by TRAIL, confirming that these anti-apoptotic proteins were functional in these experiments.

EXAMPLE XIII

Broad Activity of Polyphenylurea Compounds Against Transformed Cells

This Example shows polyphenylurea compounds have activity against many different tumor cell lines, while having little effect on normal cells.

Figure 29:
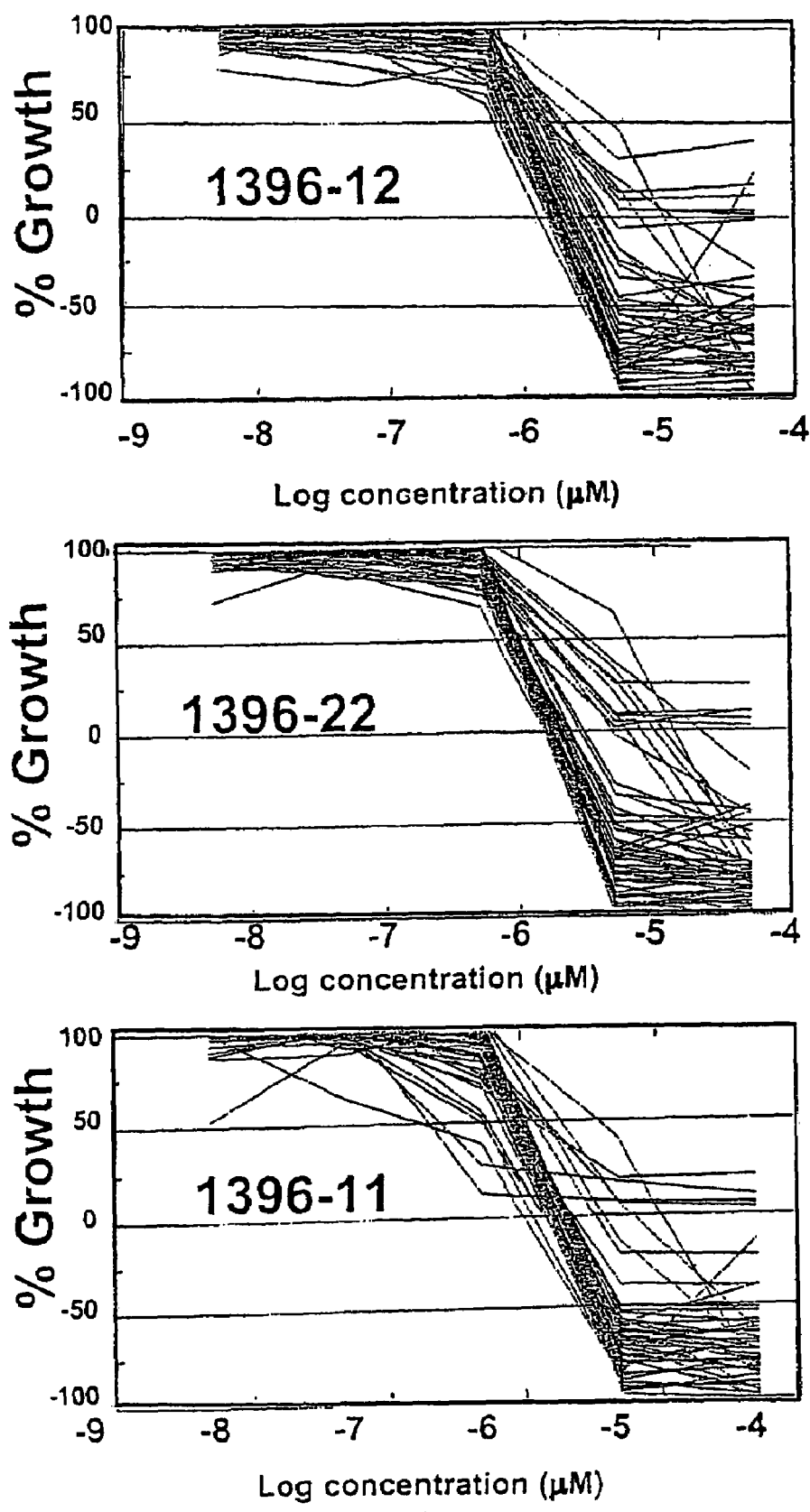
FIG. 29 shows the effects of TPI 1396-12, TPI 1396-22, and TPI 1396-11 on 60 tumor cell lines from the NCI-60 cell panel on cell growth compared to cells cultured with solvent diluent alone.

Selected polyphenylurea compounds were tested on the National Cancer Institute (NCI) panel of 60 tumor cell lines (see FIG. 28a and FIG. 29). Cells were cultured with compounds for 48 hours followed by measurement of the relative number of viable cells using a protein-based colorimetric assay, expressing data as percent growth relative to cells treated with solvent control alone. Compounds TPI 1396-11, TPI 1396-12, TPI 1396-22, and TPI 1396-34 induced reductions in viable cell numbers, with an average $LD_{50}$ (concentration required to kill 50% of the cells, after adjustment for background cell death) for the 60 cell lines of 10+/−2.8 µM (median=17 µM), 7.6+/−12 µM (median=6 µM), 11+/−2.6 µM (median=22 µM), and 22+/−5 µM (median=23 µM), respectively. Moreover, the $LD_{50}$ was <10 µM for over one-third of the tumor cells treated with the active compounds. In contrast, $LD_{50}$ was not reached for any of the 60 tumor cell lines after treatment with up to 70 µM of the structurally related control compound TPI 1396-28 (see FIG. 28a). By comparison, when using this same assay, the mean $LD_{50}$ for the anticancer drug etoposide in the NCI panel of 60 tumor cell lines is 200+/−2.5 µM, with none of the cells having $LD_{50}$<10 µM.

Compared to tumor cell lines, normal cells were relatively resistant to the polyphenylurea compounds. As shown in FIG. 28b, various types of cells including Jurkat and HeLa tumor cell lines, and normal peripheral blood lymphocytes (PBLs), bone marrow mononuclear cells, mouse embryo fibroblasts (MEFs), or human prostate epithelial cells were cultured with various concentrations of TPI 1396-34. After 2 days, cell viability was assessed by annexin-V staining.

When normal cells such as mouse embryo fibroblasts (MEFs), human prostate epithelial cells, and peripheral blood lymphocytes (PBLs) were cultured with various concentrations of active poly-phenylurea compound TPI 1396-34, the slope of the cell cytotoxicity curve was much flatter than observed for tumor cell lines (FIG. 28b). At a concentration of 10 mM, for example, the percentage cell death increased by less than one-fold above background for these types of normal cells, while killing of tumor lines such as Jurkat and HeLa increased by >4 fold. Activating lymphocytes with the mitogenic lectin, phytohemaglutinin (PHA), did not increase sensitivity to the XIAP-antagonists. Normal human bone marrow mononuclear cells (BM) tended to be more sensitive. However, even for these cells, the $LD_{50}$ was not reached at concentrations up to 40 mM. By comparison, the $LD_{50}$ of Jurkat and HeLa cells was achieved at concentrations of about 5 µM(FIG. 28b).

Since many tumor and leukemia cell lines proliferate faster than normal cells, it was investigated whether the polyphenylurea compounds could induce apoptosis of non-replicating malignant cells. Accordingly, freshly isolated chronic lymphocytic leukemia (CLL) B-cells from five patients and freshly isolated leukemic blasts from five patients with acute myelogenous leukemia (AML) were treated for 20–24 hours in vitro with compounds TPI 1396-11, TPI 1396-12, or TPI 1396-34 versus TPI 1396-28 control compound or AVPI peptide (SEQ ID NO: 4), and the percentage of cell death was measured by annexin-V/propidium iodide staining with FACS analysis (FIG. 28c) or annexin-V staining (FIG. 28d). These leukemic cell samples contained only small percentages of cycling cells, and did not replicate under standard culture conditions. As seen in FIGS. 28c and 28d, active polyphenylurea compounds induced dose-dependent cell death of primary-cultured leukemia cells in 5 of 5 CLL specimens (FIG. 28c) and 4 of 5 AML specimens (FIG. 28d) examined, with $LD_{50}$ achieved at doses of approximately 5 µM after correction for spontaneous apoptosis in culture. In contrast, the inactive control compound TPI 1396-28 and the AVPI peptide did not induce apoptosis of these leukemia cells. All samples were treated with both TPI 1396-34, TPI 1396-28, as well as the AVPI peptide, but the complete data set is shown only for AML-1. Comparable results were obtained with control compounds for the other leukemia specimens. In addition, the active polyphenylurea compounds were also active against trans-formed hematopoietic cells from mice, inducing death of mouse 70Z/3 lymphoma and immortalized 32D myeloid cells with $EC_{50}$ valves of 8 to 12 µM. Thus, cell replication is not required for sensitivity to the disclosed poly-phenylurea compounds.

EXAMPLE XIV

Polyphenylurea Compounds Sensitize Tumor Cells to Anticancer Drugs and TRAIL This example shows that polyphenylurea compounds can collaborate with conventional anticancer drugs to induce killing of tumor cells.

Figure 31A:
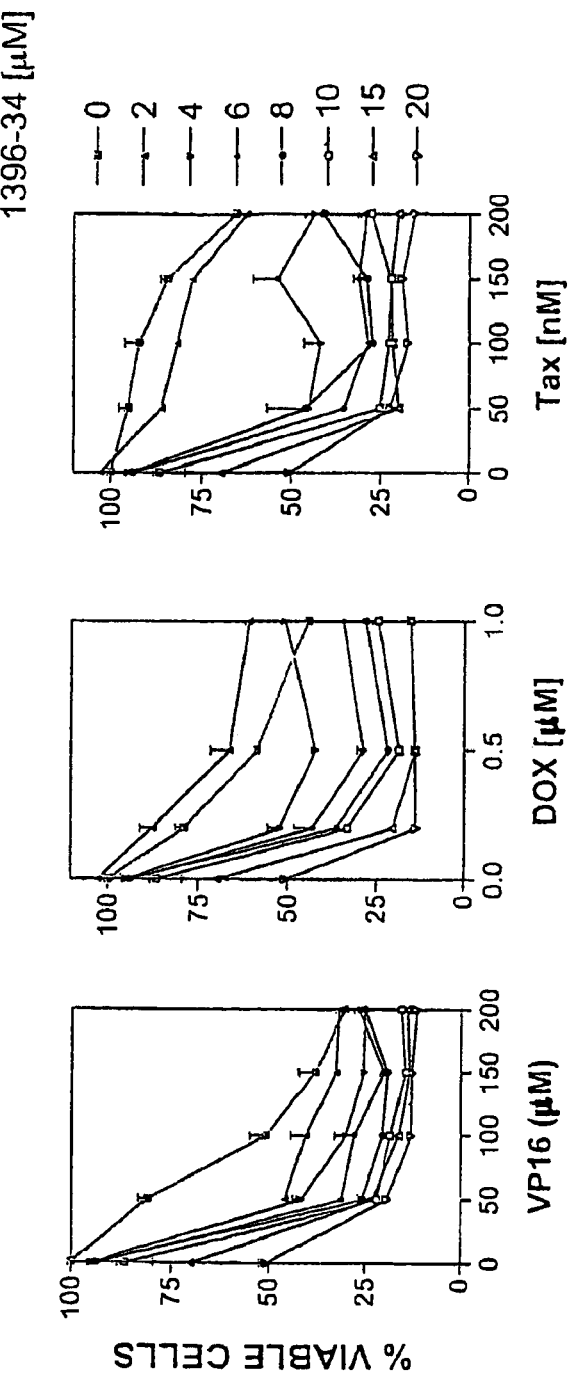
FIG. 31a, b, c and d show the effect of combination of conventional chemotherapeutic agents with TPI 1396-34 on various tumor cell lines. The viability of DU145 (a), PPC1 (b), PC3 (c), and H460 (d) cells cultured with various concentrations of TPI 1396-34 and various concentrations of chemotherapeutic drugs is shown.
Figure 31B:
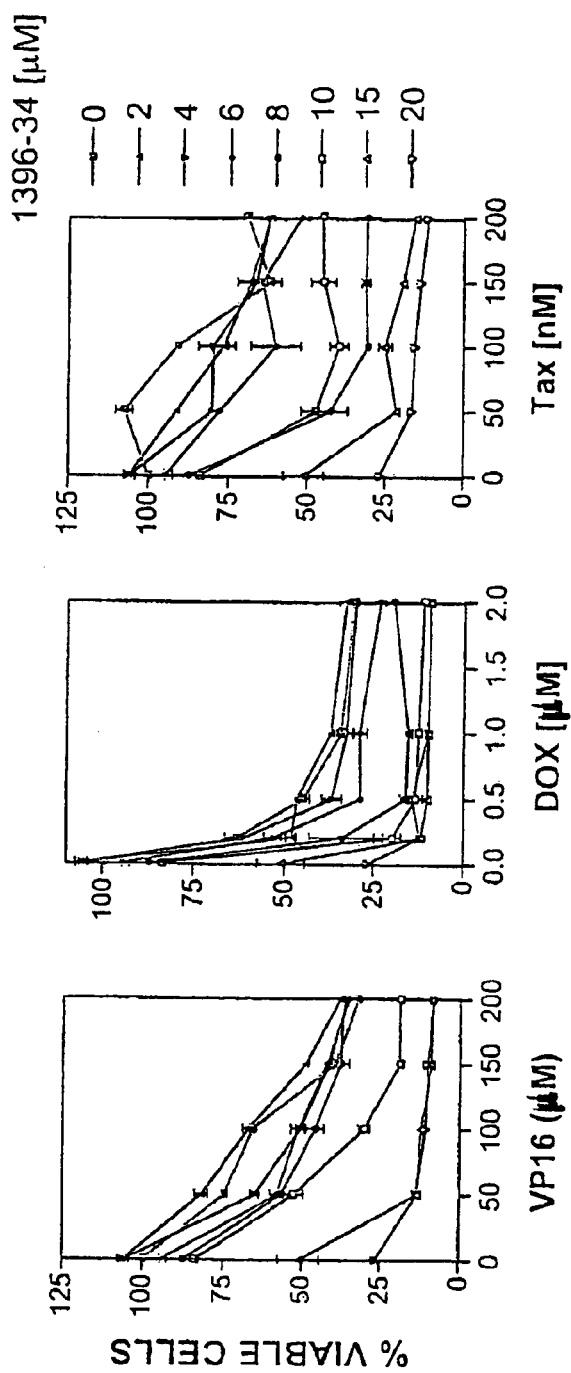
Figure 31C:
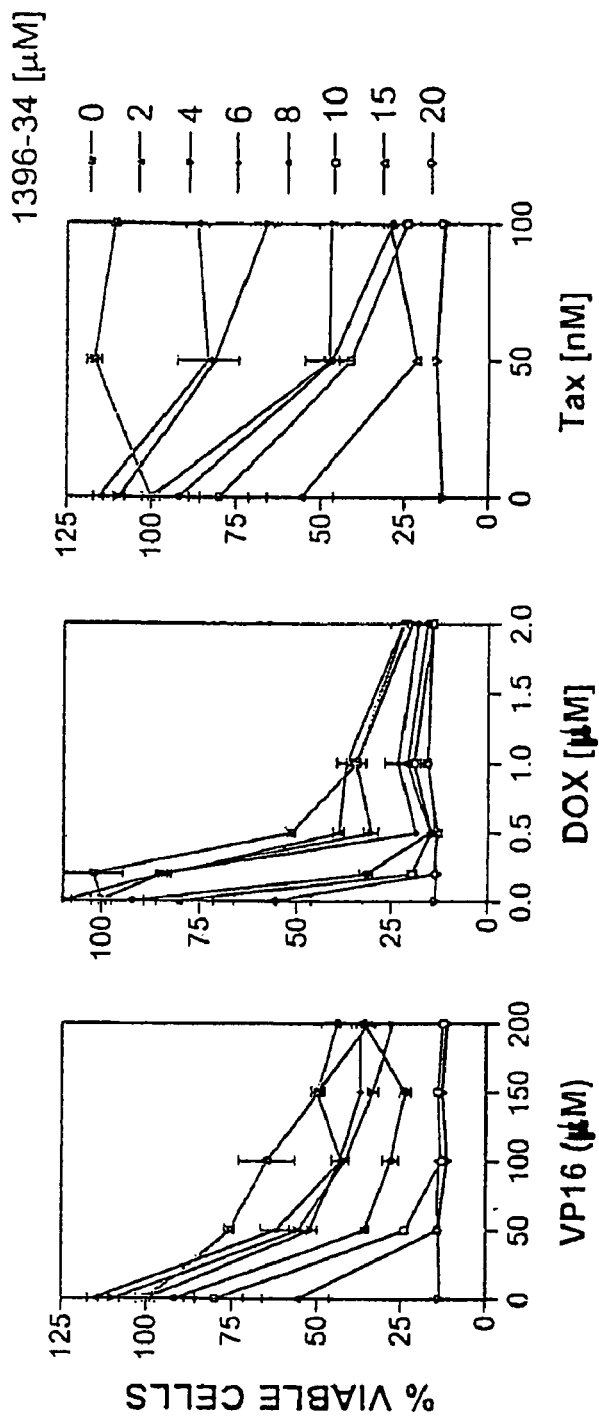
Figure 31D:
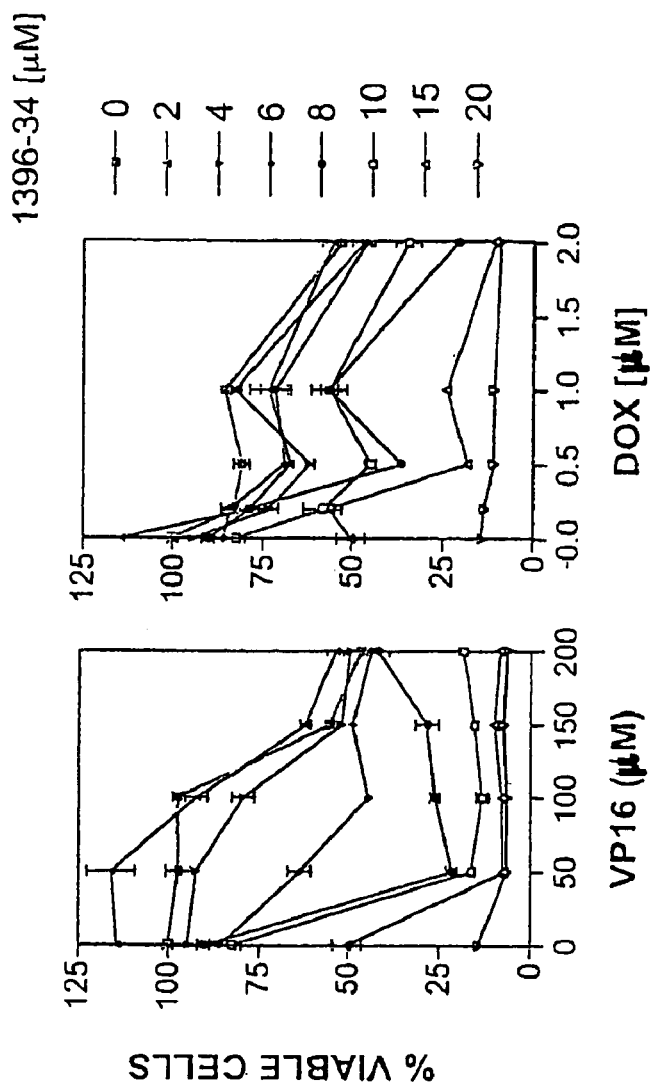

In order to test the effect of polyphenylurea compounds in combination with known anticancer drugs, Du145 prostate cancer cells were cultured for 48 hours with various concentrations of Etoposide (VP16), Doxorubicin (DOX), or Paclitaxel (TAXOL) with or without 10 µM TPI 1396-34. The percentage of viable cells relative to control was determined using a MTT (3-(4,5-dimethylthiazolyl-2)-2,5-diphenyltetrazolium bromide) assay which is commercially available (Sigma). FIG. 30a shows representative data indicating that TPI 1396-34 significantly increased dose-dependent cytotoxicity of VP16, DOX, and TAXOL in Du145 prostate cancer cells. A more complete version of the data showing results at various concentrations of TPI 1396-34 is shown in FIG. 31a. Similar results were obtained for PPC1 (FIG. 31b) and PC3 (FIG. 31c) prostate cancer cells treated with VP16, DOX, or TAXOL, and for H460 (FIG. 31d) lung cancer cells treated with VP16 or DOX. Inactive poly-phenylureas compounds failed to sensitize tumor cells to anticancer drugs.

Similar tests of the effects of polyphenyl urea compounds on apoptosis induction by the biological agent TRAIL, an apoptosis inducing member of the Tumor Necrosis Factor (TNF) family were also performed. Cancer cell lines PPC1, ALVA31 and DU145 were treated with various concentrations of TRAIL alone or in combination with TPI 1396-34 at a concentration of 1 µM. TPI 1396-34 sensitized PPC1, ALVA31, DU145, and HeLa cells to TRAIL-induced apoptosis (see FIG. 30b). Inactive control compounds did not display this activity.

EXAMPLE XV

Polyphenylurea Compounds Demonstrate Anti-Tumor Activity in Clonogenic Survival Assays and Tumor Xenograft Models This example shows that clonogenic survival of cancer cells is reduced by polyphenyl urea compounds. In addition, selected polyphenylurea compounds showed anti-tumor activity in vivo using human tumor xenografts grown in immunocompromised mice.

In addition to short-term cytotoxicity assays, selected polyphenylurea compounds were tested for effects on clonogenic survival of cancer cells in colony formation assays, which can be considered a more stringent test of anticancer activity. Two prostate cancer cell lines PC-3 and LNCaP were cultured with TPI 1396-34 for 3 days, then culture medium was changed and colonies were counted one week later. FIG. 32a shows the results obtained using various concentrations of TPI 1396-34 and one concentration (10 µM) of a control compound. As seen in FIG. 32a, TPI 1396-34 diminished clonogenic survival of these cancer lines in a concentration dependent manner, with an average $EC_{50}$ dose of 3 µM+0.5 µM(mean+std error). At a dose of 10 µM, colony formation was reduced to <5% of control, in contrast to inactive control compounds, which had relatively little effect.

Selected polyphenylurea compounds were tested for anti-tumor activity in vivo, using human tumor xenografts grown in immunocompromised mice. First, it was determined what doses of polyphenylurea compounds were tolerated by mice. It was found that 100 mg/kg delivered i.p. as a single or in divided doses resulted in no gross toxicity. For tumor xenograft studies, PPC1 prostate cancer cells (2.5 million) were injected subcutaneously into the flanks of 8 male Balb/C nu–/nu– mice. Half of the animals received i.p. injections of TPI 1396-34 in DMF (N,N-Dimethylformamide) at 30 mg/kg at day 7 and day 8, while the other half received DMF diluent alone. Tumor growth was monitored at least twice weekly by external calipers (see FIG. 32b). At 24 days after compound injections, mice were sacrificed and tumors were excised and weighed (see FIG. 32b, inset). As can be seen in FIG. 32b, treatment with TPI 1396-34 resulted in reduced tumor size compared to the DMF control.

Similar data was obtained using TPI 1396-22 (see FIG. 33a and 33b). In these experiments PPC1 prostate cancer cells (2.5 million) were injected subcutaneously into the flanks of male Balb/C nu–/nu– mice. On days 5, 6, and 7, when tumors were about 125 mm$^3$, mice were treated with 30 mg/kg of TPI 1396-22 or solvent by i.p. injection and tumor volume was measured by calipers at least twice weekly for 19 days after injection. In FIG. 33b, the mice were sacrificed at day 19 and the tumors excised and weighed.

Additional experiments were performed using a different tumor xenograft model. HCT-116 colon cancer cells (2.5 million) were injected subcutaneously in the flanks of female Balb/C nu–/nu– mice. On days 6, 7, and 8 when tumors were about 125 mm$^3$, mice were treated with 30 mg/kg of TPI 1396-34 (n=10) or solvent control (n=19) by i.p. injection. Tumor volume was measured by external calipers at least twice weekly for 19 days (see FIG. 32c). On day 19, the mice were sacrificed and the tumors were excised and weighed. Again, tumor size was reduced in mice treated with TPI 1396-34 compared to solvent control.

In summary, dosing mice for just 2 or 3 days with TPI 1396-34 or TPI 1396-22 significantly slowed the rate of growth of both PPC1 and HCT116 tumors, thus demonstrating in vivo anti-tumor activity of these chemical compounds.

EXAMPLE XVI

Structure Activity Relationship (SAR) of Individual TPI 1396 Compounds and the Generation of TPI 1509 Compounds This Example shows SAR information based on TPI 1396-1 through TPI 1396-36 (see FIG. 22 for structures of these compounds) and the structure of TPI 1509 compounds. TPI 1509 compounds are based on TPI 1396 compounds which are in turn based on the TPI 927 library. As shown by the activity screening of individual compounds TPI 1396-1 through TPI 1396-36, a number of different hydrophobic aromatic groups are acceptable for activity at the R1 and R3 positions (see Table X). Table X also shows that active compounds can be derived from a proline at the R2 position.

TABLE X

Core structure with R2 = L-Proline

| TPI 1396 # | R1 | R3 | Activity* |
|---|---|---|---|
| 10 | [4-(N-methyl-N'-phenylureido)butyl] | [(4-methoxyphenyl)methyl] | 2.8 |
| 11 | [4-(N-methyl-N'-phenylureido)butyl] | [adamantylmethyl] | 2.6 |
| 12 | [4-(N-methyl-N'-phenylureido)butyl] | [3-cyclohexylpropyl] | 2.7 |

TABLE X-continued
Core structure with R2 = L-Proline
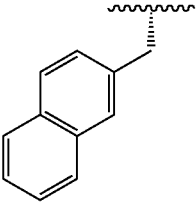
| TPI 1396 # | R1 | R3 | Activity* |
|---|---|---|---|
| 22 | 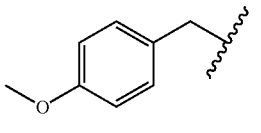 | 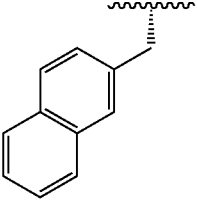 | 3.3 |
| 23 | 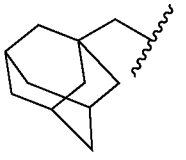 | 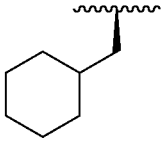 | 2.6 |
| 34 | 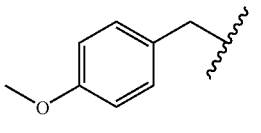 | 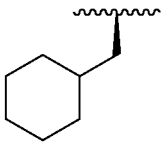 | 3.0 |
| 35 | 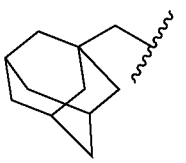 | | 2.5 |
*Relative caspase-3 activity in the XIAP derepression assay was calculated as the ratio of the Vmax in the presence of each compound divided by the Vmax of the controls having caspase-3 and XIAP.

When examining individual compounds having different functionalities at the R2 position (Table XI), it can be seen that the diphenyl ureas derived from triamines having two secondary amines and one tertiary amine are more active than the triphenyl ureas. These diphenyl ureas were derived from the reduction of proline-containing acylated dipeptide amides, followed by treatment with phenyl isocyanate.

| TPI 1396- | Structure | Activity* |
|---|---|---|
| 34 | 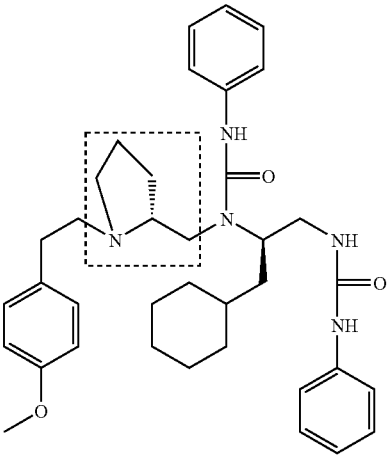 | 3.0 |
| 25 | 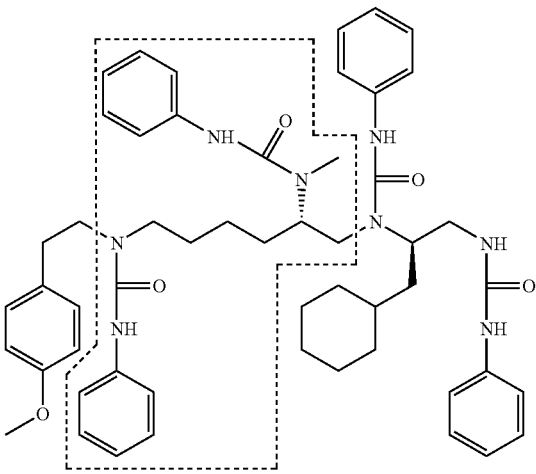 | 1.6 |
| 28 | 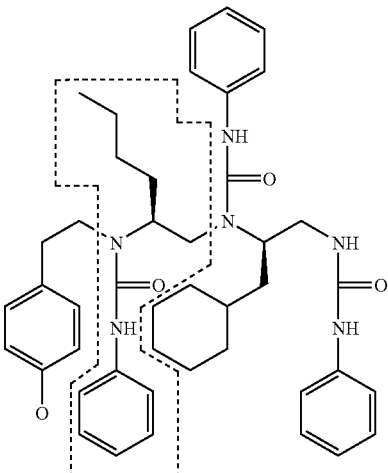 | 1.3 |

-continued

| TPI 1396- | Structure | Activity* |
|---|---|---|
| 31 | (structure) | 1.3 |

*Relative caspase-3 activity in the XIAP derepression assay was calculated as the ratio of the Vmax in the presence of each compound divided by the Vmax of the controls having caspase-3 and XIAP.

Also, a series of compounds (TPI 1509, shown in FIG. 34) synthesized using D-proline instead of L-proline were tested for activity. FIG. 34 shows the names, structures and activity of these compounds in the XIAP derepression assay. All of these compounds were active at 25 mg/ml, and the most active compounds in this assay were TPI 1509-1, TPI 1509-2, TPI 1509-3, and TPI 1509-6.

EXAMPLE XVII

Structure Activity Relationship (SAR) of Polyphenylureas

This example demonstrates compounds that can be used to address the relative importance of the main scaffold and each R group on the activity of the poly-phenylurea compounds. FIG. 35 shows compounds which are analogs of TPI 1509-7 where the properties of R1, R2 and R3 are varied separately by altering their chemical natures and therefore their physiochemical properties. A similar series of compounds was synthesized based on TPI 1396-34. The compounds are assayed for activity and another round of SAR can optionally be performed to further optimize the structure of the compounds. A desirable compound can be, for example, a compound with a lower molecule weight and better pharmacological properties than existing compounds.

EXAMPLE XVIII

TPI 1332 Peptide Compounds Interact with a Site on XIAP Distinct from the SMAC Binding Site This example demonstrates that compounds in the TPI 1332 series of tetrapeptides do not interact with the SMAC binding site on XIAP.

Peptide compounds containing unnatural amino acids in the 792 series, 792-33 and 792-35 (see FIG. 12 and 20 and Example XI), and an active compound in the TPI 1332 series, TPI 1332-69, were tested for binding activity in the SMAC binding assay as described above in Example X. For this assay, biotinylated SMAC 7-mer peptide (50 ng) was bound to 96 well plates coated with NeutrAvidin (Pierce, Rockford, Ill.) at 1 mg/ml in 100 µl per well of 50 mM HEPES pH 7.4, 100 mM NaCl, 1 mM EDTA, 10% sucrose, 0.1% CHAPS, 10 mM DTT. Then GST-XIAP was added at 0.1 mg/ml in 100 µl with or without compounds in DMSO. After incubation for 1 hour at room temperature, plates were washed with PBS with 0.05% Tween 20, and bound GST-XIAP was detected by addition of mouse anti-GST monoclonal antibody (1:2000 dilution) followed by anti-mouse horse radish peroxidase conjugated IgG and 3,3',5, 5'-tetramethylbenzidine base (TMB) substrate with detection at 450 nm on a plate reader.

As shown in FIGS. 36A–F and 37, the active compounds of the TPI 792 series and its analogs, as well as compounds of the TPI 1332 series, compete with XIAP binding to the SMAC peptide, with the exception of TPI 1332-69. In addition, as shown in FIG. 37, while TPI 1332-69 is active in the derepression assay but does not compete for the SMAC peptide binding site, TPI 1495-5 (substitution analog of TPI 1332-69 with G at position 4) is active in the derepression assay and competes for the SMAC peptide binding site. As expected, the inactive compounds in the 792 or 1332 series do not compete with XIAP binding to the SMAC peptide.

Figure 36C:
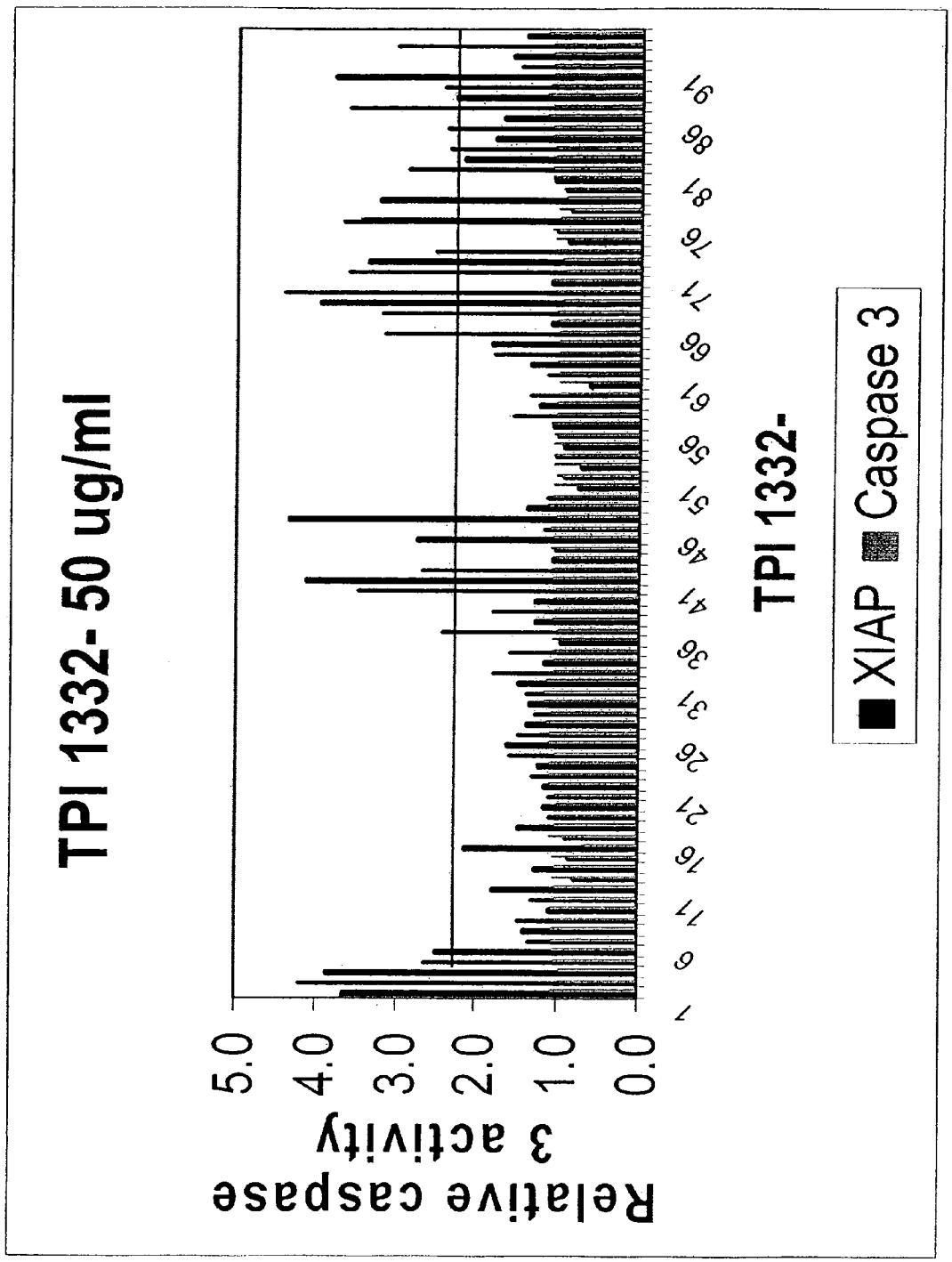
FIG. 36C shows the activity of 1332-1 through TPI 1332-93 at 50 μg/ml in the derepression assay using full length XIAP.
Figure 36D:
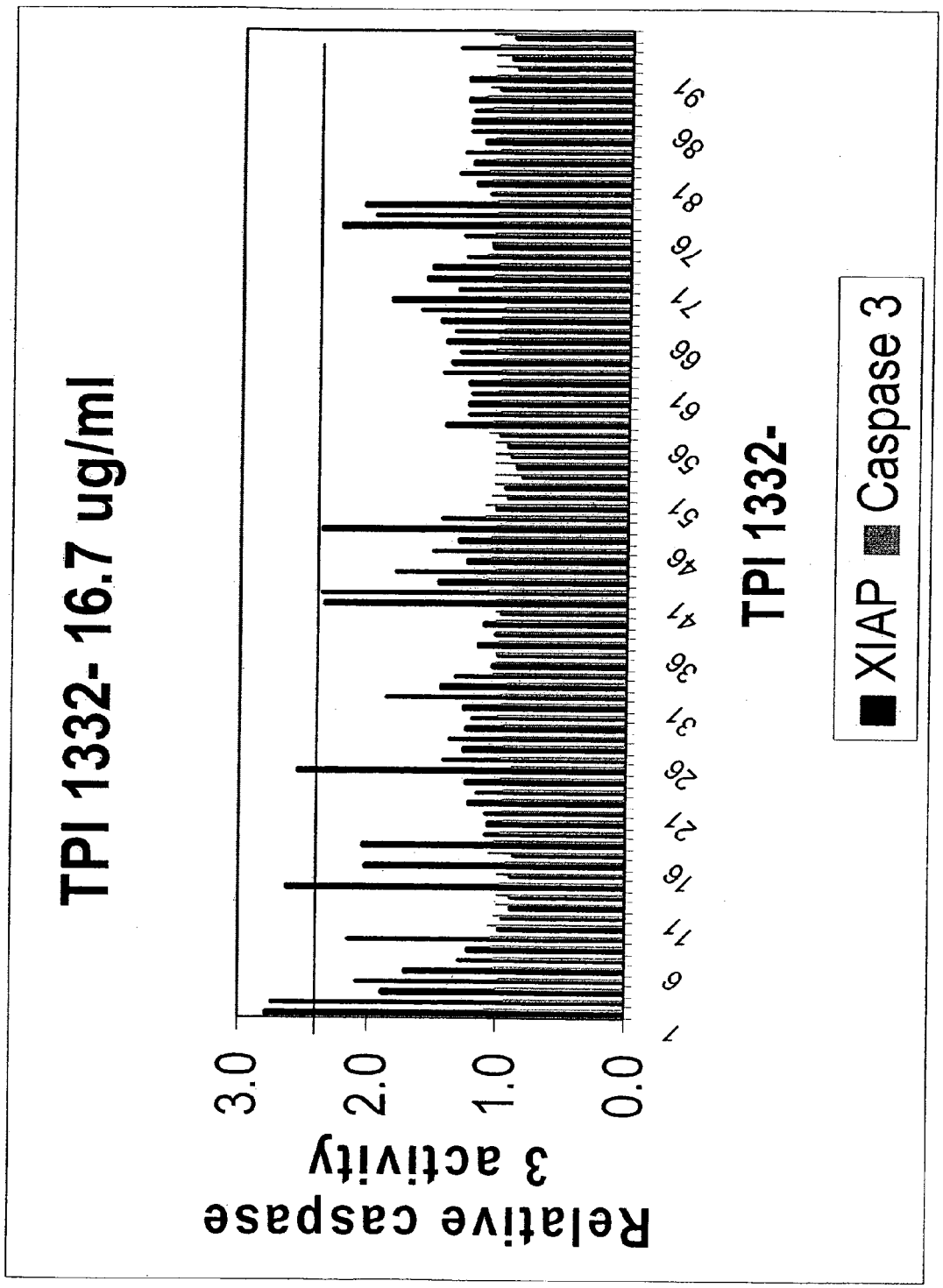
FIG. 36D shows the activity of TPI 1332-1 through TPI 1332-93 at 16.7 μg/ml in the derepression assay using full length XIAP.
Figure 36E:
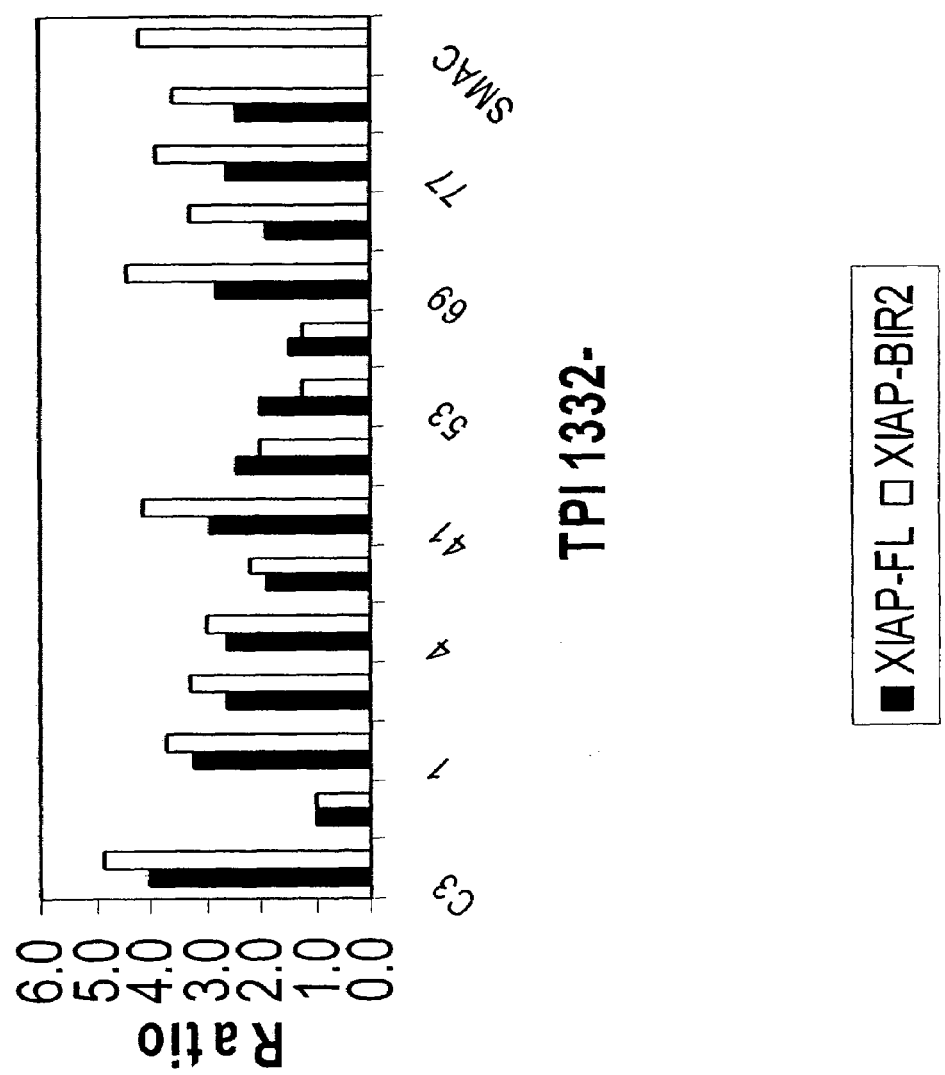
FIG. 36E shows the activity of TPI 1332-1, -4, -41, -53, -69, and 77 in the derepression assay using full length XIAP and the XIAP BIR2 domain.
Figure 36F:
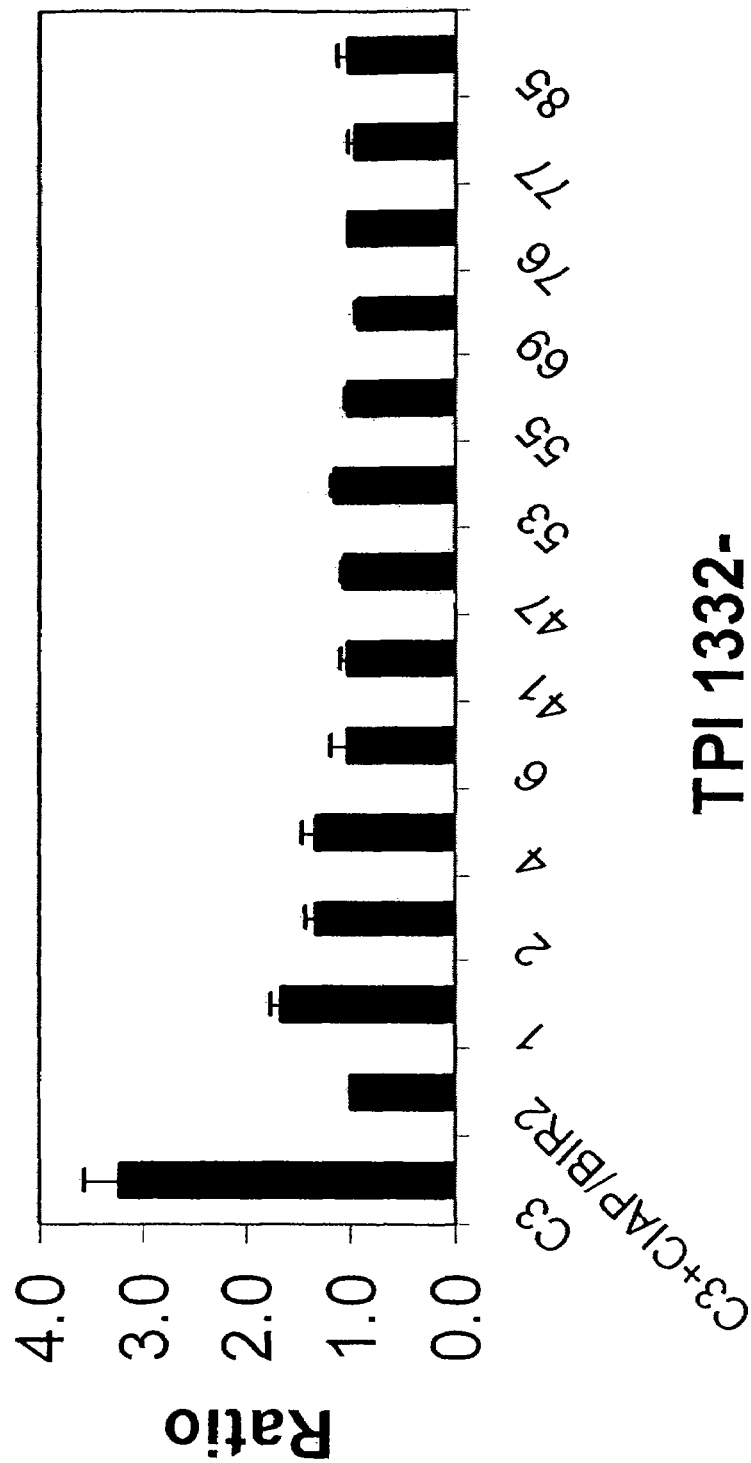
FIG. 36F shows the activity of TPI 1332-1, -2, -4, -6, -41, -47, -53, -55, -69, -76,-77 and -85using cIAP BIR2 domain.

As is shown in FIG. 36C–F, many compounds of the 1332 series were capable of reversing XIAP-mediated suppression of caspase 3. Active compounds at 50 µg/ml (FIG. 36C) included TPI 1332-1, -3, -4, -5, -11, -15, -32, -36, -38, -40, -41, -42, -45, -47, -63 to -69, -71 to -73, -76, -78, -81 to -85, -87 to -90 and -93. The activity of TPI 1332-1, -4, -41, -53, -69, and -77 was also determined in the derepression assay using XIAP-BIR2 domain, as shown in FIG. 36E. The activity of TPI 1332-1, -2, -4, -6, -41, -47, -53, -55, -69, -76, -77 and -85, in the derepression assay using the cIAP1 BIR2 domain further is shown in FIG. 36F. These data indicate that TPI 1332 and related compounds are active in derepressing caspase inhibited by XIAP or the BIR2 domain of XIAP, but do not overcome cIAP1-mediated suppression of caspase-3. It is important to note that the lack of activity observed for various compounds can be the result of the compounds being present at a two fold excess over cIAP1.

Shown in FIG. 37 are the activities of compounds derived from TPI 1332-69, referred to as TPI 1495-1 (TPI 1332-69) and TPI 1495-2 through TPI 1495-9. Whereas TPI 1332-69 was active in the caspase derepression assay but inactive in the SMAC competition assay, TPI 1495-5 was active in both the caspase derepression assay and the SMAC competition assay. These data indicate that TPI 1495-5 has a binding site on XIAP that affects the functions of both the BIR2 domain and SMAC binding domain of XIAP.

FIG. 43 shows several compounds derived from TPI 792-33 or TPI 792-35, referred to as the TPI 1453 series. As is shown, TPI 1453-1 is the same as TPI 792-33, with TPI 1453-2 through TPI 1453-5 being are modifications of TPI 792-33 that contain various natural and nonnatural amino acid substitutions; TPI 1453-5 is the same as TPI 792-35, with TPI 1453-6 through TPI 1453-9 being are modifications of TPI 792-35 that contain various natural and nonnatural amino acid substitutions. Compounds TPI 1453-1, -2, -4, -6, -7, -8, and -9 were determined to have activity in both the caspase derepression assay and the SMAC competition assay.

These data indicate that a novel negative regulatory site on XIAP, the XIAP BIR2 domain, is not targeted by SMAC. Compounds that bind to this novel negative regulatory site such as TPI 1332-36, as well as compounds that modulate both the SMAC binding site and BIR2 domain, can be used in screening assay in order to identify other compounds that can bind to this novel site.

EXAMPLE XIX

Identification of Compounds that Inhibit IAPs Other than XIAP

This example describes an assay that can be used to determine the effects of derepressors of XIAP-inhibited caspases on other IAPs.

Immunohistochemical analysis of prostate cancers indicates that cIAP1 and cIAP2 are commonly over-expressed in these tumors. Both cIAP1 and cIAP2 are caspase inhibitors (Roy, EMBO J. 16:6914–6925 (1997)) and they each bind SMAC (Du et al., Cell 102:33–42 (2000); Chai et al., Nature 406:855–862 (2000)). Moreover, molecular modeling studies indicate that some of the BIRs of cIAP1 and cIAP2 are likely to bind SMAC, having great structural similarity to XIAP. These observations indicate that derepressors of XIAP-inhibited caspases can have activity against caspases inhibited by these other IAPs.

To confirm that derepressors of XIAP-inhibited caspases have activity against caspases inhibited by these other IAPs, the following assays are performed. Competition of the compounds with the SMAC peptide for binding to BIRs on XIAP is assayed. To accomplish this, the compounds are tested in SMAC competition assays in which FITC-conjugated SMAC tetrapeptide AVPI (SEQ ID NO:4) or FITC-conjugated HtrA2 tetra-peptide AVPS (SEQ ID NO:6) are bound to BIRs from XIAP. Rather than expressing full-length XIAP, fragments of XIAP containing only the BIR2 or BIR3 domains are expressed, as described in Takahashi et al., J. Biol. Chem. 273:7787–7790 (1998) and Deveraux et al., EMBO J. 17:2215–2223 (1998). These assays will determine if the compound functions as a SMAC-mimic, and also whether the compound targets BIR2 (the domain that inhibits caspases-3 and -7), BIR3 (the domain that inhibits caspase-9), both, or neither of these domains.

Additionally, enzyme depression assays are performned using BIR2 or BIR3 domains to pinpoint the domain in XIAP that is targeted by a compound. Recombinant purified BIR2 is mixed with caspase-3, and BIR3 with caspase-9, then the activity of these proteases is measured against specific fluorogenic substrate peptides (Ac-DEVD-AFC for caspase-3 versus Ac-LEHD-AFC for caspase-9) in the presence and absence of a compound in an effort to pinpoint whether the compound targets BIR2, BIR3, both or neither of these domains in the XIAP protein. These results can be used for structure-based optimization of compounds using molecular modeling of the published structures of XIAP, BIR2 (Sun et al., Nature 401:818–821 (1999) and Riedl et al., Cell 104:791–800 (2001)), and BIR3 (Liu et al., Nature 408:1004–1008 (2000)).

With respect to cIAP1 and cIAP2, similar enzyme derepression and SMAC competition assays are performed using full-length cIAP1 and cIAP2, as well as fragments containing individual BIR domains, thus determining whether the compounds cross-inhibit these other members of the IAP-family.

If a compound does inhibit cIAP1, cIAP2, or both of these proteins, then the potency of the compound can be improved through medicinal and combinatorial chemistry. Assays can be performed to contrast retention versus loss of cIAP1/cIAP2 activity in vitro with activity of compounds in cell-based assays. Structure activity relationship studies of this type indicate whether the optimal compound has selective specificity for XIAP versus pan-reactivity against several IAPs. The compounds with these different profiles (selective versus broad-spectrum activity) are contrasted with respect to toxicity issues, to obtain a compound with a desired balance between efficacy and safety.

EXAMPLE XX

Mechanism of Action of PolyPhenyurea Compounds

To determine whether apoptosis induction by polyphenylurea compounds occurs through the intended mechanism of action, toxicity of TPI 1396-34 was tested using cells obtained from XIAP knock-out mice in a cell based assay. Mechanism-based toxicity of TPI 1396-34 and daunorubicin on mouse embryo fibroblasts (MEFs) from XIAP −/− mice and transformed wild type (+/+) mice was determined. Cells were either tested directly at low passage (FIGS. 38A and C) or after transformation by infection with a retrovirus encoding SV40 large T antigen (FIGS. 38B and D). Cells were cultured I day with various concentrations of compound TPI 1396-34 (FIGS. 38A and B) or with daunorubicin (FIGS. 38C and D). Cell viability was measured by MTT assay, expressing data as a percentage relative to control, untreated cells. Data shown in FIG. 38A–D represent mean±standard deviation of triplicate determinations.

These results demonstrate that XIAP-deficient cells are less sensitive to the polyphenylurea compound compared to wild-type MEFs, providing evidence that the compound functions through the intended mechanism of action since cells lacking the intended target (XIAP protein) are less sensitive. In contrast, if the compound induced apoptosis through a non-specific mechanism, it would be expected that XIAP-deficient cells would be more sensitive due to the absence of this anti-apoptotic protein. These findings also contrast non-transformed with transformed cells by showing that transformed cells are more sensitive to the XIAP antagonist. In contrast, conventional anticancer drugs such as daunorubicin do not display selectivity for transformed cells in these in vitro cytoxicity assays.

EXAMPLE XXI

Polyphenylurea Compounds Enhance Cytotoxicity of Antigen-Specific CTL

To determine if polyphenylurea compounds reduce resistance to apoptosis mechanisms relevant to CTL-mediated cell lysis, selected compounds were tested for their ability to enhance cytotoxicity of antigen-specific CTL.

For these experiments, tumor cells were loaded with $^{51}Cr$ then pulsed with specific antigen and incubated with antigen-specific T cells at effector:target ratios of either 5 (FIG. 39A) or 10 (FIG. 39B) in the absence of compounds (open circles; dashed lines) or in the presence of 10 µM of either inactive control compound TPI 1396-28 (squares) or active compound TPI 1396-34 (closed circles). After 4 hours, $^{51}Cr$ release was measured. Data shown in FIG. 39 are expressed as a percentage of total release induced by detergent lysis, and data represent mean±standard deviation of duplicate determinations.

As is shown in FIG. 39, TPI 1396-34 sensitizes tumor targets to CTL-mediated lysis. These results provide evidence that polyphenylurea compounds are not deleterious to CTL effector function and indicate that inhibiting XIAP reduces resistance to apoptosis mechanisms relevant to CTL-mediated cell lysis.

EXAMPLE XXII

In Vivo Activation of Caspases by Polyphenylurea Compounds in Tumors

To determine if polyphenylurea compounds induce caspase activation in tumors in vivo, TPI 1396-12 was tested a human tumor xenograft mouse model. For these studies, tumor-bearing Balb/c mice at 8 weeks of age were either injected i.p. for 3 successive days with 30 mg/kg of polyphenylurea compound TPI 1396-12 or with an equal volume of diluent (CNTL). Immunoblot analyses of tumor tissue, the results of which are shown in FIG. 40A, were performed using an antibody specific for cleaved caspase-3 or actin at 24 hours following the final injection of compound or control. These results indicate that polyphenylurea compound TPI 1396-12 induce caspase activation in tumors in vivo.

FIG. 40B shows immunohistochemistry of tumor tissue sections using H& E stained sections (B and C); anti-caspase-3 antibodies and anti-PCNA antibodies (dark stained nuclei; D and E), anti-caspase-6 antibodies (dark staining; F and G) and anti-DFF40 antibodies (dark staining; H and I). As is shown by detection of surrogate marker PCNA, polyphenylurea compound TPI 1396-12 had no effect on tumor proliferation. These results provide further evidence that polyphenylurea compound TPI 1396-12 functions through an apoptotic mechanism in vivo.

EXAMPLE XXIII

In Vivo Toxicology Analysis of Polyphenylurea Compounds

Figure 41:
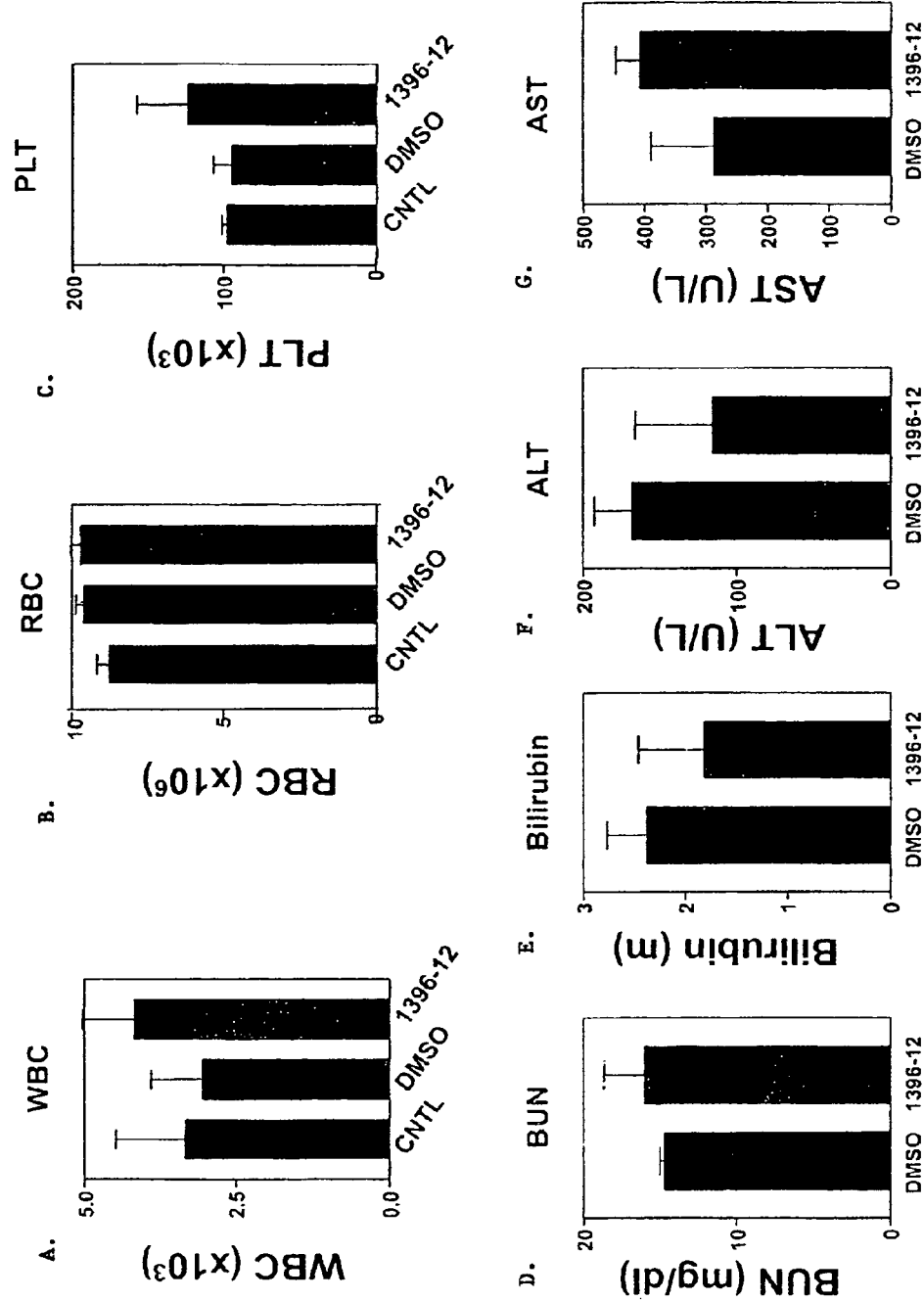
FIG. 41 shows toxicological analysis of TPI 1396-12, including white blood cell count (A); red blood cell count (B); platelet count (C); BUN (D); Bilirubin (E); ALT (F); and AST (G).

To assess in vivo stability and toxicology of polyphenylurea compound TPI 1396-12, tumor-bearing mice were treated with doses of compounds previously determined to be adequate for achieving anti-tumor activity in vivo using xenograft model and toxicological analyses were performed. In these studies, Balb/c mice (8 weeks of age) were either untreated or injected i.p. for 3 successive days with 30 mg/kg of polyphenylurea compound TPI 1396-12, or with an equal volume of diluent (PBS containing 10% DMSO, 5% TWEEN 80). At 12 hours after the final injection, mice were sacrificed and blood was analyzed for white blood cell count (WBC), red blood cell count (RBC), and platelet count (PLT). Sera were assayed for BUN, bilirubin, ALT and AST. These data, shown in FIG. 41, represent the mean±standard deviation for 3 mice. Although these data do not reach statistical significance, they indicate a trend.

Toxicology data shown in FIG. 41 indicate that polyphenylurea compound TPI 1396-12 is not toxin at the administered dosage. In addition, histological analyses of tissues confirmed these results.

These and related studies indicated that polyphenylurea compound TPI 1396-12 has a maximum tolerated dose of greater than 200–400 mg/kg in mice (non-lethal); that anti-tumor activity was demonstrated with as little as two sequential daily 30 mg/kg i.p. doses; and that polyphenylurea compound TPI 1396-12 is expected to be stable in human serum for greater than 48 hours.

EXAMPLE XXIV

Polyphenylurea Compounds Selectively Bind to BIR2

To obtain direct evidence that polyphenylurea compounds bind to the BIR2 domain of XIAP, NMR studies were performed. In these studies, polyphenylurea compounds TPI 1540-14 and TPI 1540-15 were shown to selectively bind to BIR2.

$T_{lr}$ measurements were formed at 200 ms with 400 µM polyphenylurea compound TPI 1540-14, -15 or -20 in the absence and presence of 10 µM GST-BIR2. Binding of active compounds TPI 1540-14 and TPI 1540-15 was manifested by a decrease in signal intensity in the presence of a sub-stoichiometric amount of GST-BIR2. Inactive compound TPI 1540-14 did not show this effect. As a control, an internal reference compound was added to the solution containing TPI 1540-15 (marked with a * in FIG. 42). As a control for compound binding to GST, the binding of TPI 1540-15 was also tested against GST-Bcl-B, which produced a negative result. Results for TPI 1540-14 and TPI 1540-20 are shown in FIG. 42. Results for TPI 1540-15 were similar to those observed for TPI 1540-14.

In summary, this example provides evidence that polyphenylurea compounds TPI 1540-14 and TPI 1540-15 bind directly to the BIR2 domain of XIAP.

EXAMPLE XXV

Structure Activity Relationship (SAR) of TPI 1540 Compounds

This example shows SAR information for individual TPI 1540 compounds TPI 1540-6 through TPI 1540-23. As is shown in FIG. 35B, a number of different modifications can be made without altering activity in comparison to TPI 1509-7 or TPI 1396-34 as indicated by IC50 values observed in the XIAP derepression assay or Jurkat-Annexin V assay.

These SAR data show that structures of active compounds, such as TPI 1396-34 can be simplified while retaining complete activity against the target protein both in vitro and in cell based assays. In addition, these data show that polyphenylurea compounds can be optimized with respect to Lipinsky's rules and that, accordingly, pharmacological properties of selected polyphenylurea compounds can be optimized.

EXAMPLE XXVI

Binding of BID and XIAP BIR2 Domain to Biotinylated Peptides

This example describes competition assays for XIAP-BIR2 binding to biotinylated peptides of the TPI 792, TPI 1332 and TPI 1495 series. The biotinylated peptides are referred to as the TPI 1554 series, and include TPI 1554-1 through TPI 1554-8, as shown in FIG. 44. Also shown in the table of FIG. 44 is the TPI number corresponding to the original tetrapeptides (Non-biotin Synthesis #) and the molecular weights (MW).

Binding assays were performed to determine whether the biotinylated peptides bound to the BIR domain of XIAP. Biotinylated peptides were adsorbed to Neutravidin-coated plates, and GST-XIAP BIR2 or GST-BID (control) was added. Bound GST polypeptides were detected with an anti-GST antibody. FIGS. 45A–J show that biotinylated compounds TPI 1453-1 (TPI 1554-1)(A); TPI 1453-6 (TPI 1554-2)(B); TPI 1332-4 (TPI 1554-3)(C); TPI 1332-41 (TPI 1554-4)(D); TPI 1332-69 (TPI 1554-5)(E); TPI 1332-77 (TPI 1554-6)(F); TPI 1495-19 (TPI 1554-7)(G), and TPI 1495-20 (TPI 1554-8)(H) competed for binding to XIAP-BIR2 to an extent comparable to the binding of SMAC peptides SMAC 7-mer (I) and SMAC 4-mer (J).

FIGS. 46A–C show binding of XIAP-BIR2 to biotinylated tetrapeptides TPI 1554-1 through TPI 1554-8 using 1 μg/ml XIAP BIR2 (A); 0.5 μg/ml XIAP BIR2 (B), and 0.25 μg/ml XIAP BIR2 (C) with biotinylated peptides at concentrations of 1.6 μg/ml, 0.4 μg/ml and 0.1 μg/ml. TPI 1554-3 through TPI 1554-8 had a greater extent of binding to XIAP BIR2 domain in comparison to TPI 1554-1 and -2. These results show that binding of XIAP BIR domain to biotinylated tetrapeptides TPI 1554-3 through TPI 1554-8 is comparable to the binding of SMAC peptides.

FIG. 47 shows competition assays for the binding of XIAP BIR2 domain to the biotinylated tetrapeptides in the absence or presence of a polyphenylurea compound, using biotinylated peptide TPI 1554-5 (TPI 1332-69) (A), which is a non-SMAC mimic; and biotinylated peptide TPI 1554-3 (TPI 1332-4)(B), which is a SMAC mimic. Results from these studies indicate that the polyphenylureas do not compete for binding of XIAP-BIR2 domain with either of the tetrapeptides. However, the SMAC mimic tetrapeptide TPI 1554-3 competes with binding of XIAP BIR2 domain to the biotinylated non-SMAC mimic tetrapeptide TPI 1554-5. This observation for TPI 1554-3 is consistent with the finding described herein in Example XVIII that TPI 1332-69 binds to a site on XIAP that overlaps between the SMAC and BIR2 binding sites.

EXAMPLE XXVII

Rhodamine-Labeled Binding/Competitive Binding Assay

This Example describes assays useful for determining the binding affinity of a derepressor of an IAP-inhibited caspase for an IAP, or functional fragment thereof.

A. Binding Assay

A polarization-based binding assay was used to detect binding between rhodamine labeled candidate derepressors of IAP inhibited caspase (candidate compounds) and the XIAP fragments His-BIR2, His-BIR1-2 and His-BIR1-2-3. The assay is based on the decrease in mobility that occurs for rhodamine-labeled candidate compounds when associated with XIAP or functional fragments thereof, which is detected as an increase in polarization of the rhodamine-labeled candidate compound due to binding to the target protein.

In a first assay, binding of candidate derepressors of IAP inhibited caspase was measured by a fluorescence polarization procedure. A fixed quantity of rhodamine-labeled candidate compound was titrated against varying quantities of IAP fragment compounds (His-BIR2 of XIAP, His-Traf2 (negative protein control), His-BIR1-2 of XIAP or His-BIR1-2-3 of XIAP). Binding of the candidate compound to the IAP fragment is detected as an increase in polarization (millipolars or mP) compared to the candidate compound alone, as bound fluorophore has a greater polarizing effect than unbound fluorophore. A plot of mP versus log concentration of the IAP fragment can be used to calculate the binding constant for the candidate compound for the IAP fragment.

The results of this assays are set forth in FIGS. 48, 50 and 52. Briefly, a micromolar quantity of labeled candidate compound was prepared in a buffered solution in the presence of various amounts of His-BIR2 of XIAP, BIR1 of NAP, and His-BIR1-2 of XIAP in a standard microtiter plate. (See Table XII for conditions.) His-Traf2 served as a negative control for specificity. Results similar to those seen with His-BIR1-2 of XIAP are seen with His-BIR1-2-3 of XIAP. The plates were incubated for one hour at room temperature, after which polarization of rhodamine was read in an LJL Analyst HT® multimode reader with excitation at 530 nm and emission at 580 nm. FIGS. 48, 50 and 52 show polarization values (millipolars, mP) plotted as a function of millipolars versus the log concentration of His-BIR2 of XIAP, His-Traf2 or His-BIR1-2 of XIAP. His-Traf2 was plotted as a negative control. Results similar to those seen with His-BIR1-2 of XIAP are seen with His-BIR1-2-3 of XIAP.

The structure of TPI 1332-4 is shown in FIG. 36A. The structure of TPI 1540-14 is set forth in FIG. 35A.

TABLE XII

| FIG. | Candidate Compound (Rhodamine-Labeled Candidate Compound) | Concentration of Rhodamine Labeled Candidate Compound (in Buffer) | IAP Fragment [IAP Fragment] μM |
|---|---|---|---|
| 48 | TPI 1332-4 (TPI 1566-11) | 2.4 μM (in 50 mM KPi, pH 7.4, 50 mM NaCl) | His-BIR2 of XIAP, His-Traf2 0, 0.11, 0.33, 0.99, 2.96, 8.89, 26.67 |
| 50 | TPI 1540-14 (TPI 1576 pk1, pk2) | 2.5 μM (in 50 mM Tris, pH 8.8, 50 mM NaCl, 1.25 mM DTT) | His-Traf2, His-BIR1-2 of XIAP 0, 0.14, 0.41, 1.23, 3.70, 11.11, 33.33, 100 |
| 52 | TPI 1540-14 (TPI 1576 pk1, pk2) | 2.5 μM (in 50 mM Tris, pH 8.8, 50 mM NaCl, 1.25 mM DTT) | His-BIR1-2 of XIAP, His-Traf2, BIR1 of XIAP 0, 0.14, 041, 1.23, 3.70, 11.11, 33.33, 100 |

The structure of TPI 1332-4 is shown in FIG. 36A. The structure of rhodamine-labeled TPI 1332-4 (TPI 1566-11) is shown below.

The structure of TPI 1540-14 is set forth in FIG. 35A. The structures of two species of rhodamine-labeled TPI 1540-14 (TPI 1576-37 pk1 and TPI 1576-37 pk2) are shown below.

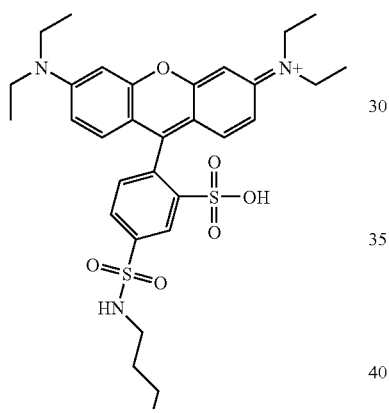

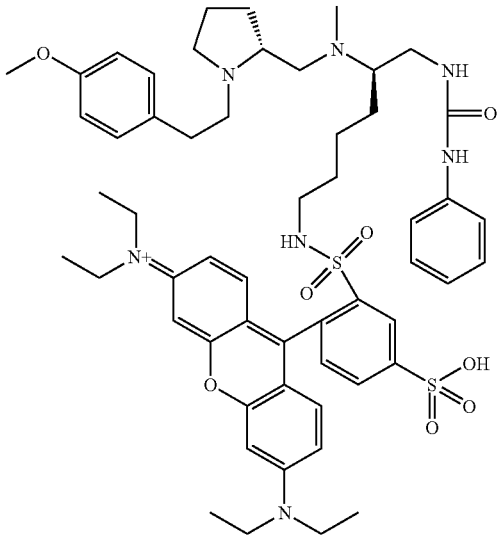

TPI 1576-37 pk1

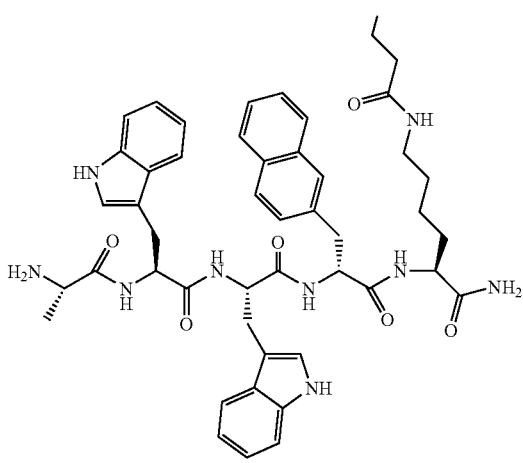

TPI 1566-11

-continued

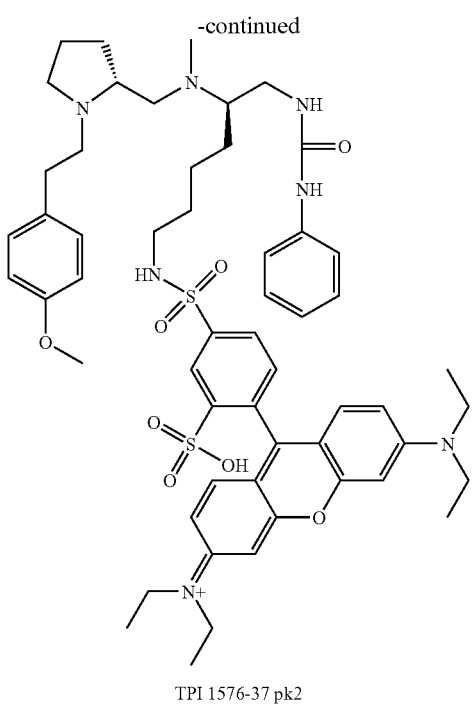

TPI 1576-37 pk2

B. Competitive Binding Assay

In a second assay, competitive binding of candidate derepressors of IAP inhibited caspase was measured by a fluorescence polarization procedure. Fixed quantities of rhodamine-labeled candidate compound and IAP fragment were titrated against varying concentrations of a known IAP-binding compound. Displacement of the candidate compound by the known IAP-binding compound was detected as a decrease in polarization, as the displaced (unbound) candidate compound will have a lower polarization than the bound candidate compound. Polarization (millipolars or mP) was plotted against log concentration (log []) of the known IAP-binding compound. A plot of mP versus log concentration of the IAP-binding compound was then used to calculate the binding constant for the candidate compound-the IAP fragment pair.

Figure 49:
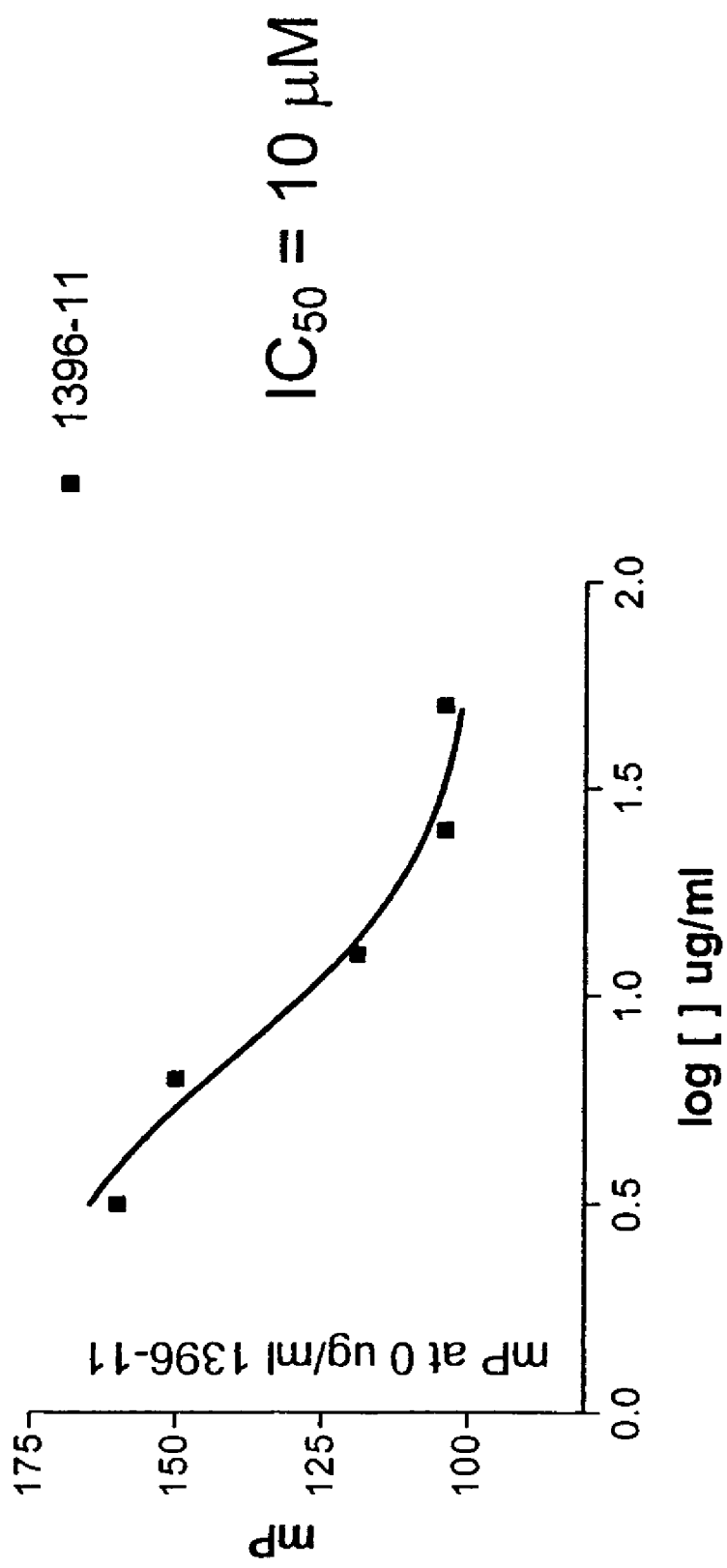
FIG. 49 shows competitive binding of rhodamine labeled TPI 1332-4(1566-11) to HIS-BIR2 of XIAP in the presence of known IAP binding compound TPI 1396-11. Rhodamine labeled TPI 1332-4 was present at 2.4 μM and His-BIR2 of XIAP at 79 μM in 50 mM KPi at pH 7.4/50 mM NaCl. TPI 1396-11 was at 0, 1.56, 3.13, 6.25, 12.5, 25, 50 and 100 μg/ml. Plates were incubated for 1 hour at room temperature and read in an LJL Analyst HT in fluorescence polarization mode with rhodamine filters (excitation 530 nm; emission 580 nm) and a rhodamine dichroic mirror at 565 nm. Data was fit in Prism™ by nonlinear regression for a sigmoidal dose-response curve with variable slope.
Figure 51:
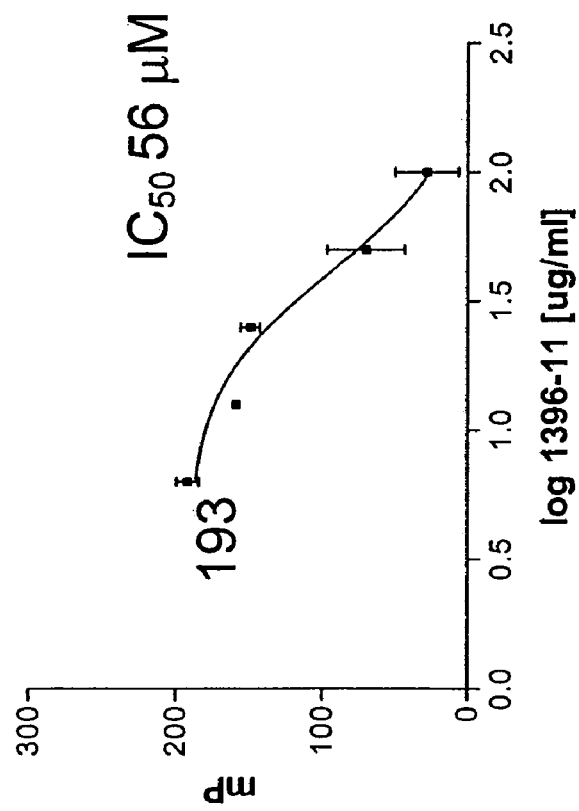
FIG. 51 shows competitive binding of labeled TPI 1540-14 (TPI 1576-37, peak 2) to His-BIR1-2 against TPI 1396-11. TPI 1576-37 pk2 was present at 2.5 μM and His-BIR1-2 of XIAP at 50 μM in 50 mM Tris at pH 8.8/50 mM NaCl/1.25 mM DTT. TPI 1396-11 was at 0, 1.56, 3.13, 6.25, 12.5, 25, 50 and 100 μg/ml. Plates were incubated for 1 hour at room temperature and read in an LJL Analyst HT in fluorescence polarization mode with rhodamine filters (excitation 530 nm; emission 580 nm) and a rhodamine dichroic mirror at 565 nm. Data was fit in Prism by nonlinear regression for a sigmoidal dose-response curve with variable slope.
Figure 53:
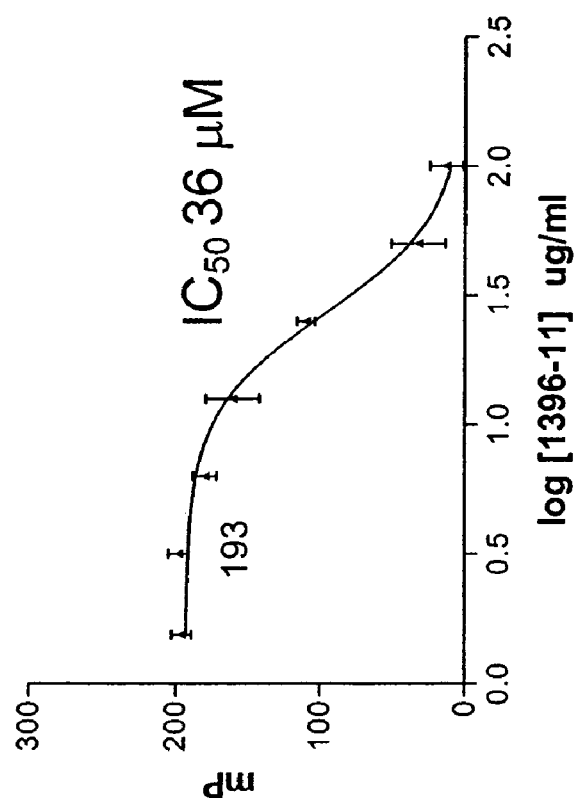
FIG. 53 shows competitive binding of labeled TPI 1540-14 (TPI 1576-41, peak 2) to His-BIR1-2 against TPI 1396-11. TPI 1576-41 pk2 was present at 2.5 μM and His-BIR1-2 of XIAP at 50 μM in 50 mM Tris at pH 8.8/50 mM NaCl/1.25 mM DTT. TPI 1396-11 was at 0, 1.56, 3.13, 6.25, 12.5, 25, 50 and 100 μg/ml. Plates were incubated for 1 hour at room temperature and read in an LJ LAnalyst HT in fluorescence polarization mode with rhodamine filters (excitation 530 nm; emission 580 nm) and a rhodamine dichroic mirror at 565 nm. Data was fit in Prism by nonlinear regression for a sigmoidal dose-response curve with variable slope.

The results of this assays are set forth in FIGS. 49, 51 and 53. Briefly, a micromolar quantity of labeled candidate compound and IAP fragment was prepared in a buffered solution in the presence of various amounts of IAP-binding compound TPI 1396-11 in a standard 96-well microtiter plate. (See Table XIII for conditions). Plates were incubated for one hour at room temperature, after which polarization of rhodamine was read in an LJL Analyst HT® multimode reader with excitation at 530 nm and emission at 580 nm. FIGS. 49, 51 and 53 show polarization values (millipolars, mP) plotted as a function of the log concentration of TPI 1396-11 in μg/ml. FIGS. 49 and 53 also show the $IC_{50}$ of the labeled candidate compounds (10 μM for TPI 1332-4, 36 μM for TPI 1540-14).

TABLE XIII

| FIG. | Labeled Candidate Compound ($I.C._{50}$) | Concentration of Rhodamine Labeled Candidate Compound (in Buffer) | [TPI 1396-11] μg/mL |
|---|---|---|---|
| 49 | TPI 1566-11 (10 μM) | 2.4 μM (in 50 mM KPi, pH 7.4, 50 mM NaCl) | 0, 1.56, 3.13, 6.25, 12.5, 25, 50, 100 |
| 51 | TPI 1576-37 pk2 | 2.5 μM (50 mM Tris, pH 8.8, 50 mM NaCl, 1.25 mM DTT) | 0, 1.56, 3.13, 6.25, 12.5, 25, 50, 100 |
| 53 | TPI 1576-41 pk2 (56 μM) | 2.5 μM (50 mM Tris, pH 8.8, 50 mM NaCl, 1.25 mM DTT) | 0, 1.56, 3.13, 6.25, 12.5, 25, 50, 100 |

EXAMPLE XXVIII

Structure Activity Relationship (SAR) of Individual TPI 1577 TPI 1567 and TPI 1572

This Example shows the structure and SAR information based on TPI 1577, TPI 1567 and TPI 1572, which are all based on TPI 1540-14. As shown by the activity screening of individual compounds belonging to the TPI 1577, TPI 1567 and TPI 1572 families, a number of different hydrophobic groups are acceptable for activity at the R1, R3, N", positions (see Table XIV).

TABLE XIV

| TPI # — MW[1] — MLogP | Structure | Activity[2] (μM) |
|---|---|---|
| TPI 1577-1 425 2.71 | | 252 |

TABLE XIV-continued
| TPI # / MW[1] / MLogP | Structure | Activity[2] (μM) |
|---|---|---|
| TPI 1577-2 / 467 / 3.31 | 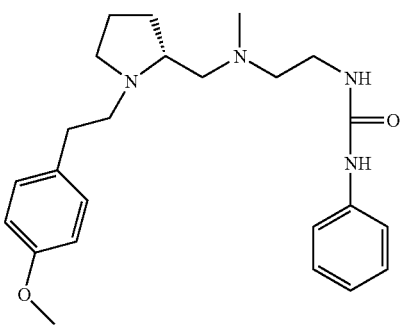 | 157 |
| TPI 1577-3 / 411 / 2.5 | 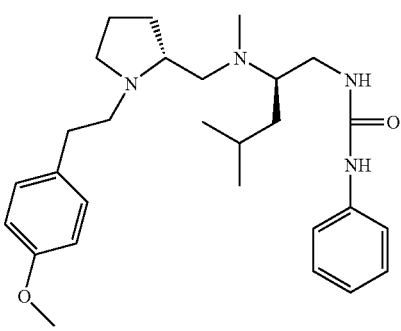 | >241 |
| TPI 1567-5 / 401 / 3.25 | 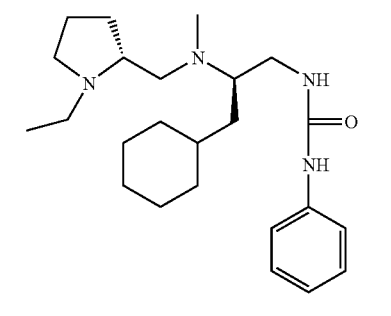 | 209 |
| TPI 1577-6 / 476 / 4.20 | 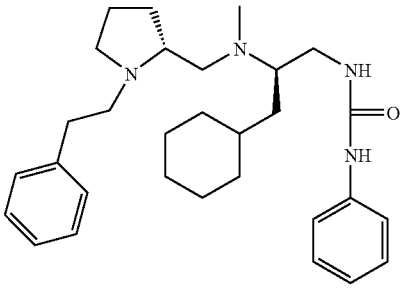 | 113 |

TABLE XIV-continued
| TPI # / MW[1] / MLogP | Structure | Activity[2] (μM) |
|---|---|---|
| TPI 1577-7 / 495 / 4.57 | 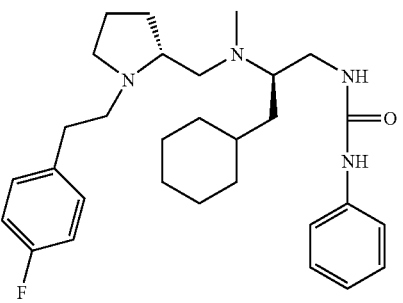 | 71 |
| TPI 1577-8 / 491 / 4.39 | 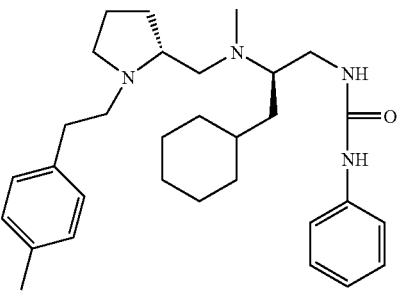 | 88 |
| TPI 1567-11 / 505 / 4.58 | 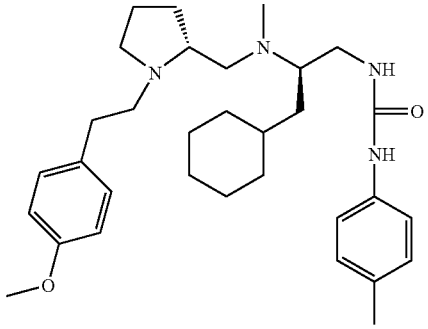 | 75 |
| TPI 1567-12 / 525 / 4.25 | 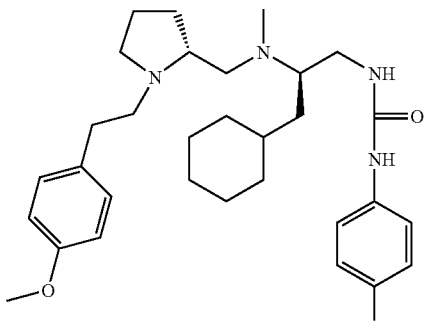 | 124 |

TABLE XIV-continued
| TPI # / MW[1] / MLogP | Structure | Activity[2] (μM) |
|---|---|---|
| TPI 1567-13 / 633 / 4.53 | 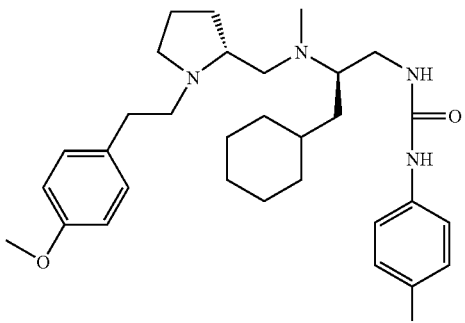 | 58 |
| TPI 1567-14 / 665 / 4.98 | 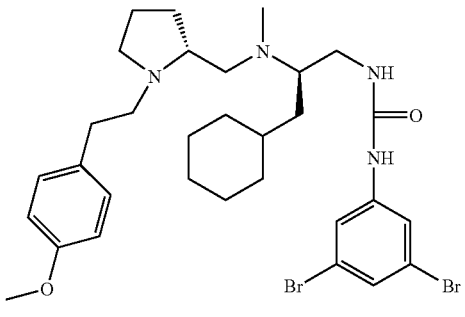 | 81 |
| TPI 1577-9 / 557 / 4.44 | 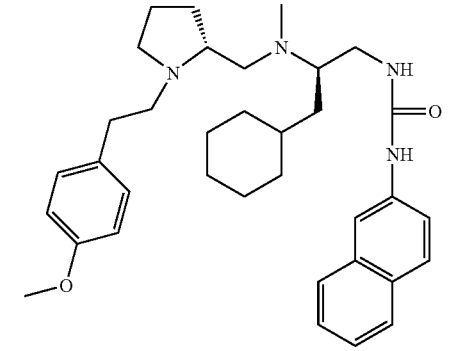 | 23 |
| TPI 1567-23 / 628 / 3.52 | 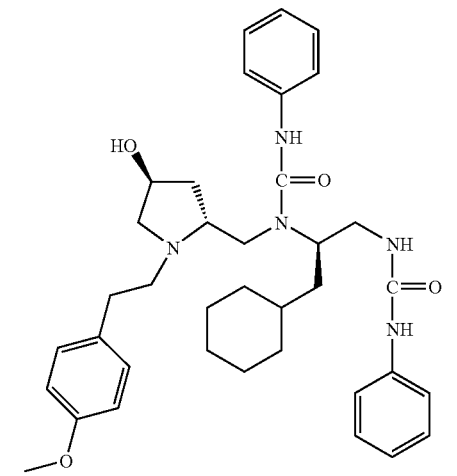 | 35 |

TABLE XIV-continued
| TPI # MW[1] MLogP | Structure | Activity[2] (µM) |
|---|---|---|
| TPI 1567-24 523 3.13 | 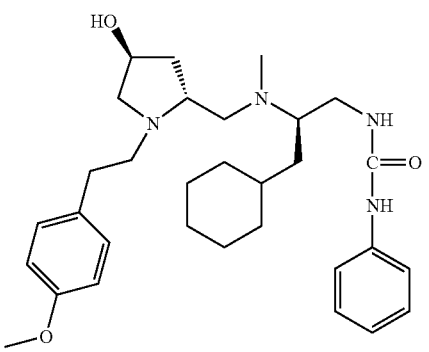 | 122 |
| TPI 1567-18 629 4.39 | 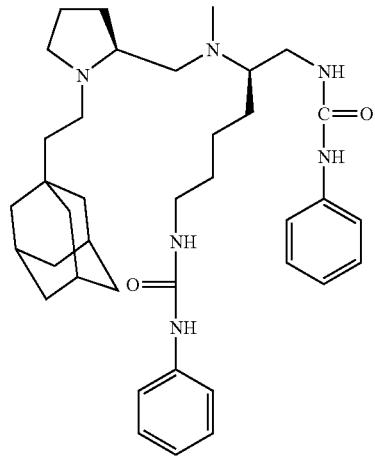 | 61 |
| TPI 1572-8 353 2.63 | 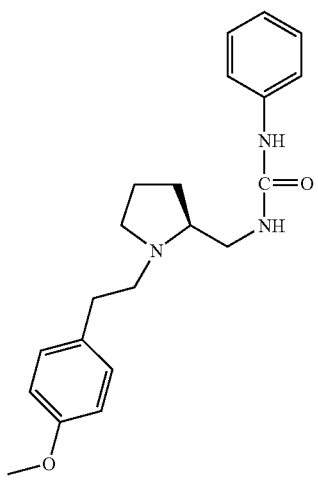 | >283 |

TABLE XIV-continued

| TPI # / MW[1] / MLogP | Structure | Activity[2] (μM) |
|---|---|---|
| TPI 1572-15 / 515 / 2.97 | (structure) | 171 |
| TPI 1572-16 / 529 / 3.16 | (structure) | 149 |
| TPI 1572-10 / 477 / 3.29 | (structure) | >210 |

TABLE XIV-continued

| TPI # MW[1] MLogP | Structure | Activity[2] (μM) |
|---|---|---|
| TPI 1572-11 505 3.68 | | 89 |
| TPI 1572-14 506 3.89 | | 103 |
| TPI 1572-17 506 3.89 | | 132 |

TABLE XIV-continued
| TPI # | | |
|---|---|---|
| MW[1] | | |
| MLogP | Structure | Activity[2] (μM) |
| TPI 1572-18 581 4.95 | 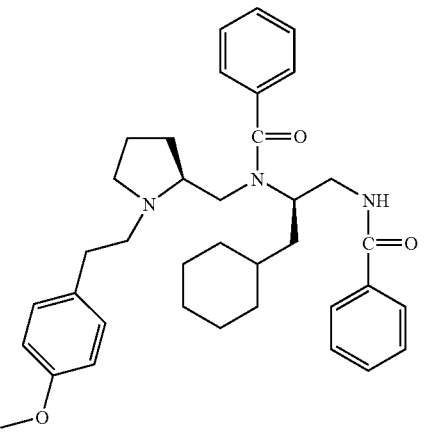 | 164 |
| TPI 1572-19 457 3.01 | 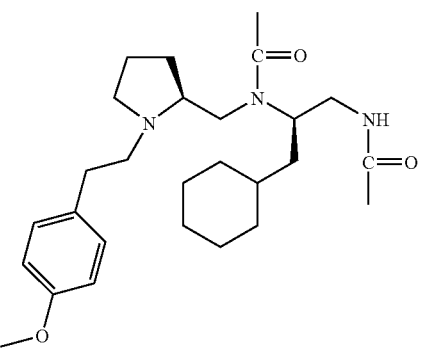 | >219 |
| TPI 1572-20 515 2.7 | 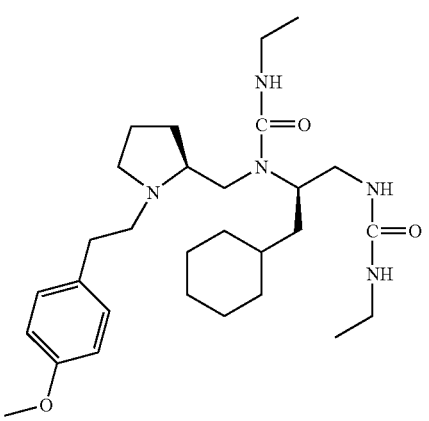 | 235 |

TABLE XIV-continued

| TPI # MW¹ MLogP | Structure | Activity² (μM) |
|---|---|---|
| TPI 1572-21 639 4.61 | | 69 |
| TPI 1572-22 647 4.7 | | 79 |

TABLE XIV-continued

| TPI # MW[1] MLogP | Structure | Activity[2] (µM) |
|---|---|---|
| TPI 1572-23 701 4.39 | (structure: 4-nitrophenyl-NH-C(=O)-N group bearing a (pyrrolidinyl with N-CH2CH2-(4-methoxyphenyl)) methyl substituent and a cyclohexylmethyl side chain, with CH2-NH-C(=O)-NH-(4-nitrophenyl)) | 94 |

[1] Molecular weight in grams/mole.
[2] Relative caspase-3 activity in the XIAP derepression assay was calculated as the ratio of the Vmax in the presence of each compound divided by the Vmax of the controls containing caspase-3 and XIAP but lacking the compounds.

Figure 54:
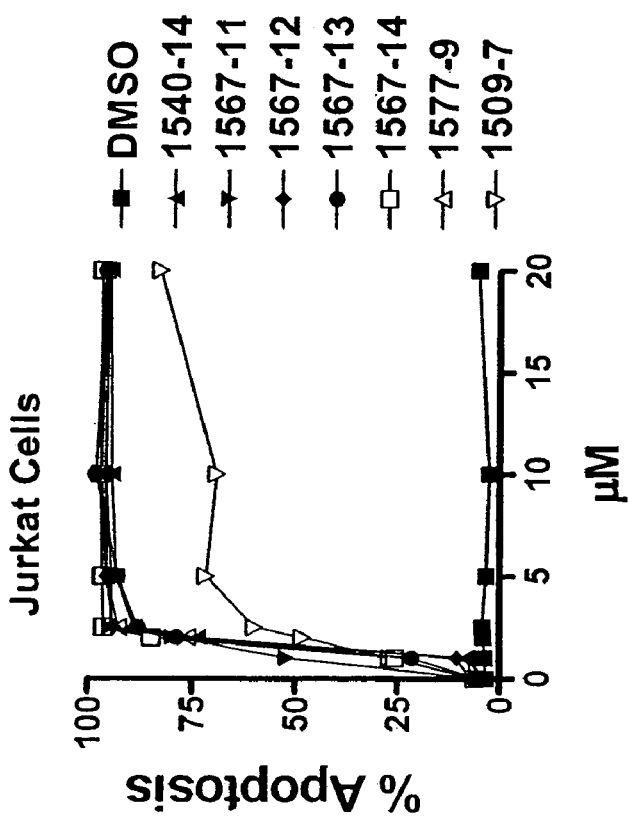
FIG. 54 shows the aptoptotic effect of several compounds of the invention. The apoptotic effect was determined as described in Example XXVIII.

Following the procedure of Example XI, TPI 1540-14, TPI 1567-11, TPI 1567-12, TPI 1567-13, TPI 1567-14, TPI 1577-9 and TPI 1509-7 were tested for their ability to induce apoptosis in Jurkat cells. The results of these tests are shown in FIG. 54. As compared to the DMSO control, each of the tested compounds proved capable of inducing apoptosis in the tested cell line at micromolar concentrations.

EXAMPLE XXIX

Scintillation Proximity Assay

This example describes a scintillation proximity assay. This method uses derepressors of IAP-inhibited caspase modified with a radiolabel, such as tritium, in a scintillation proximity assay (SPA). In a homogeneous assay, copper chelate (His-Tag) YSi SPA™ Scintillation Beads (available from Amersham-Pharmacia) are mixed with His-BIR2, His-BIR1-2 or His-BIR1-2-3 and a radiolabeled compound. Unlabeled competing compounds (candidate compounds) are then added at various concentrations in 96 well plates which are spun down, pelleting the beads, attached His-protein and bound radiolabel. Plates are then read in a scintillation counter. Reduction in bound radiolabel reflects competition by unlabeled candidate compounds. Candidate compounds that competitively displace one or more labeled derepressors are identified as ligands and potential derepressors of IAP inhibited caspase. See Alderton, W. K. and P. N. Lowe, 1999, "Scintillation Proximity Assay to Measure Nitroargine and Tetrahydrobioperin Binding to Heme Domain of Neuronal Nitric Oxide Synthase," Methods in Enzymol., 301:114–125.

EXAMPLE XXX

Scintillation Proximity Assay

This assay utilizes Ni-NTA Hi Sorb Plates™ from Qiagen to identify candidate compounds that are derepressors of IAP inhibited caspase. This is a non-homogenous assay with several washing steps. One or more of His-BIR2, His-BIR1-2 or His-BIR1-2-3 are bound to a plate. A biotin-labeled compound, a fluorophore-labeled compound or a radiolabeled compound is then bound to the protein in the presence of varying concentrations of competing unlabeled compound (candidate compound). Following at least one wash step, bound labeled compound is measured. For example, where the labeled compound is biotinylated, the read-out is via alkaline or horseradish peroxidase conjugated streptavidine (both available from Amersham-Pharmacia), which yields an absorbance in the visible range, which can be measured with a spectrophotometer. Where the labeled compound is radiolabeled, radioactive read-out is obtained with a scintillation counter. Where the labeled compound is fluorescently labeled, fluorescence read-out is obtained with a fluorescence spectrophotometer. A decrease in the read-out in the presence of competing unlabeled compound (candidate compound) reflects competition by the unlabeled compound. A candidate compound that competitively displaced labeled compound is identified as a ligand and as a potential derepressor of IAP inhibited caspase.

Throughout this application various publications have been referenced. The disclosures of these publications in their entireties are hereby incorporated by reference in this application in order to more fully describe the state of the art to which this invention pertains.

Although the invention has been described with reference to the examples provided above, it should be understood that various modifications can be made without departing from the spirit of the invention. Accordingly, the invention is limited only by the claims.

What is claimed:

1. An isolated agent comprising one of the compounds identified herein as TPI 1577-1, TPI 1577-2, TPI 1577-3, TPI 1567-5, TPI 1577-6, TPI 1577-7, TPI 1577-8, TPI 1567-11, TPI 1567-12, TPI 1567-13, TPI 1567-14, TPI 1577-9, TPI 1567-23, TPI 1567-24, TPI 1567-18, TPI 1572-8, TPI 1572-15, TPI 1572-16, TPI 1572-10, TPI 1572-11, TPI 1572-14, TPI 1572-17, TPI 1572-18, TPI 1572-19, TPI 1572-20, TPI 1572-21, TPI 1572-22 or TPI 1572-23.

2. A composition comprising an isolated agent of claim 1 in admixture with a diluent.

3. A pharmaceutical composition comprising the agent of claim 1 or 2 and a pharmaceutically acceptable carrier.

4. A complex comprising an IAP bound to an agent of claim 1.

5. The complex of claim 4, wherein said IAP is selected from the group consisting of XIAP, c-IAP-1, c-IAP-2, NIAP, BRUCE (Appollon), ML-IAP, ILP2, DIAP-1, DIAP-2 and survivin.

6. The isolated agent of claim 1, wherein said compound is TPI 1577-1.

7. The composition of claim 2, wherein said compound is TPI 1577-1.

8. The pharmaceutical composition of claim 3, wherein said compound is TPI 1577- 1.

9. The complex of claim 4, wherein said compound is TPI 1577-1.

10. The complex of claim 5, wherein said compound is TPI 1577-1.

11. The isolated agent of claim 1, wherein said compound is TPI 1572-14.

12. The composition of claim 2, wherein said compound is TPI 1572-14.

13. The pharmaceutical composition of claim 3, wherein said compound is TPI 1572-14.

14. The complex of claim 4, wherein said compound is TPI 1572-14.

15. The complex of claim 5, wherein said compound is TPI 1572-14.

16. The isolated agent of claim 1, wherein said compound is TPI 1577-2.

17. The composition of claim 2, wherein said compound is TPI 1577-2.

18. The complex of claim 4, wherein said compound is TPI 1577-2.

19. The isolated agent of claim 1, wherein said compound is TPI 1577-3.

20. The composition of claim 2, wherein said compound is TPI 1577-3.

21. The complex of claim 4, wherein said compound is TPI 1577-3.

22. The isolated agent of claim 1, wherein said compound is TPI 1567-5.

23. The composition of claim 2, wherein said compound is TPI 1567-5.

24. The complex of claim 4, wherein said compound is TPI 1567-5.

25. The isolated agent of claim 1, wherein said compound is TPI 1577-6.

26. The composition of claim 2, wherein said compound is TPI 1577-6.

27. The complex of claim 4, wherein said compound is TPI 1577-6.

28. The isolated agent of claim 1, wherein said compound is TPI 1577-7.

29. The composition of claim 2, wherein said compound is TPI 1577-7.

30. The complex of claim 4, wherein said compound is TPI 1577-7.

31. The isolated agent of claim 1, wherein said compound is TPI 1577-8.

32. The composition of claim 2, wherein said compound is TPI 1577-8.

33. The complex of claim 4, wherein said compound is TPI 1577-8.

34. The isolated agent of claim 1, wherein said compound is TPI 1567-11.

35. The composition of claim 2, wherein said compound is TPI 1567-11.

36. The complex of claim 4, wherein said compound is TPI 1567-11.

37. The isolated agent of claim 1, wherein said compound is TPI 1567-12.

38. The composition of claim 2, wherein said compound is TPI 1567-12.

39. The complex of claim 4, wherein said compound is TPI 1567-12.

40. The isolated agent of claim 1, wherein said compound is TPI 1567-13.

41. The composition of claim 2, wherein said compound is TPI 1567-13.

42. The complex of claim 4, wherein said compound is TPI 1567-13.

43. The isolated agent of claim 1, wherein said compound is TPI 1567-14.

44. The composition of claim 2, wherein said compound is TPI 1567-14.

45. The complex of claim 4, wherein said compound is TPI 1567-14.

46. The isolated agent of claim 1, wherein said compound is TPI 1577-9.

47. The composition of claim 2, wherein said compound is TPI 1577-9.

48. The complex of claim 4, wherein said compound is TPI 1577-9.

49. The isolated agent of claim 1, wherein said compound is TPI 1567-23.

50. The composition of claim 2, wherein said compound is TPI 1567-23.

51. The complex of claim 4, wherein said compound is TPI 1567-23.

52. The isolated agent of claim 1, wherein said compound is TPI 1567-24.

53. The composition of claim 2, wherein said compound is TPI 1567-24.

54. The complex of claim 4, wherein said compound is TPI 1567-24.

55. The isolated agent of claim 1, wherein said compound is TPI 1567-18.

56. The composition of claim 2, wherein said compound is TPI 1567-18.

57. The complex of claim 4, wherein said compound is TPI 1567-18.

58. The isolated agent of claim 1, wherein said compound is TPI 1572-8.

59. The composition of claim 2, wherein said compound is TPI 1572-8.

60. The complex of claim 4, wherein said compound is TPI 1572-8.

61. The isolated agent of claim 1, wherein said compound is TPI 1572-15.

62. The composition of claim 2, wherein said compound is TPI 1572-15.

63. The complex of claim 4, wherein said compound is TPI 1572-15.

64. The isolated agent of claim 1, wherein said compound is TPI 1572-16.

65. The composition of claim 2, wherein said compound is TPI 1572-16.

66. The complex of claim 4, wherein said compound is TPI 1572-16.

67. The isolated agent of claim 1, wherein said compound is TPI 1572-10.

68. The composition of claim 2, wherein said compound is TPI 1572-10.

69. The complex of claim 4, wherein said compound is TPI 1572-10.

70. The isolated agent of claim 1, wherein said compound is TPI 1572-11.

71. The composition of claim 2, wherein said compound is TPI 1572-11.

72. The complex of claim 4, wherein said compound is TPI 1572-11.

73. The isolated agent of claim 1, wherein said compound is TPI 1572-17.

74. The composition of claim 2, wherein said compound is TPI 1572-17.

75. The complex of claim 4, wherein said compound is TPI 1572-17.

76. The isolated agent of claim 1, wherein said compound is TPI 1572-18.

77. The composition of claim 2, wherein said compound is TPI 1572-18.

78. The complex of claim 4, wherein said compound is TPI 1572-18.

79. The isolated agent of claim 1, wherein said compound is TPI 1572-19.

80. The composition of claim 2, wherein said compound is TPI 1572-19.

81. The complex of claim 4, wherein said compound is TPI 1572-19.

82. The isolated agent of claim 1, wherein said compound is TPI 1572-20.

83. The composition of claim 2, wherein said compound is TPI 1572-20.

84. The complex of claim 4, wherein said compound is TPI 1572-20.

85. The isolated agent of claim 1, wherein said compound is TPI 1572-21.

86. The composition of claim 2, wherein said compound is TPI 1572-21.

87. The complex of claim 4, wherein said compound is TPI 1572-21.

88. The isolated agent of claim 1, wherein said compound is TPI 1572-22.

89. The composition of claim 2, wherein said compound is TPI 1572-22.

90. The complex of claim 4, wherein said compound is TPI 1572-22.

91. The isolated agent of claim 1, wherein said compound is TPI 1572-23.

92. The composition of claim 2, wherein said compound is TPI 1572-23.

93. The complex of claim 4, wherein said compound is TPI 1572-23.

\* \* \* \* \*